(12) United States Patent
Anant et al.

(10) Patent No.: US 8,936,941 B2
(45) Date of Patent: Jan. 20, 2015

(54) COMPOSITIONS USEFUL FOR CANCER DETECTION AND TREATMENT, A CANCER STEM CELL MODEL, AND METHODS OF PRODUCTION AND USE THEREOF

(75) Inventors: Shrikant Anant, St. Louis, MO (US); Courtney Houchen, Edmond, OK (US); Satish Ramalingam, Kansas City, KS (US); Rama Ramanujam, Dublin, OH (US); Dharmalingam Subramanlam, Overland Park, KS (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 524 days.

(21) Appl. No.: 13/027,845

(22) Filed: Feb. 15, 2011

(65) Prior Publication Data
US 2011/0283372 A1 Nov. 17, 2011

Related U.S. Application Data

(63) Continuation-in-part of application No. 12/386,550, filed on Apr. 20, 2009, now Pat. No. 7,902,166, which is a continuation-in-part of application No. 12/384,387, filed on Apr. 3, 2009, now Pat. No. 7,956,044, application No. 13/027,845, which is a continuation-in-part of application No. 12/454,355, filed on May 15, 2009, now Pat. No. 8,198,255.

(60) Provisional application No. 61/124,654, filed on Apr. 18, 2008, provisional application No. 61/123,045, filed on Apr. 3, 2008, provisional application No. 61/128,063, filed on May 16, 2008.

(51) Int. Cl.
| | |
|---|---|
| *C12N 15/00* | (2006.01) |
| *C12N 5/00* | (2006.01) |
| *G01N 33/574* | (2006.01) |
| *C12N 15/113* | (2010.01) |
| *C12N 5/095* | (2010.01) |
| *A61K 31/7088* | (2006.01) |
| *A61K 9/127* | (2006.01) |

(52) U.S. Cl.
CPC .. *A61K 31/7088* (2013.01); *G01N 2333/91215* (2013.01); *G01N 33/574* (2013.01); *C12N 2510/00* (2013.01); *C12N 15/113* (2013.01); *A61K 9/127* (2013.01); *C12N 5/0695* (2013.01); *C12N 2310/14* (2013.01); *C12N 2503/02* (2013.01)
USPC .......................................... 435/455; 435/325

(58) Field of Classification Search
USPC ................................................. 435/455, 325
See application file for complete search history.

(56) References Cited

U.S. PATENT DOCUMENTS

| 7,345,027 B2 | 3/2008 | Tolentino et al. |
| 7,511,025 B2 | 3/2009 | Wyatt et al. |
| 7,511,132 B2 | 3/2009 | Khvorova et al. |

OTHER PUBLICATIONS

Gerbe et al (Gastroenterology 137:2179-2184, 2009).*
Elbashir et al., "Analysis of Gene Function in Somatic Mammalian Cells Using Small Interfering RNAs"; Methods, vol. 26:199-213 (2002).
Battelli et al., "The RNA-binding Protein Musashi-1 Regulates Neural Development Through the Transplant Repression of p21 $^{WAF-1}$", Mol. Cell. Neurosci., vol. 31:85-96 (2006).
Mukherji et al., "A Phosphoproteomic Analysis fo the ErbB2 Receptor Tyrosine Kinase Signaling Pathways", Biochemistry, vol. 45:15529-15540 (2006).
Ratti et al., "A Role for the ELAV RNA-binding Proteins in Neural Stem Cells: Stabilization of *Msi1* mRNA", Journal of Cell Science, vol. 119:1442-1452 (2006).
Xi et al., "Differentially Regulated Micro-RNAs and Actively Translated Messenger RNA Transcripts by Tumor Suppressor p53 in Colon Cancer", Clin Cancer Research, vol. 12:2014-2024 (2006).
Smart et al., "Two Isoforms of the Cold-inducible mRNA-binding Protein RBM3 Localize to Dendrites and Promote Translation", J. Neurochem, vol. 101:1367-1379 (2007).
May, et al., "DCAMKL-1 and LGR5 Mark Quiescent and Cycling Intestinal Stem Cells Respectively", Stem Cell, pp. 1-38 (2009).
Sureban et al., "Knockdown of RNA Binding Portein Musashi-1 Leads to Tumor Regression In Vivo", Gastroenterology 134:1448-1458 (2008).
May et al., "Identification of a Novel Putative Pancreatic Stem/Progenitor Cell Marker DCAMKL-1 in Normal MousePancreas", Am. J. Physiol. Gastrointest Liver Physiol., vol. 299:G303-G310 (2010).
Mwangi et al., "DCAMKL-1: a New Horizon for Pancreatic Progenitor Indentification", Am. J. Physiol. Gastrointest. Liver Physiol. vol. 299:G301-302 (2010).
Nakanishi et al.; "DCLK1 Distinguishes Between Tumor and Normal Stem Cells in the Intestine," Nature Genetics 45:98-103 (2013).
Melcalf and De Sauvage; "A Tumor-Specific Stem Cell," Nature Genetics 45:7-9 (2013).
Vedeld et al.; "The Recently Suggested Intestinal Cancer Stem Cell Marker DCLK1 is an Epigenetic Biomarker for Colorectal Cancer," Epigenetics 9:346-350 (2014).

* cited by examiner

*Primary Examiner* — Marcia S Noble
(74) *Attorney, Agent, or Firm* — Dunlap Codding, PC

(57) ABSTRACT

DCAMKL-1 has been identified as a biomarker for stem cells, as well as cancer stem cells. Methods of detecting the presence of at least one stem cell, methods of isolating stem cells, and methods of inhibiting growth of cancer cells utilizing DCAMKL-1 are disclosed herein.

5 Claims, 54 Drawing Sheets
(51 of 54 Drawing Sheet(s) Filed in Color)

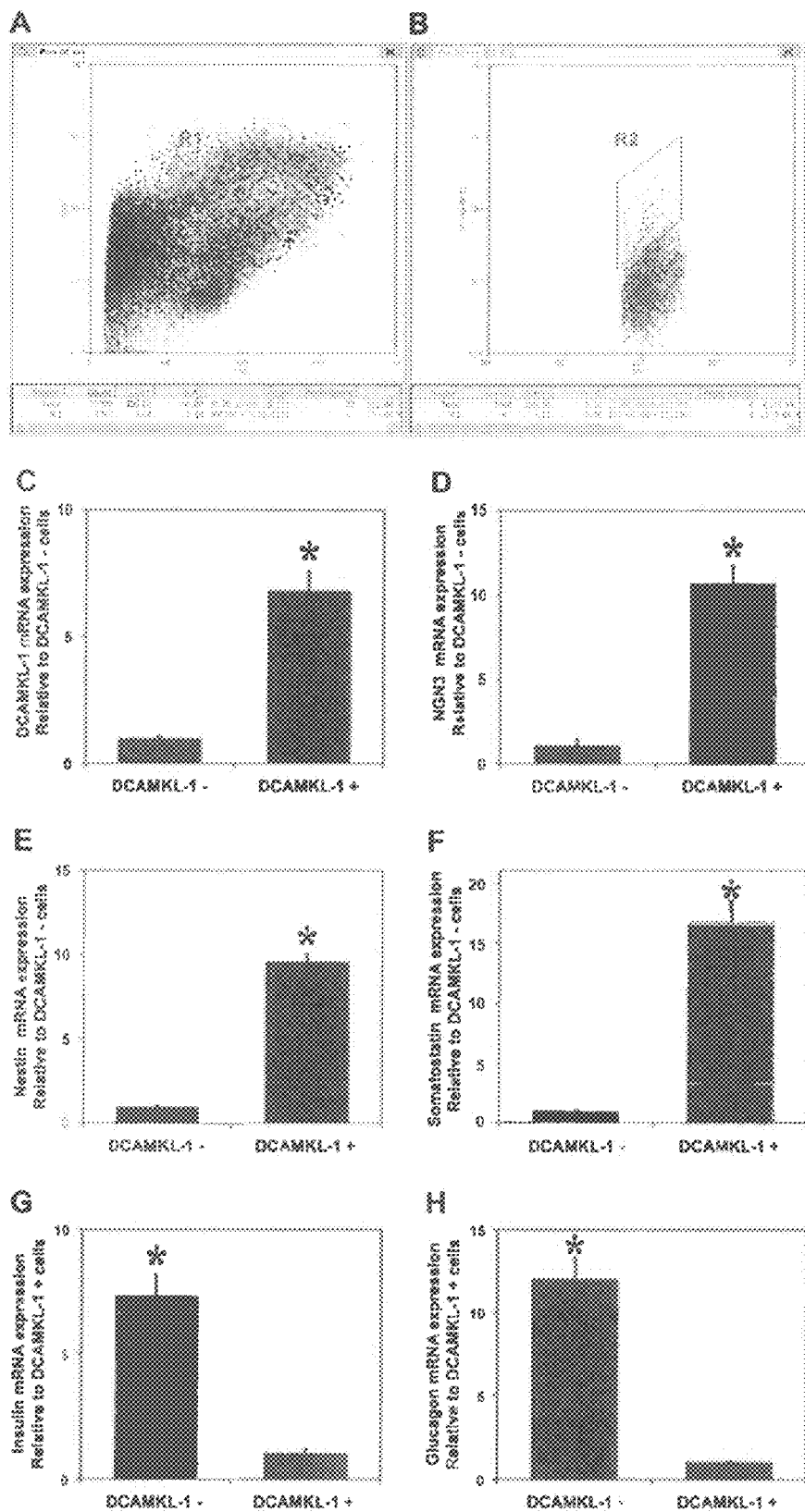

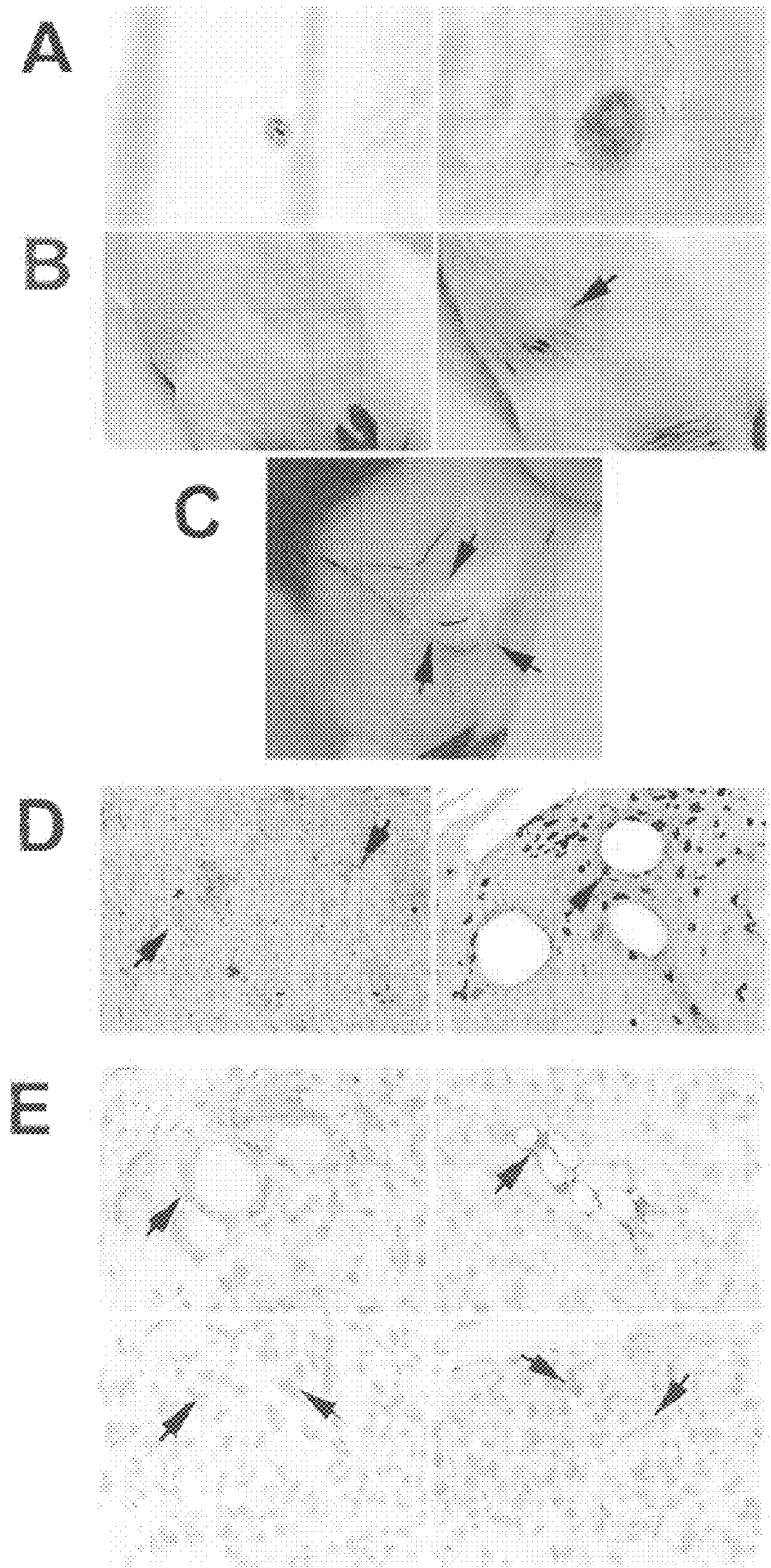

Figure 26
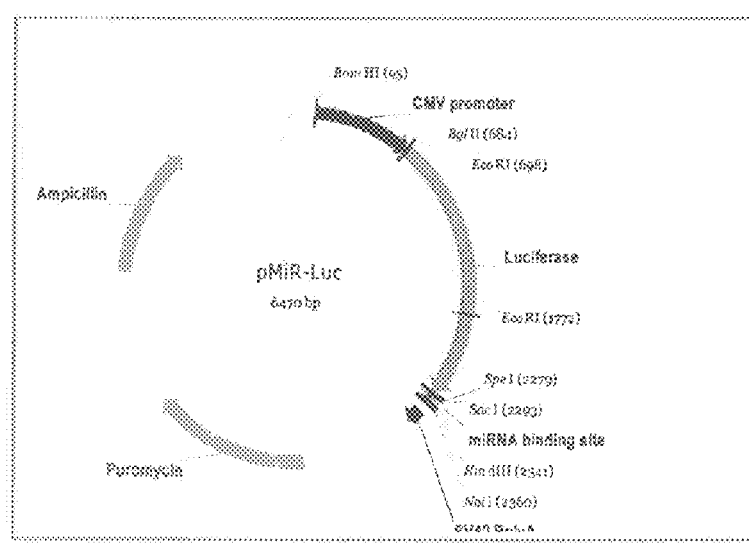
5' ----AGAAAAATCAGAGAGATCCTCATAA--AGGCCAAGAAGGGCGGAAAGTCCAAATTGCTCGAG
         Luciferase Gene
TGATGAAAGCTGCGCACTAGT--AACTATACAACCTACTACCTCA---AAGCTTAATAAAGGAT
         (SpeI)    let7a Binding Site        (HindIII)
CTTTTATTTT CATTGGATCT GTGTGTTGGT TTTTTGTATG CGGCCGCTA---- 3'
                                              (NotI)

Figure 28
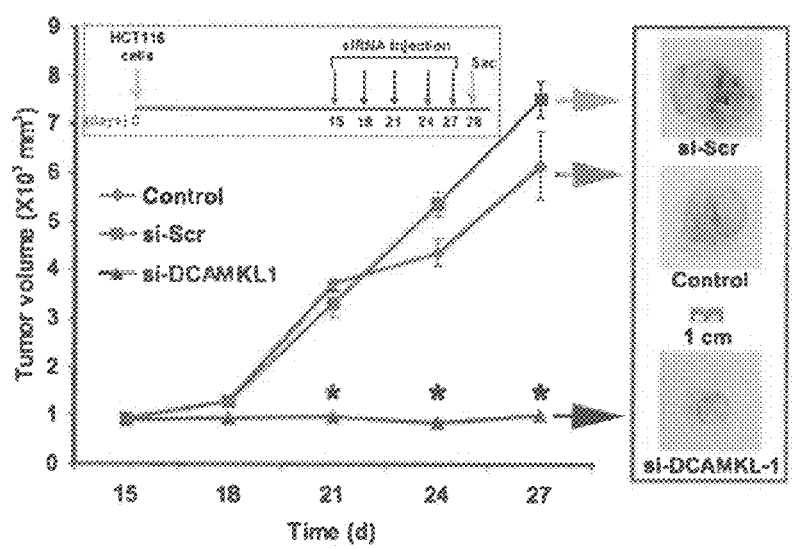
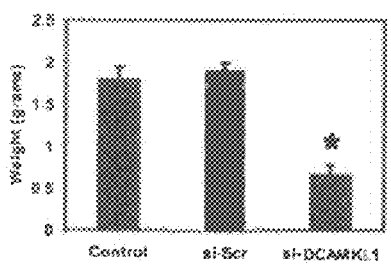
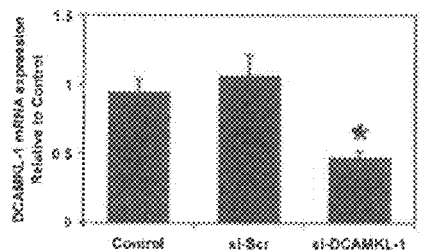
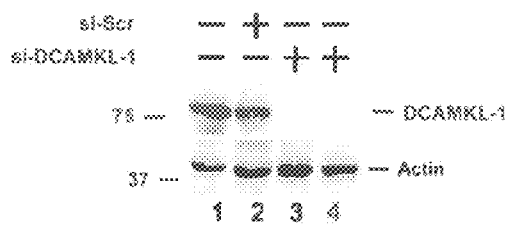

NIH3T3-RBM3 TUMOR XENOGRAFT

Figure 49
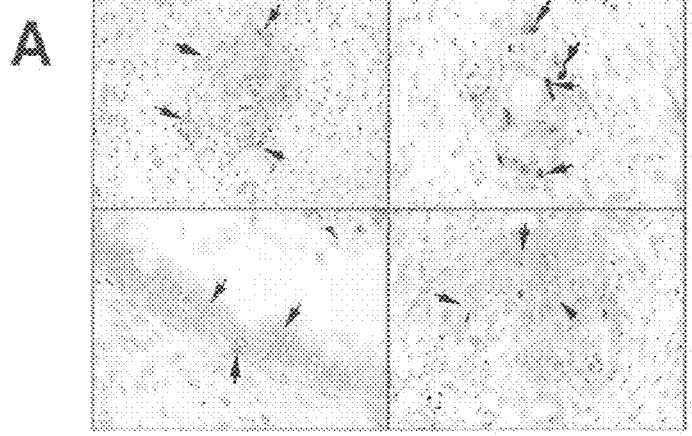
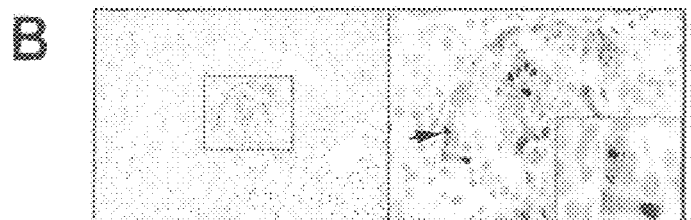
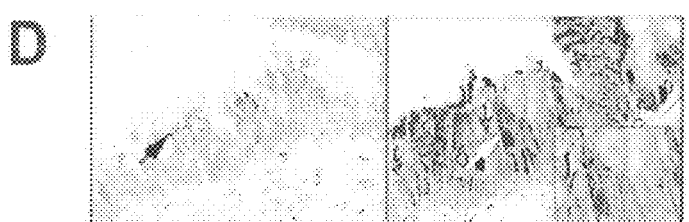
Figure 50
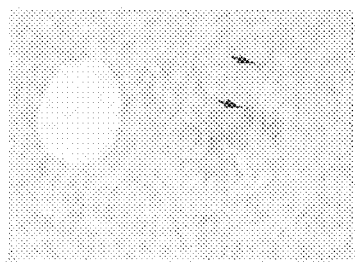

FIGURE 55
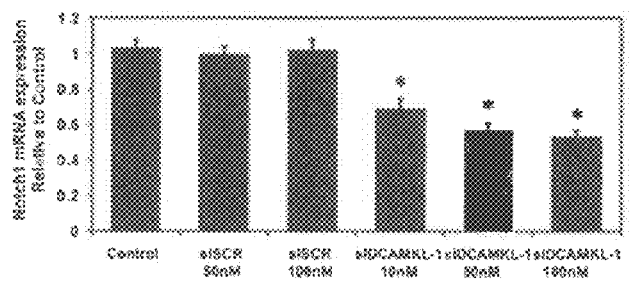
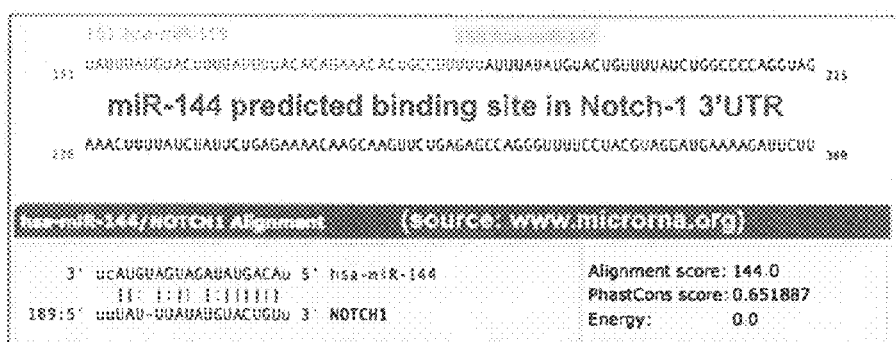
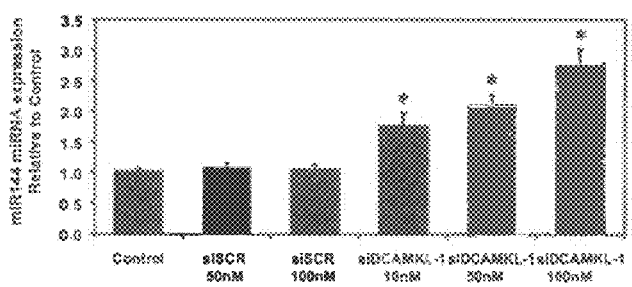
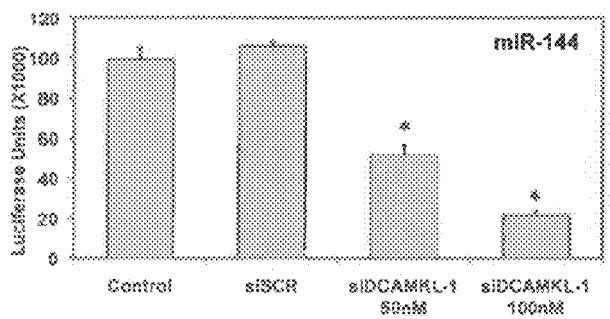

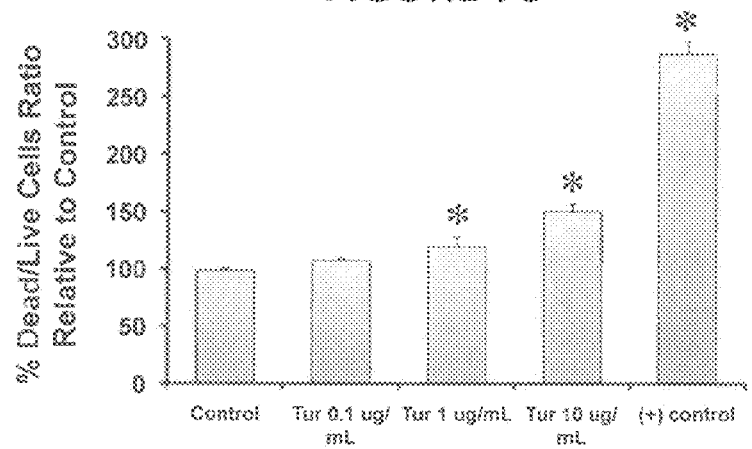
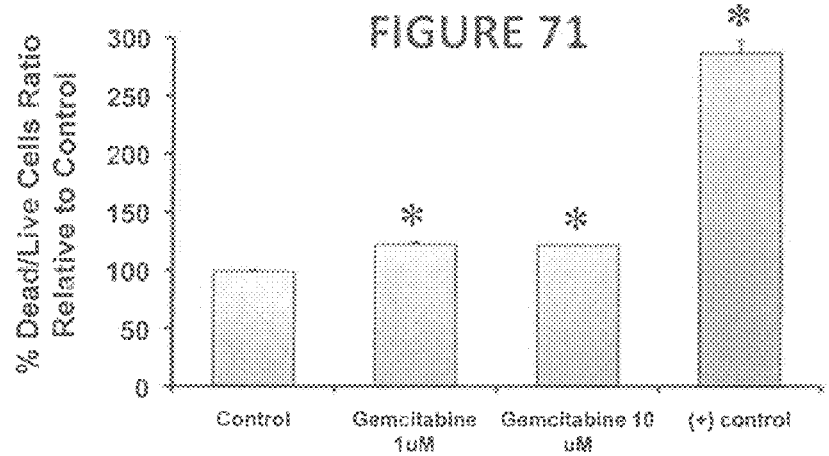
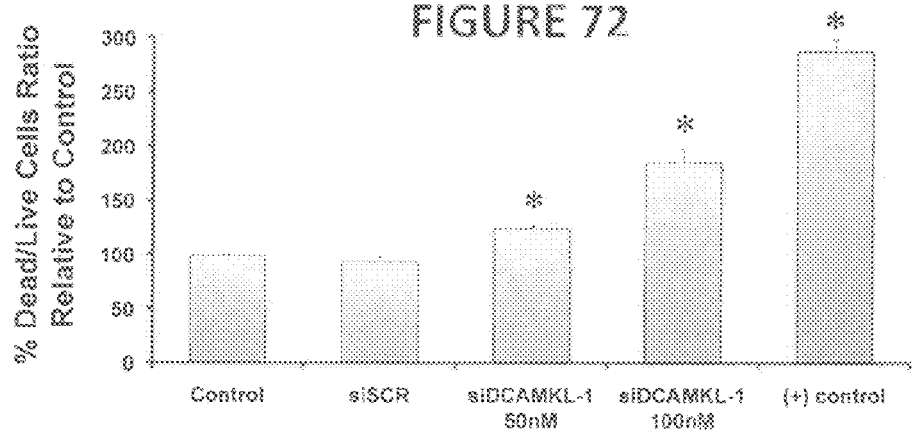

COMPOSITIONS USEFUL FOR CANCER DETECTION AND TREATMENT, A CANCER STEM CELL MODEL, AND METHODS OF PRODUCTION AND USE THEREOF

CROSS REFERENCE TO RELATED APPLICATIONS

This application is a continuation-in-part of U.S. Ser. No. 12/386,550, filed Apr. 20, 2009 now U.S. Pat. No. 7,902,166; which is a continuation-in-part of U.S. Ser. No. 12/384,387, filed Apr. 3, 2009 now U.S. Pat. No. 7,956,044; which claims benefit under 35 U.S.C. 119(e) of provisional application U.S. Ser. No. 61/123,045, filed Apr. 3, 2008. Said '550 application also claims benefit under 35 U.S.C. 119(e) of provisional application U.S. Ser. No. 61/124,654, filed Apr. 18, 2008.

This application is also a continuation-in-part of U.S. Ser. No. 12/454,355, filed May 15, 2009 now U.S. Pat. No. 8,198,255; which claims benefit under 35 U.S.C. 119(e) of provisional application U.S. Ser. No. 61/128,063, filed May 16, 2008.

The entire contents of each of the above-referenced patents and patent applications are hereby expressly incorporated herein by reference.

STATEMENT REGARDING FEDERALLY SPONSORED RESEARCH OR DEVELOPMENT

This invention was made with government support under Contract Numbers CA135559 and CA137482 awarded by the National Institutes of Health. The government has certain rights in the invention.

BACKGROUND OF THE INVENTION

1. Field of the Invention

The presently disclosed and claimed inventive concept(s) relates generally to compositions useful in cancer detection and/or treatment, as well as methods of producing and using same.

2. Brief Description of the Art

Cancer of the colon is the second most frequently diagnosed malignancy in the United States, as well as the third leading cause of cancer death. Colon cancer is a highly treatable and often curable disease when localized to the bowel. Surgery is the primary treatment and results in cure in approximately 50% of patients. However, recurrence and metastases following surgery is a major problem and often is the ultimate cause of death.

Due to its proximity, cancer of the colon often metastasizes to the small intestine. The prognosis of the cancer spreading to the small intestine is related to the degree of penetration of the tumor through the bowel wall and the presence or absence of nodal involvement. These two characteristics form the basis for all staging systems developed for colon cancer. Various characteristics also assist in prognosticating colon cancer and its spread to the small intestines. For example, bowel obstruction and bowel perforation are indicators of poor prognosis. Elevated pretreatment serum levels of carcinoembryonic antigen (CEA) and of carbohydrate antigen 19-9 (CA 19-9) also have a negative prognostic significance. However, age greater than 70 years at presentation is not a contraindication to standard therapies; acceptable morbidity and mortality, as well as long-term survival, are achieved in this patient population.

Cancer cells can also originate in the small intestine. However, this is a much rarer type of cancer. Symptoms of cancer of the small intestine typically include pain or cramps in the middle of the abdomen, weight loss without dieting, a lump in the abdomen, or blood in the stool.

Cancer of the stomach, also referred to as gastric cancer, also frequently metastasizes to the small intestine due to its proximity. This cancer is often difficult to diagnose in early stages and can be in the stomach for a long time, growing to a large size before symptoms arise. In the early stages of cancer of the stomach, an individual may experience indigestion and stomach discomfort, a bloated feeling after eating, mild nausea, loss of appetite or heartburn. In more advanced stages of stomach cancer, there may be blood in the stool, vomiting, weight loss or more severe pain.

Because of the frequency of these types of cancer (approximately 160,000 new cases of colon and rectal cancer per year alone), the identification of high-risk groups, the demonstrated slow growth of primary lesions, and the better survival of early-stage lesions, screening for gastrointestinal cancers should be a part of routine care for all adults starting at age 50, especially those with first-degree relatives with colorectal cancer.

Procedures used for detecting, diagnosing, monitoring, treating and preventing cancer of the colon, small intestine and/or stomach are of critical importance to the outcome of the patient. Patients diagnosed with early stage cancer generally have a much greater five-year survival rate as compared to the survival rate for patients diagnosed with distant metastasized cancers. New diagnostic methods which are more sensitive and specific for detecting early cancer of the stomach, small intestine and colon are clearly needed.

Patients with gastrointestinal cancers are closely monitored following initial therapy and during adjuvant therapy to determine response to therapy and to detect persistent or recurrent disease of metastasis. There is clearly a need for a cancer marker which is more sensitive and specific in detecting recurrence of these types of cancer.

Stem cells are ultimately responsible for the entire cell production process in a particular tissue. They have a potential capability of large numbers of cell division and maintenance of cell replacement during the entire life of an animal (Potten et al., 2003). The epithelial cells of intestinal villi of the small intestinal mucosa are replaced within 2-3 days, and this rapid cell turnover, in addition to self-renewal by the intestinal tissue, is governed by epithelial stem cells present in the crypts of the small intestine (Okano et al., 2005). The Musashi-1 (Msi-1) gene encodes an RNA binding protein involved in early asymmetric divisions generating differentiated cells from neural stem cells or progenitor cells. Msi-1 expression was observed in the small intestine at the fourth-sixth cell position from the bottom of the crypts and in the cells in the deepest portion of the large intestine, where the possibility of stem cells is considered to be high (Okano et al., 2005; and Marshman et al., 2002).

Several lines of evidence suggest that some tumor types are maintained by a small population of self-renewing cells or "cancer stem cells". The transformation of a normal mucosal epithelial cell to an invasive colorectal carcinoma occurs via a well-coordinated accumulation of mutations in a series of critical genes (Riehl et al., 2006). In gut, tumorigenesis arises from the stem cell population located near the base of intestine and colonic crypts (Potten et al., 2003). Msi-1 has been shown to be a positive regulator of Notch signaling through its interaction and translational repression of mammalian Numb (mNumb) messenger RNA (mRNA) (an inhibitor of Notch signaling) (Okano et al., 2002). Recently, reports have emerged showing that Msi-1 regulates neuronal development through the translational repression of p21$^{WAF1/Cip1}$ (Battelli et al., 2006; Sakakibara et al., 1996; and Imai et al., 2001). Msi-1 expression in intestinal tumors of APC$^{min/+}$ mice is thought to be caused by activation of Notch signaling. However, the definitive role of Msi-1 in colon cancer and cancer progression is currently unclear.

Dysregulated expression of oncogenes and tumor suppressors is a critical regulator of tumorigenesis. Known targets that lead to a tumorigenic phenotype include cyclooxygenase (COX)-2, interleukin (IL)-8 and vascular endothelial growth factor (VEGF) (Dixon et al., 2001; Dubois et al., 1998; Wang et al., 2005). COX-2 is the rate-limiting enzyme in the production of prostaglandins (PGs), an important mediator of various cellular processes including increased proliferation, apoptosis resistance and enhanced angiogenesis (Krysan et al., 2005; Mukhopadhyay et al., 2003b). COX-2 overexpression occurs in multiple tumors, and can be observed at various stages of tumorigenesis (Eberhart et al., 1994). While transcriptional activation of COX-2 is an early event, it is also regulated at the posttranscriptional levels of mRNA stability and translation (Dixon et al., 2000).

Distinct cis-acting AU-rich elements (ARE) sequence elements located within the 3' untranslated region (3'UTR) have been identified in the COX-2, IL-8 and VEGF mRNA that regulate mRNA stability and translation (Cok & Morrison, 2001; Dixon et al., 2001; Ristimaki et al., 1996). Specifically, the first sixty nucleotides in COX-2 3'UTR encode AREs, which regulate mRNA stability and translation (Cok & Morrison, 2001; Mukhopadhyay et al., 2003a). RNA binding protein HuR interacts with these ARE sequences to regulates the stability and translation of COX-2 mRNA (Cok & Morrison, 2001; Dixon et al., 2000). HuR is also upregulated in various cancers (Denkert et al., 2006a; Denkert et al., 2004; Erkinheimo et al., 2003; Nabors et al., 2001).

RNA binding motif protein 3 (RBM3) is a ubiquitously expressed glycine-rich protein that can bind to both RNA and DNA via an amino-terminal RNA binding domain. RBM3 was identified as a protein expressed following cold shock and was found in the complex of proteins binding to COX-2. However, the correlation of RBM3 to COX-2, IL-8 and VEGF mRNA stability, translation and cancer progression have not been demonstrated.

Defining the mechanisms that regulate stem cell fate is critical in increasing our understanding of the neoplastic process. Tumorigenesis in the gut arises specifically in the stem cell (Clarke, 2005; de Lau, 2007; and He, 2007) population located at or near the base of the intestinal and colonic crypts, while transit cell populations originating from the stem cell zone become fully differentiated and are eventually sloughed into the lumen. The short life span of transit cells, whether they are mutated or not, limits their deleterious influence in the intestinal or colonic crypt (Potten, 2003; and Booth, 2002). Because no specific gut stem cell markers have been identified definitively (Bjerknes, 2005; and Kayahara, 2003), recognizing and assaying resident intestinal stem cells is quite difficult and has raised contentious argument; however, the microcolony assay following γ-irradiation is by definition a functional evaluation of intestinal stem cell fate (Withers, 1970) and can provide a mechanism for examining the early events of tumorigenesis. Because homeostatic mechanisms of stem cell proliferation are the same processes that become dysregulated in carcinogenesis (Sancho, 2003), a complete examination of these proliferation mechanisms holds medical significance in targeting future cancer treatments; therefore, a more detailed understanding of the pathways that regulate stem cell behavior is essential.

Recently, MSI-1 (Musashi-1) has been identified as a putative stem cell marker (Potten et al., (2003) Differentiation, 71:28-41). Musashi-1 was identified as an RNA binding protein that is a translational repressor of p21. Musashi-1 regulates asymmetric division in neural precursor cells, and is expressed in intestinal crypts in the stem cell zone. Its increased expression has also been observed in tumors in APC/Min mice. However, it has not been shown to be a reliable intestinal stem cell marker.

Pancreatic adenocarcinoma has the worst prognosis of any major malignancy with a 3% 5-year survival (Hoyer et al., 2006). Major obstacles in treating pancreatic cancer include extensive local tumor invasion and early metastasis. Recently, it has been proposed that pancreatic tumors arise specifically in the stem cell population located in these tissues. There is increasing evidence that a small subset of cells termed cancer stem cells (CSCs) or cancer initiating cells (CICs) are capable of initiating and sustaining tumor growth in transplantation assays (Diehn and Clarke, 2006). CSCs share unique properties with normal adult stem cells, including the ability to self-renew and differentiate. CSCs are often refractory to current standard chemotherapeutic agents and radiation therapies, as they are designed to eradicate actively cycling cells, not slowly cycling cancer stem cells. Thus novel therapies that specifically target the cancer stem cell population, either alone or in conjunction with current strategies, may be more effective in obliterating solid tumors.

The existence of CSCs was first demonstrated in acute myelogenous leukemia (Bonnet and Dick, 1997) and subsequently verified in breast (Al-Hajj et al., 2003), pancreatic (Li et al., 2007) and brain tumors (Singh et al., 2004a; Singh et al., 2003; Singh et al., 2004b). The CD133+ subpopulations from brain tumors could initiate clonally derived neurospheres in vitro showing self-renewal, differentiation, and proliferative characteristics similar to normal brain stem cells (Singh et al., 2004a; Singh et al., 2003; Singh et al., 2004b). Furthermore, transplantation of CD133+, but not CD133−, cells into NOD/SCID mice was sufficient to induce tumor growth in vivo. In a recent study, primary human pancreatic adenocarcinomas were implanted in immunocompromised mice to assess the ability of specific cell surface markers to identify a subpopulation of pancreatic cancer cells with enhanced tumorigenic potential (Li et al., 2007). A subpopulation of CD44+CD24+ ESA+ cells was identified as putative pancreatic cancer stem cells.

Tumor cell heterogeneity present in most solid tumors creates an enormous challenge for cancer eradication. Current strategies for inducing cell death generally target only the most rapidly proliferating cells within a tumor. Indeed, radiation therapy targets proliferating cells, which are the most sensitive to ionizing radiation (Cohn et al., 1997; Houchen et al., 2000; Riehl et al., 2000; Tessner et al., 1998); however, it is clear that effective tumor-eradication strategies must address the potential survival mechanisms unique to each particular cell type within the malignant population (i.e., quiescent stem cells). Currently, most traditional cancer therapies are based on their ability to kill most of the tumor population (i.e., log kill assays), but these treatments often fail to destroy cancer stem cells, which have been shown in several tumor types to be more resistant to standard chemotherapeutic agents (Li et al., 2007). This may explain why standard chemotherapy is effective in causing tumor shrinkage but often fails to prevent tumor recurrence, possibly due to the surviving cancer stem cell's ability to regenerate the tumor even after chemotherapeutic insult. This is not an unreasonable inference when one considers the gastrointestinal tract, where a single surviving intestinal stem cell is able to reconstitute an entire gastrointestinal crypt following severe genotoxic or cytotoxic injury (Bach et al., 2000).

Characterization of stem cells from the hematopoietic system, neural stem cells from the central nervous system and neural crest stem cells have emphasized the importance of specific cell surface antigens that permit the isolation of stem cells by fluorescence activated cell sorting (FACS). A candidate pancreatic stem cell, which is characterized by its expression of the neural stem-cell marker nestin and lack of established islet- and duct-cell markers, has been described in published reports (Abraham et al., 2004; Lechner et al., 2002; Zulewski et al., 2001). Furthermore, the basic helix-loop-helix transcription factor neurogenin 3 (NGN3) controls endocrine cell fate specification in uncommitted pancreatic progenitor cells. In the pancreas, NGN3-positive cells co-express neither insulin nor glucagon, demonstrating that NGN3 marks early precursors of pancreatic endocrine cells. Moreover, NGN3-deficient mice do not develop any islet cells and are diabetic. These data taken together demonstrate that NGN-3 and nestin are critical components of the pancreatic stem/progenitor cell compartment. A convincing recent study demonstrates that the adult mouse pancreas contains islet cell progenitors and that expansion of the 13 cell mass following injury induced by ligation of the pancreatic duct results in NGN3 gene expression and the ensuing differentiation of endogenous progenitor cells in a cell-autonomous, fusion-independent manner (Xu et al., 2008). These data demonstrate that functional islet progenitor cells can be induced in pancreatic ducts following injury.

Therefore, there is a need in the art for new and improved methods of detecting and preventing tumor growth, identifying and isolating cancer stem cells, and producing and using cancer stem cell models. It is to such compositions and methods that the presently disclosed and claimed inventive concept(s) is directed.

BRIEF DESCRIPTIONS OF THE DRAWINGS

This patent or application file contains at least one drawing executed in color. Copies of this patent or patent application publication with color drawing(s) will be provided by the Patent and Trademark Office upon request and payment of the necessary fee.

FIG. 1 illustrates the expression pattern of DCAMKL-1 in normal mouse small intestine. (A) Immunohistochemical staining of normal small intestine for DCAMKL-1, arrow indicates the cell positive for DCAMKL-1 in the stem cell zone. (B) Pre-incubation with blocking peptide completely abolishes DCAMKL-1 immunoreactivity. (C) Immunohistochemical staining of normal small intestine for DCAMKL-1, brown color indicates the cells positive for DCAMKL-1 (indicated by the arrows).

FIG. 2 illustrates co-localization of Musashi-1 and DCAMKL-1 in mouse intestine. (A) Immunohistochemical staining of normal small intestine for DCAMKL-1 (brown color indicated by the arrow). (B) Immunohistochemical staining of normal small intestine for Musashi-1, brown color indicates the cells positive for Musashi-1 at the base of the crypts. (C) The cell positive for DCAMKL-1 stained red (indicated by the arrow) appears at the base of the crypt. (D) Intestinal section stained for Musashi-1 green. (E) Co-localization of DCAMKL-1 and Musashi-1 (yellow indicated by the arrow). The magnified inset image represents the single cell positive for both DCAMKL-1 and Musashi-1. (F) Co-staining of DCMAKL-1 (red color indicated by the arrow) with nuclear Hoechst 33342 (blue) staining. (G) Co-staining of Musashi-1 (green) with nuclear Hoechst 33342 (blue) staining. (H) Colocalization of DCAMKL-1 and Musashi-1 (yellow indicated by the arrow), co-stained with nuclear Hoechst 33342 (blue) staining. The magnified inset image represents the single cell positive for both DCAMKL-1 and Musashi-1 (yellow color).

FIG. 3 illustrates the fate of DCAMKL-1 positive cell following ionizing radiation (IR). (A) 6 h after whole body 6 Gy IR, morphologically appearing apoptotic cells were observed in the lower third of the intestinal crypt, but apoptosis is not observed in any of the DCAMKL-1 positive cells indicated by the arrow. (B) The small intestine stained for DCAMKL-1 (red) and TUNEL (green) to demonstrate apoptosis in the crypts 6 h following radiation. (C) Small intestine of unirradiated mice demonstrating no staining for phospho-H2AX. The crypt area is magnified in the inset. (D) 6 h post IR; small intestine demonstrates DNA damage by positive phospho-H2AX staining (DAB brown). The crypt area is magnified in the inset. (E) 6h post IR; small intestine demonstrates DNA damage in the DCAMKL-1 positive cell indicated by the arrow. The magnified inset image represents the single cell positive for both DCAMKL-1 and phospho-H2AX. (F) After 24 h after IR, the appearance of multiple DCAMKL-1 immunoreactive mitotic figures indicated by 'M' were noted adjacent to morphologically appearing apoptotic cells indicated by arrows that were also expressing DCAMKL-1.

FIG. 4 illustrates DCAMKL-1 expression in the regenerative crypts post IR. (A) 84 h following IR, no DCAMKL-1 expression could be detected in regenerative crypts. (B) Staining at 144 h after IR demonstrates restoration of DCAMKL-1 expression in the intestinal crypt indicated by arrows.

FIG. 5 illustrates the histological evaluation of small intestine of APC/min mice. (A) Scattered single cells were immunoreactive for DCAMKL-1 in the intestinal crypts (arrow) and a trend towards increased expression on villi (arrow head). (B) DCAMKL-1 staining within adenomas of APC/min mice indicated by the arrows. DCAMKL-1 was also immunoreactive in the cells within the villus epithelium surrounding the adenoma (arrow head). (C) APC/min intestinal adenoma immunostained with anti-PCNA (red) and co-stained with DCAMKL-1 (brown). The cells immunoreactive for DCAMKL-1 are indicated by the arrows. (D) Portion of (A) magnified to demonstrate the cell positive for DCAMKL-1 is not immunoreactive for PCNA. (E) Double staining of PCNA and DCAMKL-1 in putative stem cell zone of wild-type mouse demonstrates the quiescent state of the DCAMKL-1 expression cell indicated by the arrow.

FIG. 6 illustrates β-Catenin expression in the small intestine of APC/min mice localized with DCAMKL-1. (A) Normal appearing APC/min mice intestine immunostained for membrane β-Catenin (brown) and cytoplasmic DCAMKL-1 (red) co-immunostaining indicated by arrow. (B) Magnified image of (A) demonstrating the cell positive for DCAMKL-1 and β-Catenin indicated by arrow. (C) DCAMKL-1 expressing cell (arrow) along with other cells demonstrating nuclear translocation of β-Catenin within an APC/min adenoma indicated by the arrow, just adjacent to normal membrane β-Catenin staining epithelium. (D) Magnified image of (C) demonstrating the DCAMKL-1 positive cell indicated by the arrow.

FIG. 7 illustrates the colonic distribution of DCAMKL-1 and structure of cell positive for DCAMKL-1. (A) The cell positive for DCAMKL-1 appears at the midpoint of the colonic crypt in the proximal colon. (B) In distal colon, the distribution of DCAMKL-1 expression appears at the base of the colonic crypt. (C) The close views of DCAMKL-1 expressing cells within the colon and distal jejunum (D) demonstrates the axonal-like process.

FIG. 8 illustrates pancreatic DCAMKL-1 expression and specific islet cell type differentiation in adult mice. (A) DCAMKL-1 expression (brown) in the main pancreatic duct (left) (×200) and in the periphery of pancreatic islets (middle) (×400). No DCAMKL-1 expression was observed in acinar cells or accessory ducts (right) (×400). (B) Immunofluorescence demonstrating DCAMKL-1 (red) and somatostatin (green) staining of pancreatic islets. Co-localization is demonstrated in merged image. (C) DCAMKL-1 (red) and glucagon (green) immunofluorescence staining of pancreatic islets. No colocalization is observed in the merged image. (D) Immunofluorescence demonstrating DCAMKL-1 (red) and insulin (green) staining of pancreatic islets. No co-localization is observed in the merged image. Images on the far right in B-D are the magnified portion of the corresponding merged images. In the immunofluorescence staining, nuclei were stained blue with Hoechst dye.

FIG. 9 illustrates DCAMKL-1 and other putative pancreatic stem/progenitor cell markers. Newborn mice pancreas demonstrates DCAMKL-1 staining (A; arrows) and neurogenin 3 (NGN3; B; arrows) (×600). Immunofluorescence staining for DCAMKL-1 (C; red) and NGN3 (D; green) in the newborn mice pancreas. E-F: colocalization demonstrated in merged image with nucleic stained blue with Hoechst dye (×400). Adult mouse pancreatic tissue serial sections stained with DCAMKL-1 (G), NGN3 (H) and nestin (I) (×200). Immunofluoresence staining of newborn mouse pancreas demonstrated the presence of DCAMKL-1 (J) and nestin (K). L-M: colocalization demonstrated in merged image with nuclei stained blue with Hoechst dye (×400). Insets in J-M are magnified images.

FIG. 10 illustrates DCAMKL-1 and 14-3-3 σ expression in human pancreatic adenocarcinoma. (A) DCAMKL-1 expression (brown) in histologically normal appearing tissue from pancreatic cancer resection specimen (top left). Spindle-shaped cytoplasmic staining of DCAMKL-1 in neoplastic pancreatic islet tissue (top right). DCAMKL-1 expression in ductal epithelial cells of pancreatic adenocarcinoma (bottom left). Intervening stromal elements demonstrate fibrillar DCAMKL-1 immunoreactivity (bottom right). Representative cells are indicated by arrows. (B) Staining for 14-3-3 σ (purple) and DCAMKL-1 (brown) at the islet periphery in normal appearing pancreatic tissue (left). In a magnified portion of the left image, a representative cell demonstrating the cytoplasmic expression of 14-3-3 σ is indicated with arrow (right). (C) 14-3-3 σ (purple) and DCAMKL-1 (brown) expression in pancreatic adenocarcinoma (left). In a magnified portion of the left image, nuclear localized 14-3-3 σ (purple) in individual cells co-localized with cytoplasmic DCAMKL-1 (brown) indicated by arrowhead (right). Fibrillar DCAMKL-1 staining in the intervening stroma is indicated by arrows. (D) Left image demonstrates DCAMKL-1 (brown) expression in ductal epithelium of a PanIN type lesion, a representative cell is indicated by arrow. Image on the right demonstrates intense cytoplasmic and nuclear staining of 14-3-3 σ (purple) and cytoplasmic DCAMKL-1 (brown) in a PanIN lesion. Representative cell demonstrating nuclear 14-3-3 σ co-localized with DCAMKL-1 is indicated by arrow. Insets in the images on the right in the panel B, C and D are magnified images.

FIG. 11 illustrates DCAMKL-1 and vimentin expression in human pancreatic adenocarcinoma. (A) Arrow in the left image indicates a single slender DCAMKL-1 expressing cell in a PanIN type lesion. A single elongated vimentin expressing cell in the ductal epithelium of a PanIN type lesion as indicated by arrow (right). (B) Immunofluorescence staining for DCAMKL-1 (red) and vimentin (green) in a PanIN lesion. Merged images reveal distinct co-localization of DCAMKL-1 and vimentin as indicated by arrows with nuclei stained blue with Hoechst dye. (C) Immunofluorescence staining for DCAMKL-1 (red) and vimentin (green) in stromal compartment of pancreatic adenocarcinoma. Merged images demonstrate immunolocalization of DCAMKL-1 and vimentin with nuclei stained blue with Hoechst dye.

FIG. 12 illustrates DCAMKL-1 expression in Pdx48$^{Cre}$-activated KRAS$^{G12D}$ pancreatic cancer mouse model. Pancreatic tissues from 5-month-old WT littermate (A) and from 5-month-old (B) Pdx48$^{Cre}$ activated KRAS$^{G12D}$ mouse were immunostained for DCAMKL-1. (C) A magnified portion of the image (B) demonstrating cells positive for DCAMKL-1 in the pancreatic duct. (D) A magnified portion of the image (B) demonstrating cells positive for DCAMKL-1 in the islets. Brown colored cells (arrows) indicate cells positive for DCAMKL-1. These data demonstrate an increased expression of DCAMKL-1 correlated with progressive neoplastic changes.

FIG. 13 illustrates FACS-based isolation of DCAMKL-1 cells from mouse pancreas. FACS-based isolation of cells from mouse pancreas using anti-DCAMKL-1 antibody. FACS plot of sorted cells. (A) side scatter oval gate R1. (B) Polygon gate R2 represents sorted fluorescent cells (red) from gate R1 (0.36% of total cells). The graphs represent the mRNA expression levels of DCAMKL-1 (C), NGN3 (D), nestin (E), somatostatin (F), insulin (G), and glucagon (H) in DCAMKL-1+ and DCAMKL-1− sorted cells. *$P<0.01$.

FIG. 14 illustrates that DCAMKL-1 sorted cells demonstrate growth in vitro and in vivo. (A) FACS isolated DCAMKL-1 cells in suspension culture at day 1 (left) and demonstrating spheroid formation at day 21 (right). (B) Athymic nude mice 4 weeks after subcutaneous injection with either Matrigel™ alone (left) or spheroid with Matrigel™, arrow indicates nodular growth (right). (C) Image demonstrates a tan grey soft tissue outgrowth with blood vessel formation under the skin of the DCAMKL-1 spheroid-injected mouse as indicated by the arrows. (D) Image on the left demonstrates soft tissue from DCAMKL-1 spheroid injection stained with H&E for histological evaluation. Cells which appeared to be epithelial in nature formed early islet-like structures, as indicated by arrows. Image on the right demonstrates groups of cells, which lined up around central spaces and appeared to be poorly formed glands (arrow). (E) Cells around the central spaces were positive for cytokeratin-14, indicating glandular epithelial origin (top left—arrow) and PDX-1, a marker of early pancreatic development (top right—arrow). Islet formations expressed the endocrine markers somatostatin (bottom left—arrow) and secretin (bottom right—arrow). Additionally, cells within these nodules expressed the epithelial marker Ep-CAM (G), proliferation marker Ki67 (H) and DCAMKL-1 (I-J). Positive staining demonstrated by brown coloration (diaminobenzidine); all images shown at ×200 magnification.

FIG. 15 illustrates a schematic representation of cell surface expression of DCAMKL-1. The C-terminus of DCAMKL-1 is predicted to be outside the cell surface and thus allows for recognition with antibody directed to this domain, which facilitates the isolation of DCAMKL-1 cells by FACS.

FIG. 16 illustrates the expression of DCAMKL-1 in the mouse small intestine. (A): Brown indicates DCAMKL-1+ cells (arrows). (B): Quantitative representation of DCAMKL-1 expressing cells as measured by cell position in intestinal crypts. (C): Co-immunofluorescence staining for DCAMKL-1 (red—arrow, left panel) and ChrA (green—arrow head, middle panel) in crypts. No co-localization was observed in the merged image (right panel). (D): DCAMKL-1 (red—arrow, left panel) and pPTEN (green—arrow head, middle panel) in crypts. No co-localization was observed in the merged image (right panel). (E): DCAMKL-1 (red—arrow, left panel) and pAKT (green—arrow head, middle panel) in crypts. No co-localization was observed in the merged image (right panel). (F): DCAMKL-1 (red—arrow, left panel) and somatostatin (green—arrow head, middle panel) in crypts. No co-localization was observed in the merged image (right panel). (G): DCAMKL-1 (red—arrow, left panel) and secretin (green—arrow head, middle panel) on villus. No co-localization was observed in the merged image (right panel). * Nuclei in all merged images are stained blue with Hoechst 33342 DNA dye.

FIG. 17 illustrates LGR5 and DCAMKL-1 in the mouse small intestine. (A): Brown indicates LGR5+ cells (arrowheads). (B): Brown indicates DCAMKL-1+ cell (arrow). (C and D): Co-immunostaining for LGR5 (purple—arrowhead) and DCAMKL-1 (brown—arrow). No co-localization of LGR5 and DCAMKL-1 was observed in the putative stem cell zone (C) or CBC cells (D). Black box in (C) demonstrates a cell negative for both LGR5 and DCAMKL-1. (E-H): Co-immunofluorescence staining for LGR5 (green) (E) and DCAMKL-1 (red—arrow) (F). No co-localization of LGR5 and DCAMKL-1 was observed in merged images (G) and (H). * Nuclei in merged image (H) are stained blue with Hoechst 33342 DNA dye.

FIG. 18 illustrates that LGR5 and DCAMKL-1 mark proliferative and non-proliferative cells respectively in the mouse small intestine. Co-immunofluorescence staining for PCNA (green) (A) and LGR5 (red—arrowheads) (B). PCNA+LGR5+ cells are indicated with arrowheads in the merged image (C). PCNA (green) (D) and DCAMKL-1 (red—arrow) (E). A PCNA-DCAMKL-1+ cell is indicated by the arrow in the merged image (F). * Nuclei in all merged images (C and F) are stained blue with Hoechst 33342 DNA dye.

FIG. 19 illustrates that DCAMKL-1 identifies the quiescent anchored stem cell. Following mLRA, mouse intestines (distal jejunum) were immunostained for BrdUrd (brown) at day 7 (A) magnified in (B) and at day 10 (C) magnified in (D). (E-F): Mouse intestines 10 days post 8 Gy IR were co-immunostained for DCAMKL-1 (brown) and BrdUrd (purple) or PCNA (purple). (E): Arrow indicates a BrdUrd+ (label retaining) and DCAMKL-1+ cell. (F): Arrow indicates a PCNA- (quiescent) and DCAMKL-1+ cell.

FIG. 20 illustrates the isolation of intestinal stem cells using DCAMKL-1 based FACS. (A): Schematic diagram depicting the predicted cell surface expression and extracellular C-terminal domain of DCAMKL-1. (B): Western blot analyses demonstrating cell surface expression of DCAMKL-1 following biotinylation (Pierce Cell Surface Protein Isolation Kit). Biotinylated cell surface protein extract from intact cells (see FIG. 21) demonstrated the presence of DCAMKL-1 (Lane B), but not in the unbound non-biotinylated intracellular protein extract fraction (Lane N). As a positive control, EGFR a known cell surface expressing protein was detected only in the bound fraction. (C): A representative Alexa Fluor® 568 conjugated DCAMKL-1+ cell following FACS (red); nucleus is stained blue with Hoechst 33342 DNA dye post-sorting. (D): A single DCAMKL-1 sorted cell in suspension culture at day 0. (E): A spheroid containing 50-100 cells at day 21. Isotransplantation assays: (F): Matrigel™ alone injected control mouse, (G): spheroid injected mouse demonstrating nodular growth on the flank (arrow), H&E staining of excised nodules from (H) control mouse and (I) spheroid injected mouse (arrow indicates glandular formation). Spheroid injected nodule stained for (J): cytokeratin-14, (K): Msi-1, (1): Math1 and (M): L-FABP, with representative cells indicated by arrows.

FIG. 21 illustrates confocal imaging of biotinylated extracellular membrane proteins in SW480 cells. Biotinylation of intact SW480 cells (used to isolate cell surface proteins) as demonstrated by incubation with streptavidin conjugated Cy3™ (red) (A) and co-localized with the transmembrane protein E-cadherin (FITC—green) (B). Merged images with Hoechst DNA stain (blue) demonstrate that biotinylation is restricted to the extracellular membrane surface (C). Control cells without biotinylation reagent do not show staining for streptavidin conjugated Cy3™ (red) (D), but do exhibit staining for E-cadherin (green) and Hoechst (blue) (E and F).

FIG. 22 illustrates FACS-based isolation of DCAMKL-1 cells from the mouse intestine. (A): FACS plot of side scatter (chosen based on previous sorting experiments) of cells stained with Alexa Fluor® 568 conjugated DCAMKL-1 antibody. Gate R1 indicates localization of the DCAMKL-1+ fluorescing cell population. (B): These cells were further gated through R2 based on fluorescence intensity. (C): FACS plot of side scatter of unstained control cells. (D): No cells were detected within gate R2.

Figure 25:
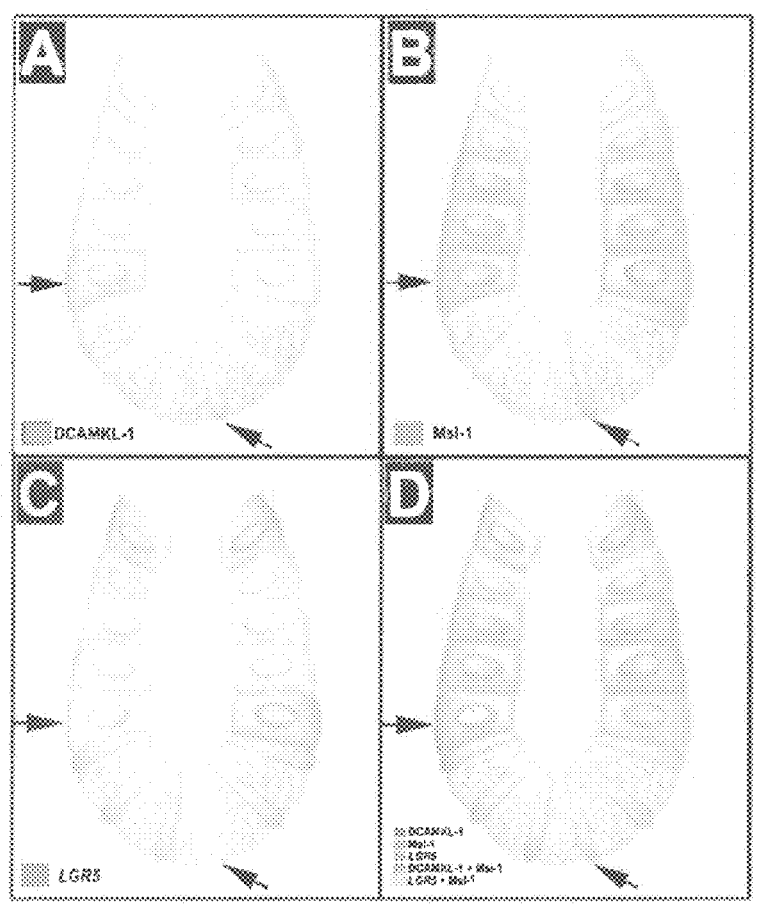

FIG. 25 provides a schematic illustration of the location of putative stem and progenitor cell markers in the mouse small intestine. (A): DCAMKL-1 (red), (B): Msi-1 (green) and (C): LGR5 (blue). (D): Merged image represents areas of predicted co-localization. Arrows indicate the position of DCAMKL-1 expressing cells.

FIG. 26 graphically illustrates a map of pLet7a-Luc Reporter Vector (LR-0037) (Signosis, Inc. CA) demonstrating the presence of the let7a binding site at the 3' UTR of Luciferase gene.

Figure 27:
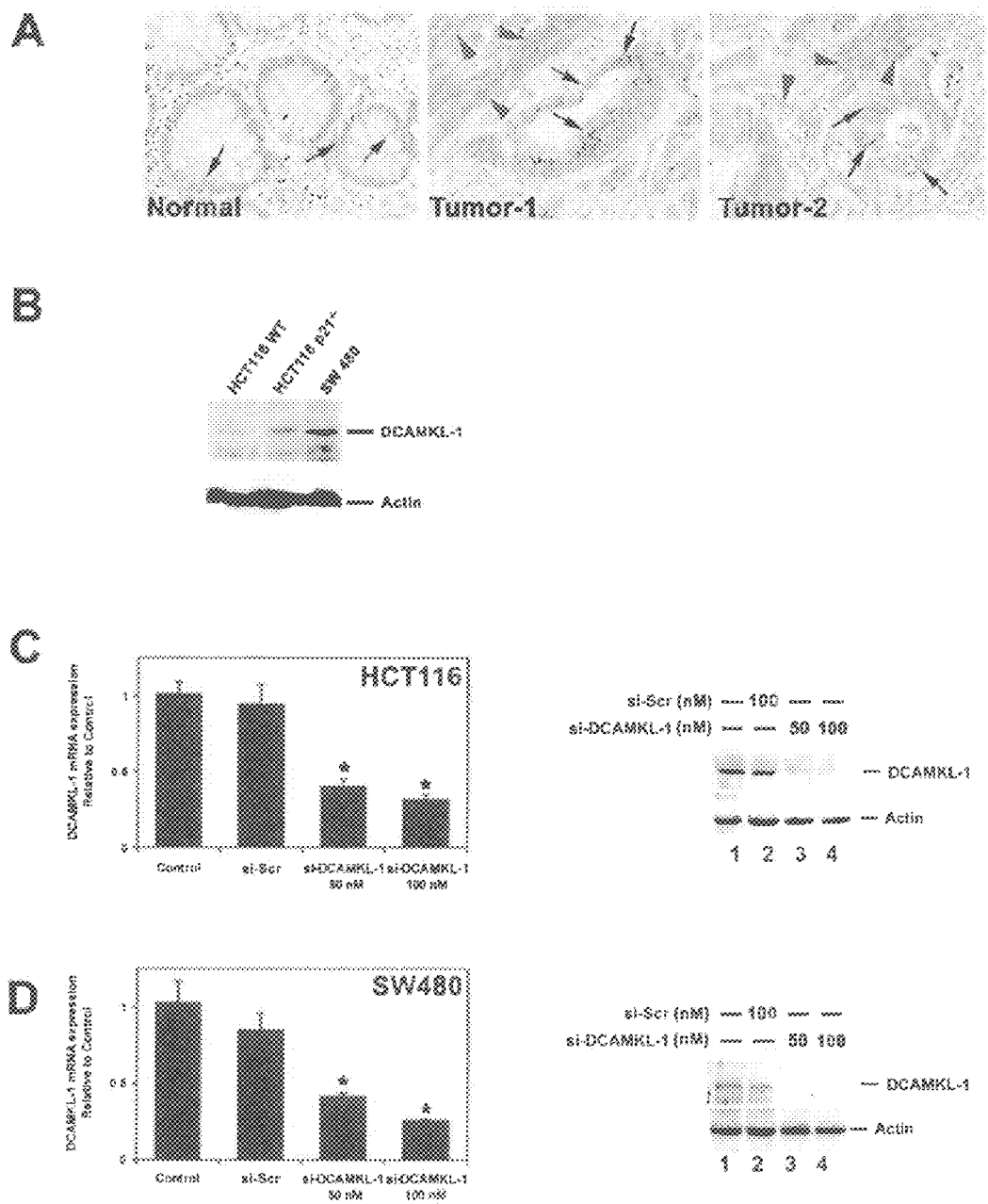

FIG. 27 illustrates that DCAMKL-1 is overexpressed in colorectal cancer. (A) Immunohistochemistry for DCAMKL-1 (brown) in normal (left panel) and two different colon cancer tissues (middle and right panels). Black arrow indicates representative epithelial cells positive for DCAMKL-1. Blue arrow head indicates the presence of DCAMKL-1 in the stromal compartment. (B) Western blot demonstrating the expression of DCAMKL-1 in three different colon cancer cell lines. Actin serves as control. (C) DCAMKL-1 specific siRNA (si-DCAMKL-1) decreases DCAMKL-1 mRNA (left panel) and protein expression (right panel) in HCT116 colon cancer cells compared to controls. (D) Similar decrease in DCAMKL-1 mRNA (left panel) and protein (right panel) observed following si-DCAMKL-1 transfection in SW480 colon cancer cells. For C and D, values in the bar graphs are given as average±SEM and * denote statistically significant differences (*$p<0.01$) compared to control. All the experiments were performed in triplicates and were repeated 3 times.

FIG. 28 illustrates that DCAMKL-1 is essential for tumor growth. (A) HCT116 cells were injected into the flanks of athymic nude mice (n=5 per group) to generate tumors. At day 15 siRNAs (si-DCAMKL-1 and si-Scr) were injected directly into the tumors and followed by injections every third day (inset). After 5 injections, tumors were excised at day 28 and are represented above. Tumor sizes with standard error are shown from data collected at the time of every injection. (B) si-DCAMKL-1 treatment resulted in significantly decreased tumor weight when compared to controls. (C) The expression of DCAMKL-1 mRNA in the tumors quantitated by real-time RT-PCR. (D) Western blot analysis for DCAMKL-1 was performed on tumors samples as indicated. For A-C, values are given as average±SEM and * denote statistically significant differences (*p<0.01) compared to control.

Figure 29:
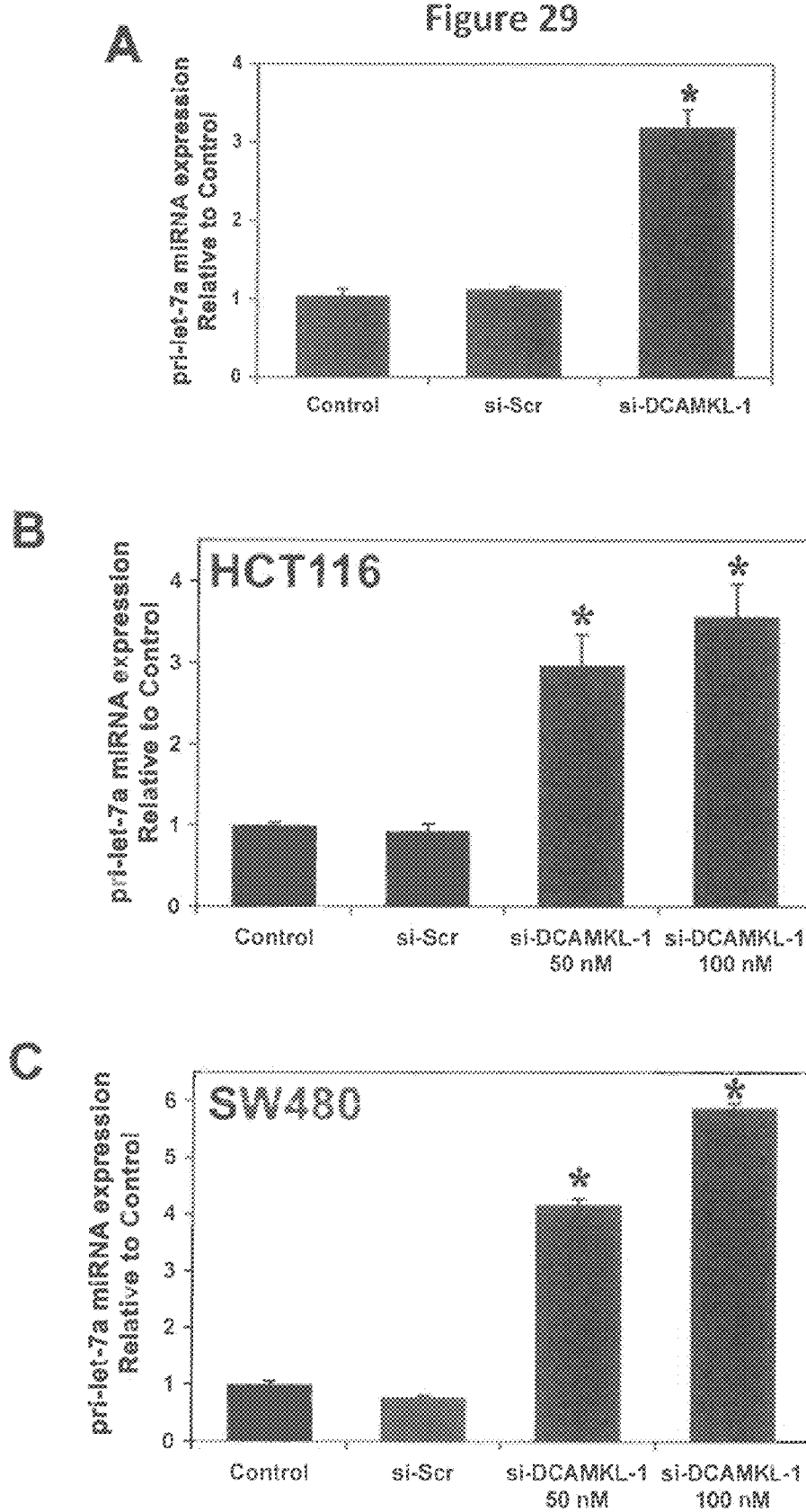

FIG. 29 illustrates that knockdown of DCAMKL-1 induces pri-let-7a miRNA. (A) Quantitative real-time RT-PCR analysis for pri-let-7a miRNA in tumor xenografts. siRNA mediated knockdown of DCAMKL-1 results in increased expression of pri-let-7a miRNA. (B) si-DCAMKL-1 treated HCT116 cells demonstrate increased expression of pri-let-7a miRNA. (C) Similar induction of pri-let-7a miRNA was observed in SW480 cells. For A-C, values are given as average±SEM and * denote statistically significant differences (*p<0.01) compared to control.

Figure 30:
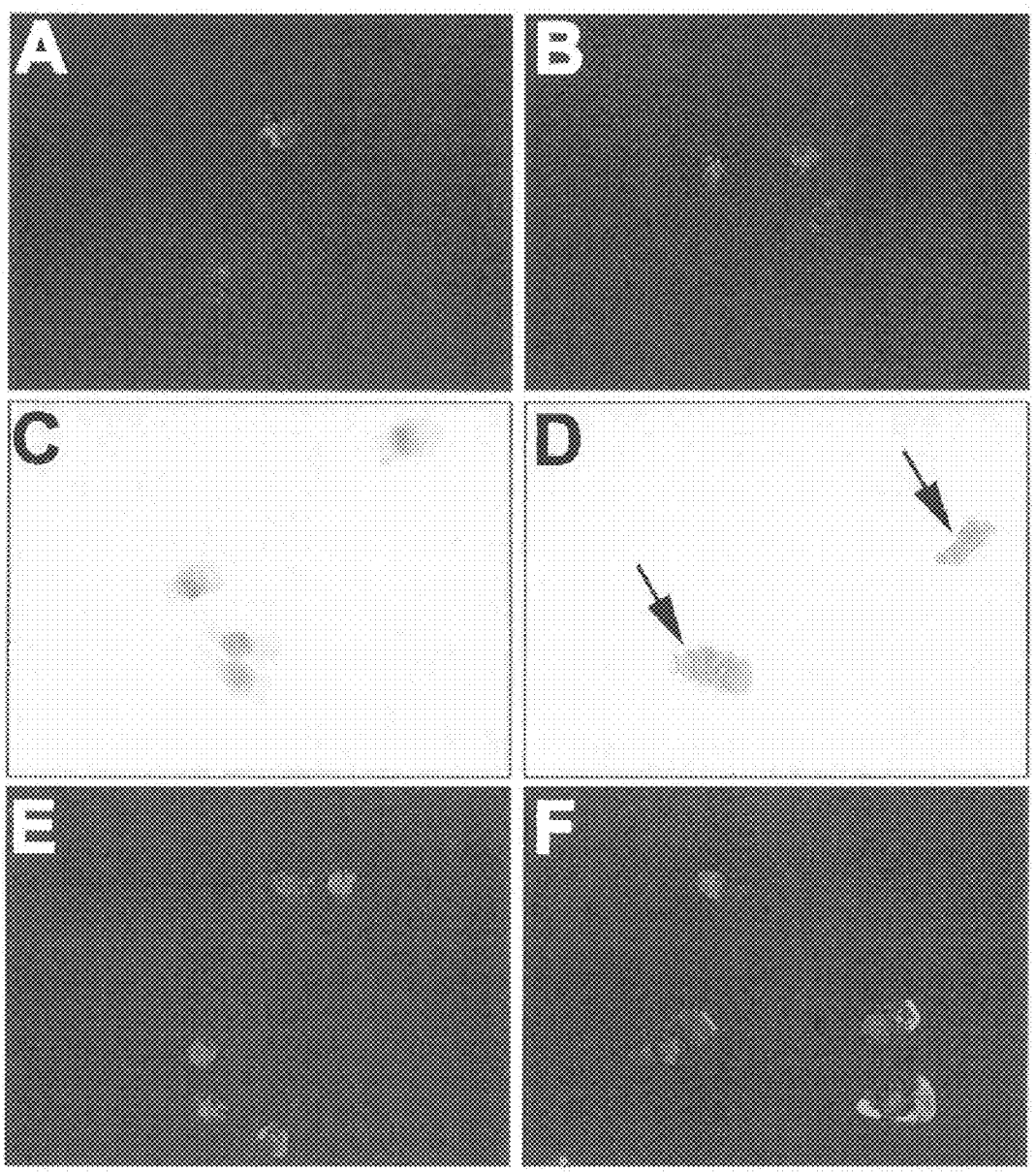

FIG. 30 illustrates that DCAMKL-1 positive cells are less differentiated. A representative image of Alexa Fluor® 568 conjugated DCAMKL-1 positively sorted cells (A) (red) and negatively sorted cells (B) following FACS. (C) Brightfield image of L-FABP immunostaining. DCAMKL-1 positive cells do not express L-FABP. (D) DCAMKL-1 negative cells express L-FABP (brown—arrows). (E) Fluorescent image of L-FABP immunostaining. DCAMKL-1 positive cells do not express L-FABP. (F) L-FABP was found in DCAMKL-1 negative cells (green). Nuclei in A, B, E and F are stained blue with Hoechst 33342 DNA dye post-sorting.

Figure 31:
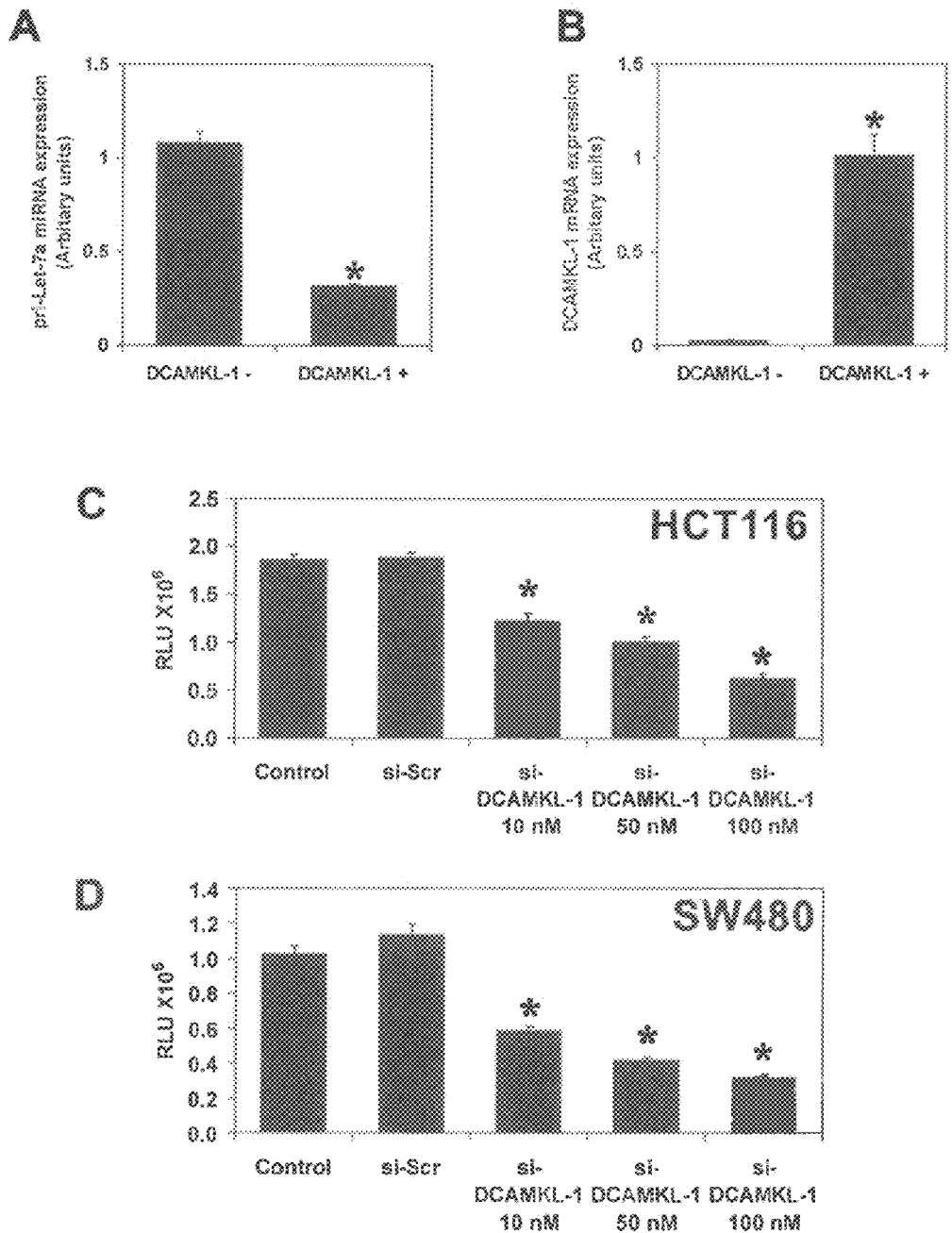

FIG. 31 illustrates that DCAMKL-1 inhibits let-7a miRNA. (A) Intestinal stem cells (DCAMKL-1+) isolated from normal mouse intestine demonstrate decreased pri-let-7a compared to more differentiated cells (DCAMKL-1-). (B) Real-time RT-PCR data demonstrate an increased expression of DCAMKL-1 mRNA in DCAMKL-1+ sorted stem cells compared to more differentiated (DCAMKL-1-) cells. siRNA mediated knockdown of DCAMKL-1 decreases luciferase activity (Relative Luciferase Units—RLU) following transfection with plasmid encoding luciferase containing let-7a binding site in HCT116 (C) and SW480 cells (D). For A-D, values are given as average±SEM and * denote statistically significant differences (*p<0.01) compared to control.

Figure 32:
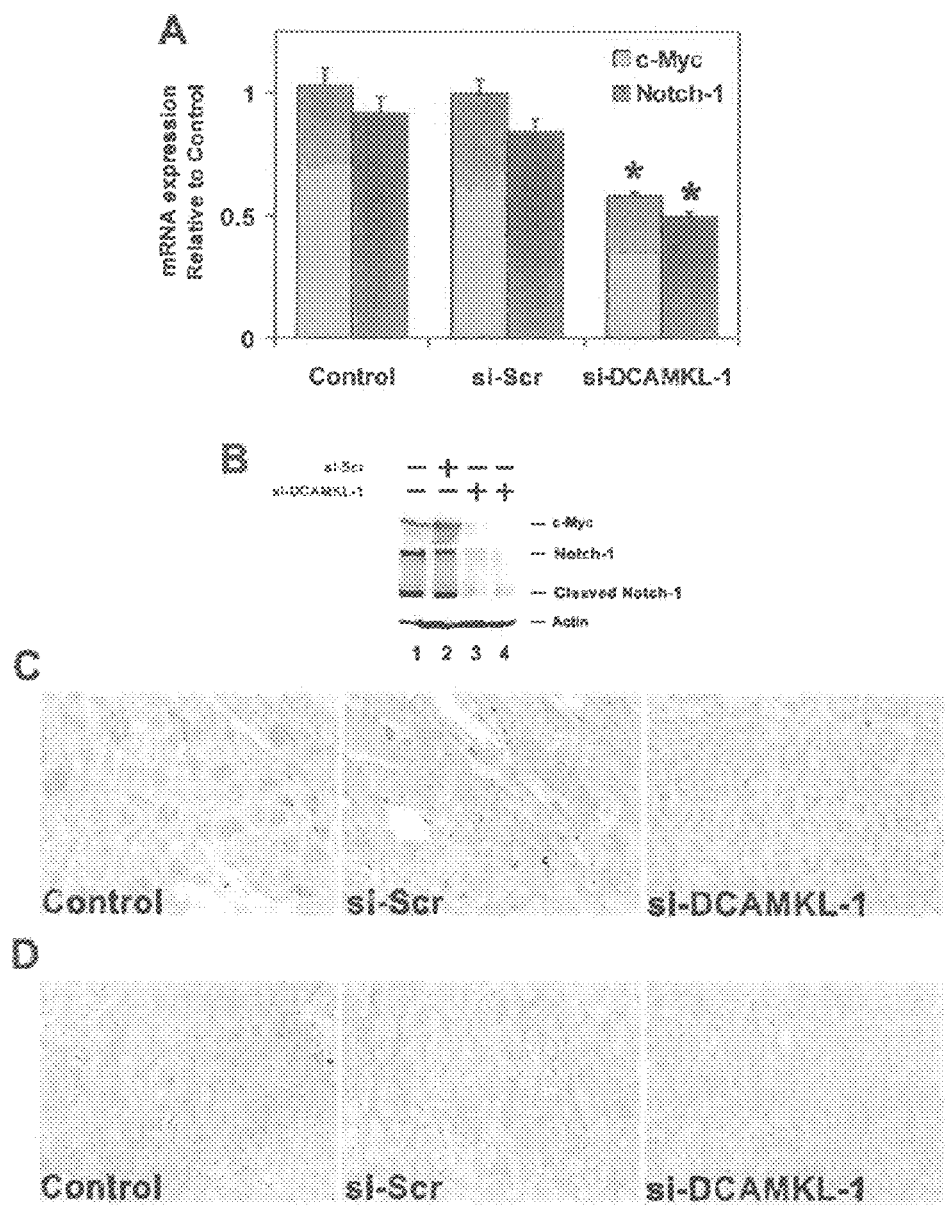

FIG. 32 illustrates that downregulation of DCAMKL-1 in tumor xenografts results in decreased expression of let-7a downstream targets. A decreased expression of c-Myc (red bars) and Notch-1 (blue bars) mRNA (A) and protein (B) was observed in HCT116 tumor xenografts following the knockdown of DCAMKL-1. (C) Decreased c-Myc expression (brown) was observed in si-DCAMKL-1 treated tumors compared to controls by immunohistochemica l analysis. (D) Immunohistochemistry for Notch-1 (brown) demonstrates a decreased expression in si-DCAMKL-1 treated tumors. *P<0.01.

Figure 33:
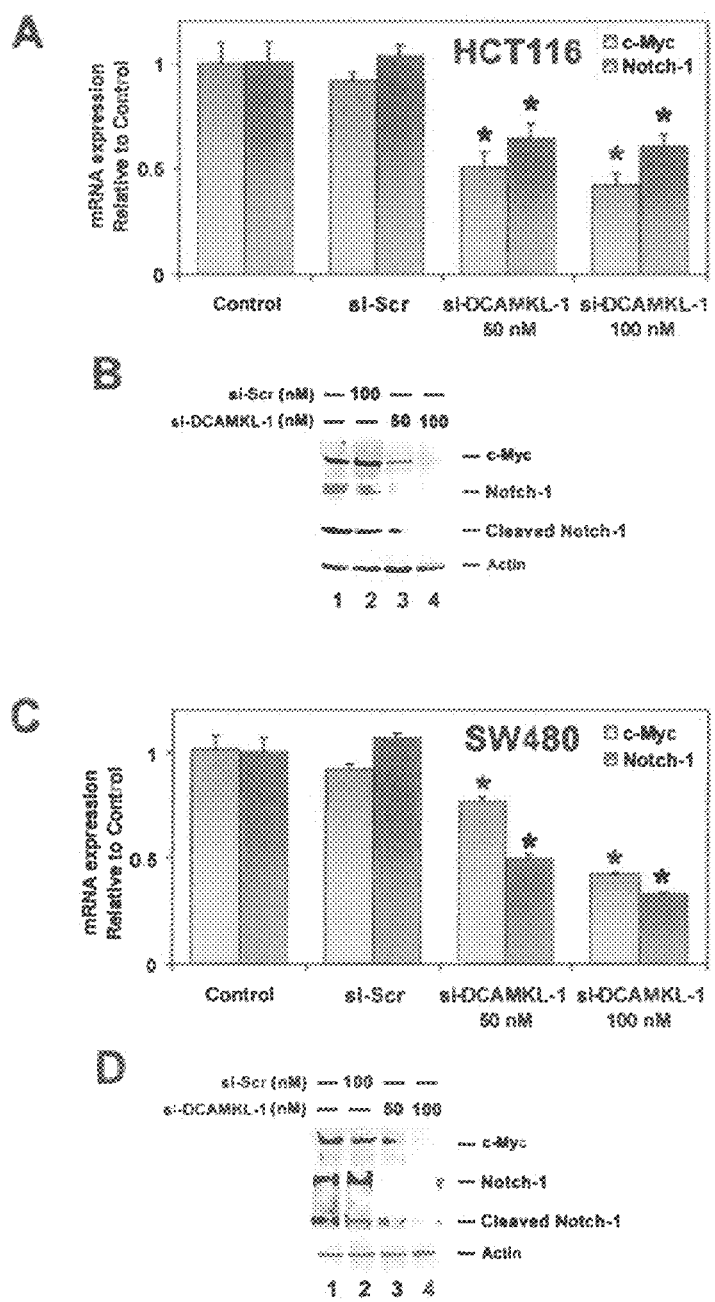

FIG. 33 illustrates that knockdown of DCAMKL-1 results in decreased let-7a downstream targets in colon cancer cells. siRNA mediated knockdown of DCAMKL-1 results in decreased c-Myc and Notch-1 mRNA (A) and protein (B) in HCT116 cells. (C and D) Similar decreases were observed in SW480 cells. *p<0.01.

Figure 34:
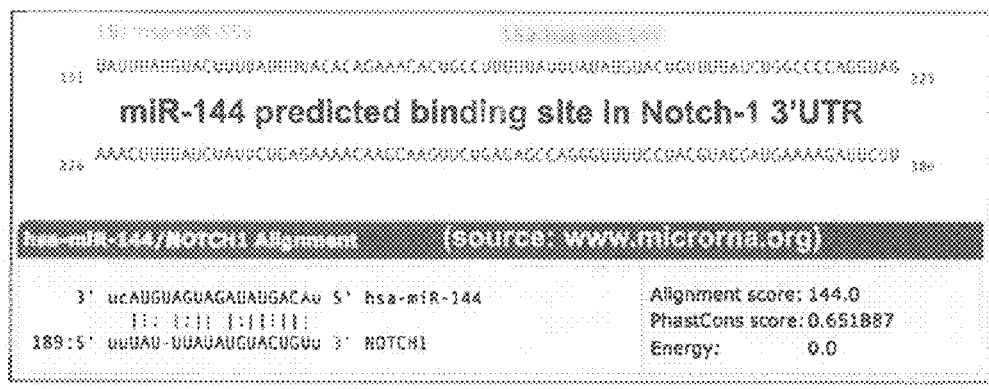

FIG. 34 depicts a putative binding site for miR-144 at $189^{th}$ base pair position on Notch-1 3'UTR (source: microRNA.org database).

Figure 35:
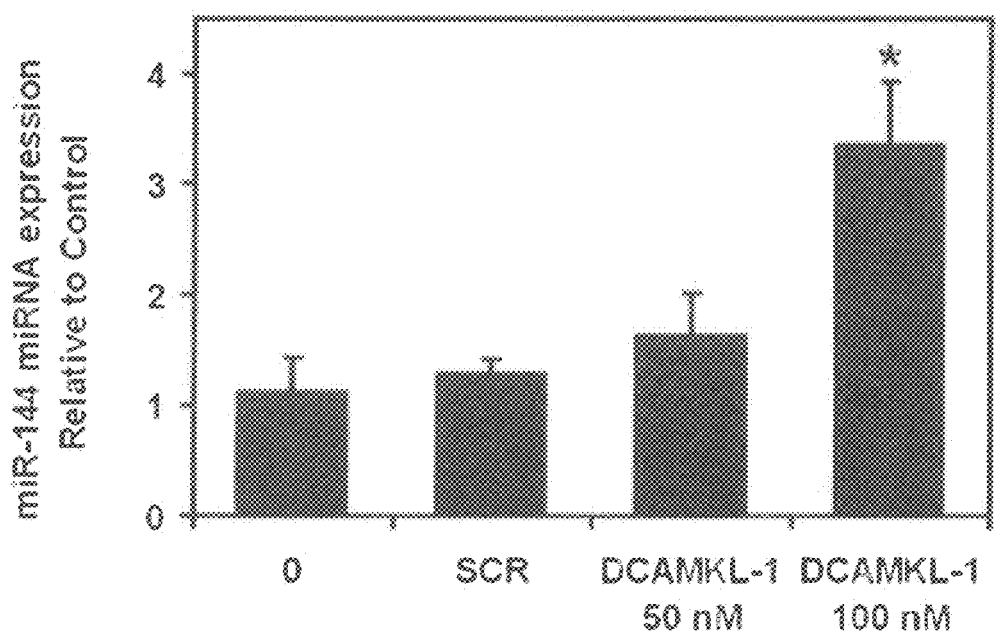

FIG. 35 graphically illustrates that knockdown of DCAMKL-1 results in increased pri-mIR-144 miRNA expression in SW480 cells. *P<0.01.

Figure 36:
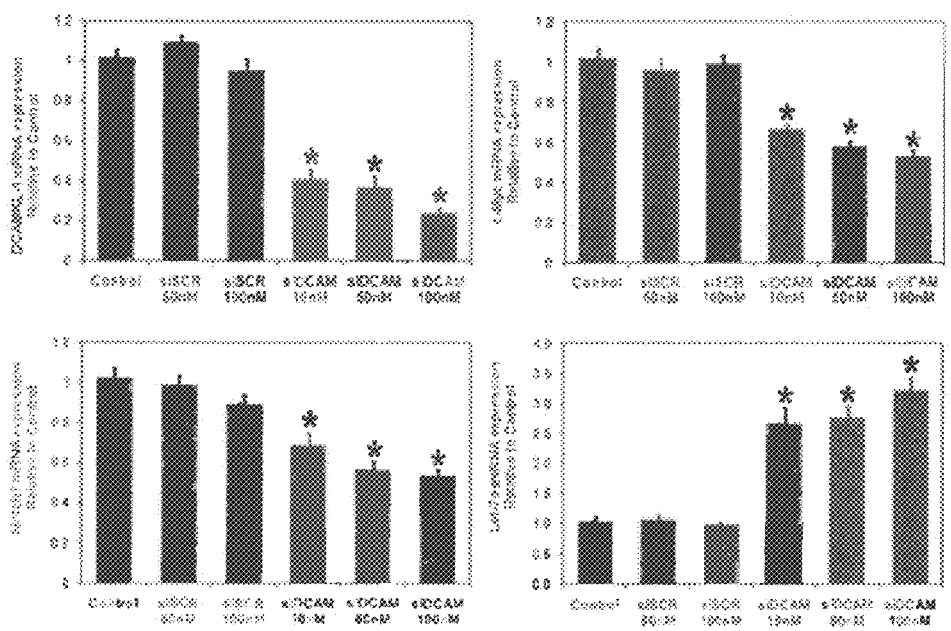

FIG. 36 graphically illustrates that downregulation of DCAMKL-1 in AsPC-1 results in decreased c-Myc and Notch-1 and increased let-7a miRNA. A decreased expression of DCAMKL-1 mRNA (A), c-Myc (B) and Notch-1 (C) following the knockdown of DCAMKL-1. (D) si-DCAMKL-1 treated AsPC1 cells demonstrated increased expression of pri-let-7a miRNA. *p<0.01.

Figure 37:
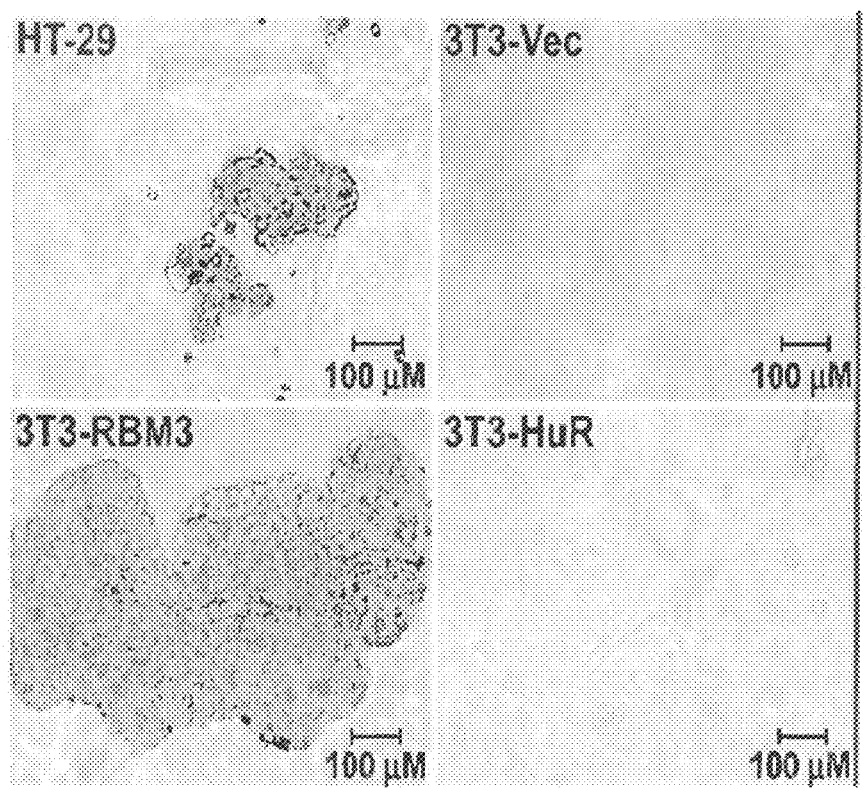

FIG. 37 illustrates that RBM3 overexpression induces oncogenic transformation. NIH-3T3-RBM3 cells develop large colonies in soft agar, which are bigger than those formed by HT-29 cells. On the other hand, HuR-overexpressing cells did not form any colonies.

Figure 38:
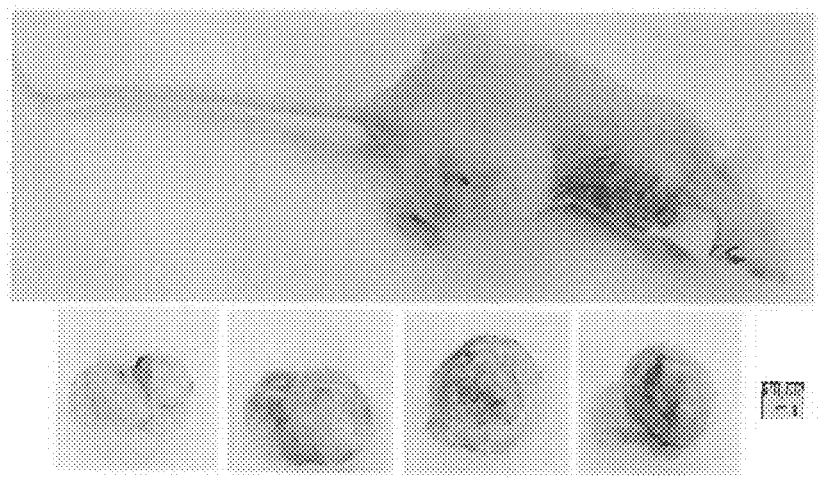

FIG. 38 depicts that RBM3 overexpressing cells develop tumors in nude mice. $1 \times 10^5$ cells were injected into the flanks of nude mice, and the animals were monitored for four weeks. Tumors were large in size.

Figure 39:
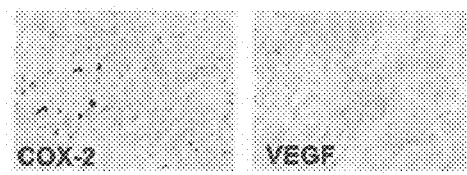

FIG. 39 depicts that COX-2 and VEGF are induced in NIH-3T3 tumors. Immunohistochemical analysis demonstrates significant upregulation of COX-2 and VEGF (brown). Furthermore, it was noted that both malignant epithelial and malignant stromal cells were present in the section.

Figure 40:
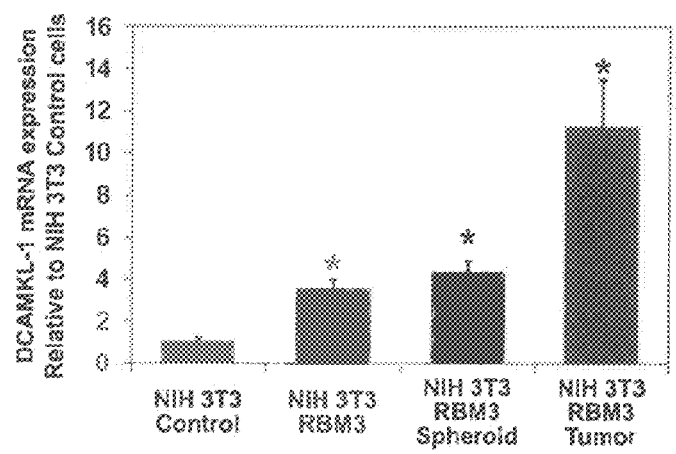

FIG. 40 graphically illustrates that DCAMKL-1 expression was increased in NIH-3T3-RBM3 tumors. Real Time RT-PCR of total RNA from the cells in culture and from the tumor was performed, and expression levels were compared to control NIH-3T3 cells.

Figure 41:
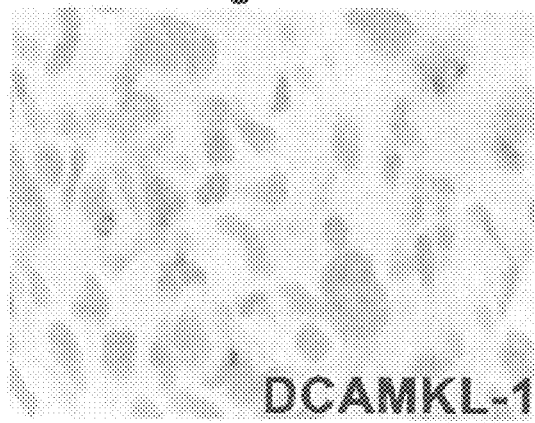

FIG. 41 illustrates DCAMKL-1 expression in NIH-3T3-RBM3 tumor tissue. Immunohistochemistry for DCAMKL-1 in NIH-3T3-RBM3 expressing tumors. Brown stain: DCAMKL-1.

Figure 42:
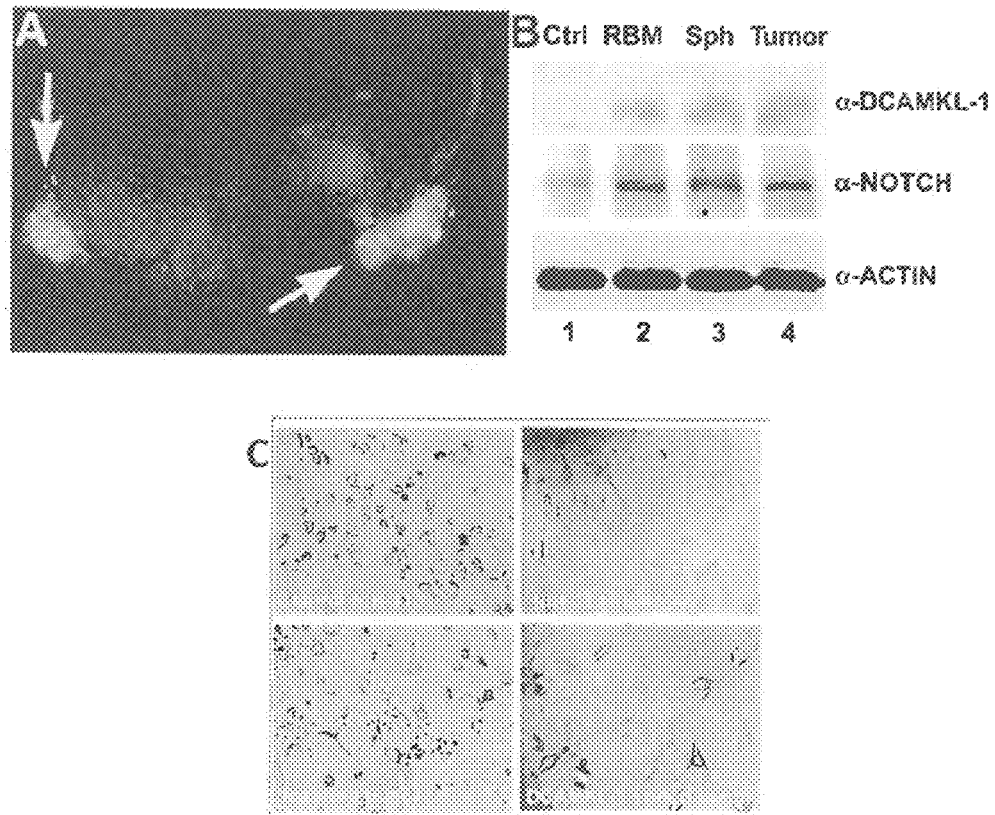

FIG. 42 illustrates that RBM3 overexpressing DCAMKL-1 positive tumor cells express Notch protein. A: Immunocytochemistry for DCAMKL-1 in the flow sorted cells. Green (arrow) was positive for DCAMKL-1 protein. Nucleus is stained with DAPI (blue). B: Western blot for DCAMKL-1 and Notch proteins. DCAMKL-1 and Notch expression was significantly upregulated in the RBM3 overexpressing cells in culture, in spheroids and in the tumor xenograft cells. Actin was used as a control for loading. C: DCAMKL-1 sorted tumor cells and NIH-3T3 RBM3 overexpressing DCAMKL-1 positive tumor cells developed neurite outgrowth-like structures in culture.

Figure 43:
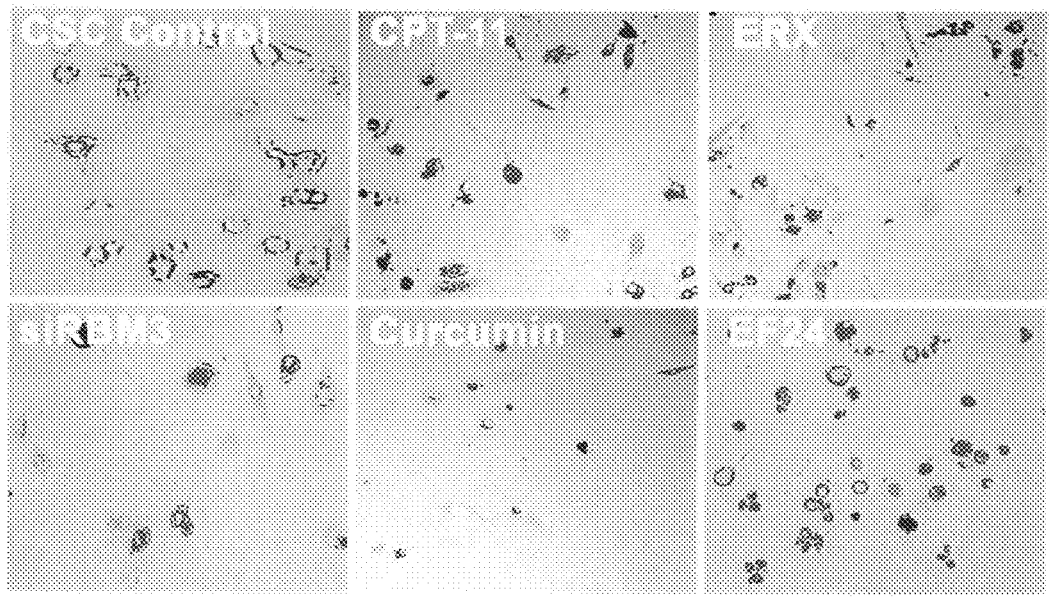

FIG. 43 depicts that curcumin and EF24 but not standard chemotherapeutic drugs kill the PICSCs™. ERX: Erbitux. CPT-11: Irinotecan.

Figure 44:
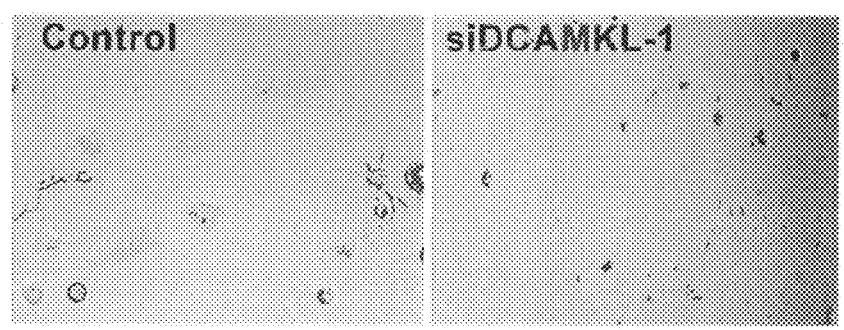

FIG. 44 illustrates treatment of RBM3 overexpressing DCAMKL-1 positive tumor cells with DCAMKL-1 siRNA (siDCAM KL-1).

Figure 45:
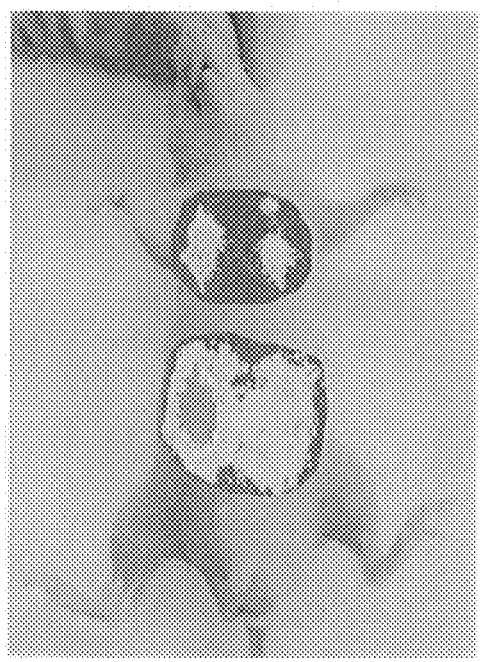

FIG. 45 represents an external image of lung and liver metastasis of NIH-3T3-RBM3-DCAMKL-1+, GFP stem cells. Image was acquired 12 days after cells were injected into the tail vein. Red color demonstrates significant fluorescence emission, while blue shows negative emission.

Figure 46:
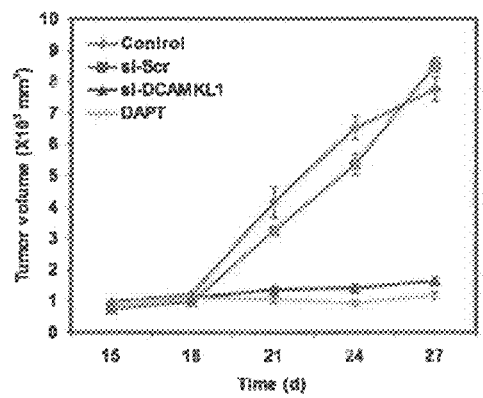

FIG. 46 graphically depicts that PICSC (AC1264) tumor xenografts generated were injected directly with siRNAs (si-DCAMKL-1 and si-Scr) and DAPT every third day (total of 5 injections). Tumor volumes with standard error are shown from data collected at the time of every injection.

Figure 47:
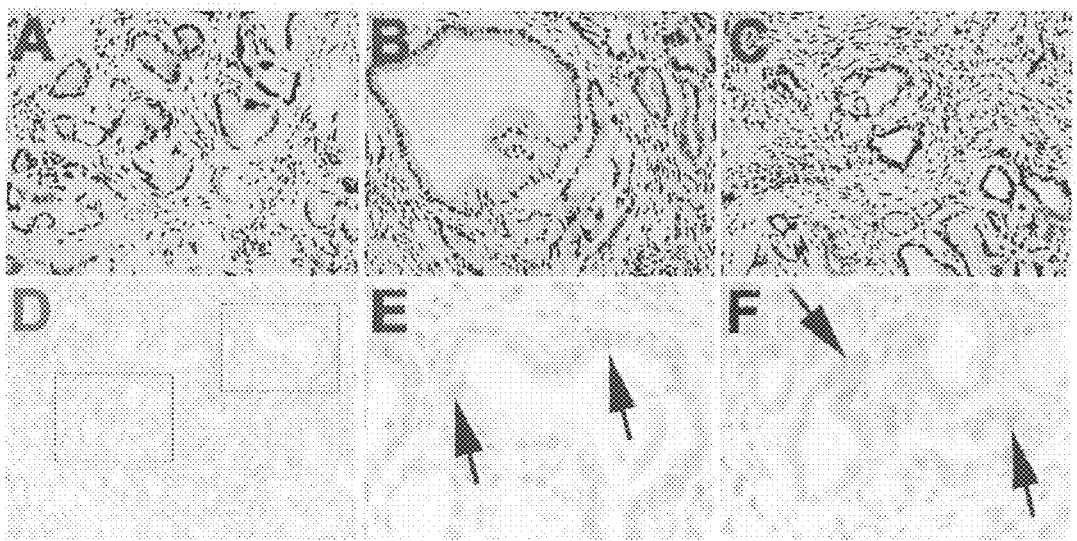

FIG. 47 depicts pancreatic tissues from 10-month-old $P48^{cre}$-LSL-KRAS$^{G12D}$ demonstrating PanIN lesion Ia (A), IIa (B) and IIIa (C). Panels A-C are H&E staining. (D) Immunostaining demonstrates the presence of DCAMKL-1 (brown—indicated by arrows) in the PanIN lesions. (E) and (F) are magnified images of a portion of D.

Figure 48:
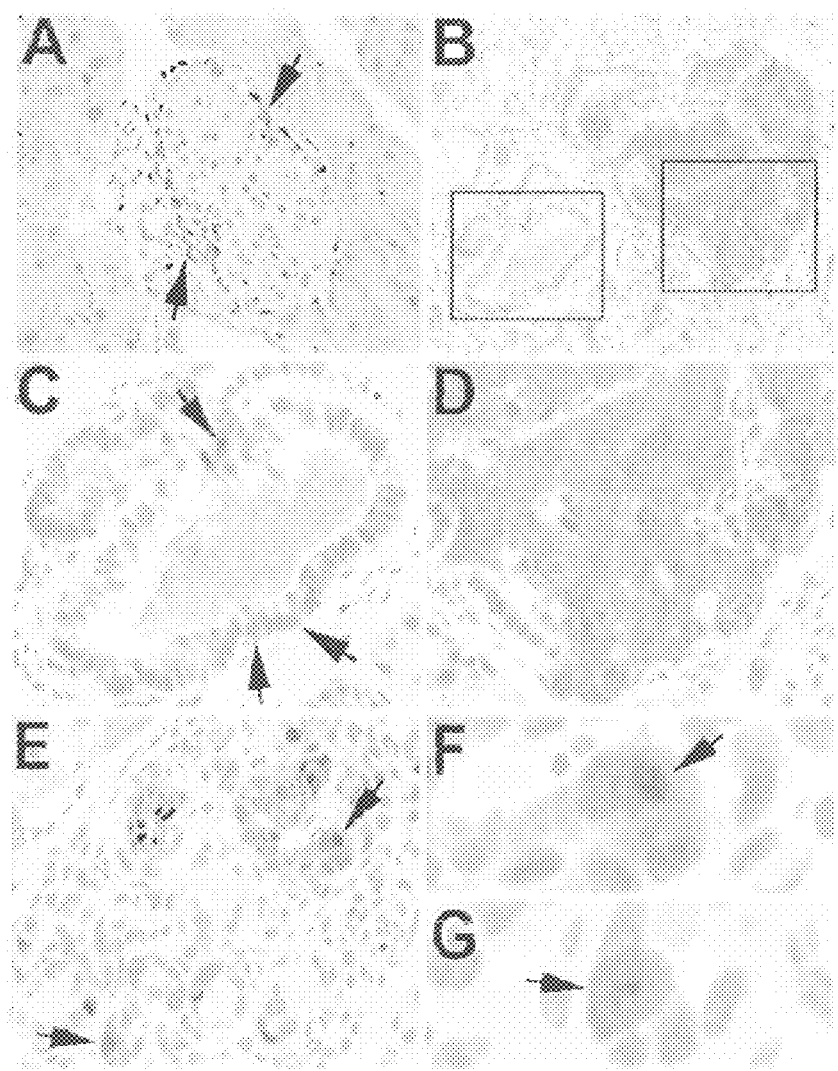

FIG. 48 illustrates DCAMKL-1 expression in P48Cre-LSL-KRAS$^{12D}$ pancreatic cancer mouse model. Pancreatic tissues from 5-month-old WT littermate (400×) (A) and from 5-month-old (100×) (B) P48$^{Cre}$-LSL-KRAS$^{G12D}$ mouse were immunostained for DCAMKL-1. (C) A magnified portion of the image (B) demonstrating cells positive for DCAMKL-1 in the pancreatic duct (400×). (D) A magnified portion of the image (B) demonstrating cells positive for DCAMKL-1 in the islets (400×). Brown colored cells (arrows) indicate cells positive for DCAMKL-1. These data demonstrate an increased expression of DCAMKL-1 correlated with progressive neoplastic changes. (E) PanIN lesions of the 5-month-old P$^{48}$Cre-LSL-KRAS$^{G12D}$ mouse expressed DCAMKL-1 (brown) and 14-3-3 σ (purple). Cells positive for DCAMKL-1 and nuclear 14-3-3 σ are indicated by arrows (400×). (F and G) Areas of co-localization in FIG. 53E (arrows) are shown as magnified images.

FIG. 49 illustrates DCAMKL-1 and 14-3-3 σ expression in human pancreatic adenocarcinoma. (A) DCAMKL-1 expression (brown) in histologically normal appearing tissue from human pancreatic cancer resection specimen (top left) (200×). DCAMKL-1 in neoplastic pancreatic islet tissue (top right) (200×). DCAMKL-1 in ductal epithelial cells (bottom left) (400×). Intervening stromal elements demonstrate fibrillar DCAMKL-1 immunoreactivity (bottom right) (200×). Representative cells are indicated by arrows. (B) 14-3-3 σ (purple) and DCAMKL-1 (brown) at the islet periphery in normal appearing human pancreatic tissue (left) (100×). Representative cell demonstrating the cytoplasmic expression of 14-3-3 σ in magnified portion of the left image (right—arrow) (400×). (C) 14-3-3 σ (purple) and DCAMKL-1 (brown) expression in human pancreatic adenocarcinoma (left) (100×). In a magnified portion of the left image, nuclear localized 14-3-3 σ (purple) co-localized with cytoplasmic DCAMKL-1 (brown) (right—arrowhead) (400×). Fibrillar DCAMKL-1 staining in the intervening stroma (arrows). (D) DCAMKL-1 (brown) expression in ductal epithelium of a PanIN type lesion in human pancreatic adenocarcinoma (left—arrow) (400×). Intense cytoplasmic and nuclear staining of 14-3-3 σ (purple) and cytoplasmic DCAMKL-1 (brown) in a PanIN lesion (right—arrow) (400×). Insets in the images on the right in the panel B, C and D are magnified images.

FIG. 50 depicts DCAMKL-1 expression in normal human pancreas. (A) DCAMKL-1 expression (brown) in histologically normal appearing tissue from human pancreatic cancer resection specimen. No DCAMKL-1 staining was observed in pancreatic ducts (200×).

Figure 51:
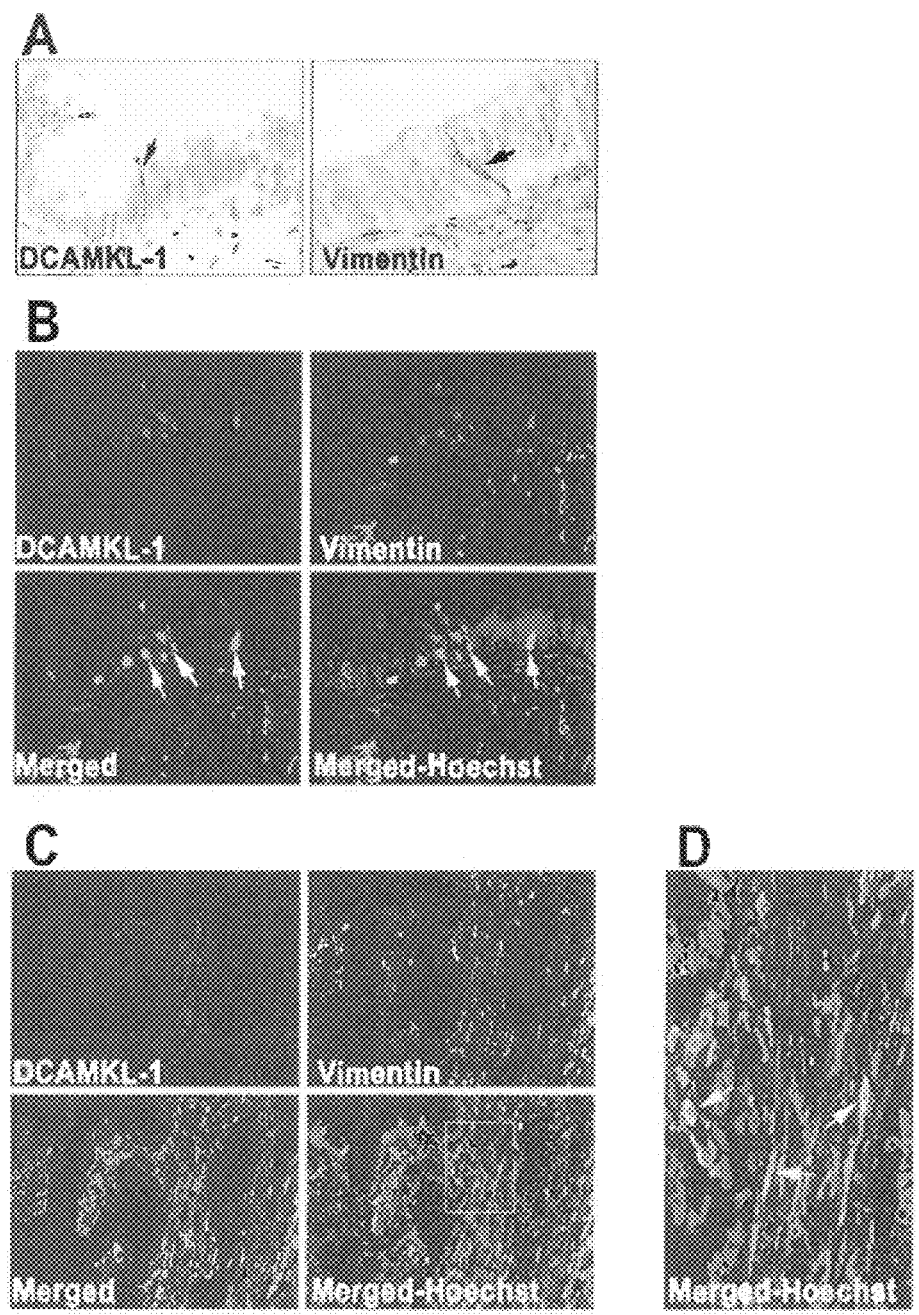

FIG. 51 illustrates DCAMKL-1 and vimentin expression in human pancreatic adenocarcinoma. (A) DCAMKL-1 expressing cell in a PanIN type lesion (left—arrow). Vimentin expressing cell in the ductal epithelium of a PanIN type lesion (right—arrow). (400×). (B) DCAMKL-1 (red) and vimentin (green) in a PanIN lesion. Co-localization demonstrated in merged image (arrows) and nuclei are stained blue with Hoechst dye (400×). (C) DCAMKL-1 (red) and vimentin (green) in stromal compartment of human pancreatic adenocarcinoma. Co-localization demonstrated in merged image and nuclei are stained blue with Hoechst dye (100×). (D) A magnified portion of bottom right of 4C demonstrating immunolocalization of DCAMKL-1 (red) and vimentin (green) indicated by arrows.

Figure 52:
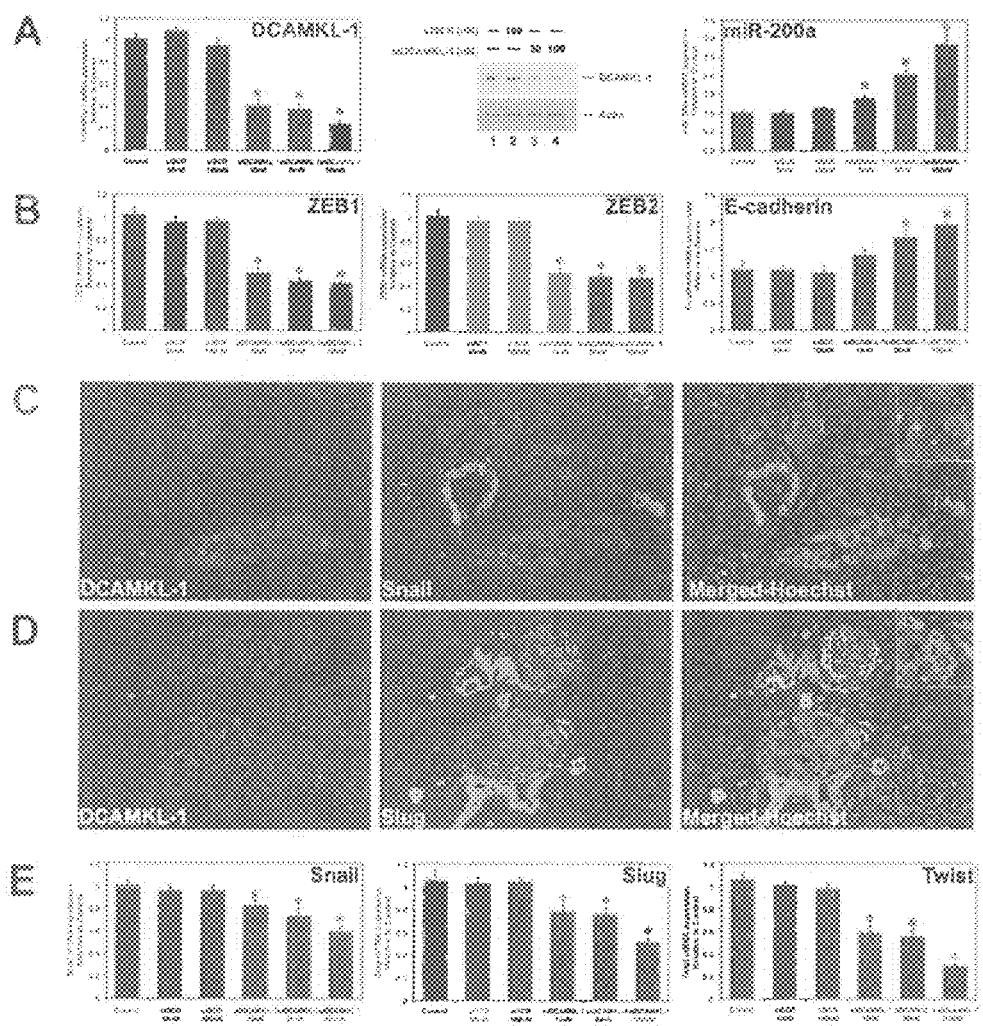

FIG. 52 demonstrates that knockdown of DCAMKL-1 inhibits EMT. (A) DCAMKL-1 specific siRNA (siDCAMKL-1) decreases DCAMKL-1 mRNA expression (left panel), decreases DCAMKL-1 protein (middle panel) and increases expression of pri-mIR-200a (right panel) compared to scrambled siRNA (siSCR)-treated or Control untreated AsPC-1 human pancreatic cancer cells. (B) AsPC-1-siDCAMKL-1 cancer cells demonstrated decreased expression ZEB1 (left panel), ZEB2 (middle panel) and rescues/upregulates E-cadherin (right panel). (C) DCAMKL-1 (red) and Snail (green) in human pancreatic adenocarcinoma. Co-localization demonstrated in merged image and nuclei are stained blue with Hoechst dye (100×). (D) DCAMKL-1 (red) and Slug (green) in human pancreatic adenocarcinoma. Co-localization demonstrated in merged image and nuclei are stained blue with Hoechst dye (100×). (E) siRNA-mediated knockdown of DCAMKL-1 decreases Snail (left panel), Slug (middle panel) and Twist (right panel) mRNA expression in AsPC-1 cancer cells. Insets in the images on the right in the panel C and D are magnified images. For panels A, B and E values given as mean±SEM, and asterisks denote statistically significant differences (*p<0.01) compared with control.

Figure 53:
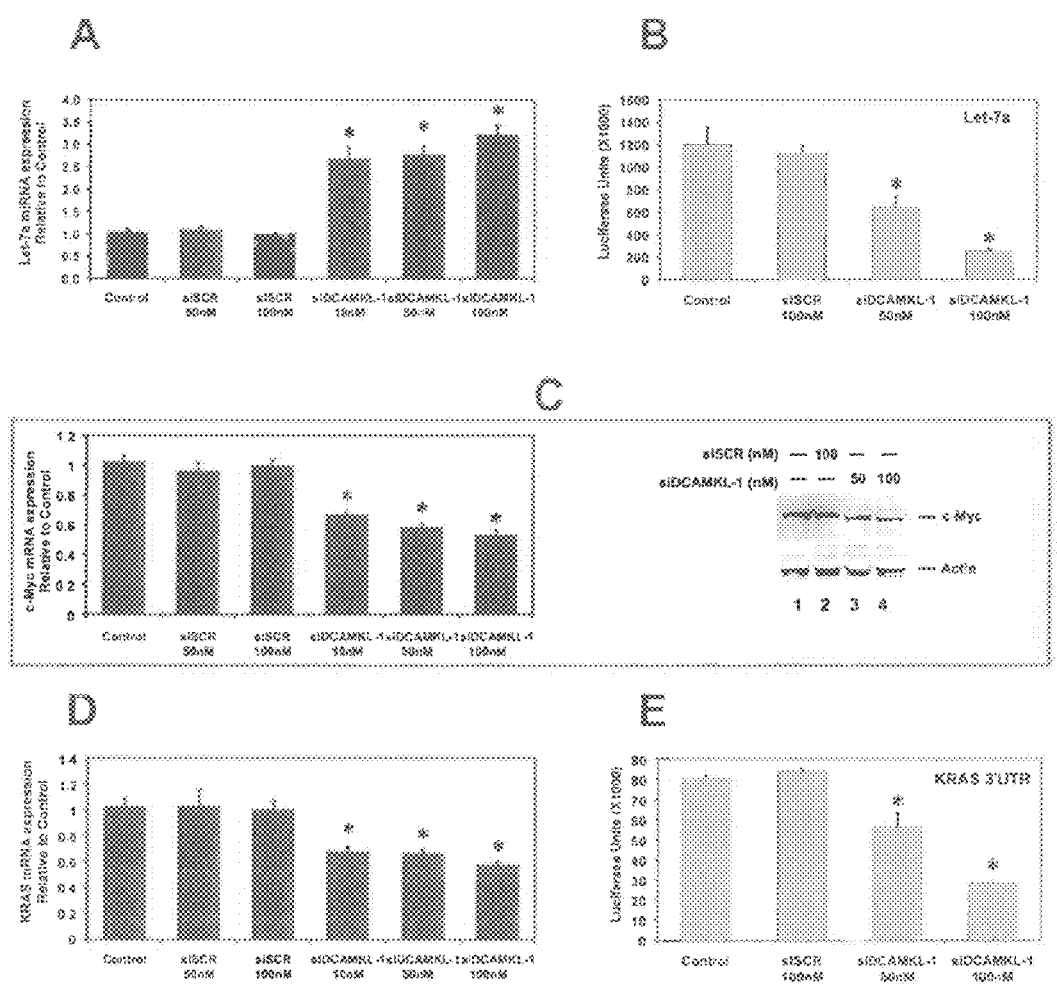

FIG. 53 depicts that DCAMKL-1 regulates oncogenes c-Myc and KRAS via let-7a miRNA. (A) siRNA-mediated knockdown of DCAMKL-1 results in upregulation of pri-mIR-let-7a. (B) Knockdown of DCAMKL-1 decreases luciferase activity (luciferase units) following transfection with plasmid encoding luciferase containing let-7a binding site in AsPC-1 cells. (C) A decreased expression of c-Myc mRNA (left panel) and protein (right panel) was observed in AsPC-1 cells following the knockdown of DCAMKL-1. (D) AsPC-1-siDCAMKL-1 cells demonstrated a decrease in KRAS mRNA. (E) Knockdown of DCAMKL-1 decreases luciferase activity (luciferase units) following transfection with plasmid encoding luciferase containing binding sites for let-7 family members (similar to KRAS 3' UTR) in AsPC-1 cells. Values represented as mean±SEM, and asterisks denote statistically significant differences (*p<0.01) compared with control.

Figure 54:
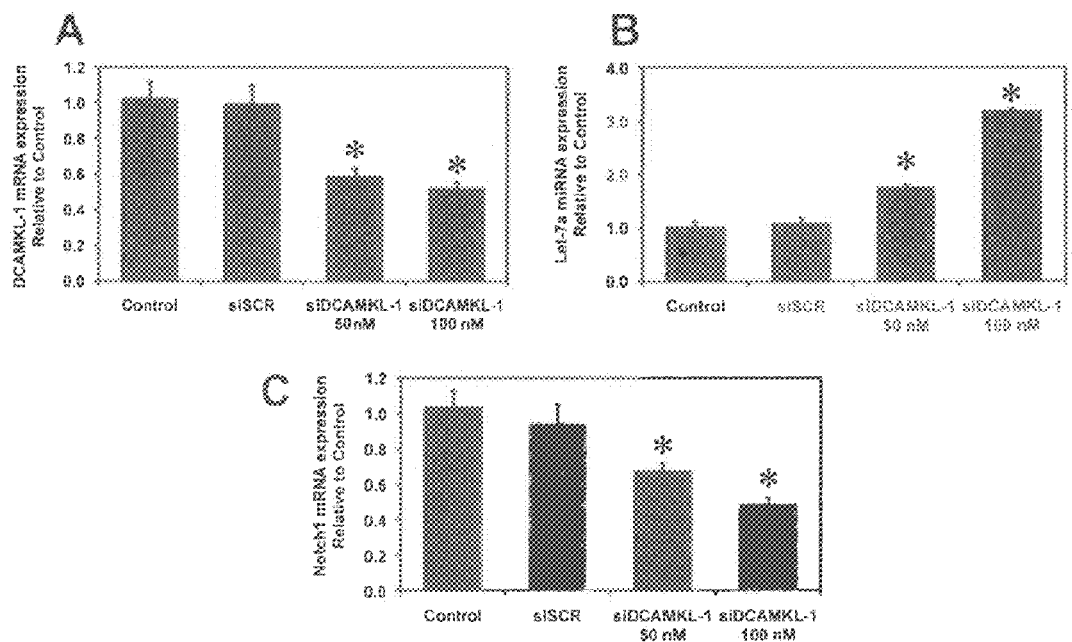

FIG. 54 illustrates that knockdown of DCAMKL-1 induces pri-let-7a miRNA and inhibits Notch1 mRNA in BxPC3 human pancreatic cancer cells. (A) Quantitative real-time PCR analysis for DCAMKL-1 in BxPC3 following treatment with siDCAMKL-1 compared to BXPC3-siSCR or control BxPC3 cells. (B) BxPC3-siDCAMKL-1 cells demonstrated a significant increase in pri-let-7a miRNA compared to BXPC3-siSCR or control BxPC3 cells. (C) BxPC3-siDCAMKL-1 cells demonstrated a significant decrease in Notch1 mRNA compared to BXPC3-siSCR or control BxPC3 cells. Values represented as mean±SEM, and asterisks denote statistically significant differences (*p<0.01) compared with control.

FIG. 55 illustrates that knockdown of DCAMKL-1 down-regulates Notch-1 via miR-144. (A) siRNA-mediated knockdown of DCAMKL-1 decreases Notch-1 mRNA in AsPC-1 cells. (B) A putative binding site for miR-144 at 189$^{th}$ base pair position on Notch-1 3' UTR (source: microRNA.org database). (C) AsPC-1-siDCAMKL-1 cells demonstrate increased expression of pri-miR-144. (D) Knockdown of DCAMKL-1 decreases luciferase activity (luciferase units) following transfection with plasmid encoding luciferase containing miR-144 binding site in AsPC-1 cells. Values represented as mean±SEM, and asterisks denote statistically significant differences (*p<0.01) compared with control.

Figure 56:
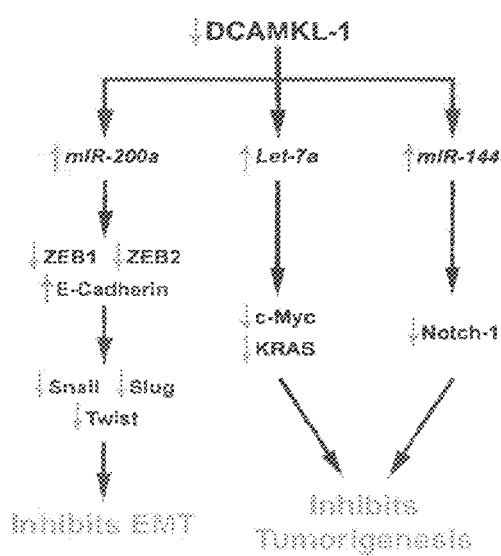

FIG. 56 illustrates that selective blockade of DCAMKL-1 results in inhibition of EMT and tumorigenesis in CSCs of pancreatic cancer.

Figure 57:
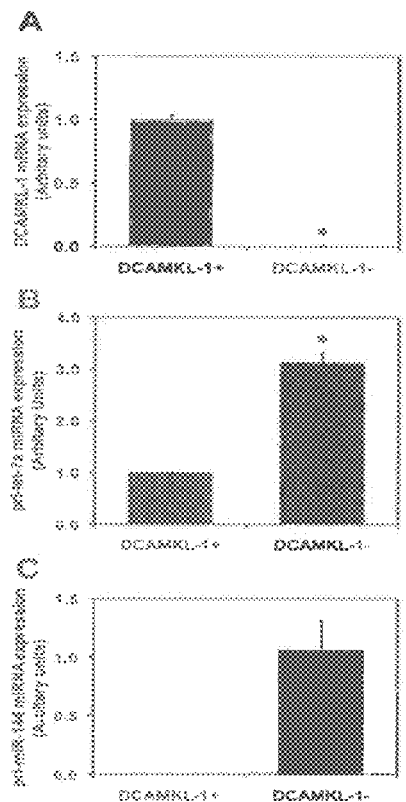

FIG. 57 illustrates that DCAMKL-1 inhibits let7a and miR-144 miRNA. (A) Quantitative real-time RT-PCR data demonstrates an increased expression of DCAMKL-1 mRNA in DCAMKL-1+ sorted cells compared to DCAMKL-1-cells. (B) DCAMKL-1-cells demonstrates a 3 fold increase in pri-let-7a miRNA compared to pancreatic stem/progenitor cells (DCAMKL-1+) isolated from normal mouse pancreas. (C) pri-mIR-144 was detected in DCAMKL-1-cells and was undetected in DCAMKL-1+ cells. Values represented as mean±SEM, and asterisks denote statistically significant differences (*p<0.01) compared with control.

Figure 58:
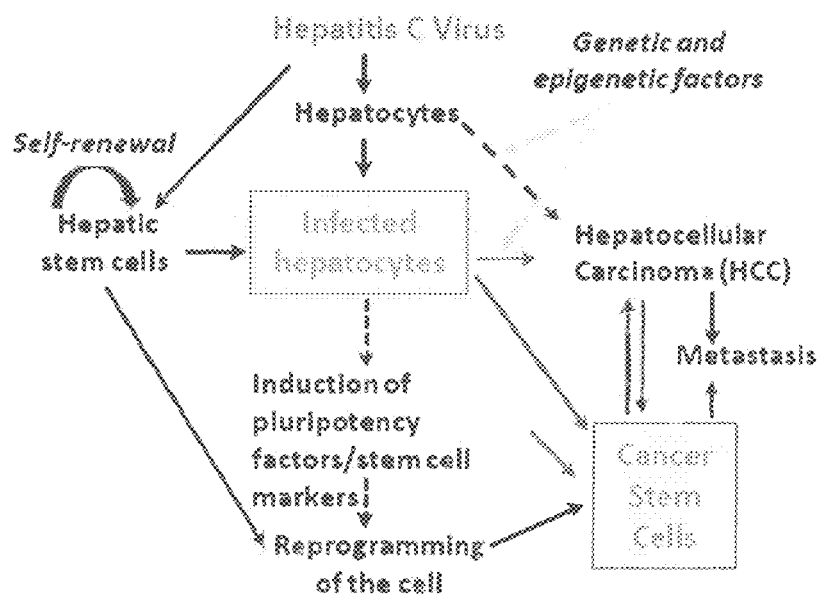

FIG. 58 graphically illustrates a proposed model for hepatitis C virus-induced HCC.

Figure 59:
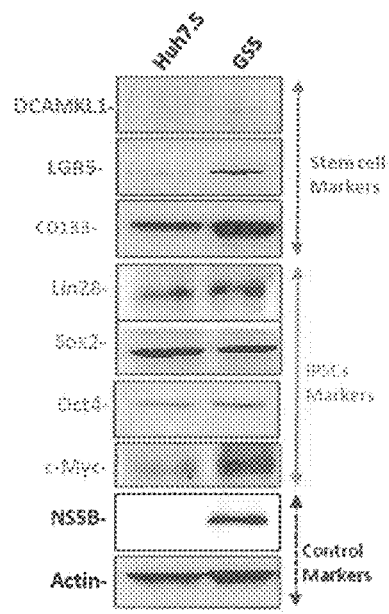

FIG. 59 depicts Western blot analysis of liver-derived hepatoma cell line (Huh7.5) and its counterpart cells expressing HCV subgenomic replicon (GS5 cell line). Expression of stem cell markers (DCAMKL1, LGR5, CD133) and induced-pluripotency (iPSCs) factors (Oct4, Sox2, c-Myc, Lin28) are shown. The presence of a viral protein NSSB in the GS5 cells mimics chronic infection of HCV in the cells.

Figure 60:
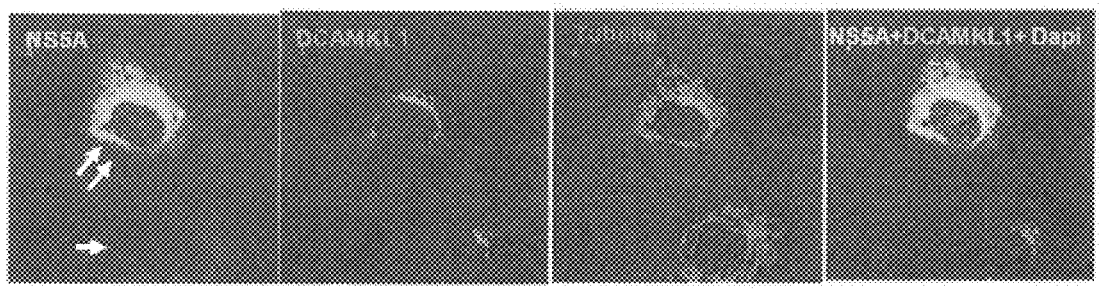

FIG. 60 depicts confocal microscopy for localization of HCV, NS5A-GFP, DCAMKL-1 and microtubules in GS5 cells as indicated. The field contains two cells; single and double arrows indicate low and high HCV replicon expressing cells, respectively, as indicated by the intensity of GFP.

Figure 61:
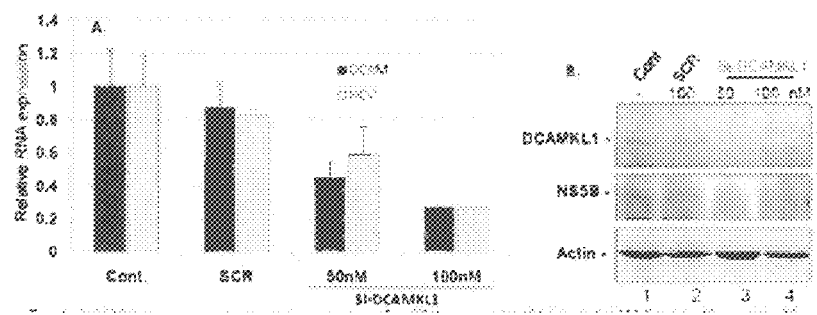

FIG. 61 illustrates that DCAMKL-1 is required for the HCV replication. A. siRNA against DCAMKL-1 (Si-DCAMKL1, 50 nM and 100 nM) or scrambled siRNA (SCR, 100 nM) were transfected into GS5 cells. Total RNAs were extracted and subjected to real-time quantitative PCR. The levels of HCV and DCAMKL-1 RNAs were considered arbitrary as one unit in untransfected GS5 cells (Cont). Actin mRNA in each sample was used as internal control for PCR. B. Western blot analysis of siRNAs tranfected and untransfected samples as indicated.

Figure 62:
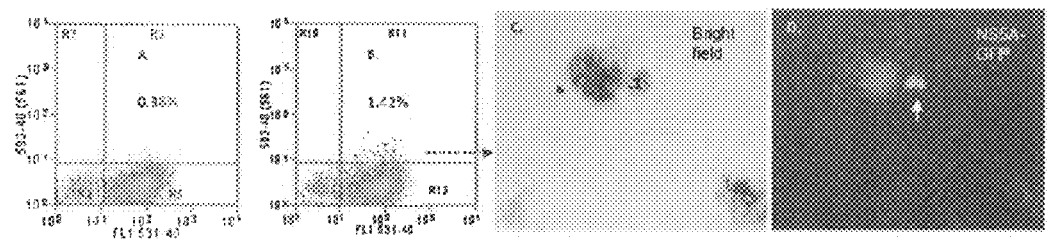

FIG. 62 illustrates spheroid formation by isolating HCV-expressing DCAMKL-1 positive cells (HCV-DCAMKL-1+). HCV replicon that expresses NSSA-GFP in hepatoma cells (GS5) were stained for surface DCAMKL-1 (with Alexa 547 secondary antibody conjugate), and GFP-DCAMKL-1 double positive cells were sorted (B). A. control (without primary antibody). One hundred cells were plated with media containing 50% Matrigel™ in a 96-well plate. Five weeks later, spheroids were photographed (C). The higher HCV expression indicated by GFP intensity is shown with an arrow in a budding spheroid (D).

Figure 63:
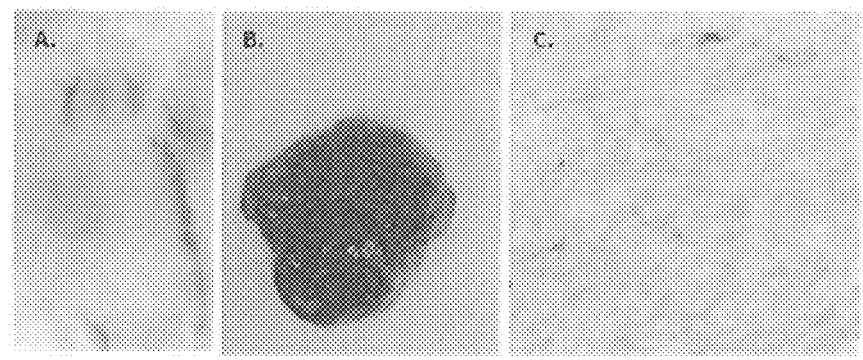

FIG. 63 illustrates that DCAMKL-1$^+$HCV$^+$ cells exhibit CSC-like features. These cells were isolated from GS5 culture by FACS, and 1 million cells were injected into the dorsal flank of a nude SCID mouse. The tumor developed after 6 weeks (A) and was harvested (B) and subjected to immunohistochemical staining (C). C, purple, DCAMKL1; Brown, activated c-Srp [pTyr418 c-Src].

Figure 64:
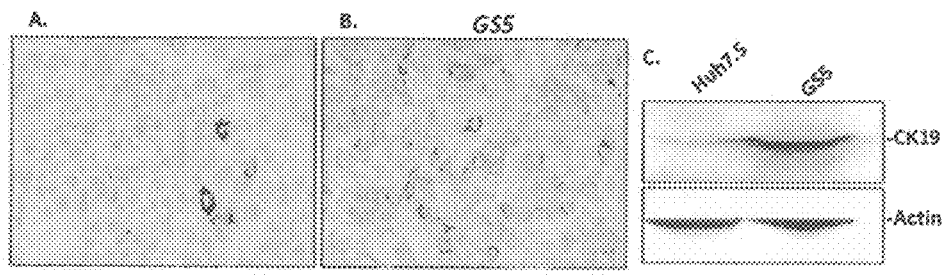

FIG. 64 depicts enhanced expressed of bile duct epithelium marker (CK19) in GS5-derived tumors (B) as compared to that of Huh7.5-derived tumor (A). Immunohistochemical staining of tumor xenografts of Huh7.5 and GS5 cell lines. Brown stain indicates CK19. Blue, nuclear stain. C, Western blot of tumor xenografts of both cells lines as indicated.

Figure 65:
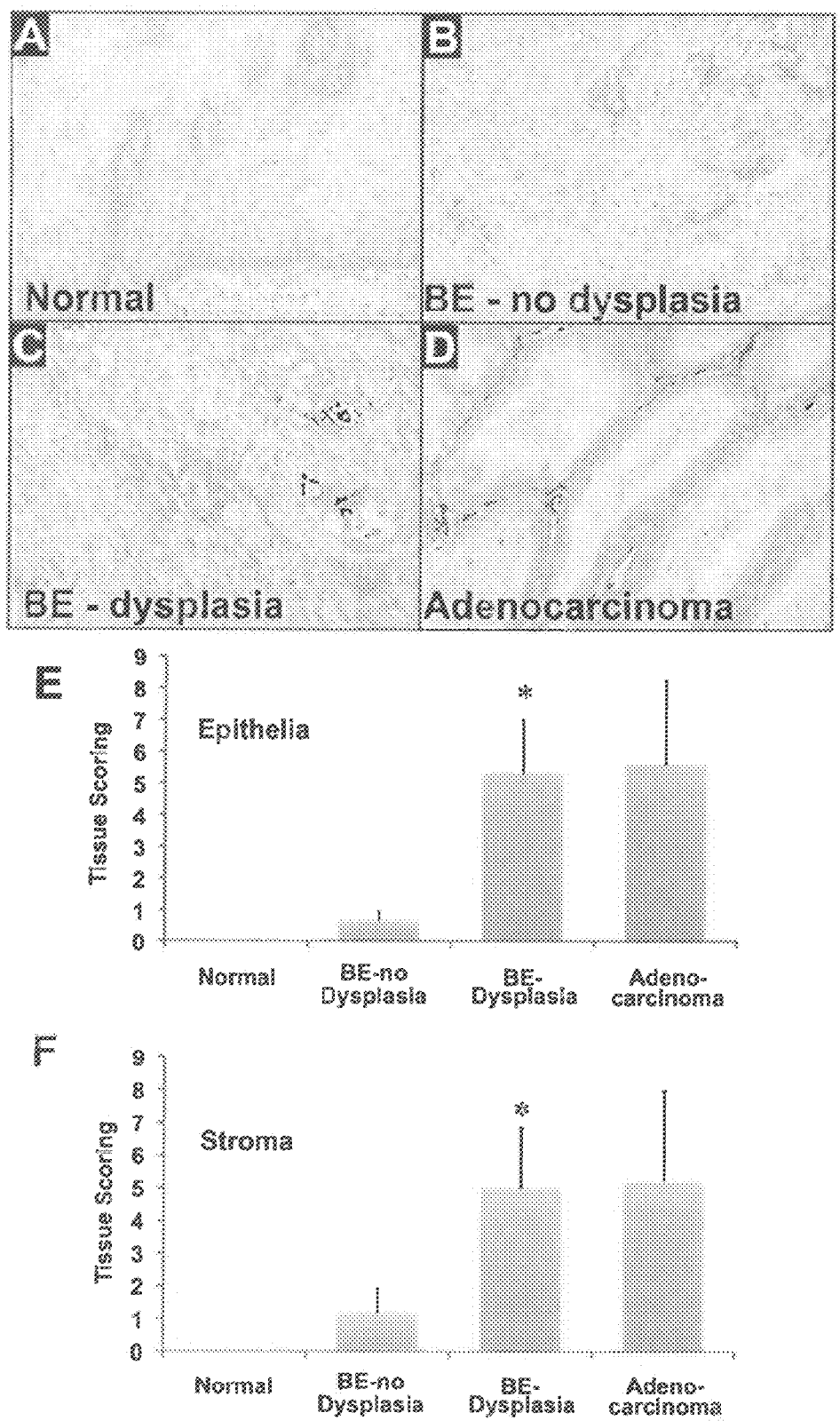

FIG. 65 graphically depicts Immunohistochemical expression of DCAMKL-1 in Normal, BE without dysplasia, BE with dysplasia and Adenocarcinoma/EAC. A: Minimal DCAMKL-1 epithelial staining in normal squamous epithelium. B-D: Increased expression of DCAMKL-1 in stroma of biopsies of BE with no dysplasia (b) and BE with dysplasia (c) as well as Adenocarcinoma/EAC in situ (d). Brown indicates cells positive for DCAMKL-1. E-F: Immunohistochemical scoring of DCAMKL-1 in epithelium (e) and stroma (f) of various tissues as indicated. Values in the bar graphs are given as average±SEM, and asterisks denote statistically significant differences (*p<0.01) compared to normal.

Figure 66:
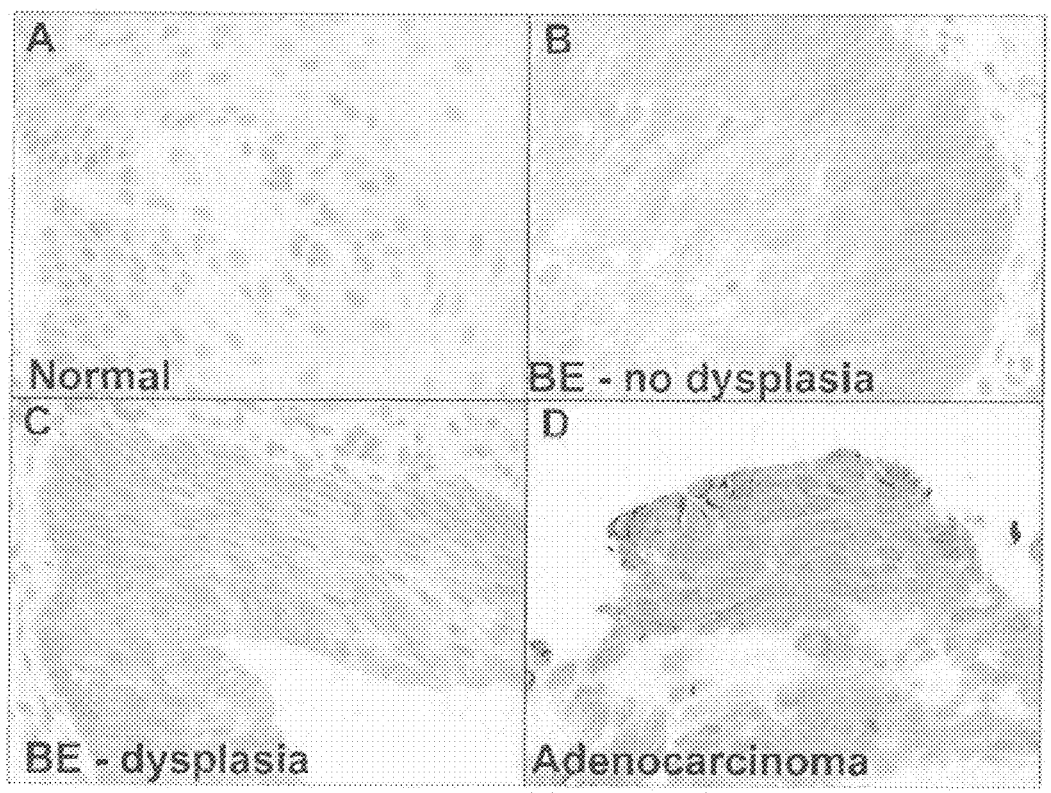

FIG. 66 depicts immunohistochemical expression of DCAMKL-1 in vascular structures within endoscopically obtained, histologically confirmed squamous esophageal mucosa, BE without dysplasia, BE with dysplasia and Adenocarcinoma/EAC. A: Minimal DCAMKL-1 in normal squamous epithelium. B-D: Increasing muscularis and vascular DCAMKL-1 expression in biopsies of BE without dysplasia (b), BE with dysplasia (c) and Adenocarcinoma/EAC (d). Brown indicates cells positive for DCAMKL-1.

Figure 67:
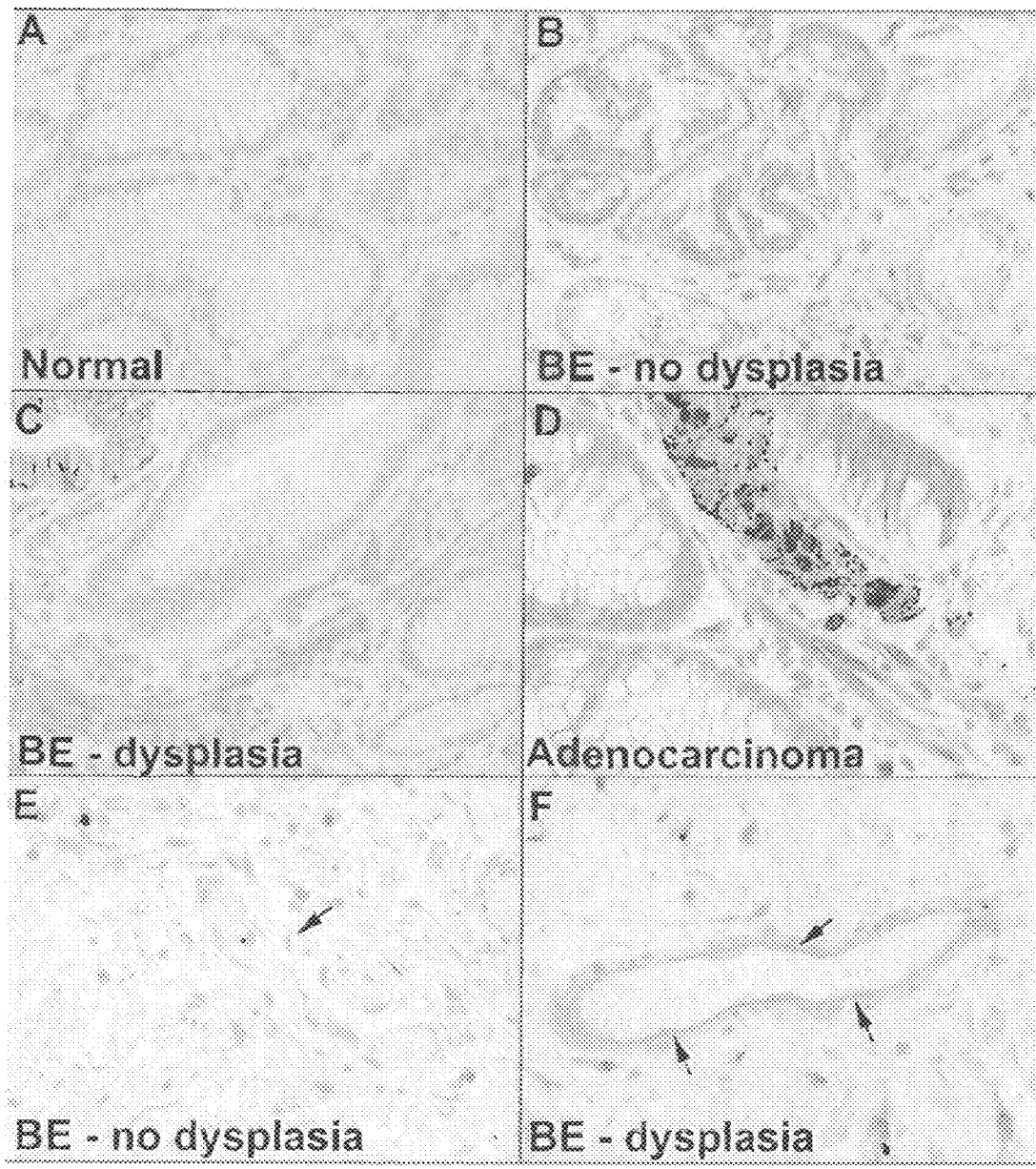

FIG. 67 depicts localization of immunohistochemical expression of DCAMKL-1 within endoscopically obtained, histologically confirmed glandular epithelium, BE without dysplasia, BE with dysplasia and Adenocarcinoma/EAC. A: Minimal DCAMKL-1 in normal squamous epithelium. B-D: Primarily epithelial DCAMKL-1 expression in BE without dysplasia (b), increased epithelial expression combined with onset of stromal expression in BE with dysplasia (c) and increased stromal expression in Adenocarcinoma/EAC (d). Minimal DCAMKL-1 immunostaining is observed in endothelial cells in patients with BE without dysplasia (arrow indicates cell positive for DCAMKL-1) (e). Increased DCAMKL-1 staining is observed endothelial cells in BE with dysplasia (f). Brown indicates cells positive for DCAMKL-1 (arrows).

Figure 68:
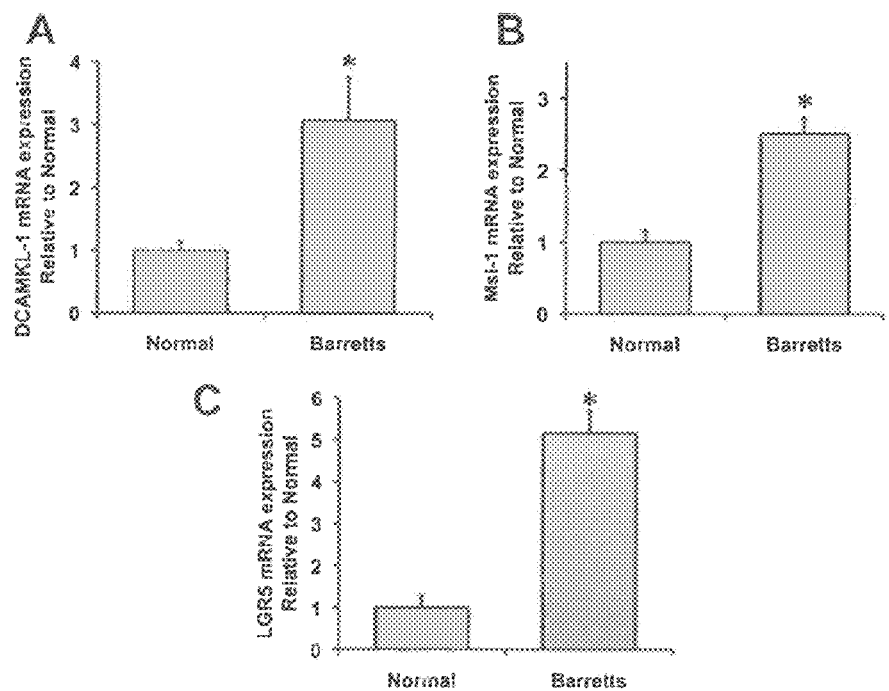

FIG. 68 illustrates that DCAMKL-1 is overexpressed in BE. A: Increased DCAMKL-1 mRNA expression in BE compared to normal. B-C: Increased Msi-1 (b) and LGR5 (c) mRNA expression in BE compared to normal. Values in the bar graphs are given as average±SEM, and asterisks denote statistically significant differences (*p<0.01) compared to normal.

Figure 69:
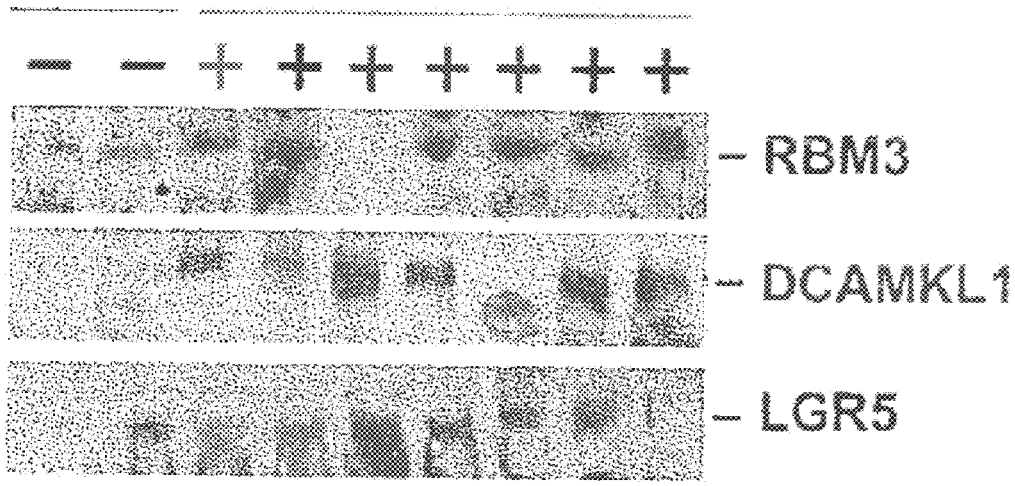

FIG. 69 illustrates RBM3, DCAMKL-1 and LGR5 levels in sera from patients with pancreatic cancer. Archived serum from patients with pancreatic cancer (+) and two healthy volunteers (−) were subjected to western blot analyses. Data demonstrates the presence of increased levels of the three proteins in the patient sera.

FIG. 70 graphically depicts the results of a cell viability assay for PICSC cells treated with turmeric.

FIG. 71 graphically depicts the results of a cell viability assay for PICSC cells treated with Gemcitabine.

FIG. 72 graphically depicts the results of a cell viability assay for PICSC cells treated with siDCAMKL-1.

Figure 73:
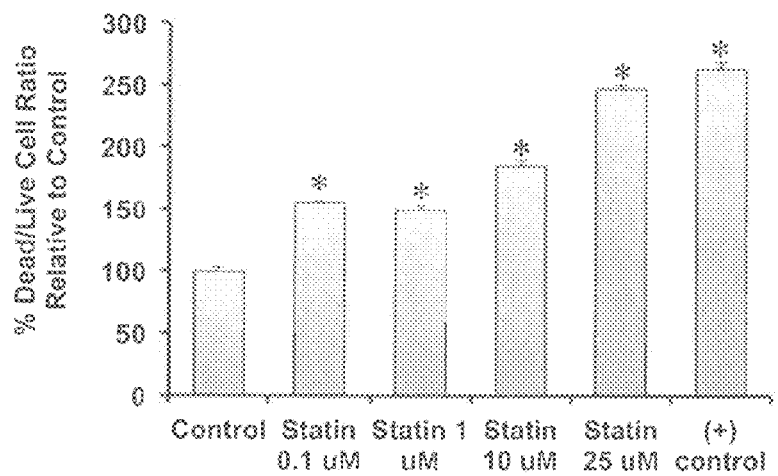

FIG. 73 graphically depicts the results of a cell viability assay for PICSC cells treated with Simvastatin.

Figure 74:
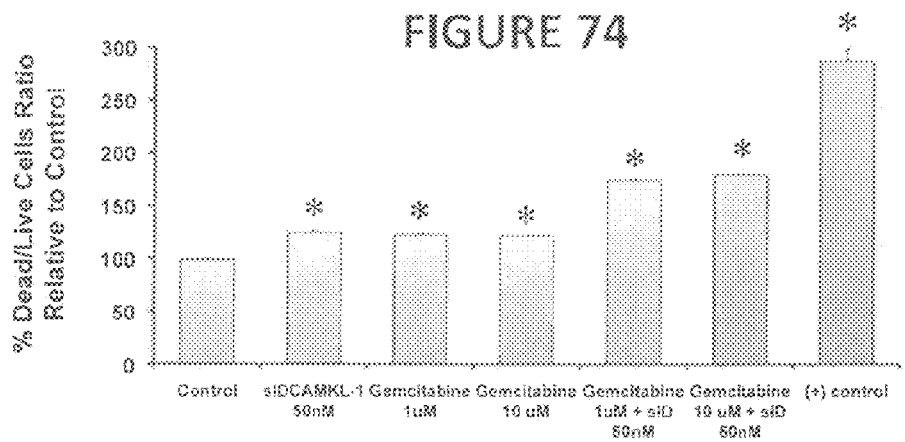

FIG. 74 graphically depicts the results of a cell viability assay for PICSC cells treated with siDCAMKL-1 in combination with increasing concentrations of Gemcitabine.

Figure 75:
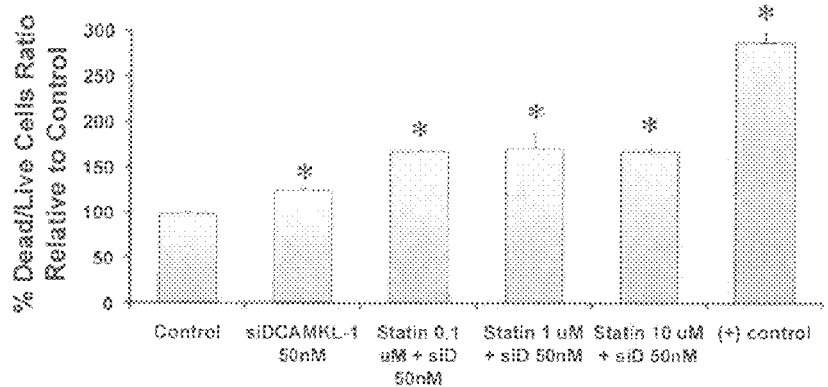

FIG. 75 graphically depicts the results of a cell viability assay for PICSC cells treated with siDCAMKL-1 in combination with increasing concentrations of Simvastatin.

Figure 76:
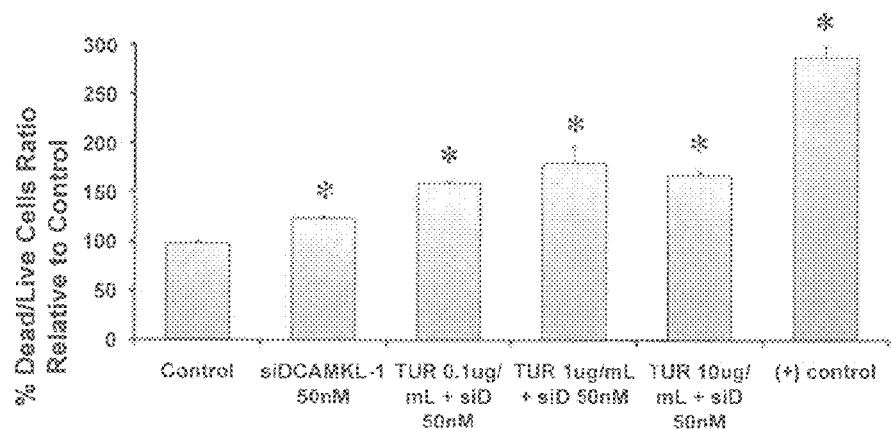

FIG. 76 graphically depicts the results of a cell viability assay for PICSC cells treated with siDCAMKL-1 in combination with increasing concentrations of turmeric.

Figure 77:
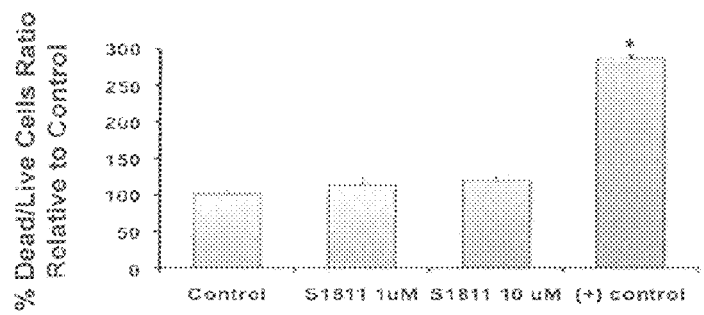

FIG. 77 graphically depicts the results of a cell viability assay for PICSC cells treated with S1811 (dye).

Figure 78:
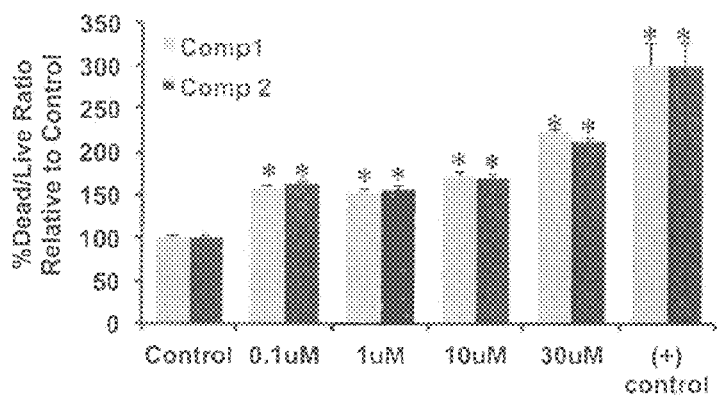

FIG. 78 graphically depicts the results of a cell viability assay for PICSC cells treated with two compounds.

Figure 79:
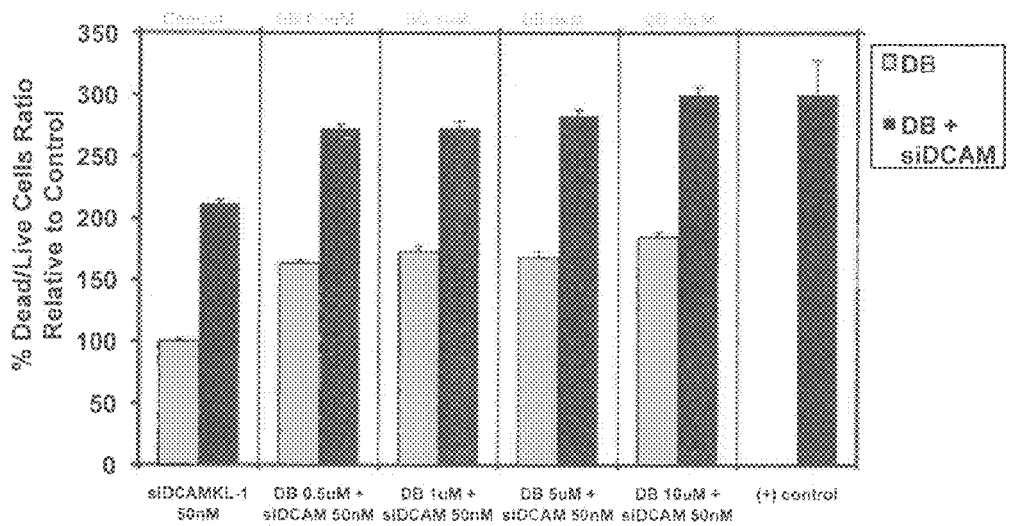

FIG. 79 graphically depicts the results of a cell viability assay for PICSC cells treated with flexible heteroarotinoids (DB).

Figure 80:
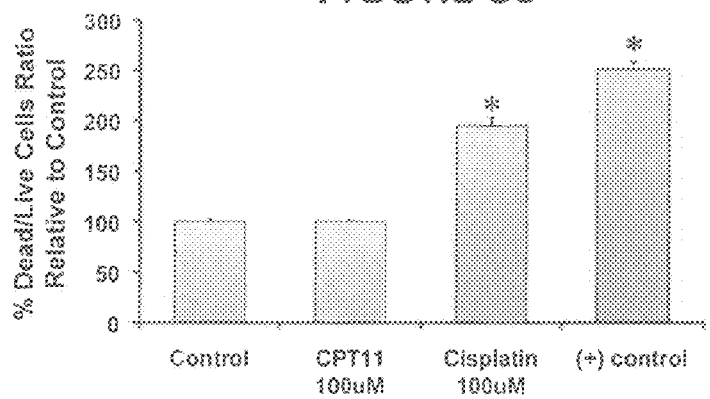

FIG. 80 graphically depicts the results of a cell viability assay for PICSC cells treated with Cisplatin.

Figure 81:
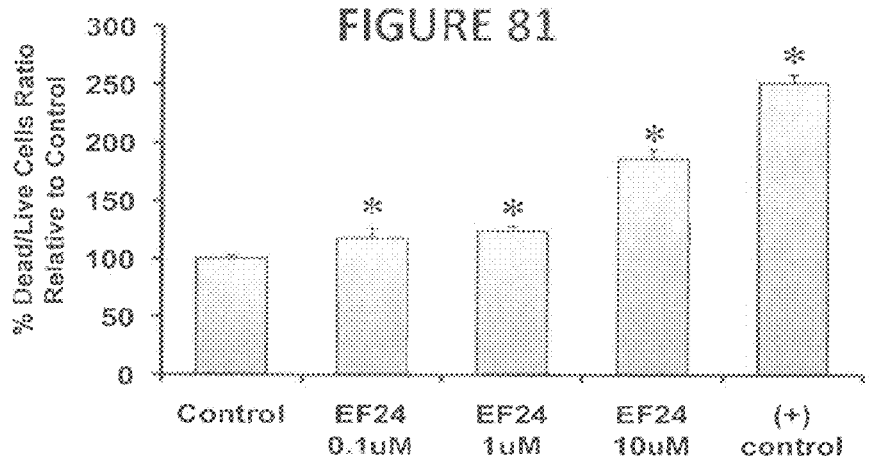

FIG. 81 graphically depicts the results of a cell viability assay for PICSC cells treated with the curcumin derivative EF24 (diphenyl difluoroketone).

Figure 82:
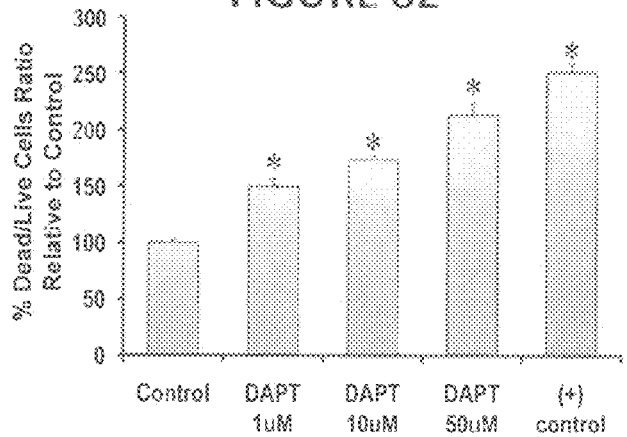

FIG. 82 graphically depicts the results of a cell viability assay for PICSC cells treated with Notch signaling inhibitor (DAPT).

Figure 83:
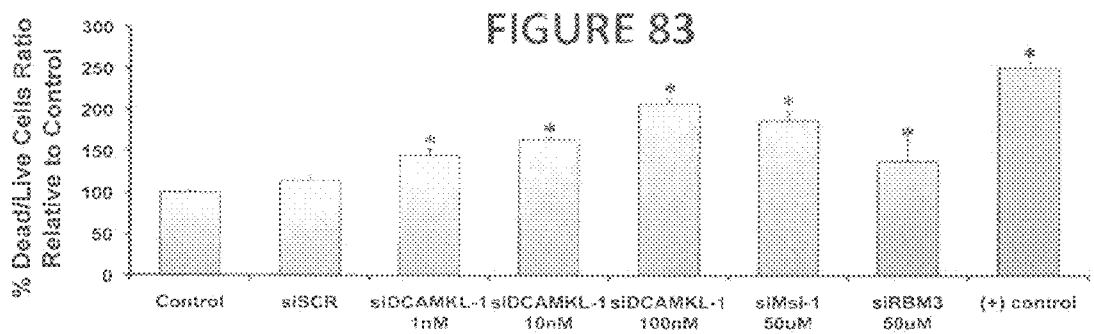

FIG. 83 graphically depicts the results of a cell viability assay for PICSC cells treated with various siRNAS (against DCAMKL-1, Musashi-1 and RBM3).

Figure 84:
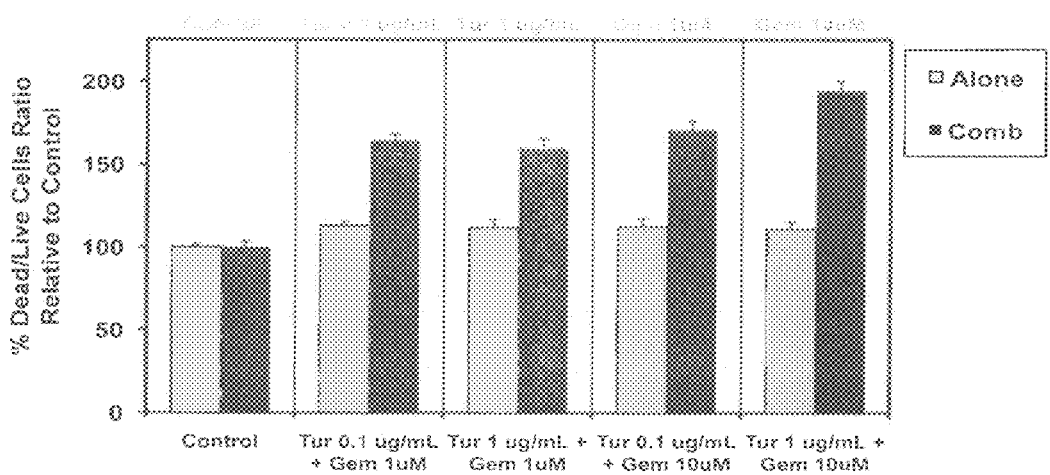

FIG. 84 graphically depicts the results of a cell viability assay for PICSC cells treated with increasing concentrations of Gemcitabine in combination with various concentrations of turmeric.

DETAILED DESCRIPTION OF THE INVENTIVE CONCEPT(S)

Before explaining at least one embodiment of the presently disclosed and claimed inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The terms "isolated polynucleotide" and "isolated nucleic acid segment" as used herein shall mean a polynucleotide of genomic, cDNA, or synthetic origin or some combination thereof, which by virtue of its origin the "isolated polynucleotide" or "isolated nucleic acid segment" (1) is not associated with all or a portion of a polynucleotide in which the "isolated polynucleotide" or "isolated nucleic acid segment" is found in nature, (2) is operably linked to a polynucleotide which it is not linked to in nature, or (3) does not occur in nature as part of a larger sequence.

The term "isolated protein" referred to herein means a protein of genomic, cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or, (4) does not occur in nature.

The term "polypeptide" as used herein is a generic term to refer to native protein, fragments, or analogs of a polypeptide sequence. Hence, native protein, fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

"Antibody" or "antibody peptide(s)" refer to an intact antibody, or a binding fragment thereof that competes with the intact antibody for specific binding. The term "antibody" is used in the broadest sense, and specifically covers monoclonal antibodies (including full length monoclonal antibodies), polyclonal antibodies, multispecific antibodies (e.g., bispecific antibodies), and antibody fragments (e.g., Fab, F(ab')2 and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. Antibody binding fragments are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The terms "DCAMKL-1", "Doublecortin-like and CAM kinase kinase-like 1", "doublecortin and $Ca^{2+}$/calmodulin-dependent kinase-like-1" and "Gene Ontogeny (GO)—enriched transcript" will be used herein interchangeably and will be understood to refer to a microtubule-associated kinase expressed in post-mitotic neurons. See for example, Shu et al. (Neuron (2006) 49:25-39; and Biol. Chem. (2006) 281:11292-300). Its presence was identified from cDNA libraries prepared from laser capture microdissected small intestinal and gastric epithelial progenitor populations.

The terms "RNA binding motif protein 3" and "RBM3" are used interchangeably herein and will be understood to refer to a putative stem cell marker. RBM3 is a ubiquitously expressed glycine-rich protein that can bind to both RNA and DNA via an amino-terminal RNA binding domain. RBM3 was identified as a protein expressed following cold shock and was found in the complex of proteins binding to COX-2.

The terms "Musashi-1" and "Msi-1" are used interchangeably herein and will be understood to refer to a putative stem cell marker. Msi-1 was identified as an RNA binding protein that is a translational repressor of p21. Msi-1 regulates assymetrical division in neural precursor cells, and is expressed in intestinal crypts in the stem cell zone.

The terms "Leucine-rich repeat-containing G-protein coupled receptor 5" and "LGR5" are used interchangeably herein and will be understood to refer to a putative stem cell marker. LGR5 is a a leucine-rich orphan G-protein-coupled receptor that specifically labels stem cells in the mouse small intestine as well as other adult tissues.

The term "14-3-3σ" refers to a putative stem cell marker. The 14-3-3 σ gene (also called stratifin) was originally characterized as the human mammary epithelial-specific marker, HME-1, and is expressed in keratinocytes and epithelial cells. 14-3-3σ is up-regulated through a p53-dependent mechanism following DNA damage, and sequesters cyclin B1/CDC2 complexes in the cytoplasm during G2 arrest. Its absence allows cyclin B1/CDC2 complexes to enter the nucleus, causing mitotic catastrophe. 14-3-3σ has also been shown to specifically interact with CDK2, CDC2 and CDK4 and to inhibit CDK activities, thereby blocking cell cycle progression, thus defining it as a new class of CKI. Deregulation of 14-3-3σ expression has been observed in a wide variety of human cancers, with both decreasing and increasing 14-3-3σ levels being associated with development of malignancy.

The term "Bmi1" will be understood to refer to a putative stem cell marker. The Bmi1 gene is known to be involved in the self-renewal of neuronal, hematopoietic and leukemic cells. Bmi1 was first identified in a mouse proviral insertion screen for lymphomagenesis. It is part of the Polycomb group gene family, and specifically a member of polycomb-repressing complex 1 (PRC1). PRC1 has an essential role in maintaining chromatin silencing.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Specific methods of using siRNAs are described in detail in U.S. Pat. No. 7,345,027, issued to Tolentino et al. on Mar. 18, 2008; U.S. Pat. No. 7,148,342, issued to Tolentino et al. on Dec. 12, 2006; U.S. Pat. No. 7,511,025, issued to Wyatt et al. on Mar. 31, 2009; and U.S. Pat. No. 7,511,132, issued to Khvorova et al. on Mar. 31, 2009; the entire contents of such patents are expressly incorporated herein by reference. These patents describe siRNAs which specifically target and cause RNAi-induced degradation of mRNA, such as RNA from VEGF and VEGF receptors, MMP-1 and BCL-2, respectively, and such siRNA compounds may be used to suppress invasion and/or metastasis of tumor cells and/or inhibit angiogenesis, in particular for the treatment of cancerous tumors, age-related macular degeneration, and other angiogenic diseases. The methods of these patents may be applied to the production and use of siRNAs in accordance with the presently disclosed and claimed inventive concept(s).

The term "biological sample" as used herein will be understood to refer to a sample of biological tissue or fluid. Biological samples include, but are not limited to, sections of tissues such as biopsy and autopsy samples, frozen sections taken for histological purposes, blood, plasma, serum, sputum, stool, tears, mucus, hair, skin, explants and primary and/or transformed cell cultures derived from patient tissues. The term "biological sample" as used herein will also be understood to include derivatives and fractions of such fluids, as well as combinations thereof. For example, the term "biological sample" will also be understood to include complex mixtures.

The phrase "providing a biological sample" as used herein refers to obtaining a biological sample for use in methods described in the presently disclosed and claimed inventive concept(s). Most often, this will be done by removing a sample of cells from an animal, but can also be accomplished by using previously isolated cells (e.g., isolated by another person, at another time and/or for another purpose), or by performing at least a portion of the methods of the presently disclosed and claimed inventive concept(s) in vivo.

As used herein, a "conjugate" refers to a molecule that contains at least one receptor-binding ligand and at least one anticancer agent that are coupled directly or via a linker and that are produced by chemical coupling methods or by recombinant expression of chimeric DNA molecules to produce fusion proteins.

As used herein, the term "covalently coupled", "linked", "bonded", "joined", and the like, with reference to the ligand and anticancer agent components of the conjugates of the presently disclosed and claimed inventive concept(s), mean that the specified components are either directly covalently bonded to one another or indirectly covalently bonded to one another through an intervening moiety or components, such as a bridge, spacer, linker or the like. For example but not by way of limitation, the ligand and the anticancer agent may be chemically coupled together via a thioether linkage as described in Mickisch et al. (1993).

As used herein, the term "anticancer agent" refers to a molecule capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent is selectively toxic against certain types of cancer cells but does not affect or is less effective against other normal cells.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The therapeutic effect may include, for example but not by way of limitation, inhibiting the growth of undesired tissue or malignant cells.

The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed inventive concept(s). This concurrent therapy can be sequential therapy where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The term "receptor" as used herein will be understood to include any peptide, protein, glycoprotein, polycarbohydrate, or lipid that is uniquely expressed or overexpressed on the surface of cancer cells and is exposed on the surface of cancer cells in a manner that will allow interaction with a circulating targeting agent, such as the conjugate.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

A "liposome" is a small vesicle composed of various types of lipids, phospholipids and/or surfactant. The components of the liposome are commonly arranged in a bilayer formation, similar to the lipid arrangement of biological membranes.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "metastasis" as used herein will be understood to refer to the spread of cancer from a primary tumor to other parts of the body. Metastasis is a sequential, multistep process in which tumor cells detach from a primary tumor, migrate through the basement membrane and extracellular matrix, and invade the lymphatic and/or blood systems. This is followed by the establishment of secondary tumors at distant sites.

The term patient includes human and veterinary subjects. "Mammal" for purposes of treatment refers to any animal classified as a mammal, including human, domestic and farm animals, nonhuman primates, and any other animal that has mammary tissue.

The term "healthy patient" as used herein will be understood to refer to a patient who is free of cancer.

The terms "treat", "treating" and "treatment", as used herein, will be understood to include both inhibition of tumor growth as well as induction of tumor cell death.

As used herein, the term "treating cancer" or "treatment of cancer" means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

"Preventing cancer" or "prevention of cancer" is intended to mean preventing the occurrence or recurrence of the disease state of cancer. As such, a treatment that impedes, inhibits, or interferes with metastasis, tumor growth, or cancer proliferation is deemed preventive.

As used herein, "managing cancer" encompasses preventing the recurrence of cancer in a patient who had suffered from cancer, lengthening the time a patient remains in remission, preventing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and preventing the occurrence of malignant cancer in patients suffering from pre-malignant or non-malignant cancers.

Administering a therapeutically effective amount or prophylactically effective amount is intended to provide a therapeutic benefit in the treatment, prevention, or management of cancer. The specific amount that is therapeutically effective can be readily determined by the ordinary medical practitioner, and can vary depending on factors known in the art, such as the type of cancer, the patient's history and age, the stage of cancer, the co-administration of other anti-cancer agents, including radiation therapy.

The presently disclosed and claimed inventive concept(s) is related to cancer-initiating cells (CICs) or cancer stem cells (CSCs), as well as production, identification and use thereof. The presently disclosed and claimed inventive concept(s) provide effective identification and treatment of cancers, as well as methods that increase sensitivity of cancer cells to cell death and reduce or eliminate resistance of cells to chemical and radiation treatment. In addition, the presently disclosed and claimed inventive concept(s) increase the efficiency of treating, curing and/or preventing cancers. Further, the presently disclosed and claimed inventive concept(s) provides a method of generating a cancer stem cell model (in a species such as but not limited to, mouse). All of the compositions and methods describe herein above rely on the use of DCAMKL-1 and at least one additional marker (such as but not limited to, RBM3, Msi-1, LGR5 and 14-3-3σ), as markers for cancer stem cells.

The presently disclosed and claimed inventive concept(s) is directed to a method of making a cancer stem cell model, such as but not limited to, a rodent cancer stem cell model. In non-limiting examples, the model may be a mouse cancer stem cell model or a rat cancer stem cell model. However, it is to be understood that any desired animal model known in the art may be utilized in accordance with the presently disclosed and claimed inventive concept(s), and thus the presently disclosed and claimed inventive concept(s) is not limited to the use of a rodent. In the method, non-tumorigenic cells are provided and transfected with an expression vector comprising a gene encoding RBM3. The cells are then cultured under conditions that allow for expression of RBM3, and overexpression of RBM3 may result in increased cell proliferation and induction of anchorage independent growth. The cultured cells are then transplanted into an animal (i.e., a rodent), and a xenograft tumor is allowed to form.

In one embodiment, the rodent may be an immunodeficient rodent. For example, if the cells being transplanted are non-allogeneic, then it is desirable for the rodent to be immunodeficient so that an immune response is not raised against the cells.

In one particular embodiment, the cells to be transplanted are mouse fibroblast cells, and the rodent is an immunodeficient mouse. In another particular embodiment, the cells to be transplanted are from a species other than mouse, and the rodent is an immunodeficient mouse.

Any gene encoding RBM3 may be utilized in accordance with the presently disclosed and claimed inventive concept(s). In one embodiment, the RBM3 may be from a mammalian source, such as but not limited to, human RBM3, mouse RBM3, rat RBM3, and the like. The DNA and amino acid sequences of human RBM3 (GenBank Accession No. NM_006743.3) have been designated SEQ ID NOS:68 and 69, respectively; the DNA and amino acid sequences of mouse RBM3 (GenBank Accession No. AB016424.1) have been designated SEQ ID NOS:70 and 71, respectively; and the DNA and amino acid sequences of mouse RBM3 (GenBank Accession No. NM_053696.1) have been designated SEQ ID NOS:72 and 73, respectively. In certain embodiments, the gene encoding RBM3 utilized in accordance with the presently disclosed and claimed inventive concept(s) may be a gene as set forth in one of SEQ ID NOS:68, 70 and 72, or a DNA sequence that is at least 80% (such as but not limited to, at least 85% or at least 90%) identical to at least one of SEQ ID NO:68, 70 and 72. In other embodiments, the gene encoding RBM that is utilized in accordance with the presently disclosed and claimed inventive concept(s) may encode the amino acid sequence of one of SEQ ID NOS: 69, 71 and 73, or an amino acid sequence that is at least 80% (such as but not limited to, at least 85% or at least 90%) identical to at least one of SEQ ID NO:69, 71 and 73. In yet other embodiments, the gene encoding RBM that is utilized in accordance with the presently disclosed and claimed inventive concept(s) may hybridize under stringent conditions to a complement of at least one of SEQ ID NOS:68, 70 and 72, or to a complement of a DNA sequence encoding the amino acid sequence of at least one of SEQ ID NOS: 69, 71 and 73.

The presently disclosed and claimed inventive concept(s) is also directed to a method of generating cancer stem cells suitable for screening agents for use in the detection or treatment of cancer. In said method, the rodent (or other desired host) cancer stem cell model is produced as described in detail herein above. The xenograft tumor produced in the cancer stem cell model is then isolated, and at least one cancer stem cell expressing DCAMKL-1 on a surface thereof is isolated from the xenograft tumor.

The presently disclosed and claimed inventive concept(s) is also directed to a method for detecting/diagnosing cancer in a patient, as well as to diagnosing a stage/progression of said cancer. The method utilizes a biological fluid from a patient (such as but not limited to, blood, plasma, serum, urine, etc.). In said method, the levels of DCAMKL-1 protein and at least one additional protein present in the biological fluid are measured, and it is determined that the patient has cancer if the levels of at least one of DCAMKL-1 and the at least one additional protein present in the biological fluid are substantially greater than controls. The at least one additional protein is associated with a stem cell and/or mesenchymal cell marker and is selected from the group consisting of RBM3, Musashi-1, LGR5, 14-3-3σ, and Bmi1. In certain embodiments, the protein levels may be measured by ELISA and/or Western blot.

In one embodiment, the method may also include detection of the specific level of DCAMKL-1, RBM3, LGR5, 14-3-3σ and/or Msi-1 proteins present, and comparison of said levels to known levels of said protein(s) present in (1) normal cells, and/or (2) cells at various stages of tumor progression and/or metastasis. For example but not by way of limitation, the method may further include measuring the two protein levels, and correlating the protein levels to the diagnosis of neoplastic disease.

The present invention further relates to an immunological kit for detecting the levels of DCAMKL-1 and the at least one additional protein. Said kit includes a DCAMKL-1 specific binding agent and a specific binding agent for the at least one additional protein.

The above-described method could also be utilized to determine the effect of chemopreventive strategies on the development of early neoplastic lesions.

The term "specific binding agent" as used herein will be understood to include any compound or agent that binds specifically to one of the desired proteins described herein (i.e., DCAMKL-1, RBM3, Msi-1, LGR5, 14-3-3σ, etc.), including but not limited to, a receptor for said protein, a lectin binding to said protein, or an antibody to said protein. As the skilled artisan will appreciate, the term "specific" is used to indicate that other biomolecules present in the sample do not significantly bind to the binding agent specific for said protein. A level of less than 5% cross-reactivity is considered not significant.

In one embodiment, the specific binding agent is an antibody reactive with the desired protein. The term antibody refers to a polyclonal antibody, a monoclonal antibody, fragments of such antibodies, as well as to genetic constructs comprising the binding domain of an antibody.

The monoclonal antibody or other specific binding agent may further comprise a label, such as but not limited to, a radiolabel or fluorescent label, to aid in visualization of tumor cells with an external imaging source, such as but not limited to, an MRI or PET scan. In this instance, the detection assays described herein may be conducted in vivo, rather than requiring removal of the tumor/biological sample from the patient.

The presently disclosed and claimed inventive concept(s) is also directed to a method of generating a personalized cancer model. In said method, a tumor or a cancerous biological sample is obtained from a patient, and cells that express DCAMK-1 protein on a surface thereof are identified and isolated by any methods known in the art or otherwise described herein. The isolated cells are then transplanted into an immunodeficient mouse (or other immunodeficient animal host), and a xenograft tumor is allowed to form. The xenograft tumor should provide an appropriate model for the patient's tumor and be suitable for screening agents for the treatment of the patient's specific cancer.

In one embodiment, the presently disclosed and inventive concept(s) is directed to methods of inhibiting tumor growth. Such methods involve an inhibition of tumor stem cells through inhibition of DCAMKL-1 and one or more RNA binding proteins in the tumor stem cells. In one embodiment, the RNA binding protein is Musashi-1 (Msi-1); in another embodiment, the RNA binding protein is RNA binding motif protein 3 (RBM3). Such methods of inhibition of RNA binding proteins result in a decrease in cancer cell proliferation and apoptosis, as well as $G_2$/M arrest, coupled with mitotic catastrophe. Inhibition of RNA binding protein(s) may also result in a decrease in mRNA stability and/or translation for the gene products of at least one of vascular endothelial growth factor (VEGF), interleukin-8 (IL-8), cyclooxygenase-2 (COX-2), Notch-1 and matrix metalloproteinase 7 (MMP7). The method of inhibiting DCAMKL-1 and one or more RNA binding proteins may include inhibition of expression of the gene encoding DCAMKL-1/RNA binding protein and/or inhibition of production of DCAMKL-1 protein/RNA binding protein.

The methods described herein may be utilized for treatment of any cancer, including but not limited to, cancers of the gastrointestinal tract, colon, pancreas, breast, prostate, lung and ovaries. Particular cancers that can be treated and managed by the methods of the presently disclosed and claimed inventive concept(s) include, but are not limited to, those associated with an increase in the expression of at least one RNA binding protein, including but not limited to, Musashi-1 (Msi-1) and RNA binding motif protein 3 (RBM3), and/or DCAMKL-1.

The presently disclosed and claimed inventive concept(s) also includes a pharmaceutical composition comprising an inhibitor DCAMKL-1 in combination with an inhibitor of at least one RNA binding protein, as described herein above. The pharmaceutical composition may further comprise at least one additional chemotherapeutic agent, as described in detail herein. In addition, the pharmaceutical composition may also further comprise a delivery agent, such as but not limited to, a liposome.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the inventive concept(s) from degradation within the gastrointestinal tract. In another example, the agents of the inventive concept(s) may be administered in a liposomal formulation to shield the agents from degradative enzymes, facilitate transport in circulatory system, and effect delivery across cell membranes to intracellular sites.

The composition, shape, and type of dosage forms of the pharmaceutical compositions of the presently disclosed and claimed inventive concept(s) will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the inventive concept(s) will vary from one another and will be readily apparent to those skilled in the art. See, e.g., Remington: The Science and Practice of Pharmacy, Alfonso R. Gennaro, editor, 20th ed. Lippincott Williams & Wilkins: Philadelphia, Pa., 2000.

Delivery of the agents of the presently disclosed and claimed inventive concept(s) into a patient can either be direct, i.e., the patient is directly exposed to an agent of the inventive concept(s) or agent-carrying vector, or indirect, i.e., cells are first transformed with the nucleic acid sequences encoding an agent of the inventive concept(s) in vitro, then transplanted into the patient for cell replacement therapy. These two approaches are known as in vivo and ex vivo therapy, respectively.

The present invention also relates to a method of treating a neoplastic disease by targeting an anticancer agent, such as but not limited to a cytotoxic agent, to a cancer stem cell in a patient with a tumor. The method includes providing a conjugate of the anticancer agent attached to a specific binding agent for at least one of DCAMKL-1, RBM3, Msi-1, LGR5 and 14-3-3σ, and administering an effective amount of such conjugate to the patient, thereby inhibiting growth of the tumor. The anticancer agent may be a chemotherapeutic agent. In addition, the conjugate could also be attached to an implantable biodegradable agent.

The above-described method of treating a neoplastic disease could also be utilized to prevent neoplastic diseases, by administering the conjugate (or any of the other compositions disclosed herein) to a patient not experiencing a cancer. Depletion of stem cells in the patient will act to deplete the potential for neoplasia and tumor formation.

While the above-described methods have been disclosed as useful with gastrointestinal (GI) and pancreatic tumors, such methods are not specifically limited to use with GI and pancreatic tumors. For example, targeted depletion of a cancer or adenoma-initiating stem cell, as described herein, would also be useful with solid tumors of both GI and non-GI origin (such as but not limited to, lung cancer).

Examples are provided hereinbelow. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

EXAMPLE 1

Colorectal cancer is a major cause of cancer death in the western world. Mutational activation of oncogenes joins with inactivation of tumor suppressor genes to produce colorectal tumors [Clark, 2006]. The transformation of normal mucosal epithelial cells into invasive colorectal carcinoma occurs via a synchronized accumulation of mutations in a series of critical genes [Fearon, 1990]. The long time span between initiation and gross development of tumors presents an enormous challenge in dissecting the critical molecular mechanisms that regulate neoplastic change.

Defining the mechanisms that regulate stem cell fate is critical in increasing our understanding of the neoplastic process. Tumorigenesis in the gut is thought to arise specifically in the stem cell [Sansom et al., 2005; de Lau et al., 2007] population located at or near the base of the intestinal and colonic crypts. Transit cell populations originating from the stem cell zone become fully differentiated and are eventually sloughed into the lumen. Transit cells' short life span, whether they are mutated or not, limits their deleterious influence in the intestinal or colonic crypt [Potten, 2003]. Because no specific gut stem cell markers have been identified definitively [Bjerknes et al., 2005; Kayahara et al., 2003], recognizing and assaying resident intestinal stem cells is quite difficult and has raised contentious argument; however, the microcolony assay following γ-irradiation (IR) is by definition a functional evaluation of intestinal stem cell fate [Withers et al., 1970] and can potentially provide a mechanism for examining the early events of tumorigenesis. Because homeostatic mechanisms of stem cell proliferation are the same processes that become dysregulated in carcinogenesis [Sancho et al., 2003], a complete examination of these proliferation mechanisms holds medical significance in targeting future cancer treatments; therefore, a more detailed understanding of the pathways that regulate stem cell behavior is essential.

As we work toward a complete understanding of these pathways that regulate stem cell behavior, one major obstacle in the study of gastrointestinal stem cell biology has been the lack of definitive markers to identify gastrointestinal stem cells. The presently disclosed and claimed inventive concept(s) confirms that DCAMKL-1 a microtubule-associated kinase expressed in post-mitotic neurons [Lin et al., 2000] is an intestinal stem cell marker. This discovery allows one to assay resident intestinal stem cells and their response to genotoxic injury. DCAMKL-1 was identified as a Gene Ontogeny-enriched (or GO-enriched) transcript expressed in comparison with GEP (gastric epithelial progenitor) and whole stomach libraries [Giannakis et al., 2006]. Immunohistochemical analysis using antibodies directed at DCAMKL-1 revealed single cell staining in scattered intestinal crypt cross-sections at or near position 4 and in gastric isthmus cells in the putative stem cell location. The radiation-injury model was chosen to investigate its effects on stem cell fate for several reasons: (1) the kinetics of radiation injury has been extensively characterized in the small intestine in mice [Potten, 1990; Wright, 2000]; (2) radiation injury can be induced uniformly throughout the gut at discreet points in time; and (3) the extent of radiation injury on crypt clonogenic survival can be varied with the dose of radiation. In this Example, immunohistochemical analysis was employed in order to visualize crypt epithelial stem cells and to determine the cell specific DCAMKL-1 expression at baseline and in response to radiation injury in adult mice.

Materials and Methods for Example 1

Immunohistochemistry: (a) Brightfield: Heat Induced Epitope Retrieval (HIER) was performed on 4 mm paraffin-embedded mouse small intestine and colon sections utilizing a pressurized de-cloaking chamber (Biocare Medical, LLC) and incubated in citrate buffer (pH 6.0) at 99° C. for 18 min. The sections were then washed three times with PBS (Sigma), and endogenous biotin activity was blocked using Avidin/Biotin blocking kit (Vector Lab) and/or with DCAMKL-1 blocking peptide (ABGENT) wherever indicated according to manufacturer's instructions. Further, endogenous peroxidase activity was quenched with 3% hydrogen peroxide. After washing, the slides were then incubated in horse normal serum (2%) and BSA (1%) at room temperature for 20 min to block non-specific binding. The sections were then exposed to primary antibodies rabbit anti-DCAMKL-1 (ABGENT), rabbit anti-Musashi-1 (ABCAM), rabbit PCNA (proliferating cell nuclear antigen) (Santa Cruz), goat β-catenin (Santa Cruz), rabbit anti phospho H2AX (Cell Signaling) overnight at refrigerator temperature. Slides were then washed three times with PBS and incubated in the appropriate secondary antibody biotinylated donkey anti-rabbit, donkey anti-goat (Jackson Immuno Research Lab) 30 min at room temperature. Slides were washed again and then incubated in SA-HRP (Dako) at room temperature for 12 min. After final wash in PBS, chromogenic development was performed utilizing DAB (brown) and/or AEC (red) substrate (Sigma). All slides were counterstained with hematoxylin (Biocare Medical), dehydrated in graded alcohols, cleared in xylene, and permanently mounted with cryoseal (Richard-Allen).

(b) Fluorescence: HIER was performed on 4 mm paraffin-embedded tissue sections utilizing a pressurized de-cloaking chamber (Biocare Medical, LLC) and incubated in citrate buffer (pH 6.0) at 99° C. for 18 min. After washing three times with PBS, the slides were then incubated in horse normal serum (2%) and BSA (1%) at room temperature for 20 min to block nonspecific binding. Sections were then sequentially exposed to rabbit anti-DCAMKL-1 (ABGENT) for 1 hr at 30° C. and its appropriate secondary Cy3 conjugated donkey anti-rabbit (Jackson Immuno Research Lab) for 30 min at room temperature. Finally fluorescein conjugated TUNEL staining was performed using "In situ Cell Death Kit" (Roche diagnostics), according to manufactures instructions. The slides were then wet-mounted and counterstained utilizing Vectashield with DAPI (Vector). For co-staining of DCAMKL-1 with Musashi-1, the slides were incubated with normal goat serum after decloaking and exposed to rabbit anti-DCAMKL-1 (ABGENT) for 1 hr at 30° C. and its appropriate secondary goat anti-rabbit Alexa Fluoro 568 (Invitrogen) for 30 min at room temperature. Further, the slides were blocked with normal goat and normal donkey serum and exposed to rabbit anti-Musashi-1 (ABCAM) for 1 hr at 30° C. and its appropriate secondary donkey anti-rabbit Alexa Fluoro 488 (Invitrogen) for 30 min at room temperature. Then the slides are washed with Hoechst 33342 for staining of the nucleus.

(c) Microscopic Examination: Slides were examined using Nikon 80i microscope base. For brightfield, 60× digital images were taken with PlanAPO objective and DXM1200C camera (Nikon). Fluorescent images were taken with 60× PlanFluoro objective and 2× optical converter for a final magnification of 120×, utilizing CoolSnap ES2 camera (Photometrics). Filter sets were used employing excitation ranges for Cy3, FITC, and DAPI. All images were captured utilizing NIS-Elements software (Nikon) and further processed using Adobe Photoshop 8.0 software.

Results for Example 1

Localization of DCAMKL-1, a putative intestinal stem cell marker. In wild-type (WT) adult mouse intestine (FIG. 1A), it was confirmed that immunoreactive DCAMKL-1 is expressed primarily in single cells in the putative stem cell zone in adult conventionally housed C57 Bl/6 mice. In rare sections villus staining was observed, particularly at the crypt villus junction (data not shown). Distinct cytoplasmic staining was observed at baseline while DCAMKL-1 expression was a rare event. Staining was present in approximately one in six intestinal crypt cross-sections on average. Immunostaining of the proposed columnar longitudinal epithelial cell interspersed between paneth cells is also observed. These columnar longitudinal epithelial cells have been previously shown to the putative stem cell marker musashi-1 (MSI-1) [Kayahara et al., 2003; Potten et al., 2003]. Preincubation with DCAMKL-1 blocking peptide (Abcam) completely abolished DCAMKL-1 immunoreactivity (FIG. 1B).

Figure 2:
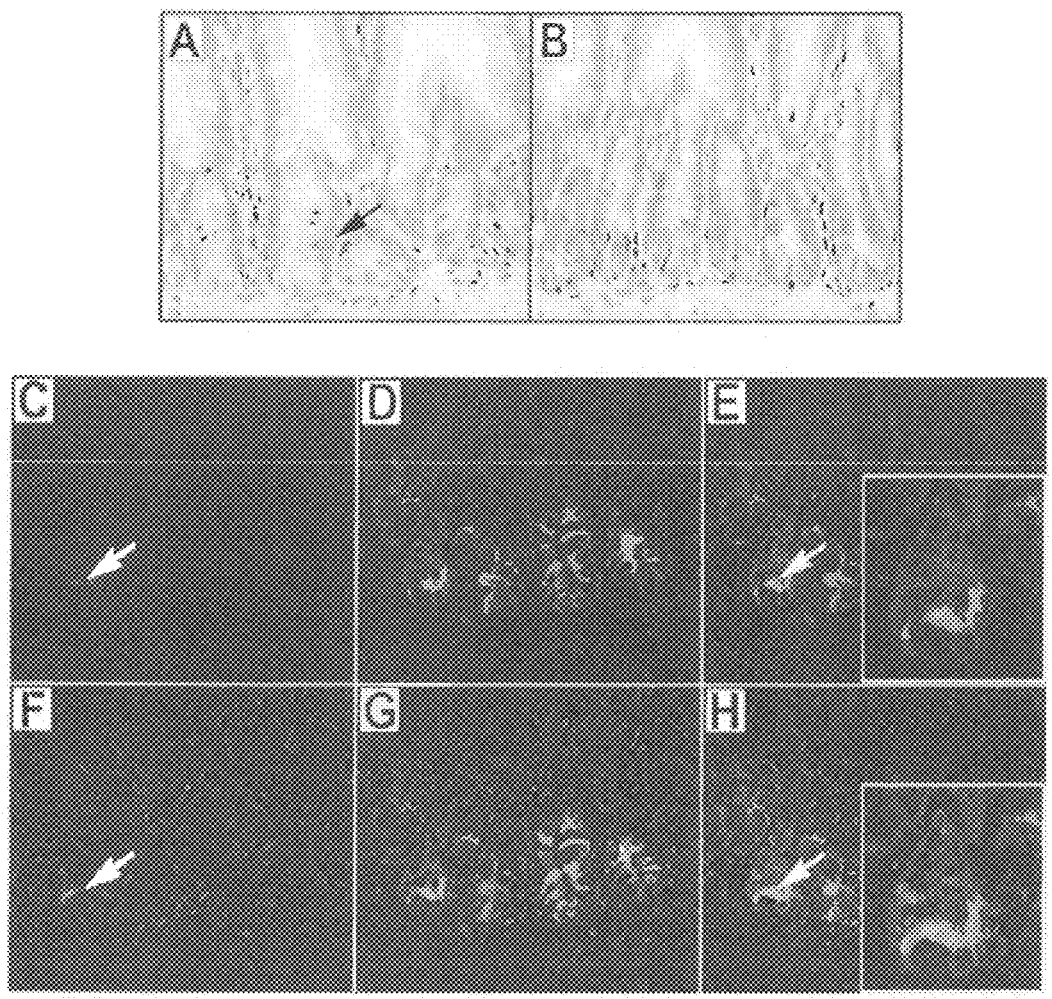

Colocalization of DCAMKL-1 and MSI-1. In order to determine whether DCAMKL-1 was expressed in the same cells that expressed the putative stem cell marker MSI-1, immunostaining for MSI-1 was performed using the intestines of adult WT uninjured mice. In FIG. 2A, distinct DCAMKL-1 staining was once again observed in the crypt. In FIG. 2B crypt epithelial staining for MSI-1 was observed in several cells at the base of the crypt including cell position 4 just above the paneth cell zone, consistent with its reported stem cell localization. Furthermore immunofluorescence microscopy and double immunostaining were used for DCAMKL-1 and MSI-1. Single cell staining for DCAMKL-1 was again observed in the stem cell zone (FIG. 2C). MSI-1 staining was also observed in the crypts (FIG. 2D). Distinct colocalization was observed however (FIG. 2H) with DCAMKL-1 and MSI-1 (orange). These data demonstrate that DCAMKL-1 is expressed in the same cell as MSI-1, but likely represents a subset of MSI-1 expressing cells. Nuclei stained with Hoechst 33342 (blue) is demonstrated in FIGS. 2F-G.

Figure 3:
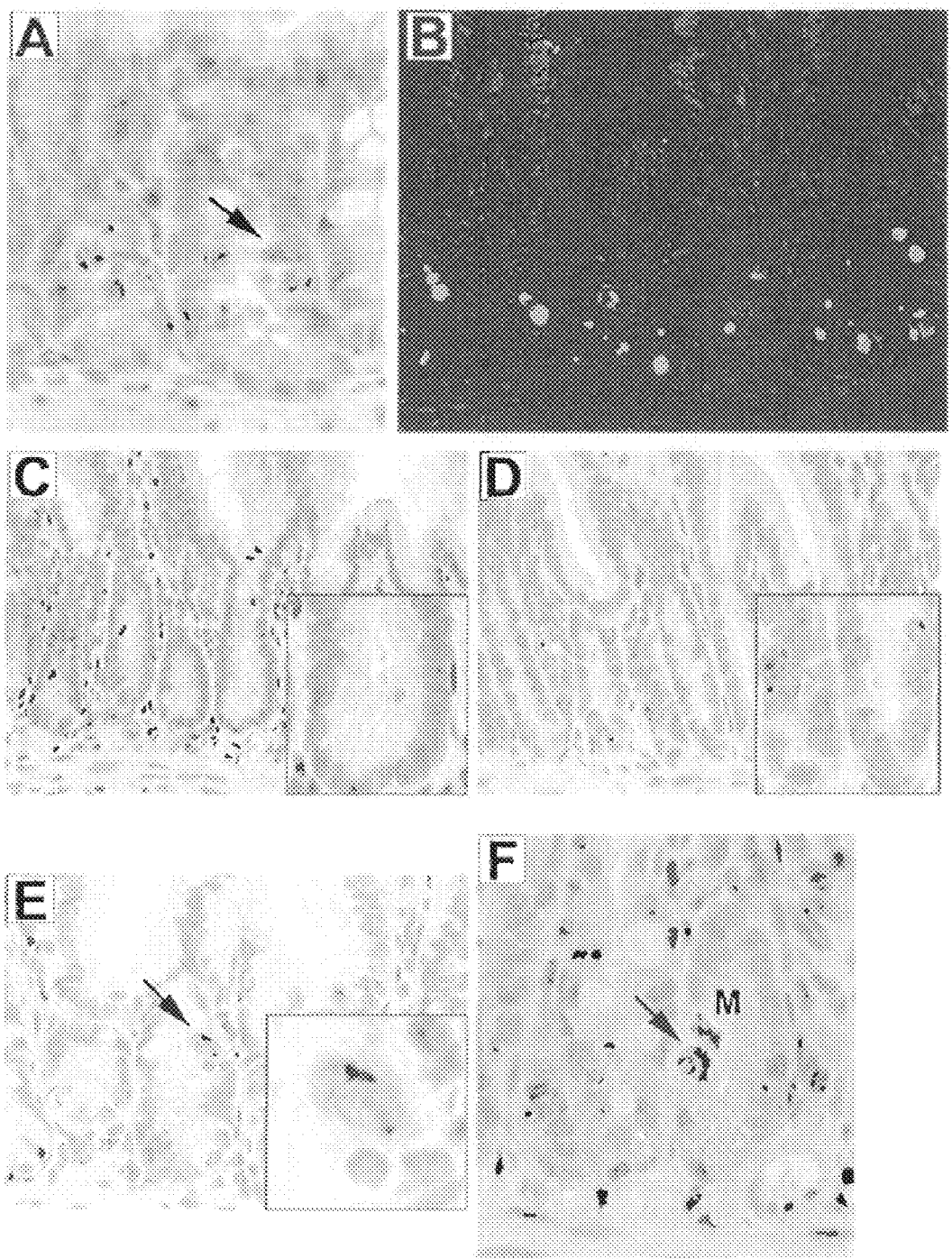

Fate of DCAMKL-1 positive cell in response to radiation injury. To investigate whether DCAMKl-1 expression was upregulated following ionizing radiation (IR), adult mice were treated with whole body 6 Gy IR, at doses sufficient to induce epithelial apoptosis in the stem cell zone [Houchen, et al, 2000; Merritt et al., 1994; Radtke et al., 2005]. Initially, the 6 hour after 6 Gy IR time point was chosen, as this is the time when maximal p53 dependent apoptosis is observed in the intestinal crypt [Merritt et al., 1994]. Here DCAMKL-1 staining similar to that observed at baseline was demonstrated (FIG. 3A). Following 6 Gy IR, morphologically appearing apoptotic cells were observed in the lower third of the intestinal crypt with a typical distribution following IR (FIG. 3A arrows). Surprisingly, apoptosis was not observed in DCAMKL-1 positive cells within the crypt in over 100 counted crypt cross-sections. In order to confirm this finding, a similar experiment was performed and stained for DCAMKL-1 and TUNEL (a marker for apoptosis). Apoptotic cells within the crypt were identified by TUNEL staining (green), and DCAMKL-1 staining (red) at single cell positions in the intestinal crypt was again observed (FIG. 3B). There was no evidence of apoptosis in DCAMKL-1 expressing cells. Furthermore, radiation-induced DNA damage was observed in the crypt at 6 hours following IR evidenced by the presence of phospho-H2AX positive cells (FIG. 3D, magnified in inset), which was not observed in unirradiated mice (FIG. 3C, magnified in the inset). The DCAMKL-1 positive cell was also positive for nuclear phospho-H2AX, but did not undergo apoptosis at that time (FIG. 3E, magnified in the inset). Indeed, this was not completely unexpected as earlier reports suggest that two important waves of apoptosis exist following IR. The first wave occurs at 4.5-6 hours (p53 dependent), and the second is near 24 hours (p53 independent). The second wave of apoptosis is thought to affect stem cells primarily [Merritt et al., 1994; Radtke et al., 2005]. In order to investigate this further, animals were examined 24 hours after IR, and immunohistochemical analysis for DCAMKL-1 was performed (FIG. 3F). In this figure morphological evidence of apoptosis and immunoreactive DCAMKL-1 staining in the stem cell zone are demonstrated; however, at this time point, there was clear evidence of apoptosis in the DCAMKL-1 positive cell (arrow). Additionally, the appearance of mitotic figures was noted, demonstrating the release of these cells from radiation-induced cell cycle arrest (FIG. 3F denoted as 'M'). The mitotic figures were often DCAMKL-1 immunoreactive, but this staining pattern was not observed in all of the mitotic figures present throughout the intestine. It should be noted that many of the cells with morphologic features consistent with mitosis were on occasion immediately adjacent to cells in the process of apoptosis, and these exhibited striking expression of DCAMKL-1. Consequently, these data suggest that by 24 hours after low dose IR (6 Gy), a few (one per cross section) stem cell/progenitor cells are removed by apoptosis and the potential descendants of these cells are able to divide and, at least transiently, express DCAMKL-1.

Figure 4:
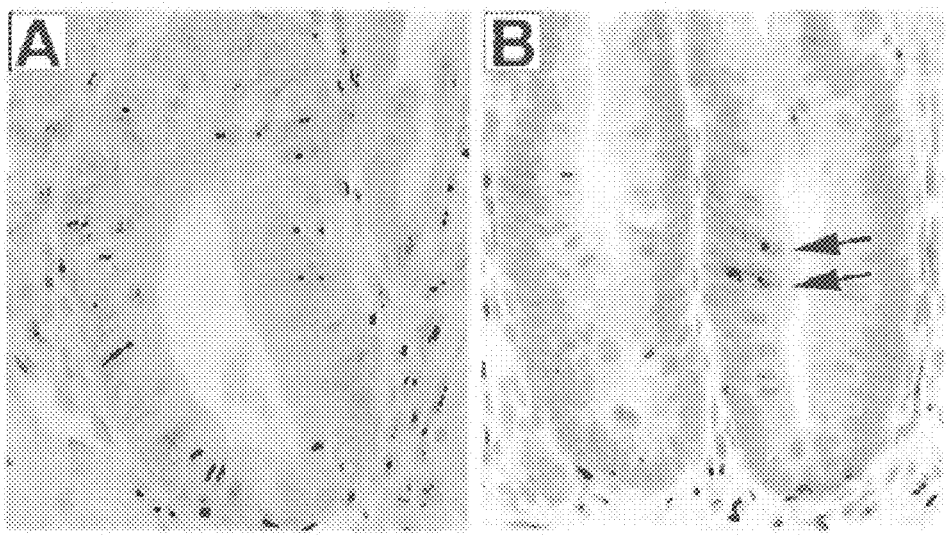

Expression pattern of DCAMKL-1 in regenerative crypts. To determine whether or not DCAMKL-1 is expressed in regenerative crypts following radiation injury, adult mice were exposed to lethal dose (12 Gy) γ-irradiation, and DCAMKL-1 expression was examined in regenerative crypt epithelial cells. 12 Gy was chosen as this dose has been demonstrated to induce crypt stem cell sterilization in a majority of intestinal crypts [Potten et al., 1994]. Regenerative crypts appear 3.5 days following radiation injury and represent the survival of at least one progenitor/stem cell per crypt. DCAMKL-1 staining was not observed in regenerative crypts following 12 Gy (FIG. 4A). These data demonstrate that DCAMKL-1 is not expressed at the protein level during the period of crypt regeneration when proliferation is at its peak. This data is consistent with the original report [Giannakis et al., 2006] and with our findings, failing to demonstrate DCAMKL-1 staining in BrdUrd positive cells (data not shown). On the other hand, it is unclear why this marker is not expressed as every cell in the regenerative crypt is not in a proliferative state. This may represent some form of loss of niche signaling in 3.5 day post-irradiated crypts lacking an intact crypt/villus axis or functional mesenchymal cells. Although it is interesting to speculate, more studies directed towards defining the regulatory mechanisms that control expression of DCAMKL-1 are required. Restoration of DCAMKL-1 expression however, within the crypts was observed 7 days post-irradiation when the morphologic features of the crypts/villus axis are returning to baseline (FIG. 4B), yet the crypts appear elongated with heaping up of nuclei. In several cross-sections DCAMKL-positive cells were not necessarily restricted to lower crypt region.

Figure 5:
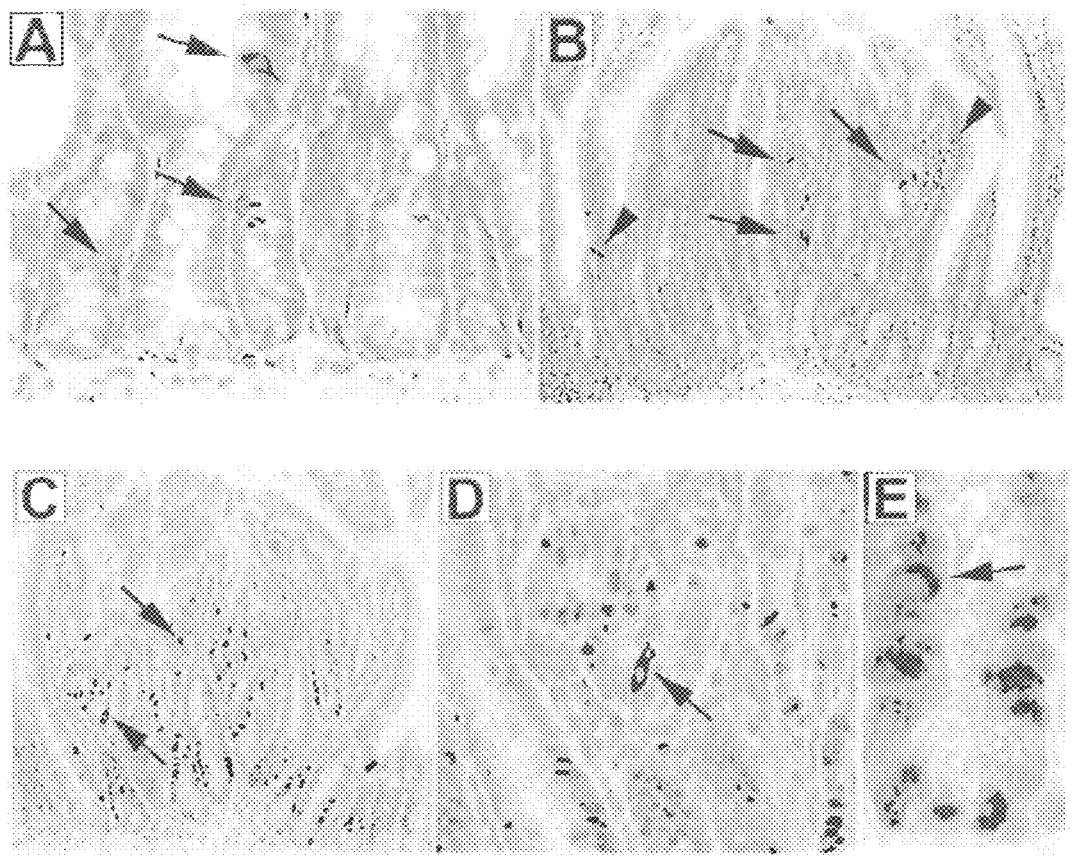

DCAMKL-1 as a putative adenoma stem cell marker. To determine whether DCAMKL-1 could be used to label putative stem cells within tumors, immunohistochemical analysis was employed to identify DCAMKL-1 in the intestines of APC/min mice. These mice have a germline mutation in the APC gene and develop numerous intestinal polyps [Clevers, 2004; Corpet et al., 2005]. APC mutations are one of the earliest genetic alterations in epithelial tumor progression [Clevers, 2006]. Indeed, greater than 60 percent of human colorectal adenomas exhibit a mutation in APC [Powell et al., 1992]. In WT mice classical single cell staining was observed in scattered crypt epithelial cells. However, in APC/min mice, a slightly different expression pattern was observed compared to WT. Although occasional single cell staining in the crypts was observed as before, there was a trend towards increased DCAMKL-1 expression on the villi (FIGS. 5A and 5B) compared to WT mice. This was often particularly evident in villus epithelial tissues adjacent to or surrounding adenomas (FIG. 5B). Note the distinct cytoplasmic staining pattern in the villus epithelium (FIG. 5A arrow head). It is unclear whether this is a function of villus expression of stem cells or a loss of crypt niche restriction in DCAMKL-1 expressing cells. It should be noted that villus epithelial DCAMKL-1 expression was occasionally observed in WT mice as well. Further studies following isolation of these cells are required to fully determine the functional significance of these villus DCAMKL-1 staining cells.

DCAMKL-1 positive cells in adenomas are quiescent. The potential stem cell origin of neoplastic tissues has become increasingly recognized [deLau et al., 2007; Radtke et al., 2005]. Accordingly, changes in the regulation of stem cells could potentially alter the risk of tumorigenesis. Immunohistochemical analysis was used to assess DCAMKL-1 expression patterns in APC/min adenomas. Distinct staining was observed (FIG. 5B), in a minority of cells within the adenoma. Given the limited expression pattern of DCAMKL-1 in adenomas, the inventors wanted to determine whether DCAMKL-1 was expressed in proliferative cells within adenomas. Double staining protocols for both DCAMKL-1 and PCNA (proliferating cell nuclear antigen) were employed in APC/min mice. As expected the majority of the adenomas expressed the proliferation marker PCNA. Indeed, there were very few cells within the adenoma that did not express PCNA. As PCNA staining is primarily nuclear, it was predicted that the cytoplasmic DCAMKL-1 would be identified in proliferating cells if co-staining was present. DCAMKL-1 was expressed in cells within the adenoma that were not proliferating and therefore quiescent (FIG. 5C, magnified in FIG. 5D). This was confirmed in normal crypt epithelial cells in which DCAMKL-1 positive cells were negative for PCNA (FIG. 5E). This is consistent with the original report in FVB/n mice where DCAMKL-1 cells were negative for BrdUrd [Giannakis et al., 2006]; however, this finding within adenomas has not been previously described.

Figure 6:
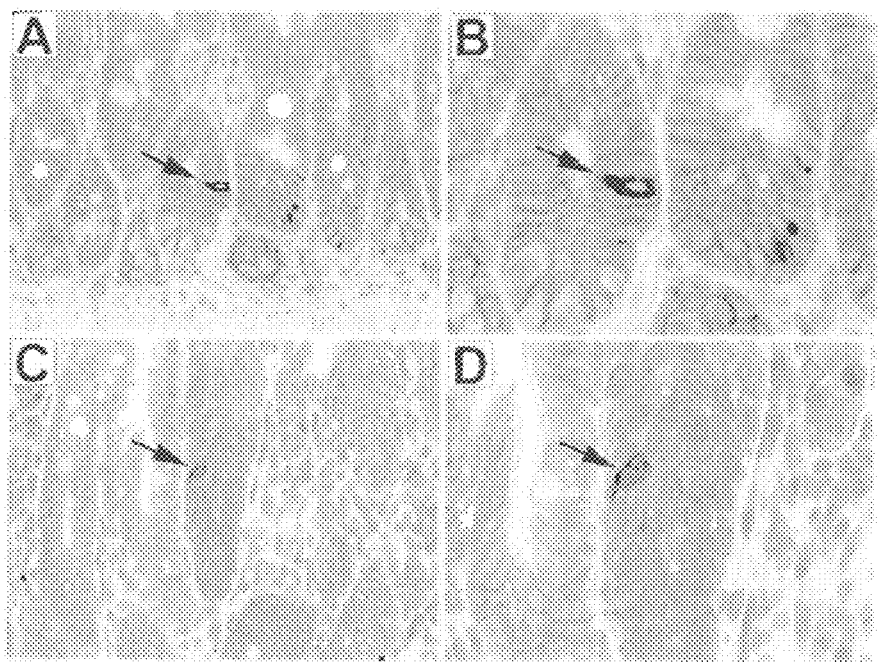

Co-expression of β-catenin and DCAMKL-1 in APC/min tumors. To determine whether nuclear localization of β-catenin could be observed in DCAMKL-1 expressing cells, the inventors sought to identify β-catenin in quiescent cells within adenomas. β-catenin translocation to the nucleus is one of the earliest steps in neoplastic transformation and is readily observed in adenomas of APC/min mice. In FIG. 6, β-catenin and DCAMKL-1 coimmunostaining is demonstrated in normal appearing intestinal crypts in APC/min mice and within a crypt adenoma. In normal appearing crypts, DCAMKL-1 immunoreactive cells exhibit typical membrane β-catenin staining, without any evidence of nuclear translocation (FIG. 6A, magnified in FIG. 6B); however, within the adenoma, nuclear β-catenin is readily identified in the DCAMKL-1 expressing cell (FIG. 6C arrow, magnified in FIG. 6D). These data taken together strongly suggest that the normal epithelial intestinal stem cell and the adenoma stem cell can be distinguished based on nuclear β-catenin and DCAMKL-1 immunostaining. Furthermore, the adenoma stem cell can be distinguished from the proliferative adenoma cells based on PCNA and DCAMKL-1 immunostaining.

Figure 7:
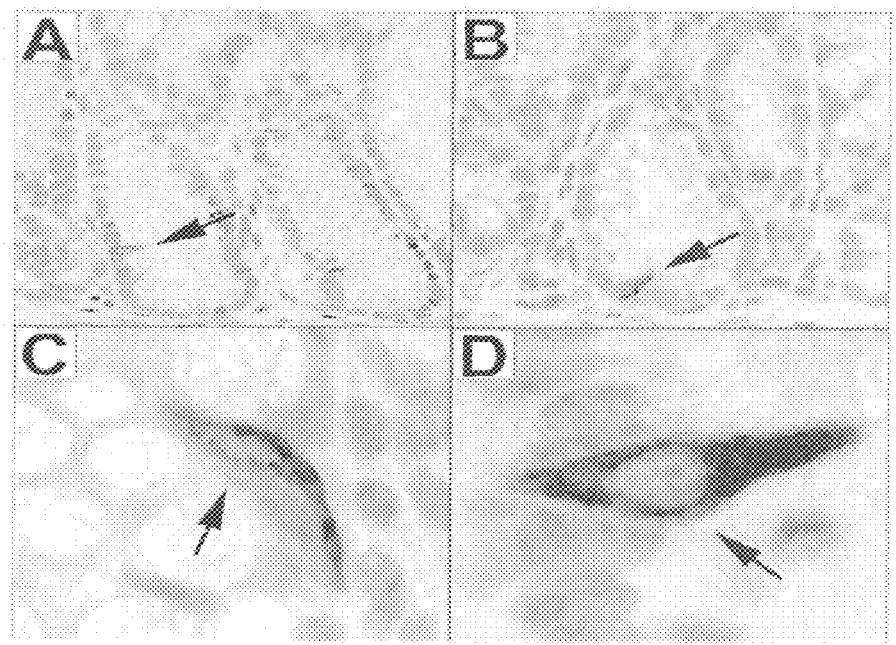

Morphology of DCAMKL-1 expressing cells. Upon closer observation the unique morphologic appearance of the DCAMKL-1 expressing cell resembles that of neural processes observed on gastric D cells [Radford et al., 2006] (FIGS. 7A-D). In FIG. 7A, DCAMKL-1 expression was observed in cells in the mid crypt in the proximal colon. In FIG. 7B, an expression was observed at the crypt base in the distal colon. Additionally, higher power views in both colon (FIG. 7C) and distal jejunum (FIG. 7D) clearly illustrate the unique morphologic staining pattern resembling axonal like processes.

Discussion of Example 1

Figure 1:
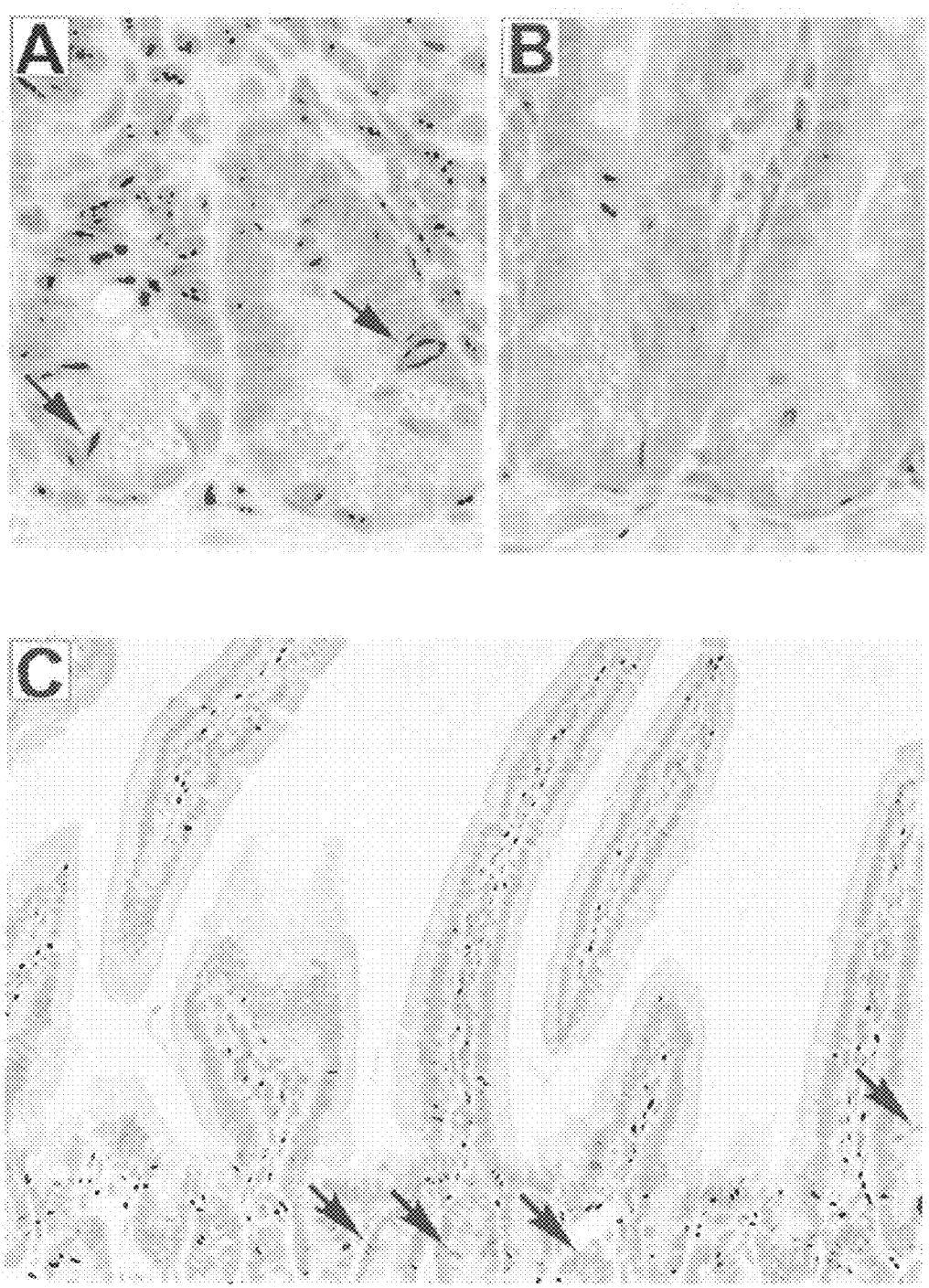

Typically, one crypt with definitive DCAMKL-1 staining was observed per 6 crypts in a typical intestinal cross-section near cell position of 4 in the crypt. Presumably, this is due to the 3-dimensional nature of the crypt and the low probability that every cross-section will contain a stem cell. Nevertheless, DCAMKL-1 immunoreactivity was consistently observed in the stem cell zone as previously noted (FIG. 1). The response to acute radiation injury is the most extensively characterized model system for studying injury repair in the rodent gastrointestinal tract. The actively proliferating cell population in the intestinal crypt rapidly undergoes apoptotic cell death following sublethal doses of IR, (<8Gy) [Ishizuka et al., 2003]. Because epithelial cells at the lower one third of the small intestinal crypts are the first to undergo apoptosis following low-dose IR (1 Gy), it is postulated that these "true" or "ultimate" stem cells prefer to undergo apoptosis rather than repair even comparatively minor damage to their DNA [Potten et al., 2002]. This trait may serve to reduce the risk of propagating a mutated clone within the crypt. If all the so-called "ultimate stem cells" [Potten et al., 2002] are destroyed, then their more radio-resistant daughter cells will assume stem cell functions and maintain the crypt; however, the molecular mechanisms that regulate this transfer of clonogenic capacity are poorly understood. In this Example, it has been demonstrated that cells positive for DCAMKL-1 underwent DNA damage along with other cells in the crypt, but did not undergo apoptosis. Whereas 24 hours following IR, the putative stem cell or cells positive for DCAMKL-1 did undergo apoptosis. Following 12 Gy IR, the DCAMKL-1 reactivity is lost in the regenerative crypts 3.5 days following IR. DCAMKL-1 expression was restored at day 7 post-irradiation when the morphologic features of the crypts/villus axis are returning to baseline. These data support the hypothesis that daughter cells are capable of taking on stem cell characteristics in response to radiation-induced deletion of the "ultimate stem cell" and also illustrates that this process occurs at some time beyond 6 hours and prior to 24 hours after low dose radiation injury. These data may potentially explain why doses of IR<8 Gy do not result in crypt sterilization of stem cells and, as a result, have little effect on clonogenic survival [Houchen et al., 2000].

This Example reports the identification of a novel intestinal stem cell marker that can be employed to test the effects of DNA damaging agents, chemotherapeutic agents and radiation injury on stem cell deletion both directly and in real time. The data presented here also support assessment of radiation-induced apoptosis of intestinal stem cells 24 hours after IR as opposed to 6 hours in intestinal cross sections. The demonstration of a more variable expression pattern of DCAMKL-1 in the normal epithelium of APC/min mice compared to WT mice suggests that APC/min mice may exhibit different mechanisms of stem cell niche regulation, particularly in the regions adjacent to adenoma. The small percentage of quiescent DCAMKL-1 expressing cells within a particular adenoma suggests that they may be the origin of the more proliferative neoplastic cells, but it remains unclear whether these cells by themselves have tumorigenic potential either outside of the adenoma or outside of the crypt niche (villi). In the normal appearing crypts of APC/min mice, β-catenin was co-expressed in the cytoplasm along with DCAMKL-1, whereas in adenomas, DCAMKL-1 positive cells demonstrated nuclear localization of β-catenin. This finding illustrates a fundamental difference between the normal and adenoma stem cell.

EXAMPLE 2

Pancreatic adenocarcinoma has the worst prognosis of any major malignancy with a 3% 5-year survival [Hoyer et al., 2006]. Major obstacles in treating pancreatic cancer include extensive local tumor invasion and early metastasis. There is increasing evidence that a small subset of cells termed "cancer stem cells" (CSCs) are capable of initiating and sustaining tumor growth in transplantation assays [Diehn et al., 2006]. CSCs share unique properties with normal adult stem cells, including the ability to self-renew and differentiate. CSCs are often refractory to current standard chemotherapeutic agents and radiation therapies, as they are designed to eradicate actively cycling cells, not slowly cycling cancer stem cells. Thus, novel therapies that specifically target the cancer stem cell population, either alone or in conjunction with current strategies may be more effective in obliterating solid tumors.

The existence of CSCs was first demonstrated in acute myelogenous leukemia [Bonnet et al., 1997] and subsequently verified in breast [Al-Hajj et al., 2003], pancreatic [Li et al., 2007] and brain tumors [Singh et al., 2004; Singh et al., 2003; Singh et al., 2004A]. The $CD133^+$ subpopulations from brain tumors could initiate clonally derived neurospheres in vitro showing self-renewal, differentiation, and proliferative characteristics similar to normal brain stem cells [Singh et al., 2004; Singh et al., 2003; Singh et al., 2004A]. Furthermore, transplantation of $CD133^+$ but not $CD133^-$ cells into NOD/SCID mice was sufficient to induce tumor growth in vivo. In a recent study, primary human pancreatic adenocarcinomas were implanted in immunocompromised mice to assess the ability of specific cell surface markers to identify a subpopulation of pancreatic cancer cells with enhanced tumorigenic potential. A subpopulation of $CD44^+CD24^+ESA^+$ cells was identified as putative pancreatic cancer stem cells [Li et al., 2007].

Tumor cell heterogeneity present in most solid tumors creates an enormous challenge for cancer eradication. Current strategies for inducing cell death generally target only the most rapidly proliferating cells within a tumor. Indeed radiation therapy specifically targets proliferating cells which are more sensitive to ionizing radiation [Houchen et al., 2000A; Riehl et al., 2000; Tessner et al., 1998; Cohn et al., 1997]; however, it is clear that effective tumor-eradication strategies must address the potential survival mechanisms unique to each particular cell type within the malignant population (i.e., quiescent stem cells) [Li et al., 2007]. This may explain why standard chemo/radio therapy is effective in causing tumor shrinkage but often fails to prevent tumor recurrence, due to the surviving cancer stem cell's ability to regenerate the tumor even after chemotherapeutic insult.

Characterization of stem cells from the hematopoietic system, neural stem cells from the central nervous system and neural crest stem cells have emphasized the importance of specific cell surface antigens that permit the isolation of stem cells by FACS [Tamaki et al., 2002; Niemeyer et al., 2001]. A candidate pancreatic stem cell, characterized by its expression of the neural stem cell marker nestin and lack of established islet and ductal cell markers, has been described [Abraham et al., 2004; Lechner et al., 2002; Zulewski et al., 2001]. Furthermore, the basic helix-loop-helix transcription factor neurogenin 3 (NGN3) controls endocrine cell fate specification in uncommitted pancreatic progenitor cells. In the pancreas, NGN3$^+$ cells co-express neither insulin nor glucagon, suggesting that NGN3 marks early precursors of pancreatic endocrine cells. Moreover, NGN3-deficient mice do not develop islet cells and are diabetic. These data taken together suggest that NGN3 and nestin are critical components of the pancreatic stem/progenitor cell compartment. A convincing recent study demonstrated that the adult mouse pancreas contains islet cell progenitors and that expansion of the β cell mass following pancreatic duct ligation resulted in ductal NGN3 gene expression and the ensuing differentiation of endogenous progenitor cells [Xu et al., 2008]. These data suggest that functional islet progenitor cells can be induced in pancreatic ducts following injury.

Example 1 demonstrates that DCAMKL-1, a microtubule-associated kinase expressed in postmitotic neurons, is an intestinal stem cell marker [May et al., 2008]. In this Example, it is demonstrated that DCAMKL-1 is also expressed in pancreatic islet epithelial cells with a distribution similar to the putative pancreatic stem cell markers NGN3 and nestin. Furthermore, DCAMKL-1 is expressed in the main pancreatic ductal epithelial cells in rodents, and a subset of cells in human pancreatic tumors. Immunoreactive 14-3-3 σ, which is increased in pancreatic cancer [Guweidhi et al., 2004], has been found in the cytoplasm and rarely in the nucleus of tumor epithelial cells in human pancreatic cancer patients. Moreover, co-expression of DCAMKL-1 and 14-3-3 σ was also observed in tumors. Additionally DCAMKL-1 staining was observed in the surface epithelium of pancreatic intraepithelial neoplasia (PanIN) type lesions (a marker of pancreatic adenocarcinoma) and the intervening stroma in human pancreatic adenocarcinoma, which co-localized with the mesenchymal marker vimentin. In the Pdx48$^{Cre}$-activated KRAS$^{G12D}$ [Hingorani et al., 2003; Jackson et al., 2001] pancreatic cancer mouse model there was a marked increase in ductal expression and a unique expansion of islet DCAMKL-1 that correlated with progressive neoplastic changes. These data taken together, demonstrate that DCAMKL-1 is a novel pancreatic stem cell marker expressed in the pancreatic duct and in islets as well as a marker of pancreatic cancer stem cells. Furthermore, this Example demonstrates the isolation of DCAMKL-1 expressing cells by FACS, which formed spheroid-like structures in suspension culture. When injected subcutaneously into flanks of nude mice, nodules formed and contained cells expressing markers of early pancreatic development (PDX-1), glandular epithelium (cytokeratin 14), and islets (somatostatin and secretin). These data taken together identify DCAMKL-1 as a novel pancreatic ductal and islet stem/progenitor cell marker that can be employed as a target for pancreatic cancer tumor eradication. DCAMKL-1 also represents a novel marker for studying the mechanisms that regulate pancreatic and/or islet regeneration.

Materials and Methods for Example 2

Experimental animals. 6-8 weeks old C57BL/6, athymic nude mice (NCr-nu) (NCI-Frederick) and Pdx48$^{Cre}$-activated KRASG12D (obtained from Dr. Rao) were used for the experiments. Mice were housed under controlled conditions, including a 12 h light/dark cycle, with ad libitum access to diet and water. All animal experiments were performed in accordance with the University's Institutional Review Board.

Tissue procurement. The human pancreatic adenocarcinoma tissue samples were derived from patients undergoing a surgical resection of the pancreas at the University of Oklahoma Health Sciences Center. The collection of samples conformed to the policies and practices of the University's Institutional Review Board (protocol number 04586).

Immunohistochemistry. Heat Induced Epitope Retrieval was performed on formalin-fixed paraffin-embedded sections utilizing a pressurized Decloaking Chamber (Biocare Medical) in citrate buffer (pH 6.0) at 99° C. for 18 min. (a) Brightfield: Slides were incubated in 3% hydrogen peroxide, then normal serum and BSA at room temperature for 20 min. After incubation with primary antibody [DCAMKL-1, insulin, glucagon, somatostatin, PDX-1 (ABCAM), 14-3-3 σ (IBL), NGN3, nestin, vimentin, cytokeratin-14 and secretin (Santa Cruz)] the slides were incubated in polymer-HRP secondary (DAKO). Slides were developed with Diaminobenzidine (Sigma). Tyramine signal amplification for NGN3 in adult mouse tissues was performed as per manufacturer's instructions (Invitrogen) (b) Fluorescence: Slides were incubated in normal serum and BSA at room temperature for 20 min. After incubation with primary antibody, slides were incubated in appropriate Alexa Fluor® conjugated secondary [488 (green) and 568 (red)].

Microscopic examination. Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon).

Real-time reverse transcription-PCR analyses. Total RNA isolated from FACS sorted pancreatic cells was subjected to reverse transcription with Superscript II RNase H-reverse transcriptase and random hexanucleotide primers (Invitrogen). The cDNA was subsequently used to perform real-time PCR by SYBR chemistry (SYBR Green I; Molecular Probes) for specific transcripts using gene specific primers and Jumpstart Taq DNA polymerase (Sigma-Aldrich, St. Louis, Mo.). The crossing threshold value assessed by real-time PCR was noted for the transcripts and normalized with β-actin mRNA. The changes in mRNA were expressed as fold change relative to control with ±SE value.

Primers used are as follows. β-actin: forward 5'-GGTGATCCACATCTGCTGGAA-3' (SEQ ID NO:16), reverse 5'-ATCATTGCTCCTCCTCAGGG-3' (SEQ ID NO:17); DCAMKL-1: forward 5'-CAGCCTGGACGAGCTGGTGG-3' (SEQ ID NO:18), reverse 5'-TGACCAGTTGGGGTTCACAT-3' (SEQ ID NO:19); NGN3: forward 5'-CGCACCATGGCGCCTCATCCCTTGG-3' (SEQ ID NO:20), reverse 5'-CAGAGGATCCTCTTCACAAGAAGTCT-3' (SEQ ID NO:21); nestin: forward 5'-CACCTCAAGATGTCCCT-3' (SEQ ID NO:22), reverse 5'-GCAGCTTCAGCTTGGGGTC-3' (SEQ ID NO:23); somatostatin: forward 5'-GGACCCCAGACTCCGTCAGT-3' (SEQ ID NO:24), reverse 5'-GGGCTCGGACAGCAGCTCTG-3' (SEQ ID NO:25); insulin: forward 5'-CCCAGCCCTTAGTGACCAGC-3' (SEQ ID NO:26), reverse 5'-TTTATTCATTGCAGAGGGT-3' (SEQ ID NO:27); glucagon: forward 5'-GGCTGGATTGCTTATAATGC-3' (SEQ ID NO:28), reverse 5'-ATCTCATCAGGGTCCTCATG-3' (SEQ ID NO:29); CD133: forward 5'-GGCTATGACAAGGATGCC-3' (SEQ ID NO:30), reverse 5'-GATCATCAATATCCAGCA-3' (SEQ ID NO:31).

Stem cell isolation from mouse pancreas. DCAMKL-1+ stem cells were isolated and propagated from mouse pancreas according to the procedures developed in neural [Singh et al., 2004; Singh et al., 2003; Singh et al., 2004A] and breast stem cell biology [Dontu et al., 2003]. The pancreas and associated duct were rapidly dissected and perfused with 3 ml of cold HBSS containing 1 mg/ml collagenase and 1 mg/ml BSA (Cellgro). The pancreatic tissues were minced and incubated in HBSS for 13 min at 37° C. Digestion was stopped with cold HBSS (Cellgro) containing 10% serum. The solution was shaken by hand for 1 min, washed 3 times with serum free HBSS and filtered through 400 mM mesh (Spectrum). The cells obtained were incubated with trypsin (Cellgro) at 37° C., pipetted to create a single cell suspension and subjected to FACS based on cell surface expression of DCAMKL-1.

FACS sorting. The single cell suspension was incubated with 1:100 dilution of Alexa Fluor® 568 conjugated DCAMKL-1 antibody targeting the C-terminal extracellular domain for 25 min and washed twice with HBSS containing 10% serum. The cells were sorted using Influx-V cell sorter (Cytopeia) and collected cells were grown in tissue culture media: DMEM (Cellgro) containing EGF (25 ng/ml), bFGF (20 ng/ml) and Insulin (5 ng/ml) (Sigma) without serum on non-treated or ultra-low adherent plates (BD Biosciences) in a suspension culture.

Isotransplantation assay. Collected cells expressing DCAMKL-1 were allowed to form spheroids in suspension culture for 21 days. Spheroids were disassociated, suspended in Matrigel™ and injected subcutaneously into the flanks of athymic nude mice (NCr-nu) (NCI-Frederick) housed in specific pathogen-free conditions. Animals were sacrificed, nodules excised, fixed in 10% buffered formalin and subjected to immunohistochemical analysis.

Results of Example 2

Figure 8:
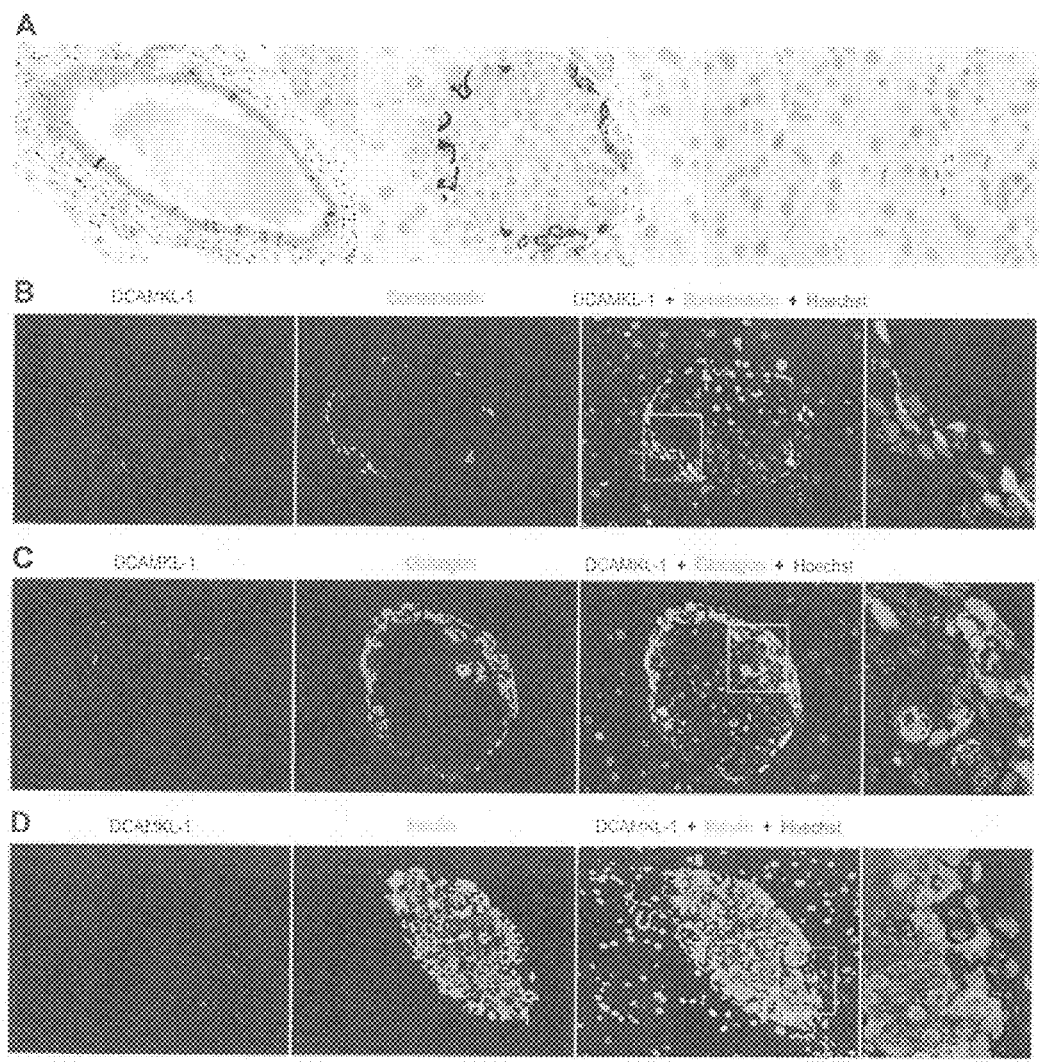

Pancreatic DCAMKL-1 expression. DCAMKL-1 is expressed in the main pancreatic duct (FIG. 8A, left) and on the periphery of pancreatic islets (FIG. 8A, middle). There was no detectable DCAMKL-1 expression within acinar cells in uninjured mice (FIG. 8A, right). In order to determine the specific islet cell sub-type, co-expression of the endocrine markers somatostatin (d-cell), glucagon (a-cell) and insulin (b-cell) was evaluated. It was found that both DCAMKL-1 (FIG. 8B, left) and somatostatin (FIG. 8B, middle) were expressed in the islet periphery. Merged images revealed co-staining of DCAMKL-1 with somatostatin (FIG. 8B, third and fourth from left). Glucagon was also found in the periphery of the islet (FIG. 8C, second from left) but did not co-localize with DCAMKL-1 (FIG. 8C, third and fourth from left). Insulin expressing cells were observed throughout the islet (FIG. 8D, second from left), but no co-immunostaining with DCAMKL-1 was observed (FIG. 8D, third and fourth from left). Thus DCAMKL-1 expressing cells do not express the two major endocrine cell markers (insulin and glucagon) but do co-localize with somatostatin expressing cells.

Figure 9:
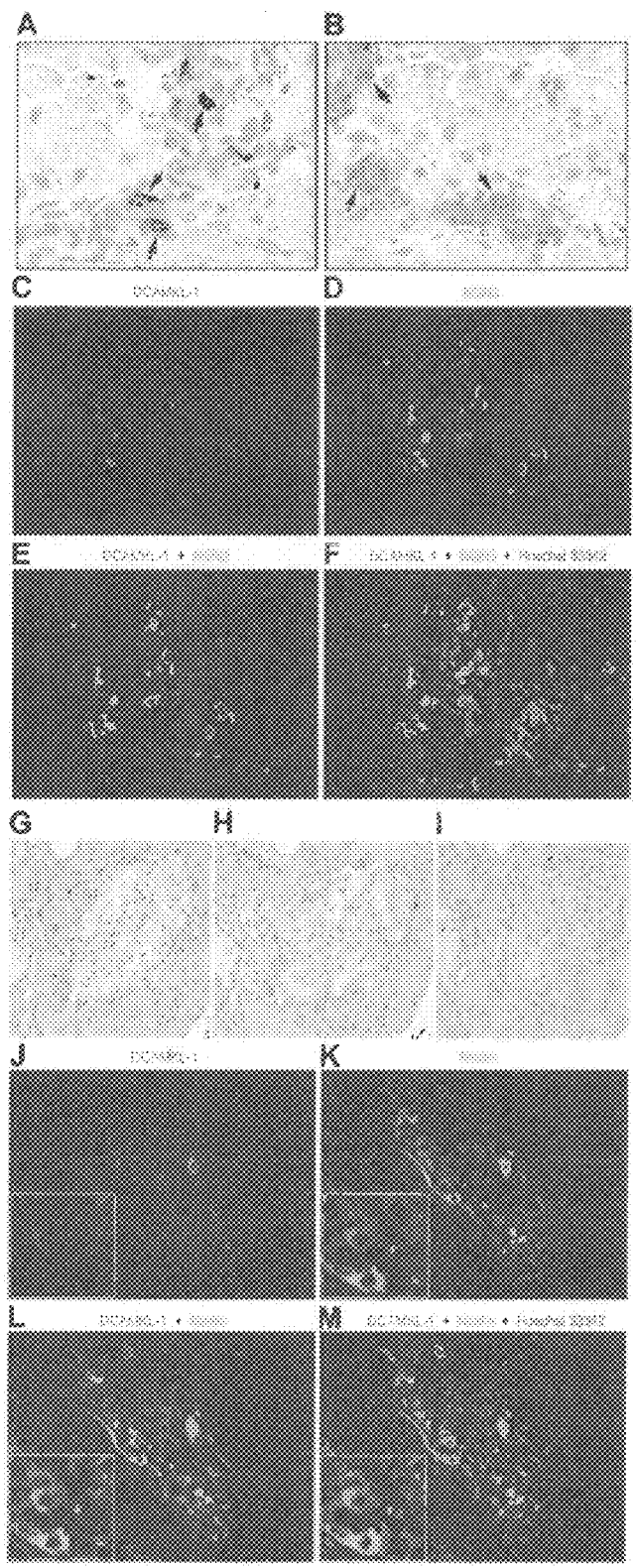

Pancreatic stem/progenitor cell markers. The basic helix-loop-helix transcription factor NGN3 controls endocrine cell fate specification. All the major islet cell types, including insulin-producing O-cells, are derived from NGN3-positive endocrine progenitor cells [Johansson et al., 2007]. It is well known that NGN3 protein expression diminishes as mice reach adulthood [Schwitzgebel et al., 2000; Jensen et al., 2000]. Immunohistochemical analysis was employed in order to determine the cell specific expression patterns of DCAMKL-1 in newborn mice, and with reference to NGN3 expression [Gu et al., 2002]. Distinct expression of DCAMKL-1 (FIG. 9A) and NGN3 (FIG. 9B) was observed in early islet formations. Immunofluorescence staining confirmed the presence of DCAMKL-1 (FIG. 9C) and NGN3 (FIG. 9D) with merged images revealing distinct co-localization within these developing tissues (FIGS. 9E and 9F).

To confirm these findings in adult uninjured mice, immunohistochemical staining was employed on serial tissue sections. Common immunolocalized staining was observed for DCAMKL-1 (FIG. 9G), NGN3 (FIG. 9H) and the pancreatic stem cell marker candidate nestin (FIG. 9I) in all three sections. Furthermore, immunofluorescence staining of newborn mouse pancreas demonstrated the presence of DCAMKL-1 (FIG. 9J) and nestin (FIG. 9K), with merged images revealing colocalization within a few cells (FIGS. 9L and 9M). These data demonstrate that DCAMKL-1 marks pancreatic islet stem/progenitor cells, based on positional evidence, and co-expression with established markers of pancreatic stem/progenitor cells.

Figure 10:
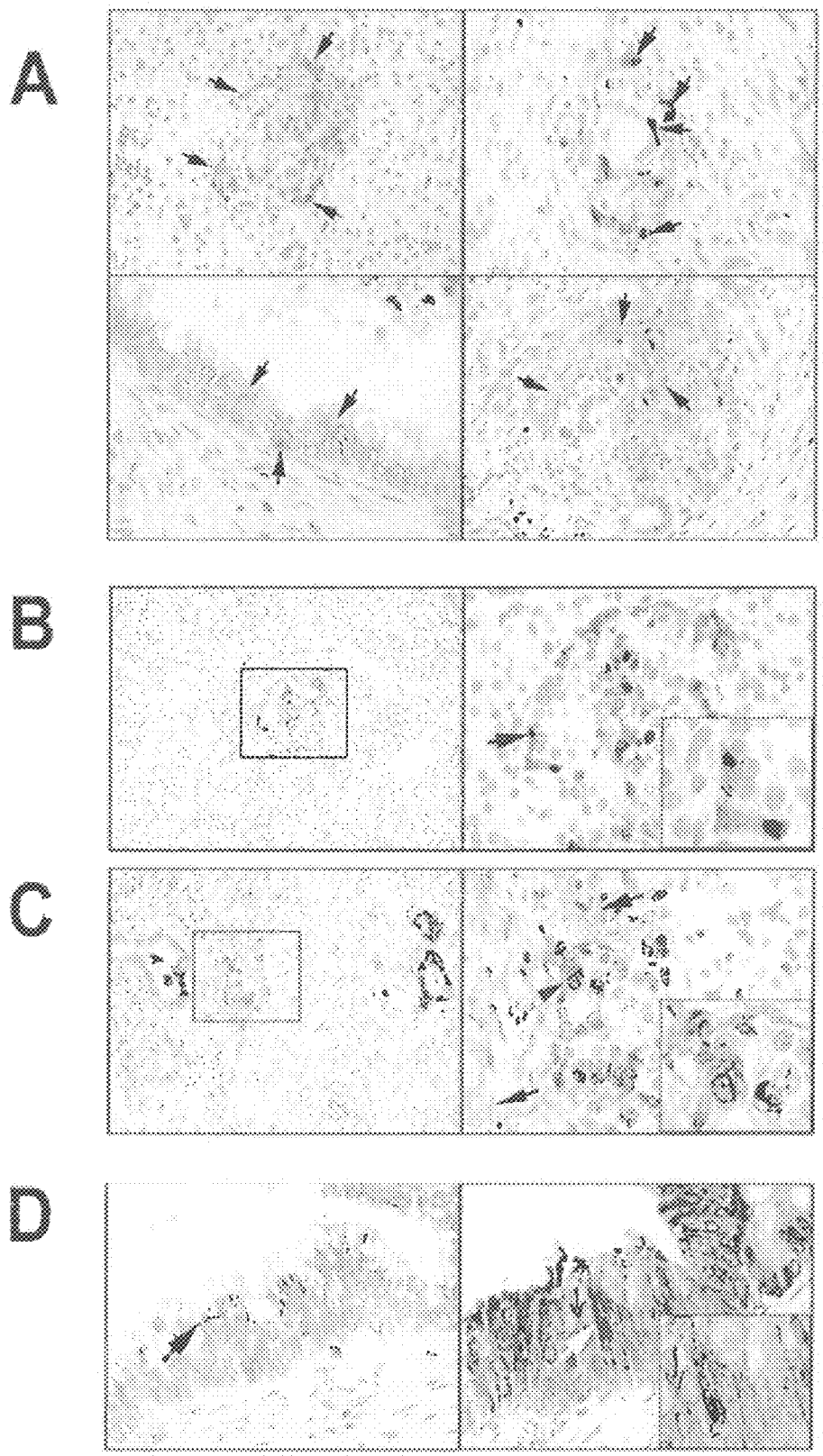

DCAMKL-1 expression in human pancreatic cancer. Next, DCAMKL-1 expression in human pancreatic adenocarcinoma was examined. Samples were obtained from patients undergoing surgical resection of pancreatic cancer provided by Dr. Russell Postier. Tumors demonstrated strong DCAMKL-1 expression. However within the histologically normal appearing resection specimen, DCAMKL-1 was observed within islets but not in the intervening stromal cells or ducts (FIG. 10A top left). Within a neoplastic focus of the tumor resection specimen however, intense spindle-shaped cytoplasmic staining of DCAMKL-1 is evident (FIG. 10A top right). DCAMKL-1 expression in ductal epithelial cells within the tumor (FIG. 10A bottom left) and in intervening stromal elements is also observed (FIG. 10A bottom right).

14-3-3 σ expression in pancreatic cancer. Previously, using DNA array technology, several groups have demonstrated increased 14-3-3 σ mRNA expression in pancreatic ductal adenocarcinoma compared to normal pancreas [Guweidhi et al., 2004]. Similarly, 14-3-3 σ protein nuclear localization has been described in pancreatic cancer [Logsdon et al., 2003]. In normal appearing pancreatic tissue of patients undergoing surgical resection, cytoplasmic staining was observed for 14-3-3 σ and DCAMKL-1 at the islet periphery, albeit in distinctly separate cells. No ducts expressing 14-3-3 σ were observed in that particular specimen (FIG. 10B left and right). Next, immunostaining was performed on a primary tumor specimen obtained from another patient with pancreatic ductal adenocarcinoma. While strong cytoplasmic expression of 14-3-3 σ (a marker of advanced PanIN lesions) was found in ductal epithelial cells, cells with nuclear localized 14-3-3 σ expression were also observed within tumor islet formations. Moreover, some of these nuclear 14-3-3 σ expressing cells also co-expressed DCAMKL-1 (FIG. 10C left and right) suggesting that nuclear translocation of 14-3-3 σ occurs in putative pancreatic cancer stem cells. Expression of DCAMKL-1 was also found in PanIN type lesions (FIG. 10D left). Additionally strong cytoplasmic 14-3-3 σ and DCAMKL-1 co-staining was observed within the lesions (FIG. 10D right). These data strongly support a role for 14-3-3 σ and DCAMKL-1 in the progression of pancreatic cancer and as a putative marker of pancreatic CSCs.

Figure 11:
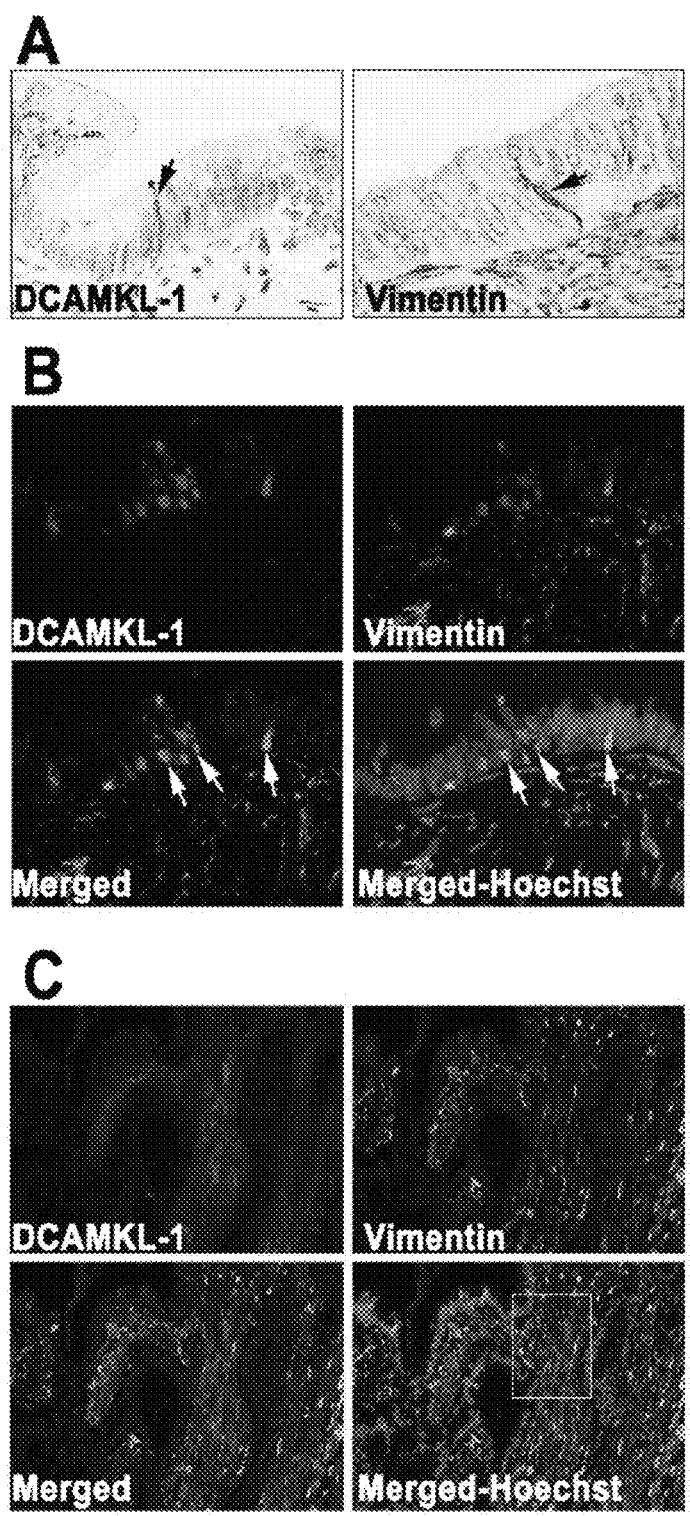
Figure 12:
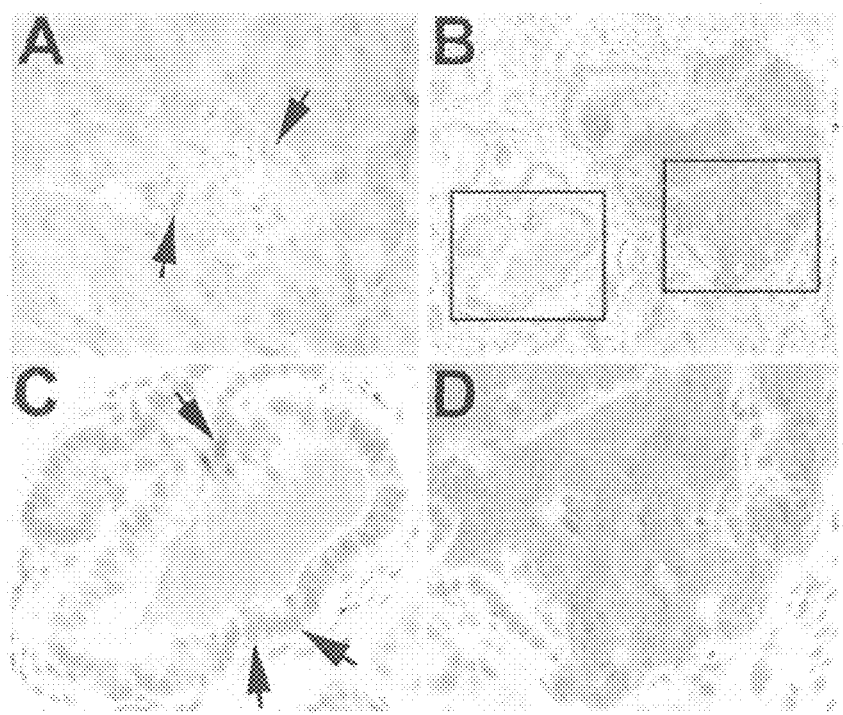

DCAMKL-1 expression in the stroma of human pancreatic adenocarcinoma tissue. Initially, DCAMKL-1+ staining was observed in elongated cells in the surface epithelium of PanIN lesions (FIG. 11A left). Further characterization of these cells by vimentin (a marker of mesenchymal lineage) immunostaining demonstrated cells that were morphologically similar to DCAMKL-1 expressing cells (FIG. 11A right). When double-labeled immunofluorescence was performed, coexpression of DCAMKL-1 and vimentin within the PanIN lesion was observed (FIG. 11B). Strong fibrillar DCAMKL-1 expression was also seen in the stromal/mesenchymal compartment of human pancreatic adenocarcinoma tissue and confirmed by vimentin co-immunostaining (FIG. 11C). These data taken together demonstrate a potential role of DCAMKL-1 in epithelial mesenchymal transition (EMT) [Turley et al., 2008].

Mouse pancreatic cancer model. The Pdx48$^{Cre}$-activated KRAS$^{G12D}$ is a well established mouse model of pancreatic cancer [Hingorani et al., 2003; Jackson et al., 2001]. These mice develop PanIN lesions (similar to humans) and pancreatic cancer after 10 weeks. Furthermore, these mice develop cancer metastasis by 32 weeks [Jackson et al., 2001; Hingorani et al., 2003]. Pancreatic tissues from 5-month-old Pdx48$^{Cre}$-activated KRAS$^{G12D}$ and their wild-type (WT) littermates were immunostained for DCAMKL-1. A marked increase in ductal expression and a unique expansion of islet DCAMKL-1 was found in the Pdx48$^{Cre}$-activated KRAS$^{G12D}$ pancreatic cancer mouse model that correlated with progressive neoplastic changes (FIG. 12A-D). These data demonstrate that DCAMKL-1 upregulation following mutant KRAS mediated tumorigenesis may represent a marker of neoplastic transformation.

Isolation and propagation of pancreatic stem/progenitor cells. Stem cells within a tissue are capable of self-renewal and differentiation. Dontu et al., [Dontu et al., 2003] isolated human mammary stem/progenitor cells from normal breast tissues. When grown in ultra low attachment plates, they formed spheroid structures termed "mammospheres". To test the hypothesis that there is a small subpopulation of distinct stem/progenitor cells within a normal uninjured rodent pancreas, the mouse pancreas was digested with ultra pure collagenase IV, and FACS based cell sorting for DCAMKL-1 was performed. On average, approximately 0.4% of total cells were sorted using this method (FIGS. 13A and 13B). To characterize the phenotype of the sorted populations, quantitative RT-PCR analyses of total RNA isolated from the DCAMKL-1+ and DCAMKL-1− cells were performed. DCAMKL-1+ population demonstrated markedly increased (~10-fold) expression of DCAMKL-1 (FIG. 13C), NGN3 (FIG. 13D), nestin (FIG. 13E), and somatostatin (FIG. 13F) compared with DCAMKL-1− cells. A 7-fold increase in insulin (FIG. 13G) and a 12-fold increase in glucagon (FIG. 13H) were observed within the DCAMKL-1− cells compared with DCAMKL-1+ cells. CD133 was not detected in DCAMKL-1+ cells, but significant CD133 expression was detected in DCAMKL-1− cells.

Figure 14:
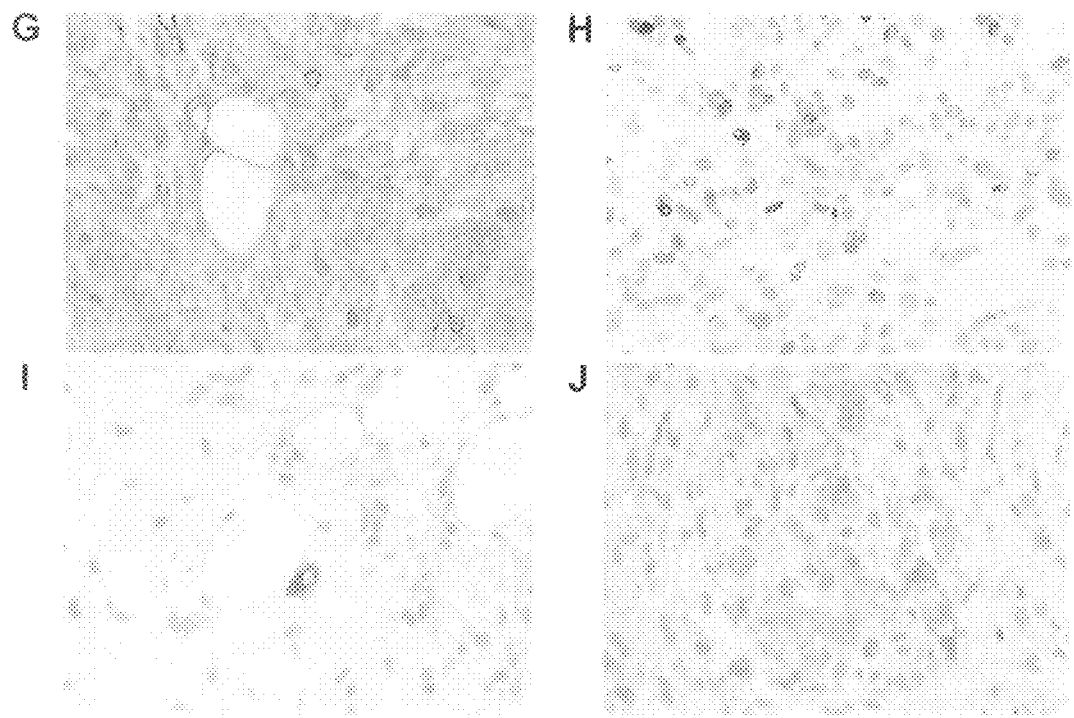

Three weeks after sorting, the formation of spheroids was observed in growth factor supplemented serum free media [Dontu et al., 2003] (FIG. 14A left-day 0 and 14A right-day 21). Spheroids were separated, suspended in Matrigel™, and injected subcutaneously into the flanks of athymic nude mice. After four weeks, nodular growth was noted at the site of injection compared to the Matrigel™ injected control (FIG. 14B left-Matrigel™ alone and 6B right—DCAMKL-1 spheroid and Matrigel™ injected). Interestingly, tangrey soft tissue outgrowth was noted that extended beyond the original injection site, which appeared to show new blood vessel formation (FIG. 14C). A total of 10 injections of pancreatic spheroids containing 50-100 cells each were performed (into right and left flanks of nude mice (n=5)). After four weeks, growth was observed in three of five nude mice for a total of six nodular growths. As a control, spheroid formation assays were performed for DCAMKL-1− cells. No spheroid formation was observed in culture, even after 12 weeks.

DCAMKL-1 sorted spheroids induce pancreatic epithelial expression in the flanks of nude mice. Histological analysis of the excised nodules revealed single cells with oval nuclei and large nucleoli, which appeared to be epithelial in nature, as well as islet-like structures (FIG. 14D). The glandular epithelial origin of these cells was confirmed by cytokeratin-14 immunoreactivity (FIG. 14E top left) [Moll et al., 2008; Purkis et al., 1990] and PDX-1, marker of early pancreatic development (FIG. 14F top right). Additionally, many of the cells within the islet structures expressed secretin [Pollack et al., 1990] (FIG. 14E bottom left) and somatostatin (FIG. 14E bottom right). Some of the cells were also positive for Ep-CAM, a marker of cells of epithelial origin (FIG. 14G). Many cells were positive for Ki67, indicating an active proliferating status (FIG. 14H). Further, cells that continued to express DCAMKL-1 were observed in both the ductlike formation (FIG. 14I) and isletlike structures (FIG. 14J). These data taken together demonstrate that DCAMKL-1 expressing cells isolated from the pancreas of normal uninjured mice by FACS and utilized in isotransplantation assays, are in fact stem/progenitor cells.

Discussion of Example 2

Solid tumors are histologically heterogeneous and include tumor cells, stroma, inflammatory infiltrates, and vascular structures. In recent years, the CSC model of tumorigenesis has received increasing attention [Tang et al., 2007]. This model suggests that tumors are initiated and maintained by a minority subpopulation of cells that have the capacity to self-renew and to generate the more differentiated progeny making up the bulk of a tumor. The CSCs, tumorigenic cancer cells, can give rise to new tumors when transplanted into immunodeficient animals [Diehn et al., 2006].

The existence of CSCs has profound implications for cancer biology and therapy due to the likelihood that eradication of CSCs is the critical determinant in achieving cure. Furthermore, CSCs may be particularly resistant to chemotherapy and radiation therapy. A recent report [Phillips et al., 2006] demonstrated that breast cancer-initiating cells were radioresistant when compared with breast cancer cells that were incapable of initiating tumors. Similarly, another report [Bao et al., 2006; Bao et al., 2006A] suggested that glioblastoma stem cells are radioresistant and may, therefore, contribute to treatment failures.

Figure 15:
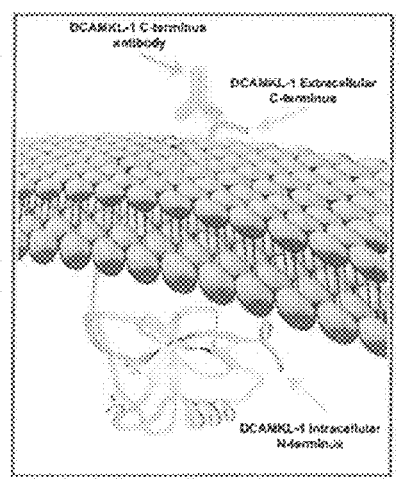

In general, cell surface proteins used for isolation of CSCs must currently be viewed as purification markers without functional implication [Diehn et al., 2006]. Therefore, it is critical to demonstrate that isolated cells from any particular tissue have the functional characteristics of CSCs. Currently, this has been most convincingly demonstrated by serial transplantation in animal models [Diehn et al., 2006]. CSCs share unique properties with normal adult stem cells, including the ability to self-renew and form spheroids. Indeed in the experiments described herein, stem cells isolated from normal mouse pancreas formed spheroids. Furthermore, 50-100 cells isolated from a particular spheroid were capable of initiating growth in the flanks of nude mice. In this Example, evidence is provided that demonstrates that DCAMKL-1, a novel stem cell marker expressed primarily in quiescent cells of the gut [May et al., 2008; Giannakis et al., 2006A], also marks normal pancreatic stem cells. One exciting outcome of this Example however, is the use of FACS for isolation of cells expressing DCAMKL-1. Although originally considered to be a cytoplasmic protein [Giannakis et al., 2006A], analysis of the DCAMKL-1 protein using TMPred program (http://www.ch.embnet.org/software/TMPRED_form.html) suggested that amino acids 534-560 represents a transmembrane domain, and amino acids 561 to 729 are outside the cell. Furthermore, it has been reported that DCAMKL-1 is expressed in adult brain with two transmembrane domains (amino acids 534-559 and 568-585), which strongly supports the suggestion that it is a cell surface expressing protein with both intra and extracellular domains [Sossey-Alaoui et al., 1999; Kim et al., 2003]. Cell surface DCAMKL-1 expression was demonstrated by Pierce® Cell Surface Protein Isolation Kit followed by Western Blot for DCAMKL-1 (data not shown). Accordingly, an Alexa Fluor® 568 conjugated anti- DCAMKL-1 antibody was generated, which targets the putative extracellular C-terminal epitope (FIG. 15). In this Example it has been demonstrated that putative stem cells isolated from the normal mouse pancreas formed early epithelial and islet-like structures and expressed markers of early pancreatic development, glandular epithelium, and islets in nude mice. In addition to expression in normal mouse pancreatic tissues, distinct DCAMKL-1 expression was also observed in representative human pancreatic cancers and the Pdx48$^{Cre}$-activated KRAS$^{G12D}$ mouse model of pancreatic cancer. Interestingly, marked coexpression of DCAMKL-1 was observed within tumors that expressed 14-3-3 σ, an inhibitor of Bad proapoptotic activity [Masters et al., 2001]. The co-localization demonstrated in this report of 14-3-3 σ and DCAMKL-1 is significant in that it could potentially define a target cell in which 14-3-3 σ related transcriptional activation within a tumor might occur. These data suggest that within a particular tumor, subsets of potential CSCs can be identified in situ. DCAMKL-1 immunostaining was observed in the intervening stroma between epithelial tumor elements, which co-expressed vimentin. These findings were indeed surprising in that DCAMKL-1 was not observed in non-epithelial cells under basal conditions. Next, ductal DCAMKL-1 was evaluated within PanIN lesions. Several thin, elongated cells that appeared to be mesenchymal were observed. To further investigate this, tumor sections were immunostained for vimentin, and cells of similar morphology were found interspersed between epithelial cells within PanIN lesions, which demonstrated distinct co-expression with DCAMKL-1. These findings suggest that DCAMKL-1 expressing cells may be undergoing EMT [Turley, et al., 2008; Reya et al., 2001]. EMT is a phenotypic conversion that facilitates organ morphogenesis and tissue remodeling in physiological processes such as embryonic development, wound healing, fibrosis, neoplasia and is associated with disease progression [Turley et al., 2008]. Desmoplasia, the appearance of fibrous, mesenchymal-like tissue in the peritumor stroma, is associated with poor clinical outcome [Poste et al., 1982]. Indeed, gene-profiling studies suggest that mesenchymal gene profiles in tumors are predictive of poor clinical outcome [Diehn et al., 2006; Theodosiou et al., 2003]. Myofibroblasts have long been thought to be derived from fibroblasts, but recent data has shown that a substantial proportion of these cells is derived from EMT and is associated with tumor progression [Polakis, 2000]. Our findings suggest that in addition to its role as a marker of pancreatic stem cells, DCAMKL-1 may additionally mark EMT within pancreatic cancer tissues.

Identification of stem cells within the normal pancreas and tumors has been generally elusive. Although recent studies using cell surface markers to isolate CSCs from tumors have been described, similar studies have not been performed utilizing normal tissues. However, in this Example, the novel stem cell marker DCAMKL-1 has been employed to identify stem cells in the normal mouse pancreas and in human and mouse pancreatic cancer.

Overall, the cancer stem cell hypothesis has many potential clinical applications, as it is becoming clear that CSCs must be removed in addition to the aberrantly proliferating cells within a particular cancer. Pancreatic cancer is an exceptionally aggressive disease and efforts directed at identification of novel therapeutic options aimed at improving the prognosis are essential. DCAMKL-1 may represent a new target for eliminating pancreatic cancer stem cells and the development of novel treatments for this devastating disease.

EXAMPLE 3

The adult intestinal epithelium is continuously and rapidly replaced by cell replication within the crypts of Lieberkühn and subsequent migration of their progeny onto the villus epithelium in the small intestine, or onto the surface epithelium in the colon [Gordon et al., 1994]. Intestinal epithelial cells are ultimately derived from multipotent stem cell(s) located near the base of each intestinal crypt [Cheng et al., 1974; Cohn et al., 1992; Schmidt et al., 1985; Winton et al., 1990]. In the adult mouse small intestine, crypt stem cells divide to produce a daughter stem cell (self-renewal) as well as a more rapidly replicating transit amplifying (TA) cell. TA cells divide in the crypt proliferative zone and their progeny ultimately differentiate into the mature intestinal epithelial cell types [Cheng et al., 1974; Potten et al., 1987; Potten et al., 1990]. Knowledge of the biological characteristics of intestinal stem cells (ISCs) has been largely acquired by inference from experiments using chimeric and transgenic mice [Gordon et al., 1994; Schmidt et al., 1985; Hauft et al., 1992]. Bjerknes and Cheng [Bjerknes et al., 1981] originally proposed the existence of a stem cell-permissive microenvironment near the crypt base at positions 1-4 interspersed between Paneth cells. These cells, termed crypt base columnar (CBC) cells were proposed as ISCs [Cheng et al., 1974A] and were found to give rise to mutant clones containing multiple cell types [Bjerknes et al., 1999].

Adult stem cells in mammals exist either in a prolonged quiescent state or are extremely slow cycling [Cheshier et al., 1999]. Based on this feature, long-term label retention assays were developed to assist in the localization of putative stem cells [Cotsarelis et al., 1990; Zhang et al., 2003]. Using this technique, Potten et al., [Potten et al., 2002] localized label-retaining cells (LRCs) or putative ISCs to a position+4 from the crypt base, directly above the Paneth cell zone [Marshman et al., 2002]. However the +4 position is an average location and may vary depending on the crypt being analyzed. It is important to note that not all +4 cells are putative stem cells.

Recent work presented by Barker et al., [Barker et al., 2007] has identified a single marker, LGR5/GPR49 gene, a leucine-rich orphan G-protein-coupled receptor, that specifically labels stem cells in the mouse small intestine as well as other adult tissues. Furthermore, using mice generated from a LGR5-EGFP-IRES-Cre-ERT2× RosaLacZ cross, they demonstrated that LGR5+ CBC cells are multipotent for all mature intestinal epithelial cell types, undergo self-renewal, persist for at least 60 days based on LacZ expression, and are resistant to irradiation [Barker et al., 2007]. Furthermore, LGR5 marked ISCs that were rapidly cycling (divide every 24 hours) under homeostatic conditions [Barker et al., 2007].

It has been demonstrated herein that doublecortin and Ca$^{2+}$/calmodulin-dependent kinase-like-1 (DCAMKL-1), a microtubule-associated kinase expressed in post-mitotic neurons [Lin et al., 2000], is a novel putative ISC marker [See Example 1, as well as Quante et al., 2008; Samuel et al., 2009; Humphries et al., 2008]. DCAMKL-1 was identified as a Gene Ontogeny-enriched transcript expressed in comparison with gastric epithelial progenitor and whole stomach libraries [Giannakis et al., 2006] and more recently in gastric stem cells [Giannakis et al., 2008]. Utilizing immunohistochemical analysis, cell-specific intestinal DCAMKL-1 expression patterns were demonstrated in adult wild type (WT) and in Apc$^{MIN/+}$ mice to visualize crypt epithelial stem cells at baseline and in response to radiation injury [May et al., 2008]. Immunoreactive DCAMKL-1 cells were found at or near position+4, at a frequency of one cell per five crypts. DCAMKL-1+ CBC cells were also observed, albeit much less frequently.

In this Example, the cell specific expression patterns of DCAMKL-1 and LGR5 were investigated in intestinal epithelial cells in uninjured adult mice. DCAMKL-1 and LGR5 mark distinctly different cells. Moreover, DCAMKL-1 did not co-localize with other key markers such as chromogranin A (ChrA), phosphorylated PTEN (pPTEN), phosphorylated AKT (pAKT), somatostatin or secretin. Furthermore, using a combination of a modified label retention assay (mLRA) and immunohistochemical analysis, it was determined that DCAMKL-1 is expressed in quiescent label retaining cells within the intestinal crypt. LGR5 identifies proliferative CBC and TA cells in the gut as evidenced by co-labeling with proliferating cell nuclear antigen (PCNA). Additionally, early glandular epithelial structures were demonstrated in nude mice isografts following fluorescence activated cell sorting (FACS) of normal mouse intestinal epithelial cells using DCAMKL-1. Thus the inventors propose that the original hypothesis of a +4 ISC should not yet be abandoned and contend that the DCAMKL-1 expressing cell represents a quiescent ISC.

Materials and Methods for Example 3

Tissue preparation and immunohistochemistry. Heat Induced Epitope Retrieval was performed on formalin-fixed paraffin-embedded sections utilizing a pressurized Decloaking Chamber (Biocare Medical) in citrate buffer (pH 6.0) at 99° C. for 18 min. (a) Brightfield: Slides were incubated in 3% hydrogen peroxide, then normal serum and BSA at room temperature for 20 min. After incubation with primary antibody [DCAMKL-1 C-terminal (Abcam), LGR5 (Abcam), BrdUrd (Upstate), PCNA (Santa Cruz), Msi-1 (Abcam), Cytokeratin 14 (Santa Cruz), Math1 (Chemicon), L-FABP (Santa Cruz)], the slides were then incubated in peroxidase-conjugated EnVision™+ polymer detection kit (DAKO). Slides were developed with Diaminobenzidine (Sigma). (b) Fluorescence: Slides were first incubated in Image-iT FX signal enhancer (Invitrogen), followed by normal serum and BSA at room temperature for 20 min. After incubation with primary antibody, slides were incubated in appropriate Alexa Fluor® conjugated secondary [488 (green) and 568 (red)].

Microscopic examination. Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon). Confocal imaging was performed using Leica TCS NT Microscope.

Modified label retention assay. C57BL/6 mice (Jackson Labs) were subjected to 8 Gy whole body gamma irradiation using a Nordion $^{137}$Cs γ-irradiator with a dose rate of 0.9 Gy per minute. Animals received twice daily BrdUrd injections beginning 24 and ending 84 hr after irradiation. This time period was chosen in order to maximize the potential of label incorporation during the crypt regeneration phase, following severe genotoxic injury. Animals were sacrificed at 7 and 10 days after the initial injury when restoration of crypt villus morphology is returning towards baseline. Co-immunostaining for BrdUrd and DCAMKL-1 was performed to identify label retaining stem cells. Additionally co-immunostaining for PCNA and DCAMKL-1 was performed to determine the proliferative status of the label retaining cells.

Stem cell isolation. Based on protocols developed in intestinal stem cell biology [Dekaney et al., 2005; Grossmann et al., 2003], stem cells were isolated and propagated from fresh mouse intestinal tissues. Intestines were opened longitudinally and cut into small strips, washed and incubated with 1 mM DTT (Sigma) for 30 min at room temperature. Tissues were further incubated with 30 mmol/L EDTA (Sigma) for 10 min at 37° C., shaken vigorously in fresh HBSS (Cellgro) and filtered through 400 μm mesh (Spectrum Labs) to separate the detached intestinal crypt epithelial cells from the tissue. The filtrate was passed through 80 μm mesh (BD Falcon) to retain the crypts and washed. The crypts were digested at 37° C. to create a single cell suspension.

FACS. The cells isolated from mouse intestine were incubated with 1:100 dilution of Alexa Fluor® 568 (Invitrogen) conjugated DCAMKL-1 antibody (Abcam) for 30 min. The cells were washed twice with HBSS containing 10% serum and sorted using Influx-V cell sorter (Cytopeia). The cells collected were grown on DMEM containing EGF (25 ng/ml), FGF (20 ng/ml) and insulin (5 ng/ml) (Sigma), on non adherent/ultra low attachment plates (BD Biosciences).

Isotransplantation assay. DCAMKL-1+ cells isolated from intestine were grown in suspension culture and formed spheroids by day 21. Mechanically dissociated spheroids (50-100 cells) were suspended in Matrigel™ and injected subcutaneously into the flanks of athymic nude mice (n=3) (NCl-Fredrick) and monitored for the appearance of nodular growth.

Cell surface protein isolation and Western Blot analysis. SW480 colon cancer cells were grown and surface proteins were labeled with sulfo-NHS Biotin (Pierce, Thermo Scientific). Cell lysates were prepared and the biotinylated proteins were separated from intracellular non-biotinylated proteins as per manufacturer's instructions (Pierce). Protein concentration was determined by BCA protein assay kit (Pierce Biotechnology Inc., Rockford, Ill.). Forty μg of the protein was size separated in a 15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 h and probed overnight with a rabbit anti-DCAMKL-1 antibody (Abcam Inc.) or with rabbit anti-EGFR antibody (Cell Signaling Technology Inc.). Subsequently, the membrane was incubated with anti-rabbit IgG horseradish peroxidase-conjugated antibodies (Amersham-Pharmacia) for 1 h at room temperature. The 82 kDa DCAMKL-1 and 175 kDa EGFR proteins were detected using ECL™ Western Blotting detection reagents (Amersham-Pharmacia).

Results of Example 3

Figure 16:
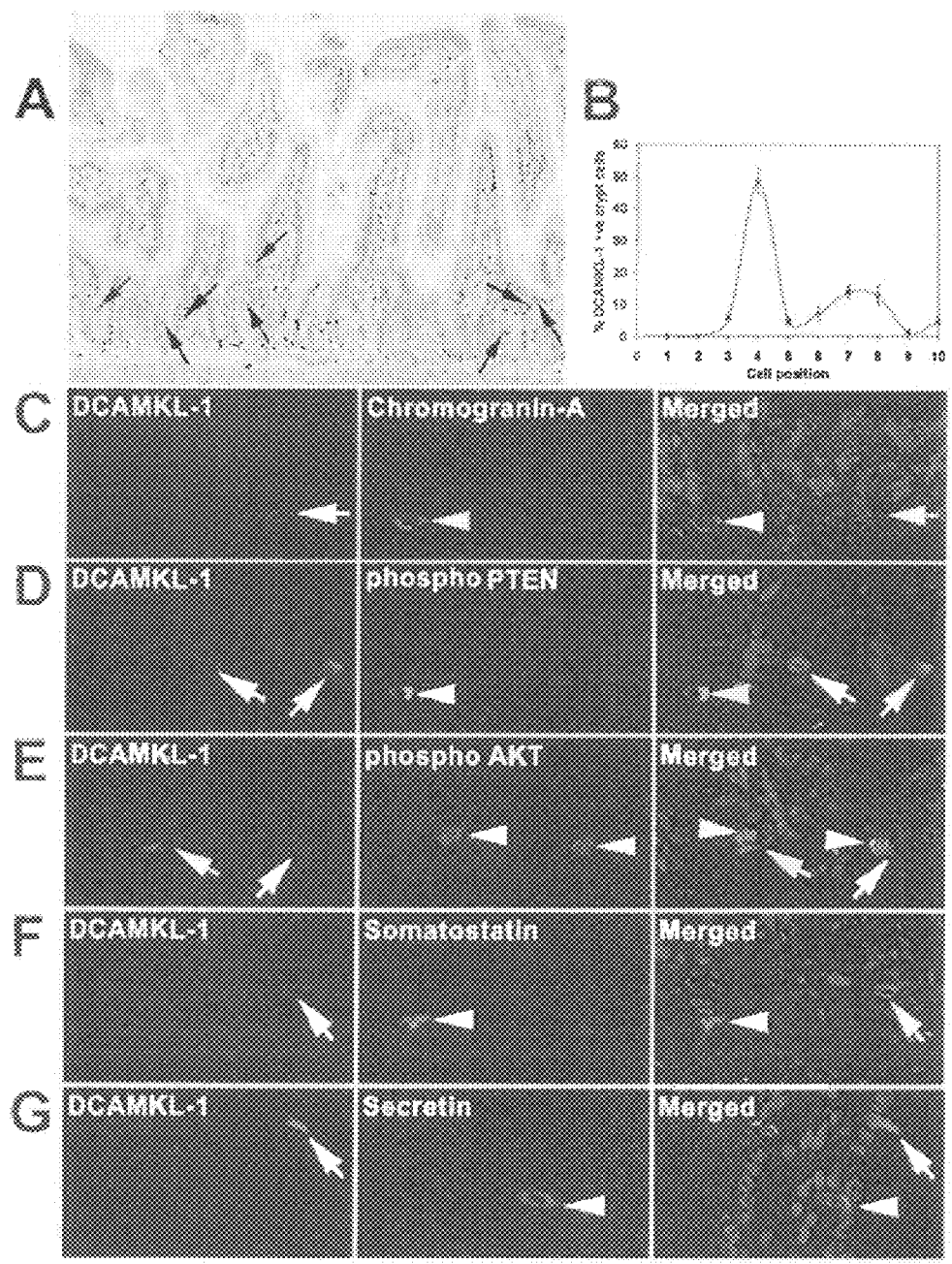

Intestinal DCAMKL-1 expression along the crypt-villus axis. Cellular distribution of DCAMKL-1 on a positional basis was determined in adult C57BL/6 mice (n=3). Longitudinal sections from the distal jejunum were prepared from each mouse and the number of immunoreactive DCAMKL-1 was determined by counting positive cells at the numbered positions (1-10), starting from the mid-point at the base of the crypt along the crypt-villus axis. Out of 500 total crypts counted, it was found that 49% of DCAMKL-1 positive cells were located at position +4 (excluding the CBCs) (FIG. 16A, 16B). DCAMKL-1 was also expressed in rare CBCs (4% of total crypts counted). As previously reported, DCAMKL-1 cells were found in the villi [May et al., 2008]. However, it was noted that DCAMKL-1 crypt with simultaneous villus expression was rare (<5% of total crypt villus units).

DCAMKL-1 marks a unique intestinal cell type. To determine whether DCAMKL-1 was co-expressed with other putative stem cell and enteroendocrine markers, double-labeled immunofluorescence staining was performed for DCAMKL-1 with ChrA, pPTEN, pAKT, somatostatin and secretin. There was no co-localization observed for any of the markers tested (FIG. 16C-16G). These data demonstrate that DCAMKL-1 marks a unique cell within the crypt.

Figure 17:
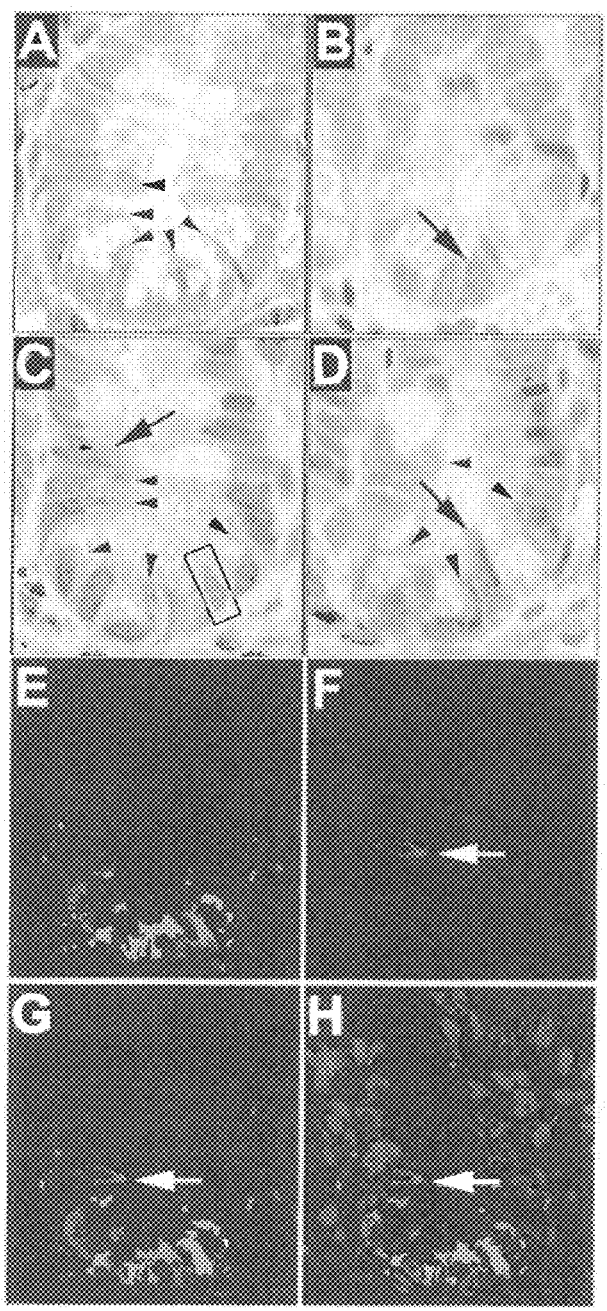

Intestinal LGR5 and DCAMKL-1 mark distinctly different cells. In the intestine, LGR5 expression was observed in crypt epithelial and in CBC cells as predicted (FIG. 17A). LGR5+ cells were also scattered throughout the mesenchyme and villus epithelial cells. This was consistent with the LacZ expression patterns described in the original LGR5 stem cell report [Barker et al., 2007], expression of LGR5 at the base of the crypt in normal human colon and small intestine [Becker et al., 2008] and the previously reported immunostaining for LGR5/GPR49 in colon and cancer tissues [McClanahan et al., 2006]. Example 1 demonstrated DCAMKL-1 expression at position+4 and in rare CBC cells [May et al., 2008] (FIG. 17B). On occasion, LGR5 expressing cells were immediately adjacent to DCAMKL-1+ cells (FIG. 17C, 17D). However, no DCAMKL-1 co-localization with LGR5 was observed in intestinal crypts (FIG. 17E-17H).

Figure 18:
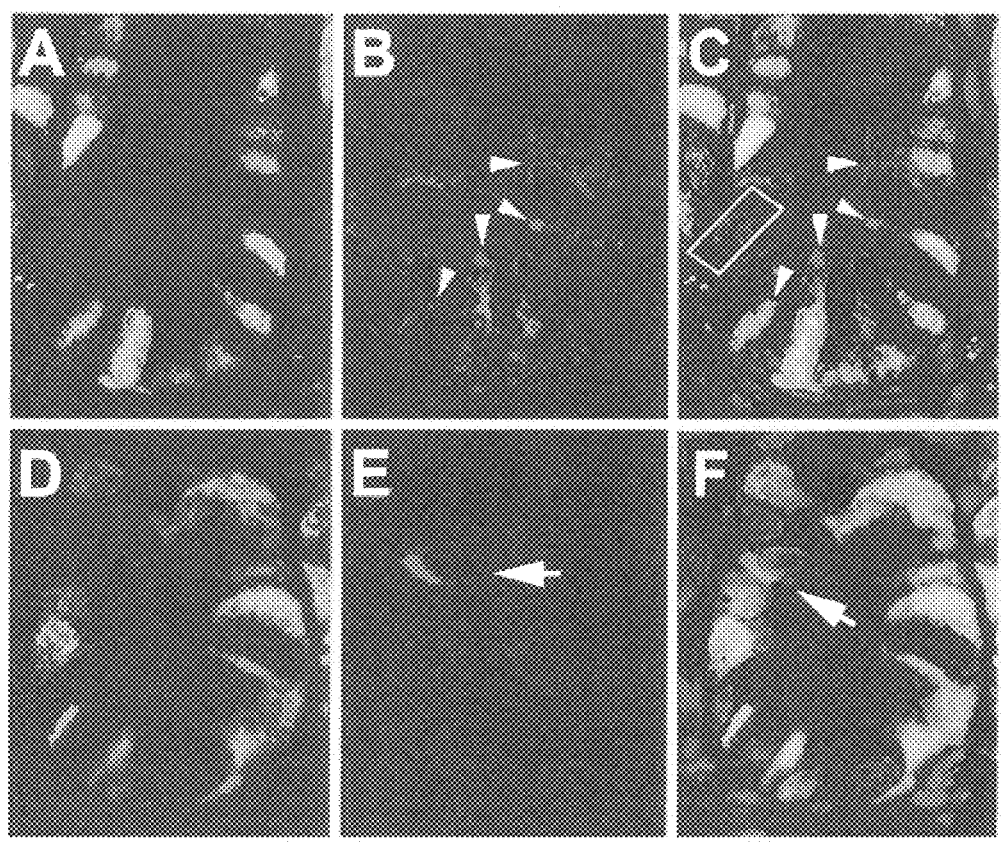

The proliferation status of LGR5 and DCAMKL-1 expressing cells. PCNA staining was performed to assess the proliferative status of LGR5 and DCAMKL-1 expressing cells in the intestine. LGR5 expressing cells were invariably PCNA+ (actively cycling) (FIG. 18A-18C). Occasionally, cells were noted at position+4 that did not express either PCNA or LGR5 (FIG. 18C white box). PCNA-cells, particularly at position+4, were distinctly DCAMKL-1+ (FIG. 18D-18F) suggesting functional quiescence at baseline. Thus, DCAMKL-1 and LGR5 identify cell populations with differing proliferation status at baseline. These findings lend support to the longstanding+4 hypothesis, which suggests that a functionally quiescent or very slowly cycling cell is primarily anchored in the stem cell niche [Potten et al., 2002; Marshman et al., 2002; Potten et al., 1997]. The inventors contend that this quiescent cell is marked by DCAMKL-1.

Figure 19:
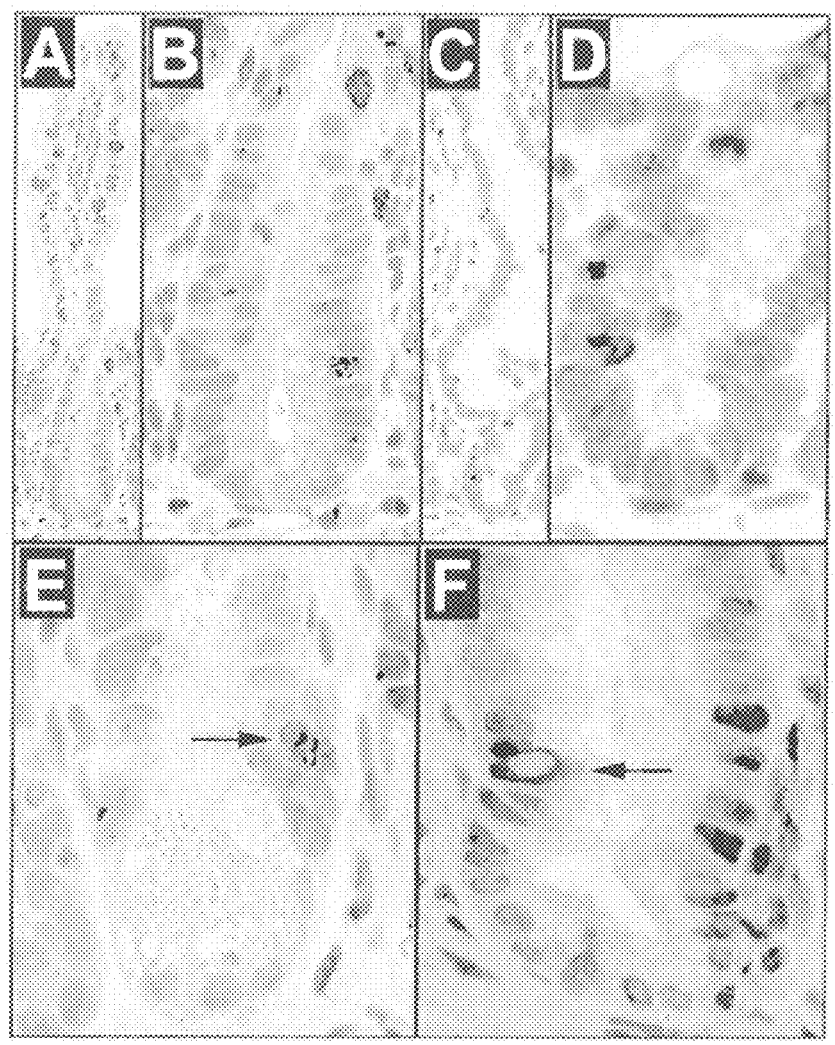

DCAMKL-1 label-retaining cells are functionally quiescent. Although the "anchored stem cell" is often found at position+4, the inventors suspect that under certain conditions this cell can exit the niche [Frye et al., 2003]. Indeed, occasionally DCAMKL-1 staining was observed outside of the crypt, particularly in APC$^{min/+}$ mice [May et al., 2008]. A modification of the traditional label retention assay (mLRA) [Cotsarelis et al., 1990; Zhang et al., 2003; Potten et al., 2002; Marshman et al., 2002] was employed by utilizing 8 Gy as the inciting dose in adult WT mice. DCAMKL-1 expression is lost in regenerative crypts by 84 hr after lethal dose IR (>8 Gy) but reappears 7 and 10 days following IR in regenerated intestine tissues [May et al., 2008]. This suggests that by 7 to 10 days after IR, the normal crypt villus units and the niche related micro-environmental signals required for DCAMKL-1 expression are restored. Example 1 demonstrated that 24 hrs after IR is a critical time point when DCAMKL-1 expressing cells undergo both mitosis and apoptosis [May et al., 2008]. Thus it was decided to pulse label 5-bromo-2'-deoxyuridine (BrdUrd) throughout the entire 24-84 hr crypt regeneration cycle. Animals were allowed to recover and were sacrificed at 7 and 10 days [Potten et al., 1988]. This period of regeneration allows for BrdUrd incorporation into dividing stem cells that would otherwise be problematic under quiescent basal conditions. At 7 days post IR, residual BrdUrd labeled cells were detected in the upper crypt and throughout the villi (FIG. 19A, 19B). However at 10 days, BrdUrd labeling had essentially disappeared, and only rare cells near the crypt base retained significant label (FIG. 19C, 19D).

Next, it was sought to determine whether the cells retaining BrdUrd label following the mLRA also expressed DCAMKL-1. At 10 days post IR, double-label immunohistochemistry was performed, and distinct co-expression of BrdUrd and DCAMKL-1 at position+4 was observed (FIG. 19E). While this cell retains label, it does not necessarily mean that it was actively proliferating. It was sought to answer this question by examining DCAMKL-1 expressing cells following the mLRA for the presence of PCNA activity. Interestingly, there was no PCNA expression in the nucleus of the DCAMKL-1+ cell. Yet clear PCNA staining could be identified in many adjacent cells (FIG. 19F). Thus the label retaining DCAMKL-1 expressing "stem cells" are again quiescent at 7 and 10 days after IR.

Figure 20:
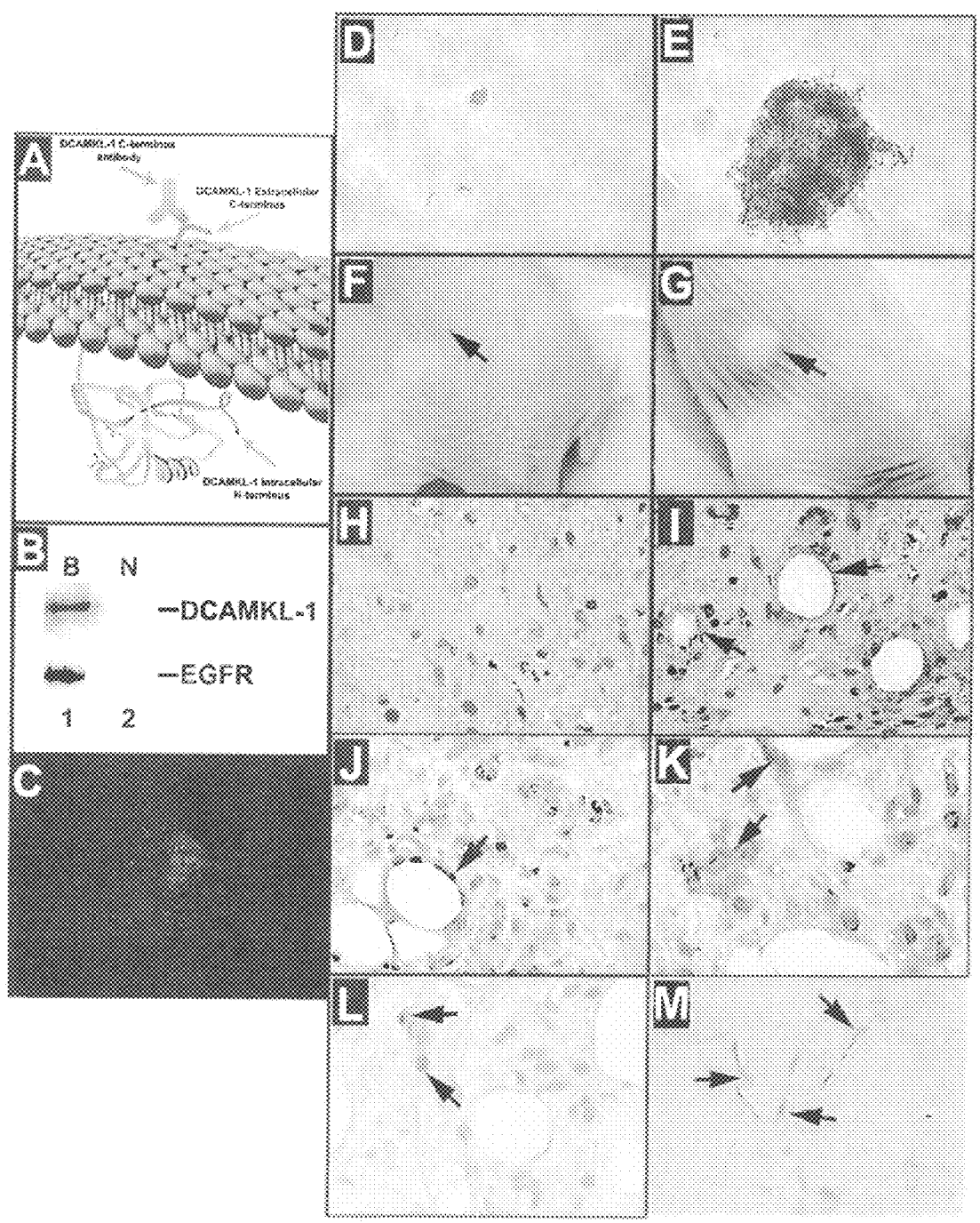
Figure 21:
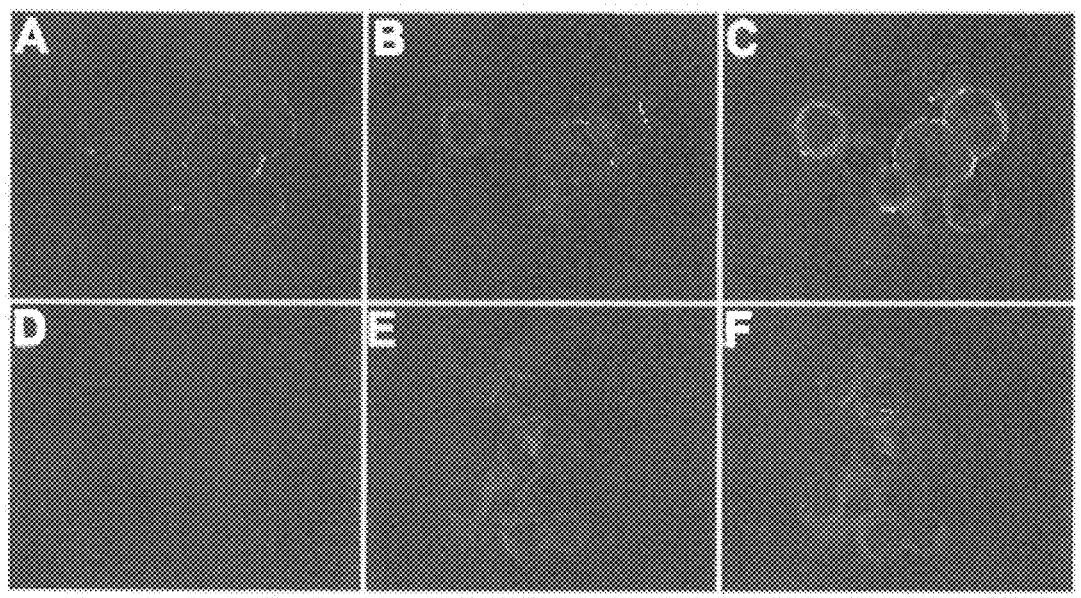

DCAMKL-1 is expressed on the cell surface and can be used to isolate stem cells. To further investigate the potential "stemness" of DCAMKL-1 expressing cells, FACS using the modified protocol of Dekaney et al. [Dekaney et al., 2005] was employed. Although originally considered to be a cytoplasmic protein [Giannakis et al., 2006], analysis of the DCAMKL-1 protein using TMPred program (http://www.ch.embnet.org/software/TMPRED_form.html) suggested that amino acids 534-560 constitutes a transmembrane domain, and amino acids 561 to 729 are extracellular. Furthermore, it has been reported that DCAMKL-1 is expressed in adult brain with two transmembrane domains (amino acids 534-559 and 568-585), suggesting that it is a cell surface expressing protein with intra and extracellular domains [Sossey-Alaoui et al., 1999; Kim et al., 2003] (FIG. 20A). To confirm the cell surface expression of DCAMKL-1, the Pierce Cell Surface Protein Isolation Kit (Pierce) was used to isolate total cell surface expressing proteins from SW480 cells (FIG. 21). Western blot analyses demonstrated the presence of DCAMKL-1 in the avidin-bound fraction, but not in the unbound fraction (FIG. 20B). This data demonstrates that DCAMKL-1 protein is indeed present on the cell surface. Epithelial growth factor receptor (EGFR), a cell surface expressing protein in the bound fraction was used as a positive control.

Figure 22:
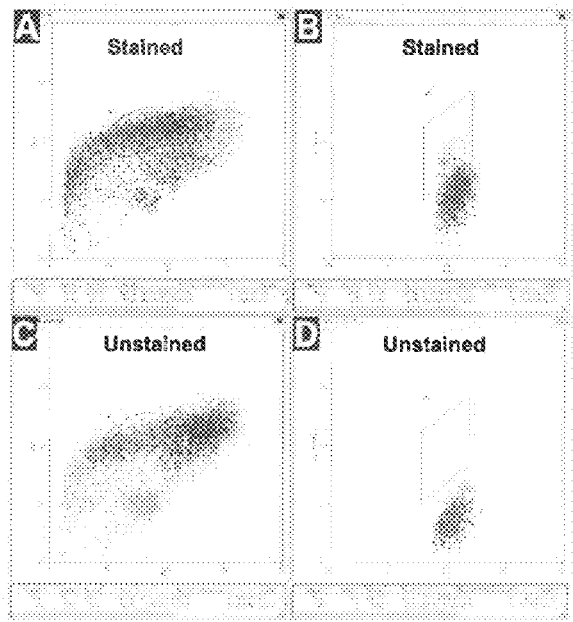
Figure 23:
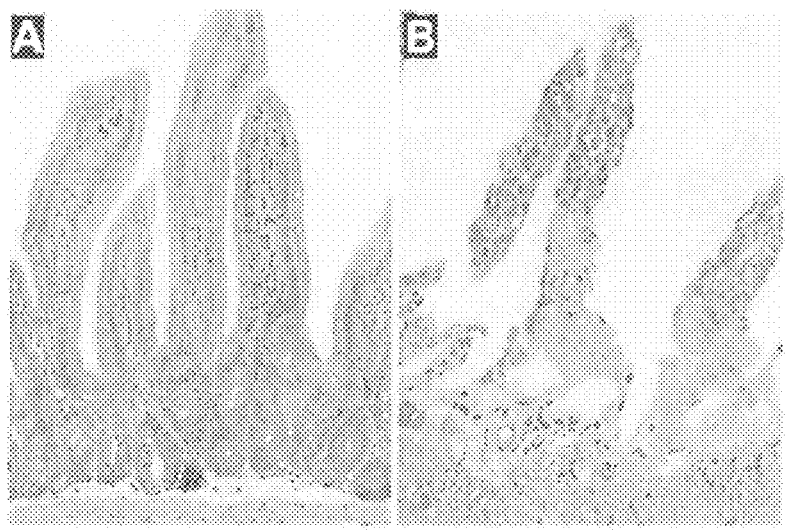
FIG. 23 illustrates mouse intestine (distal jejunum) before and after epithelial cell isolation. (A): Intact epithelium before isolation. (B): Intestine devoid of epithelial cells after isolation.
Figure 24:
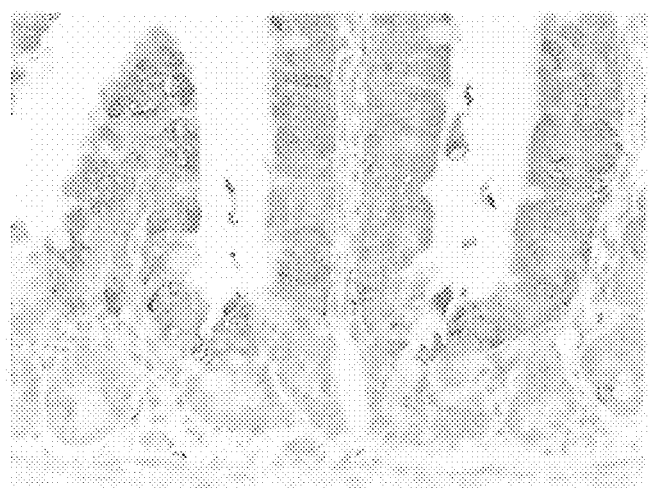
FIG. 24 illustrates mouse intestine (distal jejunum) immunostained for L-FABP (brown). Immunoreactive L-FABP is observed in occasional crypt epithelial cells; however, intense staining is observed in differentiated villus epithelial cells.

Anti-DCAMKL-1 antibody, which targets the extracellular C-terminal epitope [Lin et al., 2000; Sossey-Alaoui et al., 1999; Kim et al., 2003], was conjugated with Alexa Fluor® 568 to label intact functional stem cells from the normal mouse intestine for FACS. For sorting, gate R1 was assigned based on previous experiments, where the DCAMKL-1+ fluorescing cell population was found aggregated within that location. These cells were further gated through R2 based on fluorescence intensity (FIG. 22). Approximately 1.75% of the total cells sorted were isolated using this method (FIGS. 22-23). Sorted cells were examined by fluorescence microscopy to confirm the presence of DCAMKL-1 (FIG. 20C). The cells were then grown in suspension culture with growth factor supplemented media using the method of Dontu et al. [Dontu, 2003]. After 3 weeks, the single DCAMKL-1+ sorted cells formed spheroids (FIG. 20D, 20E); whereas DCAMKL-1-sorted cells did not (data not shown). The spheroids containing 50 to 100 cells were mechanically dissociated and subsequently injected into contralateral flanks of nude mice. After 3 weeks nodular structures were observed (FIG. 20F, 20G) in 11 of 12 spheroid injection sites (data not shown). Two weeks later, animals were sacrificed and nodules excised and subjected to immunohistochemical and histological analysis. In the control (Matrigel™ injected) nodules, an inflammatory response was observed including the presence of macrophages, but with no evidence of epithelial cells (FIG. 20H). In the spheroid injected nodules however, there were single cells with oval nuclei and large nucleoli which lined up around central spaces and appeared to represent poorly formed glands (FIG. 20I). Cytokeratin 14 immunoreactivity demonstrates that these cells were of glandular epithelial origin [Moll et al., 2008; Purkis et al., 1990] (FIG. 20J). To determine whether they expressed stem and/or TA (progenitor) cell markers, the inventors stained for the epithelial stem/progenitor cell marker Msi-1 [Sureban et al., 2008; Potten, 2003]. Significant Msi-1 immunoreactivity was observed in these epithelial structures providing additional support for the epithelial and perhaps stem/progenitor cell origin of these cells (FIG. 20K). Moreover, several cells expressed Math1 indicating an early intestinal epithelial secretory lineage commitment (goblet, enteroendocrine and Paneth cells) [Yang et al., 2001; Shroyer et al., 2005] and L-type fatty acid binding protein (L-FABP) (marker of enterocyte lineage) [Rubin et al., 1992] (FIGS. 20L, 20M and 24). These studies demonstrate that DCAMKL-1 can be used as a cell surface marker to isolate stem cells from the normal mouse intestine and investigate their lineage determination and viability in vivo.

Discussion of Example 3

In this Example, it has been demonstrated that the novel stem/progenitor markers DCAMKL-1 and LGR5 identify intestinal stem and progenitor cells, respectively. This distinction is primarily based on the proliferative status of the cells, because no in vivo genetic lineage tracing studies have yet been performed for DCAMKL-1. The major distinguishing feature presented here is that DCAMKL-1 identifies a slowly cycling or basally quiescent cell; whereas LGR5 identifies a more proliferative cell. It is important to note that these classifications do not necessarily address the question of multipotency, as it is clear that an early intestinal progenitor cell is capable of repopulating the crypt with each of the four cell types expressed in the intestine [Crossman et al., 1994]. This Example demonstrates that there may be two different populations of stem cells in the gut. One population is at or near the traditional +4 position, and is restricted primarily to the niche and may have a functional role in gut homeostasis and injury response. The second population is interspersed between the Paneth cells (CBCs) and may be responsible for Paneth cell repopulation in response to bacterial mediated injury.

These results have been supported by the recent report by Sangiorgi and Capecchi [Sangiorgi et al., 2008] identifying Bmi1 as yet another novel ISC marker. In that report using a knock-in transgenic mouse model, they presented data demonstrating that Bmi1 labels ISCs predominantly at the +4 position of the crypt. The authors suggest that Bmi1 and LGR5 label different states of ISCs. Bmi1 labels the more quiescent ISCs, while LGR5 labels ISCs more prone to enter proliferation [Sangiorgi et al., 2008]. The results of this Example are further supported by reports that the putative stem/progenitor cell markers DCAMKL-1, LGR5 and Msi-1 [Quante et al., 2008; Samuel et al., 2009; Humphries et al., 2008] are all expressed in CBC cells [Barker et al., 2007; May et al., 2008; Potten, 2003]. One exciting outcome of this Example is the use of FACS for isolation of cells expressing DCAMKL-1. Although originally considered to be a cytoplasmic protein [Giannakis et al., 2006], it has been reported that DCAMKL-1 is expressed in adult brain with two transmembrane domains (amino acids 534-559 and 568-585), making it a cell surface expressing protein with intra and extracellular domains [Sossey-Alaoui et al., 1999; Kim et al., 2003]. In this Example, cell surface isolation experiments confirm that DCAMKL-1 is indeed expressed on the cell surface. Accordingly, anti-DCAMKL-1 antibody was conjugated with Alexa Fluor® 568 for use in cell sorting experiments. This Example demonstrated that putative stem cells isolated from the normal mouse intestine by FACS form spheroids in suspension culture, and upon injection into the flanks of nude mice form early glandular epithelial structures. Moreover, these cells expressed Msi-1 [Sureban et al., 2008; Potten, 2003], Cytokeratin 14 [Moll et al., 2008; Purkis et al., 1990], Math1 [Yang et al., 2001; Shroyer et al., 2005] and L-FABP [Rubin et al., 1992], markers of intestinal epithelial lineage.

The data presented in this Example demonstrate that LGR5+ and DCAMKL-1+ cells are distinctly different and may even have different functions. However, it is predicted that both of these cell types are likely to have full multipotency and have the potential to regenerate a fully functional gastrointestinal tract following injury. The present Example demonstrates that for the first time these critical cell types can be identified in situ based on the discovery of these two novel markers. FIG. 25 presents a model for the specific expression patterns of the putative markers DCAMKL-1, Msi-1 and LGR5 in the intestinal crypts.

The importance of reliable markers for identifying both stem and progenitor cells goes well beyond their use as a tool for sorting. The unique expression of DCAMKL-1 in quiescent ISCs raises the question of whether functional quiescence is a requirement for gut homeostasis, and what factors regulate these processes. Identification of DCAMKL-1 and LGR5 expressing cells will enable for the first time the direct examination of the gene expression profiles and molecular signatures of stem and progenitor cells, respectively.

EXAMPLE 4

MicroRNAs (miRNAs) are small, non-coding RNAs that regulate gene expression in animal and plant systems [Lee et al., 2001; Lagos-Quintana et al., 2001]. miRNAs have emerged as important developmental regulators and control critical processes such as cell fate determination and cell death [Bartel, 2004]. There is increasing evidence that several miRNAs are mutated or poorly expressed in human cancers and may act as tumor suppressors or oncogenes [McManus, 2003; Takamizawa et al., 2004]. Gene expression is regulated by miRNAs through complementary elements in the 3' untranslated regions (3' UTRs) of their target messenger RNAs (mRNAs) [Vella et al., 2004]. lethal-7 (let-7), a founding member of the miRNA family, is required for timing of cell fate determination in *C. elegans* [Reinhart, 2000]. In humans, various let-7 genes have been reported to map to regions that are deleted in human cancers [Calin, 2004]. In addition, let-7 is poorly expressed in lung cancers [Takamizawa, 2004], suggesting that let-7 miRNAs may be tumor suppressors. In support of this, overexpression of let-7 inhibited cell growth of a lung cancer cell line in vitro [Takamizawa, 2004].

Mature miRNAs are produced from primary miRNA transcripts (pri-miRNAs) through sequential cleavages by the Microprocessor complex, comprising the ribonuclease III Drosha component and the double-stranded RNA (dsRNA) binding protein DGCR8 [Gregory, 2004] and Dicer [Chendrimada et al., 2005]. This coordinated enzyme complex results in the release of pri-miRNA and mature miRNA species. Posttranscriptional control of miRNA expression has been reported to occur in a tissue-specific [Obernosterer et al., 2006] and developmentally regulated fashion [Viswanathan et al., 2008; Thomson et al., 2006]. In mouse embryonic stem (ES) cells and in mouse embryonal carcinoma (EC) cells, the magnitude of the Microprocessor processing block is greatest for members of the let-7 family of miRNAs; although it is quite possible that the processing of all miRNAs may be regulated at the Microprocessor step [Viswanathan et al., 2008; Thomson et al., 2006]. It has been recently discovered that in many cancers, the miRNA profile is altered when compared to normal tissue [Calin et al., 2006]. It is becoming increasingly recognized that most cancers have a stem-cell-like compartment that is responsible for inciting and sustaining tumorigenesis [Calin et al., 2006; Jones et al., 2007]. One might hypothesize that miRNA profiles are altered in cancer stem cells (CSCs) within a particular tumor. Moreover, it is quite possible that such alterations are key factors in the initiation of the CSC. Recent evidence suggests that several miRNAs may be responsible for maintaining stem-cell-like characteristics [Bussing et al., 2008; Hatfield et al., 2005].

Furthermore, miRNA profiling of human and mouse ES cells reveals high levels of miRNAs expression, previously associated with oncogenesis and cell-cycle control [Suh et al., 2004; Calabrese et al., 2007]. Moreover, lack of let-7 miRNA expression was observed as an indicator for "stemness" in epithelial progenitor cells. Recent studies have also demonstrated that let-7 expression is absent in certain tumor cell lines, and that re-introduction of let-7 into these cells causes differentiation and reduction in proliferation and tumor-forming ability [Giannakis et al., 2006; May et al., 2008; Dekaney et al., 2005]. The regulatory mechanisms that control the maturation process of miRNA are unclear and the regulatory factors that control let-7 miRNA levels, particularly in epithelial stem/progenitor cells, are completely unknown. The study of epithelial stem cell biology has been hampered by the lack of reliable stem cell markers that distinctly define and distinguish between stem and progenitor cell populations. There has been an accelerated interest, however, in defining these populations, as it is becoming increasingly clear that many important diseases including cancers are likely driven by effects on stem and/or progenitor cells.

Example 1 demonstrated that the novel putative intestinal stem cell marker DCAMKL-1, a microtubule associated kinase expressed in post mitotic neurons [Lin et al., 2000] and in the stomach [Giannakis et al., 2006], is expressed in the intestine, colon and Apc$^{Min/+}$ adenomas [May et al., 2008]. Given the importance of stem cells in mucosal regeneration and neoplasia, it was sought to determine whether DCAMKL-1 played a functional role in tumorigenesis and whether these effects were mediated through regulation of let-7a miRNA.

Materials and Methods of Example 4

Cell culture. HCT116, HCT116 p21$^{-/-}$ and SW480 human colon adenocarcinoma cell lines were obtained from the American Type Culture Collection (ATCC) and grown in Dulbecco's modified eagle's medium (DMEM) supplemented with 10% fetal bovine serum and 100 U/mL penicillin-streptomycin in a humidified chamber at 37° C. with 5% CO$_2$.

Silencer RNA. DCAMKL-1 siRNA (si-DCAMKL-1) sequence targeting the coding region of DCAMKL-1 (Accession # NM_004734 (SEQ ID NO:1)) (GGGAGUGAGAA-CAAUCUAC (SEQ ID NO:3)) and scrambled control siR-NAs (si-Scr) not matching any of the human genes were obtained (Ambion Inc., Austin, Tex.) and transfected using Transfectol™ (Ambion Inc.).

Real-time reverse transcription-PCR analyses. Total RNA isolated either from cells or from human colon cancer cell tumor xenograft samples was subjected to reverse transcription with Superscript™ II RNase H—Reverse Transcriptase and random hexanucleotide primers (Invitrogen, Carlsbad, Calif.). The cDNA was subsequently used to perform Real-time PCR by SYBR chemistry (SYBR® Green I; Molecular Probes) for specific transcripts using gene specific primers and Jumpstart Taq DNA polymerase (Sigma-Aldrich, St. Louis, Mo.). The crossing threshold value assessed by Real-time PCR was noted for the transcripts and normalized with β-actin mRNA. The changes in mRNA were expressed as fold change relative to control with ±SEM value.

Human primers used are:

```
β-actin:
                                        (SEQ ID NO: 4)
Forward:    5'-GGTGATCCACATCTGCTGGAA-3'

(SEQ ID NO: 5)
Reverse:    5'-ATCATTGCTCCTCCTCAGGG-3'

DCAMKL-1:
                                        (SEQ ID NO: 6)
Forward:    5'-AGTCTTCCGATTCCGAGTTGAG-3'

(SEQ ID NO: 7)
Reverse:    5'-CAGCAACCAGGAATGTATTGGA-3' c-Myc:
                                        (SEQ ID NO: 8)
Forward:    5'-CACACATCAGCACAACTACGCA-3'

(SEQ ID NO: 9)
Reverse:    5'-TTGACCCTCTTGGCAGCAG-3'
```

Mouse primers used are:

```
DCAMKL-1:
                                        (SEQ ID NO: 10)
Forward:    5'-CAGCCTGGACGAGCTGGTGG-3'

(SEQ ID NO: 11)
Reverse:    5'-TGACCAGTTGGGGTTCACAT-3'
``` miRNA analysis. Total miRNA was isolated using mir-Vana™ miRNA isolation kit (Ambion Inc.). Total miRNA isolated either from cells or from human colon cancer cell tumor xenograft samples were subjected to reverse transcription with Superscript™ II RNase H—Reverse Transcriptase and random hexanucleotide primers (Invitrogen, Carlsbad, Calif.). The cDNA was subsequently used to perform Real-time PCR by SYBR chemistry (SYBR® Green I; Molecular Probes) for pri-let-7a transcript using specific primers and Jumpstart Taq DNA polymerase (Sigma-Aldrich, St. Louis, Mo.). The crossing threshold value assessed by Real-time PCR was noted for pri-let-7a miRNA and normalized with U6 pri-miRNA. The changes in pri-miRNA were expressed as fold change relative to control with ±SEM value. Primers used are:

```
pri-U6:
                                        (SEQ ID NO: 12)
Forward:    5'-CTCGCTTCGGCAGCACA-3'

(SEQ ID NO: 13)
Reverse:    5'-AACGCTTCACGAATTTGCGT-3' pri-let-7a:
                                        (SEQ ID NO: 14)
Forward:    5'-GAGGTAGTAGGTTGTATAGTTTAGAA-3'

(SEQ ID NO: 15)
Reverse:    5'-AAAGCTAGGAGGCTGTACA-3'
```

Western Blot analysis. HCT116 and SW480 cells were cultured in a 6 well plates to 40% confluency and were transfected with si-DCAMKL-1 or si-Scr for 72 h. Cells or the tumor xenograft samples were lysed and the concentration of protein was determined by BCA protein assay kit (Pierce Biotechnology Inc., Rockford, Ill.). Forty μg of the protein was size separated in a 7.5-15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 h and probed overnight with a rabbit anti-DCAMKL-1 antibody (Abcam Inc., Cambridge, Mass.) or with rabbit anti-c-Myc antibody (Santa Cruz). Subsequently, the membrane was incubated with anti-rabbit or anti-goat IgG horseradish peroxidase-conjugated antibodies (Amersham-Pharmacia) for 1 h at room temperature. The 82 kDa DCAMKL-1 and 49 kDa c-Myc proteins were detected using ECL™ Western Blotting detection reagents (Amersham-Pharmacia). Actin (43 kDa), used as loading control was identified using a goat polyclonal IgG (Santa Cruz Biotechnology Inc., Santa Cruz, Calif.).

Immunohistochemistry. Heat Induced Epitope Retrieval was performed on 4 μm formalin-fixed paraffin-embedded sections utilizing a pressurized Decloaking Chamber (Biocare Medical) in citrate buffer (pH 6.0) at 99° C. for 18 min. (a) Brightfield: Slides were incubated in 3% hydrogen peroxide, then normal serum and BSA at room temperature for 20 min. After incubation with primary antibody [DCAMKL-1 C-terminal (Abcam), anti-c-Myc (Santa Cruz Biotechnologies), L-FABP (Santa Cruz Biotechnologies)], the slides were incubated in peroxidase-conjugated EnVision™+polymer detection kit (DAKO). Slides were developed with Diaminobenzidine (Sigma). (b) Fluorescence: Slides were first incubated in Image-iT FX signal enhancer (Invitrogen), followed by normal serum and BSA at room temperature for 20 min. After incubation with primary antibody [L-FABP (Santa Cruz Biotechnologies)], slides were incubated in appropriate Alexa Fluor® conjugated secondary [488 (green)].

Microscopic Examination. Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon).

Stem cell isolation. Based on protocols developed in intestinal stem cell biology [Dekaney et al., 2005; Grossmann et al., 2003], stem cells were isolated from mouse intestine. The intestine was chopped into small strips, washed and incubated with 1 mM DTT (Sigma) for 30 min at room temperature. It was further incubated with 30 mmol/L EDTA (Sigma) for 10 min at 37° C. The strips were shaken vigorously in fresh HBSS (Cellgro) and filtered through 400 μm mesh (Spectrum Labs) to separate the detached intestinal crypt epithelial cells from the tissue. The filtrate was passed through 80 μm mesh (BD Falcon) to retain the crypts and washed. The crypts were digested at 37° C. to create a single cell suspension.

FACS. The cells isolated from mouse intestine were incubated with 1:100 dilution of Alexa Fluor® 568 (Invitrogen) conjugated DCAMKL-1 antibody (Abcam) for 30 min. The cells were washed twice with HBSS containing 10% serum and sorted using Influx-V cell sorter (Cytopeia). DCAMKL-1 positively and negatively sorted cells were collected and subjected to total mRNA and miRNA isolation. mRNA was reverse transcribed and subjected to real-time RT-PCR for DCAMKL-1. Total miRNA was subjected to real-time RT-PCR for pri-let-7a miRNA.

Xenograft tumor model. (a) Liposomal preparation: siRNA was administered into the xenografts after incorporation into 1,2-Dioleoyl-sn-Glycero-3-Phosphocholine (DOPC) (Avanti Polar Lipids, Alabaster, Ala.). DOPC and siRNA were mixed in the presence of excess tertiary butanol at a ratio of 1:10 (w/w) (siRNA/DOPC). Tween 20 (Sigma-Aldrich) was added to the mixture at a ratio of 1:19 Tween 20:siRNA/DOPC. The mixture was vortexed and frozen in an acetone/dry ice bath and lyophilized. Before administration, the siRNA preparation was reconstituted in 0.9% sterile saline and injected at a dose of 50 μl (5 μM) per injection. (b) Tumor therapy: Female athymic nude mice (NCr-nu) were purchased from the National Cancer Institute-Frederick Cancer Research and Development Center (Frederick, Md.) and housed in specific pathogen-free conditions. They were cared for in accordance with guidelines set forth by the American Association for Accreditation of Laboratory Animal Care and the USPHS "Policy on Human Care and Use of Laboratory Animals," and all studies were approved and supervised by the Institutional Animal Care and Use Committee. HCT116 cells ($6 \times 10^6$) were injected subcutaneously into the flanks of 4-6 week-old female athymic nude mice (5 mice per group). Tumors were measured with calipers and the volume was calculated as (length×width$^2$)×0.5. The tumors reached 1000 mm$^3$ after 15 days of injection of cells. These tumors were injected with 50 μl (5 μM) of siRNA preparation on every third day from day 15 for a total of 5 doses.

Luciferase reporter gene assay. pLet7a-Luc reporter vector contains a let-7a miRNA specific binding site at the 3'UTR of the firefly (*Photinus pyralis*) luciferase gene obtained from Signosis Inc (FIG. 26). HCT116 and SW480 cells were transfected with the pLet7a-Luc reporter vector, Renilla luciferase expressing plasmid pRL-TK (Promega) along with DCAMKL-1 or scrambled siRNA using Transfectol™ (Ambion Inc.). Luciferase activity was determined as per the manufacturer's instructions (Dual-Luciferase Reporter Assay System; Promega) using a Monolight 2010 luminometer (Analytical Luminescence Laboratory, San Diego, Calif.) as described earlier [Stadler et al., 2008; Sossey-Alaoui et al., 1999]. The activity, normalized to Renilla Luciferase activity, is presented as relative luciferase units relative to control with ±SEM values. Assays were performed in triplicate wells and experiments were repeated 3 times.

Statistical analysis. All the experiments were performed in triplicate. The data was analyzed by Student's t-test. Where indicated, the data is presented as mean±SEM. A p value of <0.01 was considered statistically significant.

Results of Example 4

DCAMKL-1 is overexpressed in cancer. To determine whether DCAMKL-1 was expressed in human colorectal cancers, immunohistochemical analysis was performed on human cancer tissue microarrays (Tissue Array Network and National Cancer Institute—Tissue Array Research Program). Staining revealed increased DCAMKL-1 protein (FIG. 27A; brown—indicated by black arrows) in human colorectal cancers specimens, compared to normal colonic mucosa. In tumors, the staining pattern was particularly impressive in the stroma surrounding malignant crypts (brown—indicated by blue arrow heads). Representative images of normal mucosa and two different human colorectal cancer specimens are shown in FIG. 27A. Similarly, DCAMKL-1 expression was observed in a variety of human colon cancer cell lines (FIG. 27B). HCT116 and SW480 cells were transfected with DCAMKL-1 and scrambled siRNA; then total RNA was isolated and subjected to real-time RT-PCR. A >70% reduction in DCAMKL-1 mRNA expression was noted in DCAMKL-1 siRNA (si-DCAMKL-1) treated cells (FIGS. 27C and D). A reduction in DCAMKL-1 protein was also observed following si-DCAMKL-1 transfection (FIGS. 27C and D). Scrambled siRNA (si-Scr) did not affect the expression of DCAMKL-1 mRNA or protein (FIGS. 27C and D).

siRNA mediated knockdown of DCAMKL-1 leads to tumor growth arrest. Given the increased DCAMKL-1 expression in human colorectal tumors (FIG. 27A) and in Apc$^{Min/+}$ adenomas [May et al., 2008], the inventors wanted to determine its role in tumor progression. Tumor xenografts were generated by injecting HCT116 cells ($6 \times 10^6$) subcutaneously into the flanks of athymic nude mice. After 15 days, si-DCAMKL-1 and si-Scr were injected into the xenografts.

Tumor volumes were measured using calipers at various time points before sacrifice and weights were determined after sacrifice [Sureban et al., 2008; Sureban et al., 2008A]. Administration of si-DCAMKL-1 resulted in a statistically significant reduction (p<0.01) in tumor size compared to the control or the si-Scr treated tumors (FIGS. 28A and B). Thus inhibition of DCAMKL-1 arrested HCT116 tumor xenograft growth. Total RNA isolated from these tumors was subjected to real-time RT-PCR and demonstrated a significant downregulation (55%) (p<0.01) of DCAMKL-1 mRNA expression in the si-DCAMKL-1-treated tumors compared to control and si-Scr treated tumors (FIG. 28C). This downregulation was associated with reduced expression of DCAMKL-1 protein in those tumors by Western blot analyses (FIG. 28D).

Knockdown of DCAMKL-1 induces pri-let-7a miRNA. To determine the role of DCAMKL-1 mediated regulation of pri-let-7a miRNA, control and siRNA treated HCT116 tumor xenografts were analyzed for pri-miRNA expression by real-time RT-PCR. Compared to control and si-Scr treated tumors, there was a >3-fold increase in pri-let-7a miRNA expression in DCAMKL-1 siRNA treated tumors (FIG. 29A). Next, the effects of siRNA-mediated knockdown of DCAMKL-1 on pri-let-7a miRNA expression were analyzed in HCT116 and SW480 cells. Real-time RT-PCR analysis revealed a 4-fold increase in pri-let-7a miRNA, compared to controls (FIGS. 29B and C). These data demonstrate that DCAMKL-1 negatively regulates pri-let-7a miRNA in human colon cancer cells.

DCAMKL-1 negatively regulates let-7a miRNA. As stated earlier, lack of let-7 miRNA is an indicator of "stemness" in epithelial progenitor cells [Ibarra et al., 2007; Yu et al., 2007; Stadler et al., 2008]. To determine whether pri-let-7a miRNA was expressed in stem cells, FACS based sorting was utilized to isolate DCAMKL-1 positive and negative cells, which were analyzed for pri-let-7a miRNA. The antibody used for FACS was directed against the c-terminal extracellular domain of DCAMKL-1 [Sossey-Alaoui et al., 1999; Kim et al., 2003] and conjugated to the Alexa Fluor® 568 fluorochrome. Following FACS, both sorted cell populations were examined by fluorescence microscopy. The positively sorted cells demonstrated the presence of DCAMKL-1 antibody staining, whereas the negatively sorted cells did not (FIGS. 30A and B). Furthermore, DCAMKL-1 positive cells did not express L-type fatty acid binding protein (L-FABP), a marker of enterocyte lineage known to be expressed in differentiated intestinal epithelia [Rizvi et al., 2005; Smith et al., 1996], indicating a less differentiated state (FIGS. 30C and E). In contrast, L-FABP was found to be expressed in DCAMKL-1 negative cells (FIGS. 30D and F), indicating that these cells are more differentiated compared to DCAMKL-1 positive cells.

Total miRNA isolated from DCAMKL-1 positive and DCAMKL-1 negative cells were subjected to pri-let-7a miRNA expression by real-time RT-PCR and normalized using pri-U6 miRNA. A 65% reduction in pri-let-7a miRNA was observed in DCAMKL-1 positive sorted "stem" cells relative to DCAMKL-1 negative cells (FIG. 31A). To confirm sorting specificity, total RNA isolated from the cells was subjected to real-time RT-PCR for DCAMKL-1 mRNA expression (FIG. 31B). These data demonstrate that DCAMKL-1 negatively regulates pri-let-7a miRNA in putative intestinal stem/progenitor cells.

To determine quantitatively the effect of siRNA-mediated knockdown of DCAMKL-1 on let-7a miRNA, a luciferase reporter gene assay was performed. HCT116 and SW480 cells were transfected with a plasmid containing firefly luciferase gene with a complementary let-7a binding site at the 3' UTR (FIG. 26). A dose dependent reduction in luciferase activity was observed following the knockdown of DCAMKL-1 (FIGS. 31C and D). This demonstrates that DCAMKL-1 may be a posttranscriptional regulator of let-7a miRNA downstream targets. However, other alternative mechanisms for DCAMKL-1, such as acting as a transcriptional regulator of let-7a or as a posttranscriptional regulator of let-7a maturation, cannot be ruled out.

Knockdown of DCAMKL-1 inhibits c-Myc. HCT116 tumor xenografts were evaluated for expression of the let-7a miRNA downstream oncogenic target c-Myc, following siRNA-mediated knockdown of DCAMKL-1 as described earlier. A 45% reduction in c-Myc mRNA was observed in si-DCAMKL-1 treated tumors compared to controls (FIG. 32A). An even more striking reduction of c-Myc protein was seen by Western blot and immunohistochemical analyses (FIGS. 32B and C) of siDCAMKL-1 treated tumors.

Given the role of Notch signaling in adult stem cell regulation and its implication in tumorigenesis, the effect of siRNA-mediated knockdown of DCAMKL-1 on Notch-1 was investigated. A 55% reduction in Notch-1 mRNA was observed in si-DCAMKL-1 treated tumors compared to controls (FIG. 32A). A marked reduction in Notch-1 and cleaved Notch-1 protein was observed by Western blot analysis (FIG. 32B). Furthermore, immunohistochemical analyses revealed a marked reduction of Notch-1 in si-DCAMKL-1 treated tumors compared to controls (FIG. 32D).

Reduction in c-Myc mRNA and protein was also observed in siDCAMKL-1 treated HCT116 (FIGS. 33A and 33B) and SW480 cells (FIGS. 33C and 33D). A 40% and >50% reduction in Notch-1 mRNA was observed following the knockdown of DCAMKL-1 in HCT116 and SW480 cells, respectively (FIGS. 33A and 33C). A dose dependent reduction in Notch-1 and cleaved Notch-1 protein was also seen by Western blot analysis (FIGS. 33B and 33D). These data demonstrate that knockdown of DCAMKL-1 results in a reduced expression of c-Myc by a let-7a dependent mechanism. Furthermore, siRNA mediated knockdown of DCAMKL-1 inhibits Notch-1 expression.

In order to determine the mechanism by which Notch-1 is inhibited, a computational/bioinformatics (microRNA.org database: a resource for microRNA targets and expression) analysis of the Notch-1 3'UTR was first performed. A predicted binding site for miR-144 was found in the Notch-1 3' UTR (at the 189th base pair) (FIG. 34).

The effects of siRNA-mediated knockdown of DCAMKL-1 on expression of pri-miR-144 miRNA were also analyzed. In SW480 cells, real-time RT-PCR analysis revealed a 3-fold increase in pri-mIR-144 miRNA, compared to controls (FIG. 35). This demonstrates that knockdown of DCAMKL-1 results in a reduced expression of Notch-1, possibly a miR-144 miRNA dependent mechanism in human colon cancer cells. Taken together, these data demonstrate a functional role for the novel putative intestinal stem cell marker DCAMKL-1 on Notch-1, an important regulator of epithelial proliferation and differentiation. Moreover, these data have important implications in stem cell mediated-tumorigenesis.

Human primers used for Real Time RT-PCR are: β-actin: Forward: 5'-GGTGATCCACATCTGCTGGAA-3' (SEQ ID NO:32), Reverse: 5'-ATCATTGCTCCTCCTCAGGG-3' (SEQ ID NO:33); DCAMKL-1: Forward: 5'-AGTCTTC-CGATTCCGAGTTGAG-3' (SEQ ID NO:34), Reverse: 5'-CAGCAACCAGGAATGTATTGGA-3' (SEQ ID NO:35); c-Myc: Forward: 5'-CACACATCAGCACAACTACGCA-3' (SEQ ID NO:36), Reverse: 5'-TTGACCCTCTTGGCAG- CAG-3'(SEQ ID NO:37); Notch-1: Forward: 5'-CGGGTC-CACCAGTTTGAATG-3' (SEQ ID NO:38), Reverse: 5'-GTTGTATTGGTTCGGCACCAT-3' (SEQ ID NO:39).

Knockdown of DCAMKL-1 inhibits c-Myc and Notch and induces let-7a miRNA in Pancreatic Cancer. The effect of a siRNA-mediated knockdown of DCAMKL-1 on c-Myc and Notch expression was investigated in the human pancreatic adenocarcinoma cell line AsPC-1. Similar to the colorectal cancer cell line HCT116, there was a significant and a dose dependent downregulation of the oncogene c-Myc and Notch-1 following the knockdown of DCAMKL-1. Furthermore, a significant 3 fold induction of pri-let-7a miRNA was found in these cells following the knockdown of DCAMKL-1 (FIG. 36). These data taken together demonstrate that DCAMKL-1 may play an important role in pancreatic cancer tumorigenesis.

Discussion of Example 4 miRNAs play important gene-regulatory roles by pairing to the mRNAs of protein-coding genes to direct their post-transcriptional repression [Kumar et al., 2007]. The involvement of miRNAs in human cancer has been recently described [Calin et al., 2006], with several reports indicating that miRNAs might be used as future diagnostic and therapeutic targets [Tricoli et al., 2007]. Furthermore, characteristic miRNA expression signatures in various cancers that can profoundly affect cancer cell behavior have been reported [Calin et al., 2006]. miRNAs have been shown to play an important role in regulating stem cell self-renewal and differentiation by repressing the translation of selected mRNAs in stem cells and differentiating daughter cells. Let-7a is a tumor suppressor miRNA that is blocked posttranscriptionally in ES cells and in several human cancers [Thomson et al., 2006; Calin et al., 2006; Suh et al., 2004]. The regulatory factors that control miRNA expression, maturation and function in adult stem cells and cancers are just beginning to be explored.

This Example demonstrates that the novel putative intestinal stem cell marker DCAMKL-1 is a negative regulator of let-7a miRNA expression/function. Here it is demonstrated that DCAMKL-1 expression is increased in human colorectal cancers compared to normal uninvolved tissues. This is the first demonstration of DCAMKL-1 in human colorectal cancer. In addition to the increased epithelial expression of DCAMKL-1 seen within the colorectal tumors examined, strong staining was also observed in the stroma surrounding malignant crypts. Given the importance of epithelial-mesenchymal cell interactions in cancer [Arias, 2001] and the role of the niche in epithelial stem cell fate [Rizvi et al., 2005], it is speculated that stromal DCAMKL-1 may participate in tumor progression.

Using a tumor xenograft model generated from HCT116 human colorectal cancer cells, near complete tumor growth arrest was demonstrated following siRNA-mediated knockdown of DCAMKL-1. These data strongly implicate a functional role for DCAMKL-1 in the regulation of tumor growth. Given the potential roles of let-7a miRNA in the regulation of gene expression in stem cells and cancer, the tumor xenografts were assayed for pri-let-7a miRNA expression. A significant increase in pri-let-7a miRNA was found in the tumors following siRNA-mediated inhibition of DCAMKL-1. These data confirm that pri-let-7a miRNA is indeed a tumor suppressor miRNA, which is regulated by DCAMKL-1 in colorectal cancer cells.

Cellular transformation and tumorigenesis are driven by activation of oncogenes and/or inactivation of tumor suppressors. Oncogenic c-Myc overexpression is observed in many cancers along with enhanced cell proliferation [Smith et al., 1996]. Furthermore, transcripts encoding both c-Myc and Kras are known to contain target sites for the let-7 miRNA in their 3' UTR [Kumar et al., 2007]. Such findings led us to speculate that DCAMKL-1 may affect c-Myc expression in colon cancer via a let-7a dependent mechanism. Indeed, a 45% reduction in c-Myc mRNA was found, as well as a significant decrease in protein levels in the tumors following the inhibition of DCAMKL-1. These findings were confirmed in vitro in human colorectal cancer cell lines where knockdown of DCAMKL-1 resulted in increased pri-let-7a miRNA, which corresponded with a significant reduction of c-Myc. These data taken together strongly suggests that DCAMKL-1 negatively regulates the tumor suppressor miRNA let-7a resulting in reduced expression of its downstream target oncogene c-Myc.

In order to determine the effects of DCAMKL-1 knockdown on let-7a miRNA-dependent gene silencing of let-7a downstream targets, a luciferase gene reporter assay containing a specific let-7a miRNA binding site at its 3'UTR was performed. A significant dose-dependent reduction in luciferase activity was found following knockdown of DCAMKL-1. This provides an explanation and mechanism where inhibition of DCAMKL-1 results in decreased c-Myc and possibly other let-7a downstream targets.

In this Example, it has been demonstrated that DCAMKL-1, a protein expressed in both normal stem cells and in cancer, likely promotes tumorigenesis through the regulation of pri-let-7a miRNA and c-Myc. The presence of let-7a binding sites in the c-Myc 3'UTR leads us to speculate that DCAMKL-1 is regulating c-Myc posttranscriptionally. However, other alternatives cannot be ruled out, such as direct transcriptional regulation. Nevertheless, the knockdown of DCAMKL-1 resulted in a marked reduction in c-Myc mRNA and protein in vitro and in vivo. Moreover, several other oncogenes contain let-7a binding sites in their 3'UTRs, thus it is quite possible that DCAMKL-1 may have similar effects on other oncogenic targets including Kras.

miRNAs are known to contribute to the preservation of 'sternness' and associated with self-renewal and differentiation in ES cells [Shcherbata et al., 2006]. Previous studies have also shown an overall reduction in miRNA expression in embryonic and tissue stem cells [Croce et al., 2005]. Intestinal epithelial cells were analyzed following FACS based sorting using DCAMKL-1 for pri-let-7a miRNA. A marked reduction in pri-let-7a miRNA was observed in DCAMKL-1 positively sorted "stem" cells relative to DCAMKL-1 negative cells. These data demonstrate that intestinal stem cells, like ES cells, express low levels of let-7a.

The findings presented in this Example demonstrate that regulation of miRNAs represent an exciting new strategy to combat tumorigenesis, particularly in cancers originating from cancer stem cells.

EXAMPLE 5

RBM3 is a novel proto-oncogene. It has been reported in parent application Ser. No. 12/386,550 (previously incorporated herein by reference) that the RNA binding protein RBM3 is upregulated in a wide variety of solid tumors, including but not limited to, colorectal cancers. The parent application also discloses that high levels of immunoreactive RBM3 were also observed in pancreatic, breast, lung, ovary and prostate cancers.

Overexpression of RBM3 induces a transformation phenotype: To confirm the proto-oncogenic properties of RBM3, growth studies in soft agar were performed. Originally, three different cell lines were chosen for these studies: a mouse NIH-3T3 fibroblast cell line, and two human breast cell lines where RBM3 was stably overexpressed (MCF10A and 184B5). All three cell lines were transformed and formed tight, densely packed compact multicellular spheroids where single cells could not be discriminated. In contrast, cells transfected with vector alone did not form colonies in soft agar. The results with NIH-3T3 cells are shown in FIG. 37. These studies demonstrate that RBM3 is a proto-oncogene when overexpressed. Further studies shown below demonstrate that overexpression of the RBM3 proto-oncogene results in an aggressive tumor phenotype.

RBM3 overexpressing NIH-3T3 cells develop tumors in immunocompromised mice: To determine if RBM3 overexpression causes tumors, a xenograft study was performed. $1 \times 10^5$ cells were injected into the flanks of nude mice and monitored for three weeks. Large tumors developed in all mice (FIG. 38). Pathologic analysis of the tumors by Dr. Stan Lightfoot, (staff pathologist at the University of Oklahoma Health Sciences Center) confirmed that the tumors consisted of both malignant epithelial and malignant stromal cells. Furthermore, tissue sections demonstrated high levels of COX-2 and VEGF expression (FIG. 39). Similar results were obtained with MCF10A breast epithelial cells and IEC6 colon epithelial cells following RBM3 overexpression.

Increased expression of DCAMKL-1 in RBM3-tumors: To determine the effect of RBM3 on DCAMKL-1 expression, total RNA was isolated from NIH-3T3 cells following RBM3 transfection, and Real Time RT-PCR was performed. DCAMKL-1 mRNA levels were markedly increased in NIH-3T3 cells and in spheroids following overexpression of RBM3. Moreover, there was a significant increase in DCAMKL-1 expression in tumors (FIG. 40). Confirmation that the DCAMKL-1 protein levels were high was obtained by immunohistochemistry and western blot analysis (FIG. 41). These data strongly suggest that introduction of RBM3 into a fibroblast cell line results in the cells taking on cancer stem cell epithelial characteristics.

RBM3 knockdown blocks tumor growth: Since RBM3 is overexpressed in cancers, the effect of RBM3 downregulation on the growth of HCT116 tumor cell xenografts was next determined in nude mice. After the tumors were allowed to develop (15 days), siRNA was injected in a liposome preparation. Tumors that received RBM3-specific siRNA were arrested in growth. RBM3 silencing in the tumors was confirmed by Real Time PCR and immunohistochemistry analyses. These studies have been repeated using siRNA to DCAMKL-1, and a similar reduction in xenograft growth was observed as described earlier (FIG. 28). Taken together using a siRNA mediated intra-tumor delivery system, tumor growth arrest was achieved. Thus targeting a stem cell specific protein and a proto-oncogene independently resulted in a near complete cessation of tumor growth.

DCAMKL-1 sorted cells. Given the expression of DCAMKL-1 in the tumors, single cell suspensions of the tumor were prepared and subjected to flow cytometry to isolate DCAMKL-1 positive (cancer stem cells). Flow cytometric sorting identified cells which were positive for DCAMKL-1 (FIG. 42A). Furthermore, while less than 0.3% of the NIH-3T3 cells were positive for DCAMKL-1, ~40% NIH-3T3-RBM3 cells in the tumor were DCAMKL-1 positive cells. While less than 0.3% of the NIH-3T3 cells were positive for DCAMKL-1, approximately 40% of the NIH-3T3-RBM3 cells in the tumor were DCAMKL-1 positive cells. In addition, a minor portion of these cells were positive for CD133, a five-transmembrane domain glycoprotein and a cell surface protein originally found on neuroepithelial stem cells. Only 5% of the brightest DCAMKL-1 positive cells were collected and allowed to grow in tissue culture dishes. Cells overexpressing DCAMKL-1 both before and after tumor formation in mice were observed to develop neurite outgrowth-like structures in culture (FIG. 42C). Furthermore, these cells expressed high levels of notch protein (FIG. 42B).

Notch signaling has been implicated in the regulation of cell-fate decisions such as self-renewal of adult stem cells and differentiation of progenitor cells along a particular lineage. Furthermore, Notch signaling has been previously demonstrated to promote self renewal of mammary stem cells. These data taken together imply that overexpression of RBM3 may result in dedifferentiation of NIH3T3 cells into cancer stem cells which overexpress Notch and DCAMKL-1. Additional studies presented below demonstrate that the DCAMKL-1 positive cells are potent inducers of tumor formation and metastasis, further demonstrating that they are cancer stem cells and have an aggressive phenotype. Creation of a cancer stem cell model with the capability of inducing rapidly progressive and ultimately metastatic tumors has profound implication in the study of cancer biology, particularly in cancer stem cells. The ability to study and perhaps regulate epithelial to mesenchymal transition, which is a poor prognostic feature of many cancers, is a remarkably added benefit of this tool. Furthermore, the potential of culturing and characterizing the cell line derived from the combined xenograft and FACS based sorting system allows for the development of in vitro assays to better study the response of these cells to therapy.

Curcumin derivative EF24 is a potent inhibitor of colon cancer growth: Curcumin's anti-tumor properties include cancer growth inhibition and apoptosis induction in a variety of cultured cancer cell lines in vitro. Additionally, curcumin has demonstrated the ability to inhibit tumorigenesis in vivo. However, due to poor intestinal absorption characteristics and lack of water-solubility, a synthetic compound 3,5-bis(2-fluorobenzylidene)piperidin-4-one (EF24) was generated. EF24 significantly inhibited growth tumor xenograft growth via induction of apoptosis, thus demonstrating that EF24 is a potent inducer of CSC death. The findings of EF24 efficacy in HCT 116-induced tumor xenograft growth are similar to the above-described findings of siRNA specific knockdown of DCAMKL-1, Msi-1 and RBM3. Therefore, it was evaluated whether these compounds would target PICSCs.

Standard chemotherapeutic drugs do not affect CSC growth: Although chemotherapy kills most cells in a tumor, currently it is proposed that CSCs display are relatively resistant to conventional chemotherapeutic agents. The PICSCs cells were treated with 100 µM drug (suprapharmacological dose) for 48 hours, and their growth and survival were evaluated. In spite of the high doses administered, both CPT-11 and Erbitux had no significant effect on the cells (FIG. 43). On the other hand, treatment with 30 µM curcumin, 1 µM EF24 (FIG. 43), transfection of siRBM3 (10 nM) (FIG. 43) and siDCAMKL-1 (10 nM) (FIG. 44) inhibited neurite formation, suppressed cell growth and induced cell death. These data taken together provides the rationale for use of these assays to specifically determine the effects of novel compounds and derivatives in vitro. Moreover, the in vitro testing strategies allows for a mechanistic study of such compounds.

In vivo cancer stem cell model: As described above, RDC-SCs were obtained from tumor xenograft specimens from mice that were injected with NIH3T3 cells transfected with the novel proto-oncogene RBM3 followed by DCAMKL-1 based FACS. Mice developed significant tumors by 4 weeks after subcutaneous injection of $1 \times 10^5$ cells. Moreover these mice developed rapid metastasis, as determined by histologic evaluation of multiple distant sites (FIG. 45). FACS analysis using DCAMKL-1 yielded an extraordinary high percentage of cells (35.39%) that were positive for DCAMKL-1. These data demonstrate that within this particular xenograft tumor, DCAMKL-1 expressing cells are highly represented.

To determine whether targeted DCAMKL-1 downregulation and/or Notch inhibition affected PICSCSTM generated isograft tumor growth, mice were treated with siRNA to DCAMKL-1 or the Notch inhibitor DAPT. After the tumors were allowed to develop (15 days), siRNA was injected a total of 5 times at an interval of 3 days as described earlier. Tumors that received either liposome preparation without any siRNA or those that included the scrambled siRNA continued to grow, with tumor volumes reaching $4 \times 10^3$ mm$^3$ and $6 \times 10^3$ mm$^3$, respectively (FIG. 46). On the other hand, tumors that received DCAMKL-1 specific siRNA exhibited growth arrest. Similar results were obtained following RBM3 silencing in the tumors, which was confirmed by Real Time PCR and immunohistochemistry analyses. These studies demonstrate that siRNA to DCAMKL-1 and RBM3 reduces xenograft growth induced by traditional HCT-116 cancer xenografts and in the novel RDCSC generated cancer stem cell isografts models. Furthermore, the Notch inhibitor DAPT and curcumin derivative EF24 each have potent anti-CSC growth properties, suggesting a likely role for the Notch pathway in CSC-mediated tumorigenesis. Moreover, these studies for the first time implicate a single proto-oncogene in the dedifferentiation of a fibroblast cell line into a multipotent neoplastic CSC directly in mouse models.

Mouse pancreatic cancer model: The endogenous pancreatic cancer mouse model P48$^{cre}$-LSL-KRAS$^{G12D}$ develops PanIN lesions (similar to humans) after 10 weeks, and 9 months, 70-85% of carcinoma has developed with metastasis (Rao et al., AACR 100$^{th}$ Annual Meeting, 2009). The mouse models P48$^{Cre}$ and LSL-KRAS$^{G12D}$ were originally developed in a 129V genetic background, and later this model was crossed with C57BL/6 background for more than ten generations. When compared to 129V, the mutant mouse with C57BL/6 genetic background developed more aggressive pancreatic lesions (Mice were obtained from Dr. C. V. Rao). Pancreatic tissues from 10-month-old P48$^{cre}$-LSL-KRAS$^{G12D}$ were immunostained for DCAMKL-1. An increase in ductal expression of DCAMKL-1 was observed in the PanIN lesions of the P48$^{cre}$-LSL-KRAS$^{G12D}$ pancreatic cancer mouse model that correlated with progressive neoplastic changes (FIG. 47A-F). These data demonstrate that DCAMKL-1 upregulation following mutant KRAS mediated tumorigenesis may represent a marker of neoplastic transformation.

EXAMPLE 6

This Example demonstrates that DCAMKL-1 is expressed in a subset of cells in human pancreatic tumors. 14-3-3σ was observed in the cytoplasm and rarely in the nucleus of tumor epithelial cells in human pancreatic cancer patients. Interestingly, co-expression of DCAMKL-1 and 14-3-3 σ was observed in tumors. Moreover, this example demonstrates DCAMKL-1 staining in the surface epithelium of pancreatic intraepithelial neoplasia (PanIN) type lesions and in the intervening stroma in human pancreatic adenocarcinoma. Knockdown of DCAMKL-1 in pancreatic cancer cells resulted in down regulation of Snail, Slug and Twist and induction of microRNA miR-200a, which inhibits EMT. Furthermore, knockdown of DCAMKL-1 also resulted in downregulation of the proto-oncogenes c-Myc and KRAS via up regulation of pri-let-7a and inhibition of Notch-1 via miR-144 miRNA dependent mechanisms. These data taken together identify DCAMKL-1 as a novel pancreatic cancer stem cell marker that can potentially be targeted for pancreatic cancer tumor eradication.

Materials and Methods of Example 6

Experimental animals: 6-8 weeks old athymic nude mice (NCr-nu) (NCI-Frederick) and P48$^{Cre}$-LSL-KRAS$^{G12D}$ and wild type littermate (obtained from Dr. Rao) were used. Mice were housed under controlled conditions, including a 12 h light/dark cycle, with ad libitum access to diet and water. All experiments were performed in accordance with the University's Institutional Review Board (IRB).

Tissue procurement: The human pancreatic adenocarcinoma tissues were derived from patients undergoing a surgical resection of the pancreas at the University of Oklahoma Health Sciences Center and confirmed to the policies and practices of the University's IRB (protocol number 04586). In total, histologically normal appearing human pancreatic tissues (n=3) and human pancreatic Adenocarcinoma (n=10) were utilized for this study.

Immunohistochemistry: Heat Induced Epitope Retrieval was performed on formalin-fixed paraffin-embedded sections utilizing a pressurized Decloaking Chamber (Biocare Medical—Concord, Calif.) in citrate buffer (pH 6.0) at 99° C. for 18 minutes. (a) Brightfield: Slides were incubated in 3% hydrogen peroxide, then normal serum and BSA at room temperature for 20 min. After incubation with primary antibody [DCAMKL-1 (rabbit), 14-3-3 s (rabbit) (IBL—Japan), vimentin (rabbit) (Santa Cruz Biotechnology—Santa Cruz, Calif.)] the slides were incubated either in polymer-HRP secondary (DAKO—Glostrup, Denmark) for rabbit derived or Goat Polymer Detection Kit (Biocare Medical) for goat derived antibodies as appropriate. Slides were developed with Diaminobenzidine (Sigma—St. Louis, Mo.). Tyramine signal amplification for NGN3 in adult mouse tissues was performed as per manufacturer's instructions (Invitrogen—Carlsbad, Calif.). (b) Fluorescence: Slides were first incubated in Image-iT FX signal enhancer (Invitrogen), followed by normal serum and BSA at room temperature for 20 minutes. After incubation with primary antibody [vimentin (rabbit), Snail (rabbit) or Slug (mouse) (Santa Cruz Biotechnology—Santa Cruz, Calif.)] overnight at 4° C., slides were incubated in appropriate anti-mouse/rabbit ALEXA FLUOR® conjugated secondary as appropriate [488 (green) and 568 (red) (Invitrogen)].

Microscopic examination: Slides were examined utilizing the Nikon 80i microscope and DXM1200C camera for brightfield. Fluorescent images were taken with PlanFluoro objectives, utilizing CoolSnap ES2 camera (Photometrics). Images were captured utilizing NIS-Elements software (Nikon).

Scoring: Senior Pathologist Dr. Stan Lightfoot, University of Oklahoma Health Sciences Center, performed scoring of all the immunostained slides. The scoring (DCAMKL-1 and 14-3-3σ staining) was carried out based on two different parameters: 1) staining intensity and 2) amount of tissue involved. The intensity was measured and scored from 0-3, no staining=0, weak staining=1, moderate staining=2 and strong staining=3. The amount of tissue involved was measured scored from 0-4, no tissue involved (0%)=0, <10% involved=1, 10%-50% involved=2, 51%-80% involved=3 and >80% involved=4. Finally, the intensity score was multiplied by tissue involvement score to obtain composite score (e.g. 3×4=12) (24).

Cell Culture: AsPC-1 and BxPC3 human pancreatic adenocarcinoma cell lines were obtained from the American Type Culture Collection and grown in Dulbecco's modified Eagle medium (DMEM) supplemented with 10% fetal bovine serum and 100 U/mL penicillin-streptomycin in a humidified chamber at 37° C. with 5% $CO_2$.

Silencer RNA: DCAMKL-1 small interfering RNA (siRNA) (si-DCAMKL-1) sequence targeting the coding region of DCAMKL-1 (accession No. NM_004734; SEQ ID NO:1) (GGGAGUGAGAACAAUCUACtt (SEQ ID NO:3)) and scrambled siRNAs (si-Scr) not matching any of the human genes were obtained (Ambion Inc, Austin, Tex.) and transfected using siPORT™ NeoFX™ (Ambion, Inc).

Real-time Reverse Transcription-Polymerase Chain Reaction Analyses: Total RNA isolated from human pancreatic cancer cells or cells sorted from normal mouse pancreas were subjected to reverse transcription with Superscript II RNase H-Reverse Transcriptase and random hexanucleotide primers (Invitrogen, Carlsbad, Calif.). The complementary DNA (cDNA) was subsequently used to perform real-time polymerase chain reaction (PCR) by SYBR chemistry (SYBR Green I; Molecular Probes, Eugene, Oreg.) for specific transcripts using gene specific primers and Jumpstart Taq DNA polymerase (Sigma—Aldrich, St. Louis, Mo.). The crossing threshold value assessed by real-time PCR was noted for the transcripts and normalized with β-actin messenger RNA (mRNA). The changes in mRNA were expressed as fold change relative to control with ±SEM value.

Human primers used are as follows: β-actin: forward: 5'-GGTGATCCACATCTGCTGGAA-3' (SEQ ID NO:16), reverse: 5'-ATCATTGCTCCTCCTCAGGG-3' (SEQ ID NO:17); DCAMKL-1: forward: 5'-AGTCTTCCGATTC-CGAGTTGAG-3' (SEQ ID NO:6), reverse: 5'-CAGCAAC-CAGGAATGTATTGGA-3' (SEQ ID NO:7); ZEB1: forward: 5'-AAGAATTCACAGTGGAG AGAAGCCA-3' (SEQ ID NO:40), reverse: 5'-CGTTTCTTGCAGTTTGGGCATT-3' (SEQ ID NO:41); ZEB2: forward: 5'-AGCCGATCATG-GCGGATGC-3' (SEQ ID NO:42), reverse: 5'-TTCCTCC TGCTGGGATTGGCTTG-3' (SEQ ID NO:43); E-cadherin: forward: 5'-CCTCCCATCAGCTGCCC-3' (SEQ ID NO:44), reverse: 5'-GTGATGCTGTAGAAAACCTT-3' (SEQ ID NO:45); Snail: forward: 5'-AAGGCCTTCTCTAGGCCCT-3' (SEQ ID NO:46), reverse: 5'-CGCAGGTTGGAGCGGT-CAG-3' (SEQ ID NO:47); Slug: forward: 5'-TGCTTCAAG-GACACATTA-3' (SEQ ID NO:48), reverse: 5'-CAGTGGTATTTCTTTAC-3' (SEQ ID NO:49); Twist: forward: 5'-GTCTGGAGGATGGAGGG-3' (SEQ ID NO:50), reverse: 5'-TCCTTCTCTGGAAACAATGAC-3' (SEQ ID NO:51); c-Myc: forward: 5'-CACACATCAGCA-CAACTACGCA-3' (SEQ ID NO:52), reverse: 5'-TTGAC-CCTCTTGGCAGCAG-3' (SEQ ID NO:53); KRAS: forward: 5'-GACGATACAGCTAATTCAG-3' (SEQ ID NO:54), reverse: 5'-AGACAGGTTTCTCCATC-3' (SEQ ID NO:55); Notch-1: forward: 5'-CGGGTCCACCAGTTTGAATG-3' (SEQ ID NO:38), reverse: 5'-GTTGTATTGGTTCGGCAC-CAT-3' (SEQ ID NO:39);

Mouse primers used are: β-actin: Forward: 5'-GGTGATC-CACATCTGCTGGAA-3' (SEQ ID NO:56), Reverse: 5'-AT-CATTGCTCCTCCTCAGGG-3' (SEQ ID NO:57); DCAMKL-1: Forward: 5'-CAGCCTGGACGAGCTG-GTGG-3' (SEQ ID NO:58), Reverse: 5'-TGACCAGT-TGGGGTTCACAT-3' (SEQ ID NO:59).

miRNA Analysis: total RNA isolated from human pancreatic cancer cell lines or cells sorted from normal mouse pancreas was subjected to reverse transcription with Superscript II RNase H-Reverse Transcriptase and random hexanucleotide primers (Invitrogen). The cDNA was subsequently used to perform real-time PCR by SYBR chemistry (SYBR Green I; Molecular Probes) for pri-let-7a, pri-miR-144 and pri-miR-200a transcripts using specific primers and Jumpstart Taq DNA polymerase (Sigma—Aldrich). The crossing threshold value assessed by real-time PCR was noted for pri-let-7a, pri-miR-144, pri-miR-200a miRNAs and normalized with U6 pri-miRNA. The changes in pri-miRNA were expressed as fold change relative to control with ±SEM values.

Primers used are as follows: pri-U6: forward: 5'-CTCGCT-TCGGCAGCACA-3' (SEQ ID NO:12), reverse: 5'-AACGCTTCACGAATTTGCGT-3' (SEQ ID NO:13); pri-let-7a: forward: 5'-GAGGTAGTAGGTTGTATAGTTTA-GAA-3' (SEQ ID NO:14), reverse: 5'-AAAGCTAGGAG-GCTGTACA-3' ID NO:15); pri-miR-144: forward: 5'-GCTGGGATATCATCATATACTG-3' (SEQ ID NO:60), reverse: 5'-CGGACTAGTACATCATCTATACTG-3' (SEQ ID NO:61); pri-miR-200a: forward: 5'-TTCCACAGCAGC-CCCTG-3' (SEQ ID NO:62), reverse: 5'-GATGTGCCTCG-GTGGTGT-3' (SEQ ID NO:63).

Luciferase Reporter Gene Assay: pLet7a-Luc reporter vector contains a let-7a miRNA specific binding site at the 3' UTR of the firefly (*Photinus pyralis*) luciferase gene, pMiR-144-Luc reporter vector containing miR-144 miRNA specific binding site at the 3'UTR of the firefly luciferase gene and KRAS-Luc reporter vector containing specific binding sites for let-7 family members at the 3'UTR of the firefly luciferase gene were obtained from Signosis, Inc. (Sunnyvale, Calif.). Human pancreatic cancer cell lines were transfected with the pLet7a-Luc, pMiR-144-Luc and KRAS-Luc reporter vectors separately with Renilla luciferase expressing plasmid pRL-TK (Promega) along with DCAMKL-1, or scrambled siRNA-using siPORT™ NeoFX™ transfection reagent (Ambion, Inc.). Luciferase activity was determined as per the manufacturer's instructions (Dual Luciferase Reporter Assay System; Promega) using a BioTek Synergy HT (Winooski, Vt.) as described herein above. The activity, normalized to Renilla luciferase activity, is presented as relative luciferase units relative to control with ±SEM values. Assays were performed in triplicate wells, and experiments were repeated 3 times.

Stem/progenitor cell isolation from mouse pancreas: DCAMKL-1+ stem/progenitor cells were isolated from mouse pancreas as described herein above. The pancreas and associated duct were rapidly dissected and perfused with 3 ml of cold HBSS containing 1 mg/ml collagenase XI (Sigma Aldrich) and 1 mg/ml BSA (Sigma Aldrich). The pancreatic tissues were minced and incubated in HBSS for 13 minutes at 37° C. Digestion was stopped with cold HBSS (Cellgro) containing 10% serum. The solution was shaken by hand for 1 minute, washed 3 times with serum free HBSS and filtered through 400 µM mesh (Spectrum). The cells obtained were incubated with trypsin (Cellgro) at 37° C., pipetted to create a single cell suspension and subjected to FACS based on cell surface expression of DCAMKL-1.

FACS sorting: The single cell suspension was incubated with 1:100 dilution of ALEXA FLUOR® 568 conjugated DCAMKL-1 antibody targeting the C-terminal extracellular domain for 25 minUTES and washed twice with HBSS containing 1% BSA (Sigma Aldrich). The cells were sorted using Influx-V cell sorter (Cytopeia), and collected cells were subjected to RNA analysis by real-time RT-PCR.

Statistical Analysis: All experiments were performed in triplicate. The data were analyzed by Student's t test. Where indicated, the data are presented as mean±SEM. A 'p' value of <0.01 was considered statistically significant.

Results of Example 6

DCAMKL-1 is expressed in the P48$^{Cre}$-LSL-KRAS$^{G12D}$ mouse pancreatic cancer model. The P48$^{Cre}$-LSL-KRAS$^{G12D}$ is a mouse model of pancreatic cancer that was initially developed by the Tyler Jacks laboratory (Jackson et al., (2001) Genes Dev 15:3243-8). P48$^{Cre}$-LSL-KRAS$^{G12D}$ mouse model was originally developed on the 129V genetic background and later this model was backcrossed with C57BL/6 mice for more than fifteen generations. When compared to 129V, the mutant mouse on the C57BL/6 genetic background develops more aggressive pancreatic lesions. These mice exhibit PanIN lesions after 10 weeks. Furthermore, these mice develop pancreatic adenocarcinomas with metastasis by 32 weeks. Pancreatic tissues from 5-month-old P48$^{Cre}$-LSL-KRAS$^{G12D}$ and their wild-type (WT) littermates were immunostained for DCAMKL-1. A marked increase in ductal immunoreactivity and a unique expansion of islet DCAMKL-1 was found in the P48$^{Cre}$-LSL-KRAS$^{G12D}$ pancreatic cancer mouse model that correlated with progressive neoplastic changes (FIG. 48A-D). Previously, using DNA micro arrays, several groups have demonstrated increased 14-3-3σ mRNA expression in pancreatic ductal adenocarcinoma compared to normal pancreas. Similarly, 14-3-3σ protein nuclear localization has been described in pancreatic cancer. This Example found several DCAMKL-1+ cells within the PanIN's that also expressed nuclear 14-3-3σ (FIG. 48E). Magnified images of this co-localization are shown in the FIGS. 48F and 48G. These data demonstrate that DCAMKL-1 is upregulated in pancreas of P48$^{Cre}$-LSL-KRAS$^{G12D}$ mouse and may play an important role in mutated KRAS mediated tumorigenesis.

DCAMKL-1 in human pancreatic cancer: DCAMKL-1 immunoreactivity was examined in human pancreatic adenocarcinoma by immunohistochemical analysis. Samples were obtained from patients undergoing surgical resection of pancreatic cancer provided by Dr. Russell Postier (Dept. of Surgery, The University of Oklahoma Health Sciences Center). Tumors demonstrated strong DCAMKL-1 protein localization. However, within the histologically normal appearing resection specimens, DCAMKL-1 was observed within islets but not in the intervening stromal cells or ducts (FIG. 49A, top left and FIG. 50). Within a neoplastic focus of the tumor resection specimen, however, intense spindle-shaped cytoplasmic staining of DCAMKL-1 was evident (FIG. 49A, top right). DCAMKL-1 immunoreactivity in ductal epithelial cells within the tumor (FIG. 49A, bottom left) and in intervening stromal elements was also observed (FIG. 49A, bottom right).

14-3-3σ co-localizes with DCAMKL-1 in human pancreatic cancer: In normal appearing pancreatic tissue, cytoplasmic staining was observed for 14-3-3σ and DCAMKL-1 at the islet periphery, albeit in distinctly separate cells. No ducts expressing 14-3-3σ were observed in that particular specimen (FIG. 49B, left and right). Next, primary tumor specimens obtained from another patient with pancreatic ductal adenocarcinoma were immunostained. While strong cytoplasmic immunostaining was observed for 14-3-3σ (a marker of advanced PanIN lesions) in ductal epithelial cells, cells with nuclear localized 14-3-3σ were also observed within tumor islet formations, similar to the above observation in the mouse pancreatic cancer model. Moreover, several of these nuclear 14-3-3σ expressing cells also co-expressed DCAMKL-1 (FIG. 49C, left and right), demonstrating that nuclear translocation of 14-3-3σ may occur in putative pancreatic cancer stem cells. DCAMKL-1 protein was also observed in PanIN type lesions (FIG. 49D, left). Additionally, strong cytoplasmic 14-3-3σ and DCAMKL-1 co-staining was observed within these lesions (FIG. 49D, right). These data strongly support a role for 14-3-3σ and DCAMKL-1 in the progression of pancreatic cancer and co-localization of nuclear 14-3-3σ and DCAMKL-1 as a putative marker of pancreatic CSCs.

DCAMKL-1 co-localizes with vimentin in the stroma of human pancreatic adenocarcinoma. Initially, DCAMKL-1+ staining was observed in elongated cells in the surface epithelium of PanIN lesions (FIG. 51A, left). Further characterization of these cells using vimentin, as a marker of mesenchymal lineage, demonstrated that vimentin immunoreactive cells appeared morphologically similar to DCAMKL-1 positive cells (FIG. 51A, right). When double-labeled immunofluorescence was performed, co-localization of DCAMKL-1 and vimentin within the PanIN lesion was observed (FIG. 51B). As demonstrated earlier (FIG. 49A), fibrillar DCAMKL-1 staining was observed within the stromal/mesenchymal compartment of human pancreatic adenocarcinoma. The stromal nature of these cells was confirmed by vimentin co-localization (FIGS. 51, C and D). These data taken together demonstrate that DCAMKL-1 may be involved in the desmoplastic reaction associated with human pancreatic cancer and may also play a role in EMT.

DCAMKL-1 is involved in EMT: EMT is a phenotypic conversion that facilitates organ morphogenesis and tissue remodeling in embryonic development and wound healing. A similar phenotypic conversion is also detected in fibrotic diseases and neoplasia, and is associated with disease progression and outcome (Turley et al., (2008), Nature clinical practice 5:280-90; and Poste et al., (1982) Invasion & metastasis, 2:137-76). Gene-profiling studies also suggest that mesenchymal gene profiles in tumors are predictive of poor outcome in colorectal, breast and ovarian cancers (Diehn et al., (2006) J Natl Cancer Inst, 98:1755-7; and Polakis (2000) Genes and Development, 14:1837-51).

Recent reports suggest that the downregulation of several miRNAs (miR-200a, miR-200b, miR-200c, miR-141 and miR-429) is an essential feature of EMT (Zhang et al. (2010) Oncogene, 29:937-48). Consequently, induction of these miRNAs results in inhibition of EMT (Xia et al., (2010) Biochem Biophys Res Commun, 391:535-41; and Korpal et al., (2008) J Biol Chem, 283:14910-4). It has previously been demonstrated herein that DCAMKL-1 negatively regulates tumor suppressor miRNA let-7a. To determine the potential role of DCAMKL-1 in EMT in pancreatic cancer, siRNA-mediated knockdown of DCAMKL-1 was performed, and miRNA expression of several candidate miRNAs known to play a role in EMT was evaluated. One such miRNA, miR-200a, inhibits EMT by repressing the transcription factors ZEB1 and ZEB2 with subsequent rescue of E-cadherin. This Example demonstrates that siRNA-mediated knockdown of DCAMKL-1 results in upregulation of pri-miR-200a (FIG. 52A) and downregulation of ZEB1 and ZEB2 with upregulation of E-cadherin (FIG. 52B) in the AsPC-1 human pancreatic cancer cell line.

The transcription factors Snail and Slug are key regulators of EMT and are expressed in pancreatic cancer but not in normal tissue, suggesting a role in the progression of human pancreatic tumors (34). In this Example, it is demonstrated that DCAMKL-1 co-localizes with Snail (FIG. 52C) and Slug (FIG. 52D) in human pancreatic cancer tissue. Furthermore, DCAMKL-1 knockdown results in the downregulation of Snail, Slug and Twist (FIG. 52E) in AsPC-1 cells. These data taken together demonstrate that knockdown of DCAMKL-1 inhibits EMT via a miR-200a dependent mechanism in human pancreatic cancer.

DCAMKL-1 regulates oncogenic c-Myc and KRAS: It has been demonstrated herein that DCAMKL-1 is a novel putative pancreatic stem/progenitor cell marker in the normal mouse pancreas. Furthermore, it has also been demonstrated herein that DCAMKL-1 negatively regulates let-7a miRNA (a tumor suppressor miRNA) in human colorectal cancer cells. Moreover, let-7a negatively regulates several key oncogenes including c-Myc and KRAS in various solid tumors. To determine whether DCAMKL-1 regulates let-7a miRNA in pancreatic cancer cells, control, scrambled and DCAMKL-1 siRNA-treated human pancreatic cancer cell lines (AsPC-1 and BxPC3) were analyzed for pri-miRNA expression by real-time RT-PCR. Compared to control and siSCR-treated cells, there was a 3-fold increase in pri-let-7a miRNA in DCAMKL-1 siRNA-treated cells (FIGS. 53A and 54A and B). Thus, DCAMKL-1 negatively regulates pri-let-7a miRNA in human pancreatic cancer cells. To determine quantitatively the effect of siRNA-mediated knockdown of DCAMKL-1 on let-7a miRNA, a luciferase reporter gene assay was performed. AsPC-1 cells were transfected with a plasmid containing firefly luciferase gene with a complementary let-7a binding site in the 3' UTR. A dose-dependent reduction in luciferase activity was observed following the knockdown of DCAMKL-1 (FIG. 53B). These data taken together demonstrate that DCAMKL-1 may be a posttranscriptional regulator of let-7a miRNA downstream targets in pancreatic cancer.

It has been demonstrated herein that c-Myc is a key downstream target of let-7a miRNA. To demonstrate this in pancreatic cancer cell line, control, AsPC-1-siSCR and AsPC-1-siDCAMKL-1 cells were analyzed for c-Myc expression by real-time RT-PCR. Compared to control and AsPC-1-siSCR cells, there was a significant ($p<0.01$) 50% reduction of c-Myc mRNA expression AsPC-1-siDCAMKL-1 cells (FIG. 53C).

KRAS is a critical gene that is mutated in many cancers including pancreatic cancer, and several studies have reported that up to 95% of pancreatic cancers contain KRAS mutations. KRAS is another key downstream target of let-7a miRNA. Following knockdown of DCAMKL-1, a 45% reduction in KRAS mRNA expression was observed compared to control or AsPC-1-siSCR cells (FIG. 53D). To determine the mechanism of siRNA-mediated knockdown of DCAMKL-1 on KRAS, a KRAS-Luc reporter vector containing specific binding sites for let-7 family members was transfected within the 3'UTR of the firefly luciferase gene (similar to KRAS 3' UTR). A dose-dependent reduction in luciferase activity was observed following knockdown of DCAMKL-1 (FIG. 53E). Similar results were observed in the BxPC3 human pancreatic cancer cell line (data not shown). These data taken together demonstrate that DCAMKL-1 knockdown results in downregulation of c-Myc and KRAS, two key mediators of tumorigenesis in pancreatic cancer.

DCAMKL-1 regulates Notch-1 in pancreatic cancer via miR-144: Notch signaling is frequently dysregulated in human malignancies. Notch plays a key role in several cellular developmental pathways including proliferation and apoptosis. Upregulated expression of Notch receptors and their ligands has been described in cervical, lung, colon, head and neck, renal carcinoma, acute myeloid, Hodgkins lymphoma, large-cell lymphomas, and pancreatic cancer. Notch signaling is required for initiation and progression of pancreatic ductal adenocarcinoma. Furthermore, inhibition of Notch signaling using a γ-secretase inhibitor (MRK-003) completely inhibited tumor development in Pdx1-Cre; LSL-KRAS$^{G12D}$; p53$^{lox/+}$ mouse model of pancreatic neoplasia. Given the potential roles of Notch signaling in adult stem cell regulation and tumorigenesis, the effect of siRNA-mediated knockdown of DCAMKL-1 on Notch-1 in pancreatic cancer cells was investigated.

A 50% reduction in Notch-1 mRNA in AsPC-1-siDCAMKL-1 cells was observed compared to control AsPC-1 or AsPC-1-siSCR cells (FIG. 55A). Similar results were obtained in BxPC3 cells (FIG. 54C). In order to determine the mechanism by which Notch-1 is inhibited, a computational/bioinformatics (http://www.microrna.org: A resource for microRNA targets and expression) analysis of the Notch-1 3'UTR was first performed. A predicted binding site for miR-144 was found in the Notch-1 3' UTR (at the 189th base pair) (FIG. 55B).

To investigate the role of DCAMKL-1 in the regulation of miR-144 miRNA, control, scrambled and DCAMKL-1 siRNA-treated AsPC-1 cells were analyzed for pri-miR-144 miRNA expression by real-time RT-PCR. Compared to control and AsPC-1-siSCR cells, there was a 2.5-fold increase in pri-miR-144 miRNA expression in AsPC-1-siDCAMKL-1 cells (FIG. 55C). These data demonstrate that DCAMKL-1 negatively regulates pri-miR-144 miRNA in human pancreatic cancer cells. To evaluate these findings quantitatively, a luciferase reporter gene assay was performed using AsPC-1 cells that were transfected with a plasmid containing the firefly luciferase gene with a complementary miR-144 binding site in the 3' UTR. A dose-dependent reduction in luciferase activity was observed following DCAMKL-1 knockdown (FIG. 55D), indicating that DCAMKL-1 may be a posttranscriptional regulator of miR-144 miRNA downstream targets in pancreatic cancer. Taken together, these data strongly suggest that Notch-1 is a downstream target of miR-144 miRNA and that DCAMKL-1 regulates posttranscriptional control of Notch-1.

Discussion of Example 6

Solid tumors are histologically heterogeneous and include tumor cells, stroma, inflammatory infiltrates, and vascular structures. The CSC hypothesis suggests that tumors are initiated and maintained by a minority subpopulation of cells within the tumor that have the capacity to self-renew and to generate the more differentiated, rapidly proliferating cells that make up the bulk of a tumor.

The existence of CSCs has profound implications for cancer biology and therapy due to the likelihood that eradication of CSCs is the critical determinant in achieving a cure. Recent reports have demonstrated that breast and glioblastoma CSCs are radioresistant and may therefore contribute to treatment failures (Bao et al., 2006; and Phillips et al., 2006). The cell surface marker CD133 is widely used for isolating CSCs from various cancers (Ischenko et al., 2010). Additionally, a subpopulation of CD44$^+$CD24$^+$ESA$^+$ cells was identified as putative pancreatic cancer stem cells (Li et al., 2007; and Ischenko et al., 2010). However, in general, most cell surface proteins used for isolation of CSCs serve as purification markers without functional implication (Diehn et al., 2006; and Ischenko et al., 2010). Thus it is critical to demonstrate that isolated cells from any particular cancer tissue have the functional characteristics of CSCs. Currently, this has been most convincingly demonstrated by serial transplantation in animal models (Diehn et al., 2006.

It has previously been demonstrated herein that DCAMKL-1 is upregulated in human colorectal cancers, and that siRNA mediated knockdown of DCAMKL-1 results in tumor growth arrest via let-7a miRNA dependent manner. In this Example, evidence is provided that DCAMKL-1 is upregulated in pancreatic cancer and may also identify pancreatic cancer stem cells. Interestingly, co-expression of DCAMKL-1 and 14-3-3σ, an inhibitor of Bad pro-apoptotic activity, was observed within human pancreatic adenocarcinomas (Subramanian et al., 2001; and Samuel et al., 2001). Co-localization of 14-4-3σ and DCAMKL-1 is significant, as it may represent a target cell within tumors where 14-3-3σ is transcriptionally activated. Distinct DCAMKL-1 immunostaining was also observed in the intervening stroma between epithelial tumor elements, which co-expressed vimentin. These findings were indeed surprising in that DCAMKL-1 was not observed in non-epithelial cells under basal conditions. Next, ductal DCAMKL-1 was evaluated within PanIN lesions. There, several elongated cells that also co-expressed vimentin and DCAMKL-1 were observed, demonstrating that these cells may be of mesenchymal origin. These findings demonstrate that DCAMKL-1 expressing cells may be undergoing EMT. Desmoplasia, the appearance of fibrous, mesenchymal-like tissue in the peritumor stroma, is associated with poor clinical outcome (Poste et al., 1982). Indeed, gene-profiling studies suggest that mesenchymal gene profiles in tumors are predictive of poor clinical outcome. Myofibroblasts have long been thought to be derived from fibroblasts, but recent data has shown that a substantial proportion of these cells is derived from EMT and is associated with tumor progression (Polakis, 2000).

A functional role for DCAMKL-1 in the regulation of let-7a, a key tumor suppressor miRNA in many cancers including colorectal cancer, has previously been demonstrated herein. miRNAs are important regulators of mRNAs at the posttranscriptional level by targeting them for cleavage or translational repression (Bartel, 2004). miRNAs have emerged as important developmental regulators and control critical processes such as cell fate determination and cell death (Bartel, 2004). There is increasing evidence that several miRNAs are mutated or poorly expressed in human cancers and may act as tumor suppressors or oncogenes (McManus, 2003; and Takamizawa et al., 2004). This Example demonstrates that DCAMKL-1 regulates miR-200a, let-7a and miR-144 in the AsPC-1 pancreatic cancer cell line. Each of these miRNAs has been shown to play important roles in several key aspects of tumor initiation and progression. For example, miR-200a inhibits EMT in several cancers by inhibiting transcription factors ZEB1 and ZEB2 (Xia et al., 2010; and Korpa; et al., 2008). Indeed in this Example, knockdown of DCAMKL-1 induces pri-miR-200a, resulting in down regulation of ZEB1, ZEB2, Snail, Slug and Twist in pancreatic cancer cell lines. Additionally let-7a, a tumor suppressor miRNA, has been shown to inhibit several key oncogenes. Following knockdown of DCAMKL-1, a marked increase in let-7a was observed, which resulted in downregulation of proto-oncogenes c-Myc and KRAS in pancreatic cancer cell lines using real-time RT-PCR and luciferase reporter assays. This is similar to the previous reports herein demonstrating that DCAMKL-1 regulates c-Myc via let-7a miRNA in colorectal cancer cells. These data strongly support a direct regulatory role for DCAMKL-1 in cancer via miRNA dependent mechanisms. DCAMKL-1 knockdown in AsPC-1 cells resulted in a marked decrease in Notch-1 mRNA (50%), which contains a putative predicted binding site for miR-144 in the 3'UTR. miR-144 is a regulator of embryonic-hemoglobin (-E1), through targeting the 3'-UTR of Krüppel-like factor D gene and positively regulates erythroid differentiation in hematopoietic stem cells. In order to determine whether DCAMKL-1 regulates Notch-1 through a novel microRNA, the expression of miR-144 was evaluated in AsPC-1-siD-CAMKL-1 cells. Here for the first time, it is reported that DCAMKL-1 negatively regulates Notch-1 via a miR-144 dependent mechanism. These data taken together clearly demonstrate a multi-functional role for DCAMKL-1 in regulation of miRNAs that control important genes that contribute to key aspects of tumorigenesis (FIG. 56).

As recently reported, the induction of EMT in human mammary epithelial cells resulted in a "stem-cell-like" phenotype characterized by a CD44$^{high}$ and CD24$^{low}$ cell surface marker expression pattern. Furthermore, these cells formed mamospeheres, colonies in soft agar and tumors in nude mice more aggressively than non-EMT induced cells. These studies demonstrate a direct link between the induction of EMT and the gain of stem-cell-like properties (Mani et al., 2008). These recent findings lend support to EMT in the stem cell population playing a critical role in tumorigenesis. The studies presented here provide strong evidence that DCAMKL-1 may be an important target for therapy to eradicate pancreatic cancer and perhaps other solid tumors.

The Notch signaling pathway is frequently activated in many human cancers. Notch signaling is required for initiation and progression of pancreatic ductal adenocarcinoma. Inhibition of Notch signaling using a γ-secretase inhibitor (MRK-003) completely blocked tumor development in Pdx1-Cre; LSL-KRAS$^{G12D}$; p53$^{lox/+}$ mice. siRNA-mediated knockdown of DCAMKL-1 in human pancreatic cancer cell lines resulted in 50% reduction in Notch-1 mRNA. These data demonstrate that DCAMKL-1 disruption results in inhibition of the Notch-1 pathway, thereby confirming its role as a potential target in anti-cancer strategies.

EXAMPLE 7

Hepatocellular carcinoma (HCC) is the third most common cause of cancer-related death worldwide. Infection of hepatitis C virus (HCV) that causes chronic liver diseases in most patients (>80%) is considered to be a prominent risk factor for the development of HCC. Solid tumors such as HCC are composed of a heterogeneous population of cells with distinct differentiation patterns. A hierarchical model of cancer has gained wide acceptance during recent years because of identification of cancer stem-like cells (CSCs) as 'seed elements' of most of the tumors. Unlike embryonic stem cells, which can differentiate into all cell-types of an animal, the CSCs represent a small fraction of undifferentiated cells within a tumor mass with limited stem cell characteristics and can differentiate only to a few organ-specific cell lineages. These cells are likely to cause recurrence of cancer and resistance to anti-cancer drugs. It is widely believed that frequent mutations in the hepatitis C virus (HCV) genome, suppression of innate immunity, and oxidative stress contribute to the chronic HCV infection and HCC in HCV infected patients. Failure to cure HCV infection, viral-resistance to various drugs, and HCV association with development of HCC, altogether, suggest additional problems beyond the current concept of HCV effects on liver. The consequence of HCV infection of hepatic stem/progenitor cells and HCV-induced stem cell-like features in hepatocytes is also obscure.

Since chronic HCV infection is a dominant risk factor for the development of HCC, understanding the molecular basis of HCV-induced CSC-like properties in hepatic cells will advance the ability to prevent and treat HCC. In adult liver, hepatic stem/progenitor cells (HSPCs) predominantly reside in bile duct (canal of Herring). These cells are quiescent with a low proliferating rate and are activated only when the mature epithelial cells of the liver are continuously damaged or lost. In severe acute or chronic injury, proliferation and self-renewal of HSPCs are significantly enhanced. Although HCV is a noncytopathic virus, the infection causes loss of hepatocytes and significant reduction in regenerative capacity of the liver that ultimately results in cirrhosis. These observations clearly indicate that during long-term HCV infectious process, the normal function of liver stem/progenitor cells are altered or impaired.

Using HIV-HCV pseudoviruses, Cai et al. demonstrated that a productive HCV infection can be achieved in the human embryonic stem cell (hESC)-derived hepatic progenitor cells, and that the infection is effectively neutralized by a monoclonal antibody against CD81 (a putative receptor for HCV).

Similarly, Iacovacci et al. showed efficient infectivity of HCV and its reproduction in human fetal hepatocytes. Thus, it would appear that homing of HCV in hepatic progenitor cells, which rarely undergo cell division, occurs in patients. It is possible that a subpopulation of HCV-infected hepatocytes in patients may be derived from direct infection or by asymmetric division of infected hepatic stem/progenitor cells (FIG. 58). HCV is notorious in manipulating the intracellular environment. The virus causes inhibition of innate immunity, induction of membranous web-like structures and alteration in signaling pathways. As shown herein below (FIG. 59), it is also possible that HCV can reprogram the infected cells by inducing stem/pluripotency factors. These abnormal changes may generate CSC properties in hepatocytes, resulting in development and progression of HCC as depicted in FIG. 58.

Therefore, this Example is directed to identifying and characterizing these HCV-infected CSCs, as well as defining molecular targets and signaling pathways that govern these cells.

Induction of putative stem cell/pluripotency factors by HCV: Normal adult hepatocytes are fully differentiated cells and lack expression of pluripotency factors. However, these cells can be induced to proliferate rapidly after partial hepatectomy and can also be reprogrammed into stem-like cells by forced expression of a cocktail of transcription factors. Thus, the impact of HCV on expression pattern of stem/progenitor cell markers was investigated in GS5 cells, which are derived from hepatoma cell line (Huh7.5) and support constitutive replication of a subgenomic HCV replicon under G418 selection. The replicon expresses HCV nonstructural proteins NS3 through NS5B of the HCV-1a strain and green florescent protein (GFP)-NS5A chimera. Total lysates from parent Huh7.5 and GS5 cells were subjected to Western blot analysis (FIG. 59). The levels of putative stem cell markers (DCAMKL1, LGR5 and CD133) were found to be considerably enhanced in GS5 cells compared to the control Huh7.5 cells. Interestingly, a number of transcription factors (Oct4, Sox2, Lin 28 and c-Myc) that are involved in the maintenance and self-renewal of stem cells either showed higher (c-Myc) or expression levels similar to that of Huh7.5 (FIG. 59). These results indicate that HCV may be involved in the induction and/or maintenance of stem cell features.

Putative intestinal stem cell marker DCAMKL1 is required for the HCV replication: The eccentric, punctate staining of HCV replication complexes consisting of most of the nonstructural proteins and cellular factors has been a puzzling question. It is known that these replication complexes associate with microtubules in order to replicate the HCV RNA. The DCAMKL1 protein, which binds and polymerizes tubulin into microtubule filaments, is considered as a putative marker for quiescent stem cells in the intestine, and its expression is increased in cancer stem cells. During confocal microscopy, most DCAMKL1 localization was consistently observed in the area containing replication complexes (indicated by NS5A-GFP) and high concentration of microtubules (FIG. 60). The perinuclear co-localization of DCAMKL1 with the NS5A-GFP (indicated by yellow stain) was also observed. Interestingly, disruption of microtubules in GS5 cells by vinblastin resulted in disengagement of DCAMKL1 from microtubules with concomitant inhibition of HCV replication. To confirm this observation, GS5 cells were transfected with siRNA against DCAMKL1 (siDCAMKL1) or scrambled siRNA ((SCR) for 48 hours. The siDCAMKL1 effectively inhibited expression of DCAMKL1 that was accompanied by decreases in both the HCV RNA as well as NS5B polymerase levels (FIG. 61). These observations set a precedent that DCAMKL1 is required for HCV replication, and that HCV infection might be a probable cause of enhanced DCAMKL1 expression, which is considered as a signal for the development of CSCs.

HCV-induced cancer stem cell-like properties in replicon-expressing G55 cells: The GS5 or Huh7.5 cells were labeled with anti-DCAMKL1 antibodies conjugated with Alexa Fluor 568. After removal of free conjugate, the cells were subjected to FACS analysis using red-green channels. The cells positive for both DCAMKL1 and HCV NS5A-GFP (HCV$^+$DCAMKL1$^+$) from GS5 and DCAMKL1$^+$ cells from Huh 7.5 cell lines were subjected to spheroid assays in Matrigel™ (BD Biosciences). Both cells were able to form spheroids in 3-4 weeks. The GS5 spheroids (HCV$^+$DCAMKL1$^+$) showed higher HCV NS5A-GFP expression in the budding areas (FIG. 62). Interestingly, DCAMKL1$^+$ cells from Huh7.5 cells also formed spheroids but only showed minor diffused green florescence background. These results clearly indicated that DCAMKL1$^+$ cells from hepatoma cell lines are able to form spheroids, most likely due to their CSC-like properties. The cells negative for DCAMKL failed to form spheroids under similar conditions (not shown). These HCV$^+$DCAMKL1$^+$ (GS5) or DCAMKL1 (Huh7.5), when injected into the flanks of nude SCID mice, led to tumor formation (FIG. 63, only GS5-tumor is shown). Immunohistochemical analysis of this tumor showed sporadic cells with DCAMKL1 expression embedded in an area rich in cells expressing high level of activated c-Src, a marker for aggressive tumorigenesis with metastatic potential. When both tumor xenografts (GS5 vs Huh7.5) were compared for the expression of CK19 that marks the hepatic progenitor and billiary duct epithelial cells, a surprising difference was found (FIG. 64A-B). Most GS5 tumor cells showed intense expression of CK19, whereas the Huh7.5 tumor showed only a few sporadic cells positive for this marker. This result was further confirmed by Western blot that showed a several fold increase of CK19 expression in the GS5 tumor as compared to that of Huh7.5 (FIG. 64C). Interestingly, GS5 tumors also showed a 3-5 fold increase in α-fetoprotein expression in a similar assay (data not shown). Thus, HCV-expressing progenitor and CSCs are likely to induce a distinct HCC phenotype with more aggressive characteristics than the HCC without HCV.

EXAMPLE 8

Barrett's esophagus (BE) is a premalignant lesion detected in the majority of patients with esophageal and gastro-esophageal adenocarcinoma. These cancers are associated with a low 5-year survival rate of approximately 15-20%. The incidence of esophageal adenocarcinoma (EAC) has been increasing in the United States for more than 30 years. In 2009, nearly 60% of the estimated 16,400 new esophageal cancer cases were adenocarcinomas. The risk of EAC is 30-40 fold greater in patients with BE compared to those without this condition. Progression of BE may involve development of low-grade intraepithelial dysplasia (LGID) and high-grade intraepithelial dysplasia (HGID) prior to the ultimate development of cancer. These data support the hypothesis that BE is a pre-malignant condition.

BE is diagnosed in 10-15% of reflux patients undergoing endoscopy. Moreover, among those with chronic reflux symptoms undergoing endoscopic screening, a prevalence of 5.6% was reported. Although the prevalence of BE in the United States population is not known, a population-based study from Sweden diagnosed BE in 1.6% of all participants. Applying this percentage to the US population, it is estimated that 1.5 to 2 million adults could have this premalignant lesion. Risk factors for BE include increased age, male gender, non-Hispanic white ethnicity, presence of reflux symptoms and obesity. Inverse associations regarding BE presence include red wine consumption, *H. pylori* infection and African American ethnicity.

Despite the clear association of BE and EAC, the low frequency of neoplastic progression of BE to frank EAC has created a major obstacle in predicting an individual's absolute risk of cancer when diagnosed with BE. This is compounded by the requirement of expert pathologic diagnosis of the degree of dysplasia on biopsy samples, and the potential for sampling error during endoscopy. The potential of field effects adjacent to any observable lesions increases the complexity of the diagnosis. The identification of rational molecular biomarkers based on the cell of origin to categorize patients at increased risk for progression to EAC would be a major advance. Such markers have included tumor suppressor genes (CDKN2A and TP53) along with the presence of epithelial aneuploidy or tetraploidy. The cumulative 5-year incidence of EAC was 43% and 56% in BE patients with aneuploidy and tetraploidy, respectively, compared to 5% without either finding (Sharma, 2009). However, the predictive value of these markers has not been confirmed. The previous Examples demonstrate the identification of a potential marker for both gastrointestinal and adenoma stem cells (DCAMKL-1). However, the expression of this marker in BE or EAC has not been reported. In this Example, immunohistochemical analysis was employed to determine the cell specific protein expression patterns of DCAMKL-1 in normal esophageal mucosa, BE and EAC in human esophageal biopsy tissues to explore a potential mechanistic link between a key putative intestinal stem cell marker, which is expressed in several distinct regions of the rodent and human stomach, and the eventual development of EAC from BE.

Materials and Methods of Example 8

Tissue procurement. The human Barrett's esophagus tissues were provided by Dr. Rhonda Souza at the University of Texas Southwestern Medical Center at Dallas; Dr. Steven Meltzer at Johns Hopkins Medical Center, Baltimore, Md.; and Oklahoma Veteran's Affairs Medical Center (VAMC) according to the policies and practices of the institution's IRB. Human multi-tissue microarrays (Tissue Array Network, Rockville, Md.) were purchased commercially.

Immunohistochemistry. Heat-induced epitope retrieval was performed on formalin-fixed paraffin-embedded sections by utilizing a pressurized decloaking chamber (Biocare Medical, Concord, Calif.) in citrate buffer (pH 6.0) at 99° C. for 18 minutes. For brightfield microscopy, slides were incubated in 3% hydrogen peroxide, then in normal serum and BSA at room temperature for 20 min. After incubation with primary antibody [DCAMKL-1 1:100 (rabbit), (Abcam, Cambridge, Mass.); Ki67 1:300 (rabbit) (Thermo Scientific/LabVision, Fremont, Calif.)], the slides were incubated either in polymer-horseradish peroxidase secondary (Dako, Glostrup, Denmark) for rabbit-derived or goat polymer detection kit (Biocare Medical) for goat-derived antibodies as appropriate. Slides were developed with diaminobenzidine (Sigma, St. Louis, Mo.).

Microscopic examination. Slides were examined by utilizing the Nikon 80i microscope and DXM1200C camera for brightfield microscopy. Fluorescent images were taken with PlanFluoro objectives, utilizing CoolSnap ES2 camera (Photometrics, Tucson, Ariz.). Images were captured with NIS-Elements software (Nikon Instruments, Melville, N.Y.).

Scoring. Senior Pathologist Dr. Stan Lightfoot, University of Oklahoma Health Sciences Center, performed scoring of all the immunostained slides. The scoring (DCAMKL-1 staining) was carried out based on two different parameters: 1) staining intensity and 2) amount of tissue involved. Scoring was carried out for epithelial and stromal tissues separately. The intensity was measured and scored from 0-3, no staining=0, weak staining=1, moderate staining=2 and strong staining=3. The amount of tissue involved was measured scored from 0-4, no tissue involved (0%)=0, <10% involved=1, 10%-50% involved=2, 51%-80% involved=3 and >80% involved=4. Finally, the intensity score was multiplied by tissue involvement score to obtain DCAMKL-1 staining score (e.g. 3×4=12) (Regitnig et al., 2002).

Real-time reverse transcription-PCR analysis. Total RNA isolated from human Barrett's (n=13) and paired normal tissue samples (n=13) (obtained from Stephen J. Meltzer, Johns Hopkins School of Medicine) was subjected to reverse transcription with Superscript™ II RnaseH-Reverse Transcriptase and random hexanucleotide primers (Invitrogen, Carlsbad, Calif.). The cDNA was subsequently used to perform Real-time PCR by SYBR chemistry (SYBR® Green I; Molecular Probes) for specific transcripts using gene specific primers and Jumpstart Taq DNA polymerase (Sigma-Aldrich, St. Louis, Mo.). The crossing threshold value assessed by Real-time PCR was noted for the transcripts and normalized with β-actin mRNA. The changes in mRNA were expressed as fold change relative to control with ±SEM value.

Primers used were:

β-actin:
                                              (SEQ ID NO: 4)
   Forward:    5'-GGTGATCCACATCTGCTGGAA-3'

(SEQ ID NO: 5)
   Reverse:    5'-ATCATTGCTCCTCCTCAGGG-3'

DCAMKL-1:
                                              (SEQ ID NO: 6)
   Forward:    5'-AGTCTTCCGATTCCGAGTTGAG-3'

(SEQ ID NO: 7)
   Reverse:    5'-CAGCAACCAGGAATGTATTGGA-3'

Msi-1:
                                             (SEQ ID NO: 64)
   Forward:    5'-CAGTTTCGGACCTATCTCTGAGGT-3', (SEQ ID NO: 65)
   Reverse:    5'-AAGGTGATGAAACCAAAACCCCT-3'

LGR5:
                                           (SEQ ID NO: 66)
   Forward:    5'-AACAGTCCTGTGACTCAACTCAAG-3'

(SEQ ID NO: 67)
   Reverse:    5'-TTAGAGACATGGGACAAATGCCAC-3'

Results of Example 8

DCAMKL-1 is expressed in BE and EAC. Tissues obtained from biopsy specimens (the University of Texas Southwestern Medical Center at Dallas, University of Oklahoma VAMC) and human multi-tissue microarrays (Tissue Array Network, Rockville, Md.) were immunostained for DCAMKL-1. In total, Normal squamous epithelial tissues (n=3), BE with no dysplasia (n=6), BE with dysplasia (n=6) and Adenocarcinoma (n=40) were utilized for this study. No or minimal DCAMKL-1 epithelial staining was observed in normal squamous epithelial cells (FIG. 65A). In contrast, progressively increased staining intensity was observed in BE with no dysplasia, BE with dysplasia and Adenocarcinoma (FIG. 65B-D). Distinct DCAMKL-1 stromal staining was observed in BE patients' tissues (FIG. 65B-D). When analyzed quantitatively, there was a corresponding increase in stromal staining intensity that correlated with increased epithelial staining as the pathologic diagnosis progressed from BE with no dysplasia to patients with dysplasia. In adenocarcinoma, an even greater intensity of stromal DCAMKL-1 staining was observed as compared to patients with BE with or without dysplasia (FIG. 65E-F). These data taken together demonstrate a trend towards increased stromal expression of DCAMKL-1 that correlates with progression from BE without dysplasia to EAC.

DCAMKL-1 is expressed in vascular structures in BE. Although minimal DCAMKL-1 protein was observed in the squamous epithelium of patients without BE (FIG. 66A), there were several focal areas of immunoreactive DCAMKL-1 staining within the muscularis and in intervening blood vessels within the dysplastic esophageal mucosa of patients with BE (FIGS. 66B and C). Indeed, endothelial expression of DCAMKL-1 was observed in several patients with EAC (FIG. 66D). When examined quantitatively, this pattern of DCAMKL-1 staining again correlated with progression from BE with no dysplasia to BE with dysplasia and EAC. These data taken together demonstrate the potential translocation of DCAMKL-1 expressing stem/progenitor cells to the squamous esophagus from a relatively distant source during the progression of BE. Next, the cell specific expression of patterns in EAC was determined.

In BE, DCAMKL-1 immunolocalized to the glandular cytoplasm (FIG. 67A). A substantial difference in the staining pattern between surface epithelium and the glandular epithelium in the stroma was observed (FIG. 67B). Additionally, in patients with dysplasia, increased DCAMKL-1 expression was evident in the stroma and in endothelial cells as compared to BE without dysplasia (FIG. 67C). Interestingly, in areas of focal dysplasia and particularly on surface epithelium, nuclear DCAMKL-1 staining was observed (FIG. 67D). A few endothelial cells demonstrated slight immunostaining for DCAMKL-1 in BE patients without dysplasia (FIG. 67E). However, when dysplasia was noted, most endothelial cells were positive for DCAMKL-1. This was especially true in blood vessels near the surface epithelium (FIG. 67F). Progressively increased DCAMKL-1 staining intensity, particularly in the stroma, was observed between patients with dysplasia and cancer compared to BE patients without dysplasia. This progressive increase in staining intensity was evident in both the epithelium and the stroma. Throughout the biopsy specimens, there were several cell types that may represent macrophages or perhaps mast cells that display immunoreactive DCAMKL-1. Table 1 demonstrates the scoring system for DCAMKL-1 staining in the cytoplasm of the surface epithelium, epithelium in the stroma and glandular epithelium as described earlier for individual patients.

DCAMKL-1 mRNA is upregulated in BE: Recently it has been demonstrated that RNA binding protein and putative stem cell marker Musashi1 (Msi-1) is upregulated in BE and EAC (Bobryshev et al., 2010). Furthermore, LGR5, a putative gut stem cell marker is also upregulated in BE (Becker et al., 2010). To determine whether DCAMKL-1 mRNA is overexpressed in human BE, real-time RT-PCR analyses were performed on total RNA isolated from human BE and paired normal tissues for DCAMKL-1, Msi-1 and LGR5. A significant 3 fold induction of DCAMKL-1 mRNA was observed in human BE compared to its paired normals (FIG. 68A). Similarly, a 2.5 fold increase in Msi-1 mRNA (FIG. 68B) and 5 fold increase in LGR mRNA was observed in human BE compared to its paired normal tissues (FIG. 68C). These data taken together demonstrates that putative stem cell markers like DCAMKL-1, Msi-1 and LGR5 are upregulated in human BE compared to normal.

TABLE 1

Epithelial and stromal scoring of endoscopically obtained, histologically confirmed squamous esophageal mucosa, BE without dysplasia, BE with dysplasia and Adenocarcinoma/EAC.

| Subject Identifier | Epithelial Scoring | Stromal Scoring | Histologic Diagnosis |
|---|---|---|---|
| 8-226 | 2 × 2 = 4 | 1 × 1 = 1 | BE with no dysplasia |
| 8-1510 | 0 | 0 | BE with no dysplasia |
| 8-1017-3 | 2 × 3 = 6 | 0 | BE with no dysplasia |
| 8-1017-2 | 1 × 1 = 1 | 0 | BE with no dysplasia |
| 8-140 | 0 | 2 × 2 = 4 | BE with no dysplasia |
| 8-90 | 0 | 0 | BE with dysplasia |
| 8-369-2 | 1 × 1 = 1 | 0 | BE with dysplasia |
| 8-332 | 1 × 2 = 2 | 2 × 2 = 4 | BE with dysplasia |
| 8-272 | 0 | 0 | BE with dysplasia |
| 8-332-3 | 1 × 1 = 1 | 0 | BE with dysplasia |
| 8-1497-4 | 4 × 3 = 12 | 0 | BE with dysplasia |
| 8-1497-3 | 3 × 2 = 6 | 0 | BE with dysplasia |
| 8-1130 | 3 × 4 = 12 | 3 × 4 = 12 | Adenocarcinoma |
| 8-2686 | 1 × 3 = 3 | 0 | Adenocarcinoma |
| 8-4456 | 4 × 3 = 12 | 4 × 3 = 12 | Adenocarcinoma |
| 9-414-1G | 1 × 1 = 1 | 1 × 1 = 1 | Adenocarcinoma |
| 9-414-1C | 0 | 1 × 1 = 1 | Adenocarcinoma |

Discussion of Example 8

This Example is the first report that immunoreactive DCAMKL-1, although minimally expressed in normal distal esophageal squamous mucosa, is markedly expressed in BE epithelium. Furthermore, an increased epithelial and stromal expression pattern was observed in patients with progression of dysplasia. Moreover, a marked increase in stromal DCAMKL-1 was observed in EAC.

Despite the tremendous increase in EAC incidence over the past three decades, identification of the cellular origin of BE and the role of such a cell during progression to EAC remains elusive. BE is a premalignant lesion detected in the majority of patients with EAC, conferring increased risk for cancer development. EAC is associated with a very low rate of survival once detected clinically. BE progression is associated with increasing severity of dysplasia prior to the development of cancer.

Surveillance programs are the mainstay for monitoring the progression of BE from no dysplasia to high grade dysplasia. It is expected that patients with HGD will be offered a surgical option after confirmation of the diagnosis by two expert pathologists. Newer experimental ablative therapies may be an option for patients at high surgical risk or for those who decline surgery. The limitations of these approaches and the lack of medical therapy illustrate the need for additional techniques that stratify the risk of progression and confirm the presence of dysplasia either within the specimen or potentially in the bloodstream. The recent emerging stem cell hypothesis of solid tumor cancers has only recently been explored in esophageal cancer.

The squamous epithelium of the normal esophagus undergoes metaplasia to form intestinal type mucosa in patients with BE. Recent challenges to this hypothesis suggest that the cell of origin may be a proximal gastric stem cell that migrates across the EG junction and essentially crosses the squamocolumnar junction. These stem cells then proliferate and give rise to the intestinal type epithelia that is Barrett's epithelium. It has recently been shown in animal models that the Barrett's epithelium may actually be bone marrow derived stromal cells that convert to epithelium and promote aggressive growth of BE (Barbera et al., 2010; Souza et al., 2008; and Hutchinson et al., 2010). Thus, identification of the cell(s) of origin is key to gaining a more complete understanding of the molecular features of BE including initiation and progression to EAC. In this Example, immunohistochemical evidence of a unique cellular expression pattern of the novel intestinal stem cell marker DCAMKL-1 has been developed. Although expressed in many gut tissues and pancreas, up regulation of DCAMKL-1 has been demonstrated by the inventors, particularly in the stromal desmoplastic compartment in many solid tumors (Data not shown) (May et al., 2008; and May et al., 2010). This represents the rationale for examining DCAMKL-1 expression in BE. The data in this Example demonstrate that the normal squamous esophagus expresses minimal DCAMKl-1 protein while in BE, DCAMKl-1 is readily detected during immunohistochemical analysis. Although staining is primarily epithelial, there is also clear evidence, in early BE, of distinct stromal staining. In addition to the epithelial and stromal staining, evidence of endothelial and blood vessel expression of DCAMKL-1 was observed in some patients. As the BE with no dysplasia progresses to BE with dysplasia on pathologic exam, an increase in both the stromal and epithelial expression is observed. Thus, this Example (as well as the previous Examples) demonstrates that there is a clear increased expression pattern of this novel putative stem cell marker that has been reported to have a functional role in colon and perhaps pancreatic cancer progression.

The finding that DCAMKL-1 is expressed in low levels in pre-malignant tissues makes it an intriguing candidate for investigation as a tissue specific biomarker for BE. This can potentially be used as a surrogate after confirmation of the diagnosis using conventional pathologic techniques. Finally, this marker may have a role in the confirmation of eradication of focal lesions following endoscopic ablative therapies. Endoscopic techniques have been developed recently to eradicate BE with HGID and EAC with varying levels of success. However, eradication does not always occur, and its durability remains in question. Therefore, identification of cellular markers indicating the presence of a neoplastic stem/progenitor cell either before or after endoscopic ablation would clearly enhance the clinical and endoscopic management of these individuals.

Previous efforts attempting to categorize patients at increased risk for progression to EAC using genetic markers have met with limited results. These have included tumor suppressor genes, aneuplody or tetraploidy. To date, there are no studies identifying an increased esophageal stem cell cohort during the progression from normal squamous mucosa through dysplasia to EAC. Identification of such a marker histologically and in serum could eventually allow for a non-invasive assessment of general EAC risk in patients with gastroesophageal reflux disease.

The presently disclosed and claimed inventive concept(s) disclose that there is a gastrointestinal type stem cell originating from the proximal stomach, EG junction, or bone marrow and that represents the precursor cell type for the intestinal metaplasia associated with BE and EAC. The central focus on DCAMKL-1, a microtubule associated kinase that is upregulated in colon cancer, as a marker for said cell type is due to the expression observed in many epithelial tissues including intestine, colon and pancreas. In mice, knockdown of DCAMKL-1 results in cessation of HCT-116-mediated tumor xenograft growth. Furthermore, reduction of DCAMKL-1 correlates with increased expression of the tumor suppressor miRNA Let-7a and a reduction in oncogenic c-Myc RNA and protein. Given the expression pattern in several gastrointestinal tissues, this Example sought to determine the cell specific expression pattern in the normal squamous esophagus and in columnar epithelium from patients with BE with LGID, HGID and EAC. Using a series of tissue microarray slides obtained from several laboratories and the Tissue Array Network, immunohistochemical analysis was performed to investigate DCAMKLI-1 protein levels in human patients. Given the potential for interactions between epithelial stem cells and stroma on tumor progression, DCAMKL-1 may play a key role in the initiation and progression of BE and EAC. The observations of increased and accumulation DCAMKL-1 provide a potential mechanistic link between esophageal injury/inflammation and carcinogenesis risk in proximal gastric epithelial cells.

In order to further evaluate the expression patterns of stem/progenitor proteins in BE, mRNA expression of DCAMKL-1, Msi-1 and LGR5 was evaluated in patients with BE compared to normal. Relative mRNA expression determined using quantitative real-time RTPCR demonstrated upregulation of each of these mRNAs in patients with BE. These data provide strong support for the involvement of stem/progenitor proteins in BE metaplasia.

Overall, these data present a detailed immunohistochemical analysis of the putative gastrointestinal stem cell marker DCAMKL-1 in the distal esophagus in patients with BE and EAC. These findings demonstrate a candidate for evaluating the role of stem cells in BE initiation and progression to adenocarcinoma.

EXAMPLE 9

The presently disclosed and claimed inventive concept(s) is directed to a method of diagnosing various cancer(s) using one or more blood biomarkers. It is proposed herein that stem-cell derived tumors will shed and/or secrete stem cell-derived proteins/peptides into the blood/serum, and that these proteins/peptides can be used as blood biomarkers for early diagnosis of certain cancers. One mechanism for shedding stem cell proteins into the blood involves exoprotease cleavages.

As preliminary studies, the presence of RBM3, DCAMKL-1 and LGR5 were demonstrated in the serum of nude mice that bore colon cancer tumor xenografts.

In this Example, archived serum from patients with pancreatic adenocarcinoma (7) and two healthy volunteers was assayed for the presence of RBM3, DCAMKL-1 and LGR5 as stem cell biomarker proteins using immunoblot. DCAMKL-1 and LRG5 were not detected in the sera from the normal healthy volunteers. However, increased levels of all three proteins were observed in the patient sera when compared to controls (FIG. 69). These data demonstrate the feasibility of the methods of the presently disclosed and claimed inventive concept(s) to use one or more proteins as prognostic markers for various cancers.

EXAMPLE 10

This Example is directed to stem cell assays utilizing PICSCs generated in accordance with the presently disclosed and claimed inventive concept(s). The PICSCs were generated as described herein above (i.e., transformation of NIH-3T3 cells with RBM3 gene, followed by transplantation into a nude mouse, then sorting of cells obtained from generated tumors utilizing DCAMKL-1).

The PICSCs were exposed to various compounds/anti-cancer agents, and cell viability assays were then performed using the LIVE/DEAD® Viability/Cytotoxicity Assay from Molecular Probes/Invitrogen (Eugene, Oreg.). The LIVE/DEAD® Viability/Cytotoxicity Assay is an assay that provides a two-color fluorescence cell viability that is based on the simultaneous determination of both live and dead cells.

Briefly, PICSCs cells were grown in a 96 well microtitre plate (SARSTEDT, Newton, N.C.) to about 40% confluency and treated with anti-cancer agents/compounds for 48 hours. Subsequently, chromogenic substrates Calcein AM and Ethidium homodimer-1 (EthD-1) was added to the cells. Calcein AM is well retained within the live cells, producing uniform green fluorescence in live cells (measured at 515 nM). EthD-1 enters cells with damaged membranes and undergoes an enhancement of fluorescence upon binding to nucleic acids, thereby producing a bright red fluorescence in dead cells (measured at 617 nM). The fluorescence measurement was carried out using a microtitre plate reader (Synergy HT, BIO-TEK, Vinooski, Vt.).

In FIGS. 70-84, the PICSCs were treated with increasing concentrations of various compounds or combinations of compounds for 48 hours, and the data presented therein is represented as a % Dead/Live cells ratio following said treatment. In each figure, hydrogen peroxide is used as a positive control ((+) control) which induces complete cell death. Values in each figure are given as average±Standard Error Mean, and asterisks denote statistically significant differences (*p<0.01) compared with control.

In FIG. 70, increasing levels of PICSC cell death were observed in response to treatment with increasing levels of turmeric. A significant increase in PICSC cell death was observed in response to treatment with the chemotherapeutic agent Gemcitabine (FIG. 71). In FIG. 72, increasing levels of PICSC cell death were observed in response to treatment with increasing levels of CODCK-1000 (siDCAMKL-1; described herein previously). In addition, increasing levels of PICSC cell death were observed in response to treatment with increasing levels of Simvastatin (FIG. 73). Synergistic increases in PICSC cell death were observed in response to treatment with CODCK-100 (siDCAMKL-1) in combination with Gemcitabine, Simvastatin or Turmeric (FIGS. 74, 75 and 76, respectively). In FIG. 77, increasing levels of PICSC cell death were observed in response to treatment with increasing levels of S1811 (dye). In FIG. 78, increasing levels of PICSC cell death were observed in response to treatment with increasing levels of Protoporphyrin compounds 1 and 2. In FIG. 79, a synergistic increase in PICSC cell death was observed in response to treatment with a combination of CODCK-1000 (siDCAMKL-1) and Flexible heteroarotinoids (DB). In addition, increasing levels of PICSC cell death were observed in response to treatment with the anti-cancer agent Cisplatin, while no cell death was observed following treatment with the anti-cancer drug CPT11 (FIG. 80). In FIG. 81, increasing levels of PICSC cell death were observed in response to treatment with increasing levels of the Curcumin derivative EF24 (diphenyl difluoroketone). In FIG. 82, increasing levels of PICSC cell death were observed in response to treatment with increasing levels of Notch signaling inhibitor (DAPT).

In FIG. 83, increasing levels of PICSC cell death were observed in response to treatment with increasing levels of siRNAs against DCAMKL-1, Musashi-1 (Msi-1) and RBM3 (produced as described herein and in the parent applications U.S. Ser. Nos. 12/386,550; 12/384,387; and 12/454,355, all of which were previously incorporated herein by reference). Finally, FIG. 84 demonstrates that there was a synergistic increase in PICSC cell death observed in response to treatment with a combination of Gemcitabine and Turmeric.

The results provided in this Example clearly provide ample evidence of the validity of the assays described and claimed herein utilizing the stem cell model generated in accordance with the presently disclosed and claimed inventive concept(s).

Thus, in accordance with the presently disclosed and claimed inventive concept(s), there have been provided methods of identifying a gastrointestinal, pancreatic and/or cancer stem cell marker, and methods of use thereof, that fully satisfy the objectives and advantages set forth hereinabove. Although the inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the inventive concept(s).

What is claimed is:

1. A method of generating gastrointestinal cancer stem cells suitable for screening agents for use in the detection or treatment of cancer, comprising the steps of:
    transfecting non-tumorigenic cells with an expression vector comprising a gene encoding RBM3;
    culturing the non-tumorigenic cells under conditions that allow for expression of RBM3;
    transplanting the cultured cells expressing RBM3 into a rodent and allowing a xenograft tumor to form;
    isolating the xenograft tumor; and
    isolating at least one cell expressing DCAMKL-1 on a surface thereof from the xenograft tumor, wherein the DCAMKL-1+ cell is a gastrointestinal cancer stem cell.

2. The method of claim 1 wherein, in the step of transplanting the cultured cells expressing RBM3 into a rodent, the rodent is further defined as a mouse.

3. The method of claim 2, wherein the non-tumorigenic cells are further defined as mouse fibroblast cells.

4. The method of claim 3 wherein, in the step of transplanting the cultured cells expressing RBM3 into a mouse, the mouse is further defined as an immunodeficient mouse.

5. The method of claim 2, wherein the non-tumorigenic cells are from a species other than mouse, and wherein the mouse into which the cells are transplanted is further defined as an immunodeficient mouse.

* * * * *

UNITED STATES PATENT AND TRADEMARK OFFICE
CERTIFICATE OF CORRECTION

PATENT NO.          : 8,936,941 B2
APPLICATION NO.     : 13/027845
DATED               : January 20, 2015
INVENTOR(S)         : Shrikant Anant et al.

It is certified that error appears in the above-identified patent and that said Letters Patent is hereby corrected as shown below:

In the Specification:
Column 5, line 23: Delete "13" and replace with -- β --
Column 10, line 4: After "Msi-1," delete "(1):" and replace with -- (L): --
Column 13, line 67: Delete "mIR-200a" and replace with -- miR-200a --
Column 14, line 21: Delete "mIR-let-7a." and replace with -- miR-let-7a. --
Column 15, line 3: Delete "pri-mIR-144" and replace with -- pri-miR-144 --
Column 15, line 16: Delete "NSSB" and replace with -- NS5B --
Column 15, line 36: Delete "NSSA" and replace with -- NS5A --
Column 29, line 52: Delete "Alexa Fluoro" and replace with -- Alexa Fluor® --
Column 29, line 56-57: Delete "Alexa Fluoro" and replace with -- Alexa Fluor® --
Column 30, line 8: Delete "BI/6" and replace with -- BL/6 --
Column 37, line 24: Delete "(NC1-Frederick)" and replace with -- (NCI-Frederick) --
Column 37, line 52: Delete "O-cells," and replace with -- β-cells, --
Column 44, lines 16-17: Delete "(NC1-Frederick)" and replace with -- (NCI-Frederick) --
Column 44, line 25: Delete " 䊎g" and replace with -- μg --
Column 46, line 6: Delete ""sternness"" and replace with -- "stemness" --
Column 54, line 50: Delete "pri-mIR-144" and replace with -- pri-miR-144 --
Column 56, line 38: Delete "'sternness'" and replace with -- 'stemness' --
Column 60, line 6: Delete "(NC1-Frederick)" and replace with -- (NCI-Frederick) --
Column 62, line 10: After "GCTGTACA-3'" insert -- (SEQ --

Signed and Sealed this
Nineteenth Day of May, 2015

Michelle K. Lee
*Director of the United States Patent and Trademark Office*

UNITED STATES PATENT AND TRADEMARK OFFICE
CERTIFICATE OF CORRECTION

PATENT NO.        : 8,936,941 B2
APPLICATION NO.   : 13/027845
DATED             : January 20, 2015
INVENTOR(S)       : Shrikant Anant et al.

Page 1 of 1

It is certified that error appears in the above-identified patent and that said Letters Patent is hereby corrected as shown below:

In the Specification:
Column 5, line 23: Delete "13" and replace with -- β --
Column 10, line 4: After "Msi-1," delete "(1):" and replace with -- (L): --
Column 13, line 67: Delete "mIR-200a" and replace with -- miR-200a --
Column 14, line 21: Delete "mIR-let-7a." and replace with -- miR-let-7a. --
Column 15, line 3: Delete "pri-mIR-144" and replace with -- pri-miR-144 --
Column 15, line 16: Delete "NSSB" and replace with -- NS5B --
Column 15, line 36: Delete "NSSA" and replace with -- NS5A --
Column 29, line 52: Delete "Alexa Fluoro" and replace with -- Alexa Fluor® --
Column 29, lines 56-57: Delete "Alexa Fluoro" and replace with -- Alexa Fluor® --
Column 30, line 8: Delete "BI/6" and replace with -- BL/6 --
Column 37, line 24: Delete "(NC1-Frederick)" and replace with -- (NCI-Frederick) --
Column 37, line 52: Delete "O-cells," and replace with -- β-cells, --
Column 44, lines 16-17: Delete "(NC1-Frederick)" and replace with -- (NCI-Frederick) --
Column 44, line 25: Delete " ㎍" and replace with -- μg --
Column 46, line 6: Delete ""sternness"" and replace with -- "stemness" --
Column 54, line 50: Delete "pri-mIR-144" and replace with -- pri-miR-144 --
Column 56, line 38: Delete "'sternness'" and replace with -- 'stemness' --
Column 60, line 6: Delete "(NC1-Frederick)" and replace with -- (NCI-Frederick) --
Column 62, line 10: After "GCTGTACA-3'" insert -- (SEQ --
Column 70, line 5: Delete "G55" and replace with -- GS5 --
Column 70, lines 6-7: Delete "Alexa Fluor" and replace with -- Alexa Fluor® --
Column 78, line 1: After "compounds" delete "I" and replace with -- 1 --

This certificate supersedes the Certificate of Correction issued May 19, 2015.

Signed and Sealed this
Twenty-fifth Day of August, 2015

Michelle K. Lee
*Director of the United States Patent and Trademark Office*

SEQUENCE LISTING

```
<160> NUMBER OF SEQ ID NOS: 78

<210> SEQ ID NO 1
<211> LENGTH: 8082
<212> TYPE: RNA
<213> ORGANISM: Homo sapiens

<400> SEQUENCE: 1
uuucaaugag gacgggccga ggcacauccc ugcacuagug gccgcaaccg aggcgccgcg      60
cuccagcagc ugcugccgcc cagcccggcc ccgccgccgc cccccagccc ugcagccccg     120
cagccccggc cgcgcccagc ccggcgagga cagcaccagg aggcggcccc cagcgcggcc     180
acaaagaccc ccggcggcgu cucuccgcgg accgguccua cuugaagucc aucaugucccu     240 ucggcagaga cauggagcug gagcacuucg acgagcggga uaaggcgcag agauacagcc     300
gagggucgcg ggugaacggc cugccgagcc cgacgcacag cgcccacugc agcuucuacc     360
gcacccgcac gcucagacg cucagcuccg agaagaaggc caagaaaguu cguuucuauc     420
gaaacggaga ucgauacuuc aaagggauug uguaugccau cucccagac cgguuccgau     480 cuuugaggcc ccugcuggcu gauuugaccc gaacucuguc ggauaacgug aauuugcccc     540
agggagugag aacaaucuac accauugaug ggcucaagaa gauuccagc cuggaccaac     600
```

-continued

```
ugguggaagg agagaguuau guaugug gcu ccaugagcc cuucaagaaa cuggaguaca    660
ccaagaaugu gaaccccaac uggucgguga acgucaagac caccucggcu ucucgggcag    720
ugucuucacu ggccacugcc aaaggaagcc cuucagaggu gcgagagaau aaggauuuca    780
uucggcccaa gcuggucacc aucaucgaaa guggcgugaa gccacggaaa gcugucagga    840
uucugcugaa caagaaaacg gcucauuccu ugagcaggu ccaccgau aucaccgaug       900 ccaucaagcu ggacucggga guggugaaac gccuguacac guuggauggg aaacaggug a   960 ugugccuuca ggacuuuuuu ggugaugaug acauuuuuau ugcaugugga ccggagaagu   1020
uccguuacca ggaugauuuc uugcuagaug aaagugaaug ucgagggua aaguccacuu    1080 cuuacaccaa aauagcuuca ucaucccgca ggagcaccac caagagccca ggaccgucca   1140
ggcguagcaa guccccugcc uccaccagcu caguuaaugg aaccccuggu agucagcucu   1200
cuacuccgcg cucaggcaag ucgccaagcc caucacccac cagcccagga agccugcgga   1260
agcagaggag cucucagcau ggcggcuccu cuacgucacu ugcguccacc aaagucugca   1320
gcucgaugga ugagaacgau ggcccuggag aagaagugu c ggaggaaggc uuccagauuc   1380
cagcuacaau aacagaacga uauaaagucg gaagaacaau aggagaugga aauuuugcug   1440
uugucaagga augugua gaa agaucgacug cuagagagua ugcucugaaa auuaucaaga   1500
aaagcaaaug ucgaggcaaa gagcacauga uccagaauga agucuauau uuaagaagag   1560 ugaagcaucc caauaucguu cuucugauug aggaugga ugccaacu gaacuguauc      1620 uugcaugga auuaguaaag gggggagacc uuuuugaugc cauuacuucc acuaacaaau    1680
acaccgagag agacgccagu gggaugcugu acaaccuagc cagcgccauc aaauaccugc   1740
auagccugaa caucguccac cgugauauca agcagagaa ccugcugg ug uaugagcacc   1800 aagauggcag caaaucacug aagcugggug acuuuggacu ggccaccauu guagacggcc   1860
cccuguacac agucuguggc accccaacau acgggcucc agaaaucauu gcagagacug   1920
gauacggccu caaggugac aucugggcag cagguguaau cacuuauauc cugcugugug   1980
guuucccucc auuccgugga aguggugaug accaggaggu gcuuuugau cagauuuuga   2040 uggggcaggu ggacuuuccu ucuccauacu gggauaaugu uuccgauucu gcaaaggagc   2100
ucauuaccau gaugcuguug gucgaugua g aucagcgauu ucugcguu caaguacuug    2160 agcaucccug gguuaaugau gauggccucc cagaaaauga acaucagcug ucaguagcug   2220
gaaagauaaa gaagcauuuc aacacaggcc ccaagccgaa uagcacagca gcuggaguuu   2280 cugcauagc acuggaccac gggguuuacca ucaagagauc agggucuuug gacuacuacc   2340
agcaaccagg aaugauuugg auaagaccac cgcucuugau aaggagaggc agguuuccg    2400 acgaagacgc aaccaggaug ugaggagccg guacaaggcg cagccagcuc ucccgaacu    2460 caacucggaa ucggaagacu acuccccaag cucccccgag acuguucgcu ccccuaacuc   2520
gcccuuuuaa uaagacccuu uuacucaaag uccuagcuua acccuuugag acucugagau   2580 uuuuucccc caaauuugug uaaaacaguu ucaucugauc uaucuagcgc ucaaugcuug   2640
aauggcagaa cugaaagugu uuucaggau cuuuguagcg guuucccuu acugaauaag    2700 augacacgug gugauguga agauggua auug cugcua uagagccuc aaagggguuaa    2760 ggccaauuug caauuuuuuu uuaaacuuag aagcaaugaa uguuucauc agucaagcua   2820 ggaucugcag uauguaauau agcacuuguu aaccc ucuga gugcauagaa uuuuauugag   2880
aauucuuguu ugggaauuuu ucaggccuuu ggaugua uac acacauguuu cuugauuuua   2940
```

```
cugcagauca agggguguug uuagaugcug aaauguccag aaaagaagga cauuuagaau    3000
gauaucuugu uuguccuuuu cuguggguuu agaacguggc agguuuauaa cuucgacaca    3060
cgcacgguuc uuucuucuuc acaauccuau ucagaaacag auuuuuuuuu ucauuagaga    3120
uaugacuguc aguugcagug aguucugcau cccaagugga gggaauuggg uuuguggcaa    3180
agagcuugac ccaggaaaua gauggugccc cccaaauugu cuccacauga agauguacug    3240
augacgcccc agaaaugcug cuuccauauc agcugcugcu agcgccagcg cagacucuca    3300
gggagucacc acagcuuguc uugugcuugg ugagugaggg ucucucuacu cagugucaga    3360
caucuacagg aaagaaacaa cugguggaaa agagcaauaa auugcccggu gcucugcagg    3420
gcuggaauuu caaacagaaa gagggaauaa gauccuguga uuuucucac cugcuuuucc     3480 acgcacugug ucaucacug ugcaaucuac aucuaguaug aaauccacac auaggagagc     3540
uggggcacaa ggggacugga ggcaguugcu uugcaagaug gcugaggaga aagcacacug    3600
ggaacacaau ccagaauguu cuaacaauaa guuucagug aauaaaccac uggcaagaca     3660 auccaugug caccuuuagg uuaccauauau agucccuag gaagaucagg augaaagacc      3720
uagaugauac cccugaggau aaaaccucca uccccuaaaa ugauuuuuuu uaaauaccac    3780
ugucuuuagc ugccaggag gucagagugu uuuucuguc uuugggccaa guccugucug       3840
agaccuguau uuucacucuu guuaccaaau cuaucucccu agugcagugu cuccaggccu    3900
gaguuucuuc uggaacagau uccauuuuag aaugggauu cacagguucu gugcaucacc     3960
acagugcuca gagaggauuc uccuggggug cuuagaggc aggugcccaa cucaaaugua     4020
uucccaaggu uugcugggcu cugggauccca cgagacaacc agagagggau aucucaugaa   4080
auuugcaucu gguggcugaa caguaccuau guucucuguu uugaauauac uuuaauaccu    4140
gagagucuua aaauuuguga acaacguuuc uauaguccuu uauuucaaa ugcacauuga     4200 ucuucacuug cugcauuuuu acuuucaac ccugaaacua uggucuacau aauauggau       4260 uuuuaaauca caugcauua cuuuugcaac accaucacca aaauuuuug ucuuuuuaca       4320 uuuagguuca ucucuggu cuguguugc cugacaugua aaaagcauau cguuauuga         4380 gguuuuuuc ccccccuuuu agagcauccg gaagugauaa cacgcaaaau cacaaaguag     4440
cauaaaucag uaaauuaguu gaguuguuuu uggggggag uggggguag ggggcacaga      4500 acaccagaaa gaguguuggu guguaggua auuccauauu aaugaggaac acgaacuag       4560 uuggaaauua cugcuuucuc uagaaauaua aagcaaagca cuauuccaag gcuauggagu    4620
agcucuacag ccuggccuca acucuaaaag ugugaagaau gcaauggggca gagaccuacc   4680 ugcaguggac ugucauuuuc cuuucuuucu cugaauuacu gcuuuucug ugggcauuaa     4740 cuauauugcu acagcaucua guguacgag ccugcggugc auggcucagg ccuuuuccca      4800
ucgacgucua gggggacucu ggaccgugug aagcuagggg uguuucuca gcacacugca     4860 gaagggcagc ucaagaaau gcagggccca uucagcaugg ggaucccagc acaucacugu     4920
agaauuugag ugaucuaugc ugaauaaaca guggaaugug accagucaag uagaaaucuu    4980
gaguaaucag auggaaugca aucuuucuaa cauuaagcua ccaagauccu gaaugucaga    5040
gauguacuca gaggguuaac agacaagcac aaggcaugcu gacuacauug guguauccag    5100
auugcuuugc uuuuagccag ugcuuucaa uuuuuuucuc gacauucuug ggauaguuca    5160
aguuugaaau aauuaagugg uggguucuu uaaggaauuu cuauaaccaa auugaucuua     5220 uuuugauuu cacuuaucau agaacaaaua uguaucauua uggcaguga ucuauguaau      5280 uaucaauuua aucaucacca ccgguguuuc cauauuuuu cccaaguauu uaauauagcu     5340
```

-continued

| | | | | |
|---|---|---|---|---|
| cucuuauggu | gguggccugg | ugauggggac | cgucuuucuu | uuacugacac | augaccaauc | 5400 |
| auaugguauu | uucaagggaa | uuuuaagauu | caucuuuuca | guuugauagu | agacuaguua | 5460 |
| aggaagaacu | cuuucauuac | uugcaucgug | uaaaucaucu | cuguagacau | guguucauau | 5520 |
| uaaugaacac | auuuuuucuc | aacauuguag | cagaaaucau | uuuauucguc | augaucaaug | 5580 |
| aauaugugau | uugcuccaga | ucguuagaag | gaaaaguaag | auuucaguca | ucaaaaaugu | 5640 |
| uuuuaccgua | gcccucaucu | aacuuacacg | uggugcauau | uaaaauaagc | agagaaaaaa | 5700 |
| aaaugugaau | aaacuacuga | aaacacuugg | uguuugugu | ucaugagac | cuccugcaa | 5760 |
| ccugcucccc | augguggca | guuacaggc | ccaucagaua | uuguugaaag | aaagcaauau | 5820 |
| auccaugaau | gaaggcuaaa | auugcaaucc | uuuacccuuu | gaggcauauu | ucaguugaaa | 5880 |
| acaaaagaa | aagaaaauuu | ggcuagagg | gucacagagc | ucccauauga | ccaagucuca | 5940 |
| agcacauuaa | aucaugguug | uuuacuggcc | aagggcgucc | acuagacaac | ucuaucccuu | 6000 |
| gcgcugaagc | ucaaucgugc | ugagggagag | cuuucuuaau | auuacugugu | ugcucuuagc | 6060 |
| ccuucucugg | guuaggaucu | gucagcauuu | cuaugauaaa | cuccuauucu | caaagguuuu | 6120 |
| uaauuugacc | auaaaaaugu | gccccaggcu | gaaguuugcu | auacagggcu | guaccaaaga | 6180 |
| gugaagguuu | acuuccuucu | cuuccaacu | ucuucccau | ucccaagga | aaagaacaac | 6240 |
| aaaaaaaucu | gguauggucc | cuccuuaaua | gugauucag | aauuuggaa | agcaccaaga | 6300 |
| uccaagaugg | uaguuuaau | guaguuacuc | auucgcacac | auuuuuaaa | uuuaaugggu | 6360 |
| caccuggcau | auauuugaga | uaacauaucu | uuucuauaau | uuguaaguca | auaauuuuuu | 6420 |
| uaacugcuac | augauauuuu | uuuuugccca | agauuuuaa | aagacuugaa | guuggucagu | 6480 |
| ucaaaacuca | gauuuuucua | cacauugucu | gccaugucca | uuaggaguuu | gggaaaaua | 6540 |
| cucucacaca | gacccuuacu | uugcaugcag | uuuagagggu | aagauacgug | cuucuuuugg | 6600 |
| ggauaaagau | uuccuacuu | aauugucaaa | uuucauggag | ccauucuagu | cuguggga | 6660 |
| aaauagugau | uaaaagcacu | uccaaaauua | acauuuuug | acaauucaga | uaugaaaaga | 6720 |
| agcaggggaa | aauaauacac | uuuacucuuu | ucuugcuuaa | aggcaaacaa | aucaaugaaa | 6780 |
| cuugaggaca | cacuaaacau | uugauaacug | caaaugugcu | uuaaaauug | guucaauggu | 6840 |
| gcuuacacau | gaaacgguaa | caaauggggu | uccuaggacg | ucagaaggaa | ucuuuaguuu | 6900 |
| guauguaauu | acacacuaga | ggaggaggug | cuuuuaagcc | agucuuuau | uuuuaaucau | 6960 |
| cucaaauaug | caaccauaca | ugcaguaaca | uuaaggucg | uaaacuggug | gaaacagga | 7020 |
| acuucagugg | agaggcuuaa | augccucugg | uuagaguggg | gguuuugu | uguuuguuua | 7080 |
| uuguugggu | ucaacacuga | gcaucauuuc | ugugaucaag | uuucuaacug | gcauguguuu | 7140 |
| ugaucaugag | guuuaccaua | ucuugcccau | acagacaaau | gagagaucua | guucauuuu | 7200 |
| guucccuaaa | gaaagaacac | ucucuaaaau | uaaaucauac | cuguaaauuu | cuucagcauu | 7260 |
| uguuucuguu | caaugaaauu | gagacccuua | auguugcuuu | aauguaaaau | ugaauauuuu | 7320 |
| gucgugauua | uacuuuaaua | auuuaaagua | aguaauaguu | cuaaagucuu | cacguuugcu | 7380 |
| acuaagagaa | aauagaauuu | uaagguugau | gauaaagaug | cuauaauguc | aguucacucc | 7440 |
| aguccaauca | aauguaguaa | gaaaagucc | uugaauaguu | cucuagggac | aauuucucac | 7500 |
| ugccauuga | cauuaaucuu | uggugauuc | ucagaaaaaa | uaaaagaaa | uugaaacugg | 7560 |
| uccaagguua | uagucauauc | cucgauaacu | uuugaaaaaa | aauuuauua | ggaaauuaau | 7620 |
| acuagccuuu | uucauucugg | cugaaagaaa | auuauuaaag | gauuaguuga | gugugaaauu | 7680 |

-continued

```
caacaguauu uugcucauac auacuaaaaa ggugcguagg gacuuggcgc auuuaaacaa    7740
guuucugaaa gguuucaauu ugacucaaga aaaaaauuca auauuucuuu ugaaaauacu    7800
gaauuuauca cuugcugcau ggaucagaug gcauagguua aucuuugauu uucagaaucc    7860
uaaugaaaua acuuucaaac aauuugguguc cuuaauuaaa ggugggaauga gauccaauuu   7920 uuccccuaa uccuucaguu uaagcugaua caugagguu aaugugggaau gaaaucaucu      7980 gugauauauu auguucauuu aucaacugag cuuuuuugau guugccuguu uuuauguaaa    8040
acauguucuu aaaguuaaua aaauaauagu acuuggugua aa                       8082
```

<210> SEQ ID NO 2
<211> LENGTH: 729
<212> TYPE: PRT
<213> ORGANISM: Homo sapiens

<400> SEQUENCE: 2

```
Met Ser Phe Gly Arg Asp Met Glu Leu Glu His Phe Asp Glu Arg Asp
1               5                   10                  15

Lys Ala Gln Arg Tyr Ser Arg Gly Ser Arg Val Asn Gly Leu Pro Ser
            20                  25                  30

Pro Thr His Ser Ala His Cys Ser Phe Tyr Arg Thr Arg Thr Leu Gln
        35                  40                  45

Thr Leu Ser Ser Glu Lys Lys Ala Lys Lys Val Arg Phe Tyr Arg Asn
    50                  55                  60

Gly Asp Arg Tyr Phe Lys Gly Ile Val Tyr Ala Ile Ser Pro Asp Arg
65                  70                  75                  80

Phe Arg Ser Phe Glu Ala Leu Leu Ala Asp Leu Thr Arg Thr Leu Ser
                85                  90                  95

Asp Asn Val Asn Leu Pro Gln Gly Val Arg Thr Ile Tyr Thr Ile Asp
            100                 105                 110

Gly Leu Lys Lys Ile Ser Ser Leu Asp Gln Leu Val Glu Gly Glu Ser
        115                 120                 125

Tyr Val Cys Gly Ser Ile Glu Pro Phe Lys Lys Leu Glu Tyr Thr Lys
    130                 135                 140

Asn Val Asn Pro Asn Trp Ser Val Asn Val Lys Thr Thr Ser Ala Ser
145                 150                 155                 160

Arg Ala Val Ser Ser Leu Ala Thr Ala Lys Gly Ser Pro Ser Glu Val
                165                 170                 175

Arg Glu Asn Lys Asp Phe Ile Arg Pro Lys Leu Val Thr Ile Ile Arg
            180                 185                 190

Ser Gly Val Lys Pro Arg Lys Ala Val Arg Ile Leu Leu Asn Lys Lys
        195                 200                 205

Thr Ala His Ser Phe Glu Gln Val Leu Thr Asp Ile Thr Asp Ala Ile
    210                 215                 220

Lys Leu Asp Ser Gly Val Val Lys Arg Leu Tyr Thr Leu Asp Gly Lys
225                 230                 235                 240

Gln Val Met Cys Leu Gln Asp Phe Phe Gly Asp Asp Ile Phe Ile
                245                 250                 255

Ala Cys Gly Pro Glu Lys Phe Arg Tyr Gln Asp Asp Phe Leu Leu Asp
            260                 265                 270

Glu Ser Glu Cys Arg Val Val Lys Ser Thr Ser Tyr Thr Lys Ile Ala
        275                 280                 285

Ser Ser Ser Arg Arg Ser Thr Thr Lys Ser Pro Gly Pro Ser Arg Arg
    290                 295                 300
```

```
Ser Lys Ser Pro Ala Ser Thr Ser Val Asn Gly Thr Pro Gly Ser
305                 310                 315                 320

Gln Leu Ser Thr Pro Arg Ser Gly Lys Ser Pro Ser Pro Ser Thr
                325                 330                 335

Ser Pro Gly Ser Leu Arg Lys Gln Arg Ser Ser Gln His Gly Gly Ser
                340                 345                 350

Ser Thr Ser Leu Ala Ser Thr Lys Val Cys Ser Ser Met Asp Glu Asn
                355                 360                 365

Asp Gly Pro Gly Glu Glu Val Ser Glu Glu Gly Phe Gln Ile Pro Ala
        370                 375                 380

Thr Ile Thr Glu Arg Tyr Lys Val Gly Arg Thr Ile Gly Asp Gly Asn
385                 390                 395                 400

Phe Ala Val Val Lys Glu Cys Val Glu Arg Ser Thr Ala Arg Glu Tyr
                405                 410                 415

Ala Leu Lys Ile Ile Lys Lys Ser Lys Cys Arg Gly Lys Glu His Met
                420                 425                 430

Ile Gln Asn Glu Val Ser Ile Leu Arg Arg Val Lys His Pro Asn Ile
        435                 440                 445

Val Leu Leu Ile Glu Glu Met Asp Val Pro Thr Glu Leu Tyr Leu Val
450                 455                 460

Met Glu Leu Val Lys Gly Gly Asp Leu Phe Asp Ala Ile Thr Ser Thr
465                 470                 475                 480

Asn Lys Tyr Thr Glu Arg Asp Ala Ser Gly Met Leu Tyr Asn Leu Ala
                485                 490                 495

Ser Ala Ile Lys Tyr Leu His Ser Leu Asn Ile Val His Arg Asp Ile
        500                 505                 510

Lys Pro Glu Asn Leu Leu Val Tyr Glu His Gln Asp Gly Ser Lys Ser
                515                 520                 525

Leu Lys Leu Gly Asp Phe Gly Leu Ala Thr Ile Val Asp Gly Pro Leu
        530                 535                 540

Tyr Thr Val Cys Gly Thr Pro Thr Tyr Val Ala Pro Glu Ile Ile Ala
545                 550                 555                 560

Glu Thr Gly Tyr Gly Leu Lys Val Asp Ile Trp Ala Ala Gly Val Ile
                565                 570                 575

Thr Tyr Ile Leu Leu Cys Gly Phe Pro Pro Phe Arg Gly Ser Gly Asp
                580                 585                 590

Asp Gln Glu Val Leu Phe Asp Gln Ile Leu Met Gly Gln Val Asp Phe
        595                 600                 605

Pro Ser Pro Tyr Trp Asp Asn Val Ser Asp Ser Ala Lys Glu Leu Ile
        610                 615                 620

Thr Met Met Leu Leu Val Asp Val Asp Gln Arg Phe Ser Ala Val Gln
625                 630                 635                 640

Val Leu Glu His Pro Trp Val Asn Asp Asp Gly Leu Pro Glu Asn Glu
                645                 650                 655

His Gln Leu Ser Val Ala Gly Lys Ile Lys Lys His Phe Asn Thr Gly
                660                 665                 670

Pro Lys Pro Asn Ser Thr Ala Ala Gly Val Ser Val Ile Ala Leu Asp
        675                 680                 685

His Gly Phe Thr Ile Lys Arg Ser Gly Ser Leu Asp Tyr Tyr Gln Gln
        690                 695                 700

Pro Gly Met Tyr Trp Ile Arg Pro Pro Leu Leu Ile Arg Arg Gly Arg
705                 710                 715                 720

Phe Ser Asp Glu Asp Ala Thr Arg Met
```

```
<210> SEQ ID NO 3
<211> LENGTH: 19
<212> TYPE: RNA
<213> ORGANISM: Homo sapiens

<400> SEQUENCE: 3
gggagugaga acaaucuac                                                      19

<210> SEQ ID NO 4
<211> LENGTH: 21
<212> TYPE: DNA
<213> ORGANISM: Homo sapiens

<400> SEQUENCE: 4
ggtgatccac atctgctgga a                                                   21

<210> SEQ ID NO 5
<211> LENGTH: 20
<212> TYPE: DNA
<213> ORGANISM: Homo sapiens

<400> SEQUENCE: 5
atcattgctc ctcctcaggg                                                     20

<210> SEQ ID NO 6
<211> LENGTH: 22
<212> TYPE: DNA
<213> ORGANISM: Homo sapiens

<400> SEQUENCE: 6
agtcttccga ttccgagttg ag                                                  22

<210> SEQ ID NO 7
<211> LENGTH: 22
<212> TYPE: DNA
<213> ORGANISM: Homo sapiens

<400> SEQUENCE: 7
cagcaaccag gaatgtattg ga                                                  22

<210> SEQ ID NO 8
<211> LENGTH: 22
<212> TYPE: DNA
<213> ORGANISM: Homo sapiens

<400> SEQUENCE: 8
cacacatcag cacaactacg ca                                                  22

<210> SEQ ID NO 9
<211> LENGTH: 19
<212> TYPE: DNA
<213> ORGANISM: Homo sapiens

<400> SEQUENCE: 9
ttgaccctct tggcagcag                                                      19

<210> SEQ ID NO 10
<211> LENGTH: 20
<212> TYPE: DNA
<213> ORGANISM: Homo sapiens

<400> SEQUENCE: 10
```
cagcctggac gagctggtgg                                           20

<210> SEQ ID NO 11
<211> LENGTH: 20
<212> TYPE: DNA
<213> ORGANISM: Homo sapiens

<400> SEQUENCE: 11
tgaccagttg gggttcacat                                           20

<210> SEQ ID NO 12
<211> LENGTH: 17
<212> TYPE: DNA
<213> ORGANISM: Homo sapiens

<400> SEQUENCE: 12
ctcgcttcgg cagcaca                                              17

<210> SEQ ID NO 13
<211> LENGTH: 20
<212> TYPE: DNA
<213> ORGANISM: Homo sapiens

<400> SEQUENCE: 13
aacgcttcac gaatttgcgt                                           20

<210> SEQ ID NO 14
<211> LENGTH: 26
<212> TYPE: DNA
<213> ORGANISM: Homo sapiens

<400> SEQUENCE: 14
gaggtagtag gttgtatagt ttagaa                                    26

<210> SEQ ID NO 15
<211> LENGTH: 19
<212> TYPE: DNA
<213> ORGANISM: Homo sapiens

<400> SEQUENCE: 15
aaagctagga ggctgtaca                                            19

<210> SEQ ID NO 16
<211> LENGTH: 21
<212> TYPE: DNA
<213> ORGANISM: Homo sapiens

<400> SEQUENCE: 16
ggtgatccac atctgctgga a                                         21

<210> SEQ ID NO 17
<211> LENGTH: 20
<212> TYPE: DNA
<213> ORGANISM: Homo sapiens

<400> SEQUENCE: 17
atcattgctc ctcctcaggg                                           20

<210> SEQ ID NO 18
<211> LENGTH: 20
<212> TYPE: DNA
<213> ORGANISM: Homo sapiens

<400> SEQUENCE: 18
cagcctggac gagctggtgg                                          20

<210> SEQ ID NO 19
<211> LENGTH: 20
<212> TYPE: DNA
<213> ORGANISM: Homo sapiens

<400> SEQUENCE: 19
tgaccagttg gggttcacat                                          20

<210> SEQ ID NO 20
<211> LENGTH: 25
<212> TYPE: DNA
<213> ORGANISM: Homo sapiens

<400> SEQUENCE: 20
cgcaccatgg cgcctcatcc cttgg                                    25

<210> SEQ ID NO 21
<211> LENGTH: 26
<212> TYPE: DNA
<213> ORGANISM: Homo sapiens

<400> SEQUENCE: 21
cagaggatcc tcttcacaag aagtct                                   26

<210> SEQ ID NO 22
<211> LENGTH: 17
<212> TYPE: DNA
<213> ORGANISM: Homo sapiens

<400> SEQUENCE: 22
cacctcaaga tgtccct                                             17

<210> SEQ ID NO 23
<211> LENGTH: 19
<212> TYPE: DNA
<213> ORGANISM: Homo sapiens

<400> SEQUENCE: 23
gcagcttcag cttggggtc                                           19

<210> SEQ ID NO 24
<211> LENGTH: 20
<212> TYPE: DNA
<213> ORGANISM: Homo sapiens

<400> SEQUENCE: 24
ggaccccaga ctccgtcagt                                          20

<210> SEQ ID NO 25
<211> LENGTH: 20
<212> TYPE: DNA
<213> ORGANISM: Homo sapiens

<400> SEQUENCE: 25
gggctcggac agcagctctg                                          20

<210> SEQ ID NO 26
<211> LENGTH: 20
<212> TYPE: DNA
<213> ORGANISM: Homo sapiens -continued

```
<400> SEQUENCE: 26 cccagcccttt agtgaccagc                                           20

<210> SEQ ID NO 27
<211> LENGTH: 20
<212> TYPE: DNA
<213> ORGANISM: Homo sapiens

<400> SEQUENCE: 27
tttattcatt gcagaggggt                                            20

<210> SEQ ID NO 28
<211> LENGTH: 20
<212> TYPE: DNA
<213> ORGANISM: Homo sapiens

<400> SEQUENCE: 28
ggctggattg cttataatgc                                            20

<210> SEQ ID NO 29
<211> LENGTH: 20
<212> TYPE: DNA
<213> ORGANISM: Homo sapiens

<400> SEQUENCE: 29
atctcatcag ggtcctcatg                                            20

<210> SEQ ID NO 30
<211> LENGTH: 18
<212> TYPE: DNA
<213> ORGANISM: Homo sapiens

<400> SEQUENCE: 30
ggctatgaca aggatgcc                                              18

<210> SEQ ID NO 31
<211> LENGTH: 18
<212> TYPE: DNA
<213> ORGANISM: Homo sapiens

<400> SEQUENCE: 31
gatcatcaat atccagca                                              18

<210> SEQ ID NO 32
<211> LENGTH: 21
<212> TYPE: DNA
<213> ORGANISM: Homo sapiens

<400> SEQUENCE: 32
ggtgatccac atctgctgga a                                          21

<210> SEQ ID NO 33
<211> LENGTH: 20
<212> TYPE: DNA
<213> ORGANISM: Homo sapiens

<400> SEQUENCE: 33
atcattgctc ctcctcaggg                                            20

<210> SEQ ID NO 34
<211> LENGTH: 22
<212> TYPE: DNA
```

```
<213> ORGANISM: Homo sapiens

<400> SEQUENCE: 34
agtcttccga ttccgagttg ag                                              22

<210> SEQ ID NO 35
<211> LENGTH: 22
<212> TYPE: DNA
<213> ORGANISM: Homo sapiens

<400> SEQUENCE: 35
cagcaaccag gaatgtattg ga                                              22

<210> SEQ ID NO 36
<211> LENGTH: 22
<212> TYPE: DNA
<213> ORGANISM: Homo sapiens

<400> SEQUENCE: 36
cacacatcag cacaactacg ca                                              22

<210> SEQ ID NO 37
<211> LENGTH: 19
<212> TYPE: DNA
<213> ORGANISM: Homo sapiens

<400> SEQUENCE: 37
ttgaccctct tggcagcag                                                  19

<210> SEQ ID NO 38
<211> LENGTH: 20
<212> TYPE: DNA
<213> ORGANISM: Homo sapiens

<400> SEQUENCE: 38
cgggtccacc agtttgaatg                                                 20

<210> SEQ ID NO 39
<211> LENGTH: 21
<212> TYPE: DNA
<213> ORGANISM: Homo sapiens

<400> SEQUENCE: 39
gttgtattgg ttcggcacca t                                               21

<210> SEQ ID NO 40
<211> LENGTH: 25
<212> TYPE: DNA
<213> ORGANISM: Homo sapiens

<400> SEQUENCE: 40
aagaattcac agtggagaga agcca                                           25

<210> SEQ ID NO 41
<211> LENGTH: 22
<212> TYPE: DNA
<213> ORGANISM: Homo sapiens

<400> SEQUENCE: 41
cgtttcttgc agtttgggca tt                                              22

<210> SEQ ID NO 42
<211> LENGTH: 20
```

<212> TYPE: DNA
<213> ORGANISM: Homo sapiens

<400> SEQUENCE: 42
agccgatcat ggcggatggc                                                  20

<210> SEQ ID NO 43
<211> LENGTH: 23
<212> TYPE: DNA
<213> ORGANISM: Homo sapiens

<400> SEQUENCE: 43
ttcctcctgc tgggattggc ttg                                              23

<210> SEQ ID NO 44
<211> LENGTH: 17
<212> TYPE: DNA
<213> ORGANISM: Homo sapiens

<400> SEQUENCE: 44
cctcccatca gctgccc                                                     17

<210> SEQ ID NO 45
<211> LENGTH: 20
<212> TYPE: DNA
<213> ORGANISM: Homo sapiens

<400> SEQUENCE: 45
gtgatgctgt agaaaacctt                                                  20

<210> SEQ ID NO 46
<211> LENGTH: 19
<212> TYPE: DNA
<213> ORGANISM: Homo sapiens

<400> SEQUENCE: 46
aaggccttct ctaggccct                                                   19

<210> SEQ ID NO 47
<211> LENGTH: 19
<212> TYPE: DNA
<213> ORGANISM: Homo sapiens

<400> SEQUENCE: 47
cgcaggttgg agcggtcag                                                   19

<210> SEQ ID NO 48
<211> LENGTH: 18
<212> TYPE: DNA
<213> ORGANISM: Homo sapiens

<400> SEQUENCE: 48
tgcttcaagg acacatta                                                    18

<210> SEQ ID NO 49
<211> LENGTH: 17
<212> TYPE: DNA
<213> ORGANISM: Homo sapiens

<400> SEQUENCE: 49
cagtggtatt tctttac                                                     17

<210> SEQ ID NO 50

-continued

<210> SEQ ID NO 50
<211> LENGTH: 17
<212> TYPE: DNA
<213> ORGANISM: Homo sapiens

<400> SEQUENCE: 50
gtctggagga tggaggg                                                   17

<210> SEQ ID NO 51
<211> LENGTH: 21
<212> TYPE: DNA
<213> ORGANISM: Homo sapiens

<400> SEQUENCE: 51
tccttctctg gaaacaatga c                                              21

<210> SEQ ID NO 52
<211> LENGTH: 22
<212> TYPE: DNA
<213> ORGANISM: Homo sapiens

<400> SEQUENCE: 52
cacacatcag cacaactacg ca                                             22

<210> SEQ ID NO 53
<211> LENGTH: 19
<212> TYPE: DNA
<213> ORGANISM: Homo sapiens

<400> SEQUENCE: 53
ttgaccctct tggcagcag                                                 19

<210> SEQ ID NO 54
<211> LENGTH: 19
<212> TYPE: DNA
<213> ORGANISM: Homo sapiens

<400> SEQUENCE: 54
gacgatacag ctaattcag                                                 19

<210> SEQ ID NO 55
<211> LENGTH: 17
<212> TYPE: DNA
<213> ORGANISM: Homo sapiens

<400> SEQUENCE: 55
agacaggttt ctccatc                                                   17

<210> SEQ ID NO 56
<211> LENGTH: 21
<212> TYPE: DNA
<213> ORGANISM: Mus musculus

<400> SEQUENCE: 56
ggtgatccac atctgctgga a                                              21

<210> SEQ ID NO 57
<211> LENGTH: 20
<212> TYPE: DNA
<213> ORGANISM: Mus musculus

<400> SEQUENCE: 57
atcattgctc ctcctcaggg                                                20

```
<210> SEQ ID NO 58
<211> LENGTH: 20
<212> TYPE: DNA
<213> ORGANISM: Mus musculus

<400> SEQUENCE: 58
cagcctggac gagctggtgg                                               20

<210> SEQ ID NO 59
<211> LENGTH: 20
<212> TYPE: DNA
<213> ORGANISM: Mus musculus

<400> SEQUENCE: 59
tgaccagttg gggttcacat                                               20

<210> SEQ ID NO 60
<211> LENGTH: 22
<212> TYPE: DNA
<213> ORGANISM: Homo sapiens

<400> SEQUENCE: 60
gctgggatat catcatatac tg                                            22

<210> SEQ ID NO 61
<211> LENGTH: 24
<212> TYPE: DNA
<213> ORGANISM: Homo sapiens

<400> SEQUENCE: 61
cggactagta catcatctat actg                                          24

<210> SEQ ID NO 62
<211> LENGTH: 17
<212> TYPE: DNA
<213> ORGANISM: Homo sapiens

<400> SEQUENCE: 62
ttccacagca gcccctg                                                  17

<210> SEQ ID NO 63
<211> LENGTH: 18
<212> TYPE: DNA
<213> ORGANISM: Homo sapiens

<400> SEQUENCE: 63
gatgtgcctc ggtggtgt                                                 18

<210> SEQ ID NO 64
<211> LENGTH: 24
<212> TYPE: DNA
<213> ORGANISM: Homo sapiens

<400> SEQUENCE: 64
cagtttcgga cctatctctg aggt                                          24

<210> SEQ ID NO 65
<211> LENGTH: 23
<212> TYPE: DNA
<213> ORGANISM: Homo sapiens

<400> SEQUENCE: 65
aaggtgatga aaccaaaacc cct                                           23
```

<210> SEQ ID NO 66
<211> LENGTH: 24
<212> TYPE: DNA
<213> ORGANISM: Homom sapiens

<400> SEQUENCE: 66
aacagtcctg tgactcaact caag                                          24

<210> SEQ ID NO 67
<211> LENGTH: 24
<212> TYPE: DNA
<213> ORGANISM: Homo sapiens

<400> SEQUENCE: 67
ttagagacat gggacaaatg ccac                                          24

<210> SEQ ID NO 68
<211> LENGTH: 1588
<212> TYPE: DNA
<213> ORGANISM: Homo sapiens

<400> SEQUENCE: 68
gggaacgttc cgggacgttc tcgctacgta ctctttatca atcgtcttcc ggcgcagccc      60
cgtccctgtt ttttgtgctc ctccgagctc gctgttcgtc cgggtttttt acgttttaat    120
ttccaggact tgaactgcca tgtcctctga agaaggaaag ctcttcgtgg gagggctcaa    180
ctttaacacc gacgagcagg cactggaaga ccacttcagc agtttcggac ctatctctga    240
ggtggtcgtt gtcaaggacc gggagactca gcggtccagg ggttttggtt tcatcacctt    300
caccaaccca gagcatgctt cagttgccat gagagccatg aacggagagt ctctggatgg    360
tcgtcagatc cgtgtggatc atgcaggcaa gtctgctcgg ggaaccagag gaggtggctt    420
tggggcccat gggcgtggtc gcagctactc tagaggtggt ggggaccagg gctatgggag    480
tggcaggtat tatgacagtc gacctggagg gtatggatat ggatatggac gttccagaga    540
ctataatggc agaaaccagg gtggttatga ccgctactca ggaggaaatt acagagacaa    600
ttatgacaac tgaaatgaga catgcacata atatagatac acaaggaata atttctgatc    660
caggatcgtc cttccaaatg gctgtattta taaaggtttt tggagctgca ccgaagcatc    720
ttattttata gtatatcaac cttttgtttt taaattgacc tgccaaggta gctgaagacc    780
ttttagacag ttccatcttt ttttttaaat tttttctgcc tatttaaaga caaattatgg    840
gacgtttgta gaacctgagt attttttcttt ttaccagttt tttagtttga gctcttaggt    900
ttattggagc tagcaataat tggttctggc aagtttggcc agactgactt caaaaaatta    960
atgtgtatcc agggacattt taaaaacctg tacacagtgt ttattgtggt taggaagcaa   1020
tttcccaatg tacctataag aaatgtgcat caagccagcc tgaccaacat ggtgaaaccc   1080
catctgtact aaacataaaa aaattagcct ggcatggtgg tgtacgcctg taatcccagt   1140
gacttgggag gctgaggcag gagaatcgct tgaacccggg aggcggaggt tgcagtgagc   1200
taagatcgcg ccactgtact ccagcctggg caacagcgag actccatctc aaaaaaaaag   1260
gaaatgtgta tcaagaacat gattatccag cggtattttc taattcagat catcaaactg   1320
attatataga agagttggct ttaaaatgtt tgcaaatgtc ttttttttttt taatactgga   1380 agaaaaaata ttctgttgtg tctcatacag tgcttaggat gtctttcaca gagcttatta   1440
aaaagatgaa acctgagaac aaactgcttt attcttactc agcccatttt gcaaattaaa   1500
agtgggggca gaggtgggcg gatcacctga ggtcaggagt tcgagaccag cctggccaac   1560
agggcaaaac cccatctcta ctaaaaat        1588

<210> SEQ ID NO 69
<211> LENGTH: 157
<212> TYPE: PRT
<213> ORGANISM: Homo sapiens

<400> SEQUENCE: 69

Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Val Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Phe Gly Ala
                85                  90                  95

His Gly Arg Gly Arg Ser Tyr Ser Arg Gly Gly Gly Asp Gln Gly Tyr
            100                 105                 110

Gly Ser Gly Arg Tyr Tyr Asp Ser Arg Pro Gly Gly Tyr Gly Tyr Gly
        115                 120                 125

Tyr Gly Arg Ser Arg Asp Tyr Asn Gly Arg Asn Gln Gly Gly Tyr Asp
    130                 135                 140

Arg Tyr Ser Gly Gly Asn Tyr Arg Asp Asn Tyr Asp Asn
145                 150                 155

<210> SEQ ID NO 70
<211> LENGTH: 1158
<212> TYPE: DNA
<213> ORGANISM: Mus musculus

<400> SEQUENCE: 70
gcctcgaggc aagaattcgg cagaggttcg agctcgtcgt ctctgccgtc ctctgacttt        60
taatttccag gacttgcctt ctgccatgtc gtctgaagaa gggaaactct tcgtaggagg       120
gctcaacttc aacaccgatg aacaggcact tgaagaccac ttcagcagct ttgggcctat       180
ctctgaggtg gttgttgtca aggaccggga gactcaaaga tcccgggggtt ttggcttcat       240 caccttcaca aacccagagc atgcctcaga tgcgatgaga gctatgaatg gagagtccct       300
ggatgggcgc caaatccgag ttgatcatgc aggaaagtct gccaggggat ccagaggggg       360
tgcctttggt gggcgtggtc gcagttactc tagaggtggt ggagaccagg gatatggaag       420
tggaagatat gacagtcgtc ctggaggata tggatatggg tatgggcggt ctagagacta       480
cagtggcagc cagggtggct atgaccgcta ctcaggagga aattacagag acaattatga       540
caactgagat ggggcatgca cacaaaatat acacaaggaa taacacttct gatccaggat       600
cgtccttgca aattgctgta tttataaaga ttttggagc tgcgctgaaa cgtctgtttt       660
agtacatcaa gttctatttt tgaattgagc tcccaaggta gtttgttaaa gaactttag       720 aaagctccat gtgttctttta aacattttt ccctttttaaa aacaaatttt aagacatttg       780
ttacagtccc aatattttc cttttatcag aattttgtt taggcactca ggattattgt       840
ttctggccaa agaaaaaag tggccaggct aaatcagttt ttaagttga tgtgtattta       900

-continued

```
gggacatttt aaaaccttgt aaacaatgtt tatcatggcc agaaagtgat ttctgaatgt      960
acctatgaac aatccgagtc aagatcatga ttgcttagag atgtttttta ttaaagatca     1020
ccatcctgat tatatagaag agcttcttta aaatgtttgt gaatgtcatt ttttaatact     1080
ggaagaaaag tattctgttg tgtctgatgt gtttaggatg tcctttatgg agctaattaa     1140
aagatgaaac ctgaacac                                                   1158
```

<210> SEQ ID NO 71
<211> LENGTH: 153
<212> TYPE: PRT
<213> ORGANISM: Mus musculus

<400> SEQUENCE: 71

```
Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Asp Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Ser Arg Gly Gly Ala Phe Gly Gly
                85                  90                  95

Arg Gly Arg Ser Tyr Ser Arg Gly Gly Gly Asp Gln Gly Tyr Gly Ser
            100                 105                 110

Gly Arg Tyr Asp Ser Arg Pro Gly Gly Tyr Gly Tyr Gly Tyr Gly Arg
        115                 120                 125

Ser Arg Asp Tyr Ser Gly Ser Gln Gly Gly Tyr Asp Arg Tyr Ser Gly
    130                 135                 140

Gly Asn Tyr Arg Asp Asn Tyr Asp Asn
145                 150
```

<210> SEQ ID NO 72
<211> LENGTH: 1185
<212> TYPE: DNA
<213> ORGANISM: Rattus norvegicus

<400> SEQUENCE: 72

```
ggcgtcttcc cgcgccgcag tctctctgtt ctcccggttc cttagagctc gtcgtctctg       60
cagtcttctg acttttaatt tccaggactt ggattctgcc atgtcttctg aagaaggaaa      120
actcttcgtg ggagggctca acttcaacac tgatgagcag gcacttgaag accacttcag      180
cagcttcggg cctatctctg aggtggttgt tgtcaaggac cgggagactc aaagatcccg      240
gggttttggc ttcatcacct tcacaaaccc agagcatgcc tccgatgcca tgagagccat      300
gaatggagag tccctggatg gcgccaaat ccgtgtggac catgcaggca agtctgccag      360
gggaaccaga gggggtgcct ttggggccca tgggcgtggt cgcagctact ctagaggtgg      420 tgagaccag ggatatggaa gtggaagata cgacagccga cctggaggct atggatatgg      480
gtatgggcgg tctagagact acagtggcag aagccagggt ggctatgacc gctactcagg      540
aggaaattac agagacaatt atgacaactg agatggggca tgcacacaat atacacaagg      600
aataacactt ctgatccagg atcgtccttg caaattgctg tatttataaa gattttttgga     660 gctgcgctga aacgtctgtt ttagtacatc aagttctatt tttgaattga gctcccaagg      720
```

-continued

```
tagtttgtta aagaacttta agaaagctcc atgtgttctt taaacacttt tccccctttt      780
aaagacaaat tttaagacat ttgttaacgg tcccaatatt tttccttta tcagaattt       840 tgttgaggca ctcaggatta ttgttgctgg ccaagagaaa aaagtggcca ggataaatca      900
agttttttaa attaatgtgt attttgggac attaaaaatt tgtaaatgat gttttctcat      960
ggccagaaag tgatttctga atgtacctat gaacaatcta catcaagatc atgattacta     1020
gagatgtttt ttattaaaga tcactgtcct gattatatag aagagcttct ttaaaatgtt    1080
tgtgaatgtc atttttaat actggaagaa aaagtattct gttgtgtctg atgtgtttag     1140
gatgtccttt atggagctaa ttaaaagatg aaacctgaac acaaa                     1185
```

<210> SEQ ID NO 73
<211> LENGTH: 156
<212> TYPE: PRT
<213> ORGANISM: Rattus norvegicus

<400> SEQUENCE: 73

```
Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Val Lys Asp Arg Glu Thr Gln Arg Ser Arg Gly
        35                  40                  45

Phe Gly Phe Ile Thr Phe Thr Asn Pro Glu His Ala Ser Asp Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Ala Phe Gly Ala
                85                  90                  95

His Gly Arg Gly Arg Ser Tyr Ser Arg Gly Gly Gly Asp Gln Gly Tyr
            100                 105                 110

Gly Ser Gly Arg Tyr Asp Ser Arg Pro Gly Gly Tyr Gly Tyr Gly Tyr
        115                 120                 125

Gly Arg Ser Arg Asp Tyr Ser Gly Arg Ser Gln Gly Gly Tyr Asp Arg
    130                 135                 140

Tyr Ser Gly Gly Asn Tyr Arg Asp Asn Tyr Asp Asn
145                 150                 155
```

<210> SEQ ID NO 74
<211> LENGTH: 168
<212> TYPE: DNA
<213> ORGANISM: Artificial Sequence
<220> FEATURE:
<223> OTHER INFORMATION: pLet7a-Luc Reporter Vector (LR-0037) (Signosis,
      Inc. CA)

<400> SEQUENCE: 74

```
agaaaaatca gagagatcct cataaaggcc aagaagggcg gaaagtccaa attgctcgag       60
tgatgaaagc tgcgcactag taactataca acctactacc tcaaagctta ataaaggatc      120
ttttattttc attggatctg tgtgttggtt ttttgtatgc ggccgcta                    168
```

<210> SEQ ID NO 75
<211> LENGTH: 75
<212> TYPE: RNA
<213> ORGANISM: Homo sapiens

<400> SEQUENCE: 75

```
uauuuaugua cuuuuauuuu acacagaaac acugccuuuu uauuuauaug uacuguuuua        60
ucuggcccca gguag                                                        75

<210> SEQ ID NO 76
<211> LENGTH: 75
<212> TYPE: RNA
<213> ORGANISM: Homo sapiens

<400> SEQUENCE: 76
aaacuuuuau cuauucugag aaaacaagca aguucugaga gccaggguuu uccuacguag        60
gaugaaaaga uucuu                                                        75

<210> SEQ ID NO 77
<211> LENGTH: 20
<212> TYPE: RNA
<213> ORGANISM: Homo sapiens

<400> SEQUENCE: 77
ucauguagua gauaugacau                                                   20

<210> SEQ ID NO 78
<211> LENGTH: 19
<212> TYPE: RNA
<213> ORGANISM: Homo sapiens

<400> SEQUENCE: 78
uuuauuuaua uguacuguu                                                    19
```